(12) United States Patent
Evindar et al.

(10) Patent No.: US 7,759,370 B2
(45) Date of Patent: Jul. 20, 2010

(54) SPHINGOSINE-1-PHOSPHATE (SIP) RECEPTOR AGONISTS

(75) Inventors: Ghotas Evindar, Waltham, MA (US); Hongfeng Deng, Acton, MA (US); Sylvie Bernier, Woburn, MA (US); Gang Yao, Sudbury, MA (US); Aaron Coffin, Brighton, MA (US); Hongfang Yang, Burlington, MA (US)

(73) Assignee: Praecis Pharmaceuticals, Waltham, MA (US)

( * ) Notice: Subject to any disclaimer, the term of this patent is extended or adjusted under 35 U.S.C. 154(b) by 51 days.

(21) Appl. No.: 11/888,909

(22) Filed: Aug. 1, 2007

(65) Prior Publication Data

US 2008/0096938 A1 Apr. 24, 2008

Related U.S. Application Data

(60) Provisional application No. 60/821,101, filed on Aug. 1, 2006, provisional application No. 60/827,919, filed on Oct. 3, 2006, provisional application No. 60/896,431, filed on Mar. 22, 2007, provisional application No. 60/959,291, filed on Jul. 12, 2007.

(51) Int. Cl.
*A61K 31/185* (2006.01)
*A61K 31/433* (2006.01)
*C07D 285/18* (2006.01)
*C07F 9/38* (2006.01)

(52) U.S. Cl. ............... 514/363; 514/576; 548/136; 562/11

(58) Field of Classification Search ............. 514/363, 514/364, 365; 548/125, 136, 202
See application file for complete search history.

(56) References Cited

U.S. PATENT DOCUMENTS

| 6,617,336 B1 * | 9/2003 | Bovy et al. ............... 514/314 |
| 2006/0135786 A1 * | 6/2006 | Saha et al. ............... 548/341.1 |

OTHER PUBLICATIONS

The New England Journal of Medicine, Noseworthy et al, p. 949, vol. 343, No. 13, (2000).*

* cited by examiner

*Primary Examiner*—Yong Chu
(74) *Attorney, Agent, or Firm*—Linda E. Hall; Robert J. Smith

(57) ABSTRACT

The invention provides compounds formula I, their preparation, and their use as pharmaceutically active immunosuppressive agents for the treatment of autoimmune disorders, organ transplant rejection, disorders associated with an activated immune system, as well as other disorders modulated by lymphopenia or S1P receptors.

4 Claims, No Drawings

SPHINGOSINE-1-PHOSPHATE (S1P) RECEPTOR AGONISTS

RELATED APPLICATIONS

This application is related and claims priority to U.S. provisional application Ser. No. 60/821,101, filed Aug. 1, 2006, U.S. provisional application Ser. No. 60/827,919, filed Oct. 3, 2006, U.S. provisional application Ser. No. 60/896,431, filed Mar. 22, 2007 and U.S. provisional application Ser. No. 60/959,291, filed Jul. 12, 2007, the entire contents of each of which are incorporated herein by this reference.

BACKGROUND OF THE INVENTION

The sphingosine-1-phosphate (S1P) receptors 1-5 constitute a family of seven transmembrane G-protein coupled receptors. These receptors, referred to as S1P-1 to S1P-5, are activated via binding by sphingosine-1-phosphate, which is produced by the sphingosine kinase-catalyzed phosphorylation of sphingosine. S1P receptors are cell surface receptors involved in a variety of cellular processes, including cell proliferation and differentiation, cell survival, cell invasion, lymphocyte trafficking, and cell migration. Sphingosine-1-phosphate is found in plasma and a variety of other tissues, and exerts autocrine and paracrine effects, including regulating the secretion of growth factors.

Administration of S1P to an animal results in sequestration of lymphocytes into the lymph nodes and Peyers patches without causing lymphocyte depletion. This activity, which is of potential utility in treating diseases or conditions associated with inappropriate immune response, including transplant rejection, autoimmune diseases, as well as other disorders modulated by lymphocyte trafficking, is believed to proceed via activation of the S1P-1 receptor. Administration of S1P in vivo has been shown to cause hypotension and bradycardia, which are believed to be due to signaling through one or more of the other S1P receptors, i.e. S1P-2 to S1P-5. Accordingly, there is a need for compounds which are potent and selective agonists of the S1P-1 receptor.

SUMMARY OF THE INVENTION

These and other needs are met by the present invention. In some aspects, the present invention is directed to a compound of formula I:

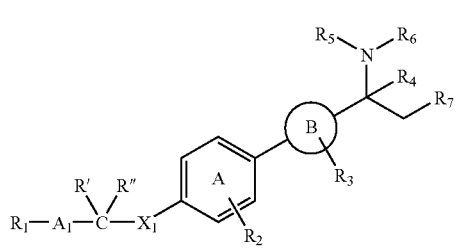

or a pharmaceutically acceptable salt thereof, wherein:

$R_1$ is hydrogen, halogen, cyano, alkyl, aryl, heteroaryl, cycloalkyl, heterocycloalkyl, aralkyl, heteroalkyl, —O-alkyl, —O-aryl, —O-heteroaryl, —S-alkyl, alkylene-O-alkyl, alkylene-$CO_2H$, alkylene-$CO_2$alkyl, alkyl$SO_2$, alkylenesulfonyl, alkylene-CO-amino, alkylene-CO-alkylamino, alkylene-CO-dialkylamino, alkylene-NH—$CO_2H$, alkylene-NH—$CO_2$alkyl —$CO_2$alkyl, —OH, —C(O)-alkyl, —C(O)O-alkyl, —$CONH_2$, —CO-alkylamino, —CO-dialkylamino, amino, alkylamino, or dialkylamino, any of which may be optionally substituted on carbon with 1, 2, or 3 groups selected from halo, alkyl, haloalkyl, —$CF_3$, aryl, —CN, —OH, or —O-alkyl;

A is $(C_1-C_{20})$alkylene, $(C_2-C_{20})$alkenylene, or $(C_2-C_{20})$alkynylene, each of which may be optionally substituted on carbon with 1, 2, o3 groups selected from OH, $CO_2H$, $CO_2$alkyl, halogen, amino, alkylamino, dialkylamino, —O-alkyl, alkylene-O-alkyl, alkylene-OH, or alkylene-$CO_2H$;

$X_1$ is a bond or is $CH_2$, O, —$CH_2O$—, S, —S(O), —$S(O)_2$, —C(O)—, —C(O)O—, or $NR_x$, wherein $R_x$ is H or $(C_1-C_6)$ alkyl;

R' and R" are each independently hydrogen, halogen, alkyl optionally substituted on carbon with halogen, alkyl, or taken together with the carbon to which they are attached form C=O or a 3, 4, 5, or 6-membered ring, optionally containing 1 or 2 heteroatoms selected from 0 NH, N-alkyl, SO, or $SO_2$, any of which may be optionally substituted on carbon with alkyl or halogen $R_2$ is cyano, alkyl, aryl, heteroaryl, cycloalkyl, heterocycloalkyl, aralkyl, heteroalkyl, —O-alkyl, —O-aryl, —O-heteroaryl, aralkoxy, heteroaralkoxy, —S-alkyl, alkylene-O-alkyl, alkylene-$CO_2H$, alkylene-$CO_2$alkyl, alkyl$SO_2$, alkylenesulfonyl, alkylene-CO-amino, alkylene-CO-alkylamino, alkylene-CO-dialkylamino, alkylene-NH—$CO_2H$, alkylene-NH—$CO_2$alkyl —$CO_2$alkyl, —OH, —C(O)-alkyl, —C(O)O-alkyl, —$CONH_2$, —CO-alkylamino, —CO-dialkylamino, amino, alkylamino, and dialkylamino, any of which may be optionally substituted on carbon with 1, 2, or 3 groups selected from halo, alkyl, OH, or —O-alkyl;

$R_3$ is absent, hydrogen, halogen, cyano, alkyl, aryl, heteroaryl, cycloalkyl, heterocycloalkyl, aralkyl, heteroalkyl, —O-alkyl, —O-aryl, —O-heteroaryl, aralkoxy, heteroaralkoxy, —S-alkyl, alkylene-O-alkyl, alkylene-$CO_2H$, alkylene-$CO_2$alkyl, alkyl$SO_2$, alkylenesulfonyl, alkylene-CO-amino, alkylene-CO-alkylamino, alkylene-CO-dialkylamino, alkylene-NH—$CO_2H$, alkylene-NH—$CO_2$alkyl —$CO_2$alkyl, —OH, —C(O)-alkyl, —C(O)O-alkyl, —$CONH_2$, —CO-alkylamino, —CO-dialkylamino, amino, alkylamino, and dialkylamino, any of which may be optionally substituted on carbon with 1, 2, or 3 groups selected from halo, alkyl, OH, or —O-alkyl;

is phenyl or pyridyl;

is aryl, heteroaryl, heterocyclo, or cycloalkyl, any of which may be optionally substituted on carbon with 1, 2, or 3 groups selected form halogen, alkyl, O-alkyl, $CO_2H$, $CO_2$alkyl, halogen, amino, alkylamino, dialkylamino, —O-alkyl, alkylene-O-alkyl, alkylene-OH, or alkylene-$CO_2H$, provided that

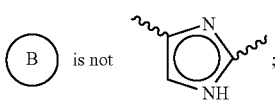

R₄ is hydrogen, cyano, alkyl, aryl, heteroaryl, alkylene-O-alkyl, alkylene-OH, aryl, alkylene-O-alkyl, —CO₂H, —CO₂-alkyl, alkylene-CO₂H, or alkylene-CO₂-alkyl, alkylene-OC(O)R wherein R is hydrogen or alkyl; cycloalkyl, heterocycloalkyl, alkylene-NH₂, alkylene-alkylamino, or alkylene-dialkylamino, any of which may be optionally substituted on carbon with 1, 2, or 3 groups selected from OH, CO₂H, CO₂alkyl, halogen, amino, alkylamino, dialkylamino, —O-alkyl, alkylene-O-alkyl, alkylene-OH, or alkylene-CO₂H;

R₅ and R₆ are each independently selected from the group consisting of hydrogen, alkyl, alkylene-OH, aryl, alkylene-O-alkyl, —CO₂H, CO₂-alkyl, alkylene-OC(O)alkyl, cycloalkyl, heterocyclo, —C(O)-alkyl, —C(O)-aryl, C(O)-aralkyl, —C(O)—Oalkyl, —C(O)—Oaryl, —C(O)—Oaralkyl, alkylene-amino, alkylene-alkylamino, and alkylene-dialkylamino, any of which may be optionally substituted on carbon with halogen, alkyl, hydroxyl, CO₂H, CO₂alkyl or alkoxy; or R₅ and R₆, together with the nitrogen to which they are attached, may form a 3, 4, 5, or 6-membered saturated or unsaturated ring, optionally containing 1 or 2 additional heteroatoms selected from O, S, NH, or N-alkyl, and optionally substituted on carbon with halogen, alkyl, hydroxyl, or alkoxy;

R₇ is selected from the group consisting of —OH, —O-alkyl, alkylene-OH, —CO₂H, alkylene-CO₂H, —C(O)O-alkyl, -alkylene-CO₂-alkyl, —C(O)O-aryl, —CH₂=CHCO₂H, —CH₂=CHC(O)O-alkyl, —CH₂=CHC(O)O-aryl, —OPO₂R$_{p1}$R$_{p2}$, —OPO₃R$_{p1}$R$_{p2}$, —CH₂PO₃R$_{p1}$R$_{p2}$, —OPO₂(S)R$_{p1}$R$_{p2}$, and —C(Z')(Z")PO₃R$_{p1}$R$_{p2}$, any of which may be optionally substituted on carbon with halogen, alkyl, hydroxyl, carboxy, or alkoxy; and wherein Z' is hydroxyl or halogen;

Z" is H or halogen;

R$_{p1}$ and R$_{p2}$ are each independently hydrogen, C₁-C₆-alkyl, aryl, or one of the following groups:

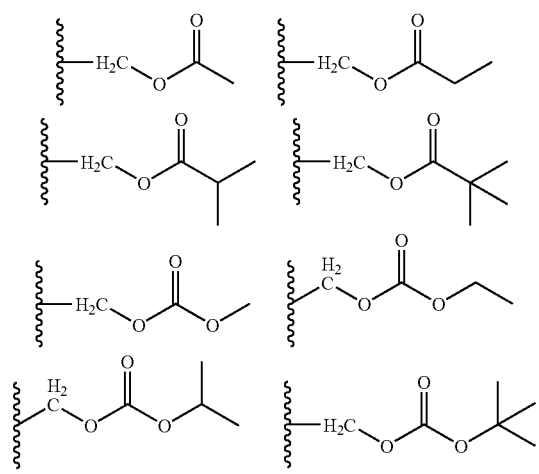

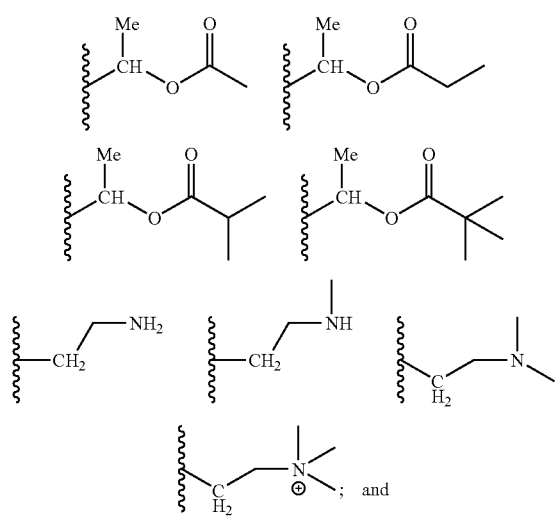

Y is heterocyclo or heteroaryl.

In some embodiments, R₂ is alkyl substituted with 1, 2 or 3 halo groups. In some embodiments, R₂ is trifluoromethyl.

In other aspects, the present invention is directed to a compound of formula II:

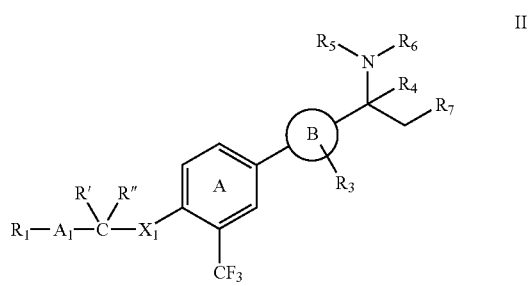

or a pharmaceutically acceptable salt thereof, wherein:

R₁ is hydrogen, halogen, cyano, alkyl, aryl, heteroaryl, cycloalkyl, heterocycloalkyl, aralkyl, heteroalkyl, —O-alkyl, —O-aryl, —O-heteroaryl, —S-alkyl, alkylene-O-alkyl, alkylene-CO₂H, alkylene-CO₂alkyl, alkylSO₂, alkylenesulfonyl, alkylene-CO-amino, alkylene-CO-alkylamino, alkylene-CO-dialkylamino, alkylene-NH—CO₂H, alkylene-NH—CO₂alkyl —CO₂alkyl, —OH, —C(O)-alkyl, —C(O)O-alkyl, —CONH₂, —CO-alkylamino, —CO-dialkylamino, amino, alkylamino, or dialkylamino, any of which may be optionally substituted on carbon with 1, 2, or 3 groups selected from halo, alkyl, haloalkyl, —CF₃, —CN, —OH, or —O-alkyl;

A is (C₁-C₂₀)alkylene, (C₂-C₂₀)alkenylene, or (C₂-C₂₀)alkynylene, each of which may be optionally substituted on carbon with 1, 2, or 3 groups selected from OH, CO₂H, CO₂alkyl, halogen, amino, alkylamino, dialkylamino, —O-alkyl, alkylene-O-alkyl, alkylene-OH, or alkylene-CO₂H;

X₁ is a bond or is CH₂, O, —CH₂O—, S, —S(O), —S(O)₂, —C(O)—, —C(O)O—, or NR$_x$, wherein R$_x$ is H or (C₁-C₆) alkyl;

R' and R" are each independently hydrogen, halogen, alkyl optionally substituted on carbon with halogen, alkyl, or taken together with the carbon to which they are attached form C=O or a 3, 4, 5, or 6-membered ring, optionally containing 1 or 2 heteroatoms selected from 0 NH, N-alkyl, SO, or $SO_2$, any of which may be optionally substituted on carbon with alkyl or halogen $R_3$ is absent, hydrogen, halogen, cyano, alkyl, aryl, heteroaryl, cycloalkyl, heterocycloalkyl, aralkyl, heteroalkyl, —O-alkyl, —O-aryl, —O-heteroaryl, aralkoxy, heteroaralkoxy, —S-alkyl, alkylene-O-alkyl, alkylene-$CO_2H$, alkylene-$CO_2$alkyl, alkyl$SO_2$, alkylenesulfonyl, alkylene-CO-amino, alkylene-CO-alkylamino, alkylene-CO-dialkylamino, alkylene-NH—$CO_2H$, alkylene-NH—$CO_2$alkyl —$CO_2$alkyl, —OH, —C(O)-alkyl, —C(O)O-alkyl, —$CONH_2$, —CO-alkylamino, —CO-dialkylamino, amino, alkylamino, and dialkylamino, any of which may be optionally substituted on carbon with 1, 2, or 3 groups selected from halo, alkyl, OH, or —O-alkyl;

is phenyl or pyridyl;

is aryl, heteroaryl, heterocyclo, or cycloalkyl, any of which may be optionally substituted on carbon with 1, 2, or 3 groups selected form halogen, alkyl, O-alkyl, $CO_2H$, $CO_2$alkyl, halogen, amino, alkylamino, dialkylamino, —O-alkyl, alkylene-O-alkyl, alkylene-OH, or alkylene-$CO_2H$, provided that

$R_4$ is hydrogen, cyano, alkyl, aryl, heteroaryl, alkylene-O-alkyl, alkylene-OH, aryl, alkylene-O-alkyl, —$CO_2H$, —$CO_2$-alkyl, alkylene-$CO_2H$, or alkylene-$CO_2$-alkyl, alkylene-OC(O)R wherein R is hydrogen or alkyl; cycloalkyl, heterocycloalkyl, alkylene-$NH_2$, alkylene-alkylamino, or alkylene-dialkylamino, any of which may be optionally substituted on carbon with 1, 2, or 3 groups selected from OH, $CO_2H$, $CO_2$alkyl, halogen, amino, alkylamino, dialkylamino, —O-alkyl, alkylene-O-alkyl, alkylene-OH, or alkylene-$CO_2H$;

$R_5$ and $R_6$ are each independently selected from the group consisting of hydrogen, alkyl, alkylene-OH, aryl, alkylene-O-alkyl, —$CO_2H$, $CO_2$-alkyl, alkylene-OC(O)alkyl, cycloalkyl, heterocyclo, —C(O)-alkyl, —C(O)-aryl, C(O)-aralkyl, —C(O)—Oalkyl, —C(O)—Oaryl, —C(O)—Oaralkyl, alkylene-amino, alkylene-alkylamino, and alkylene-dialkylamino, any of which may be optionally substituted on carbon with halogen, alkyl, hydroxyl, $CO_2H$, $CO_2$alkyl or alkoxy; or $R_5$ and $R_6$, together with the nitrogen to which they are attached, may form a 3, 4, 5, or 6-membered saturated or unsaturated ring, optionally containing 1 or 2 additional heteroatoms selected from O, S, NH, or N-alkyl, and optionally substituted on carbon with halogen, alkyl, hydroxyl, or alkoxy;

$R_7$ is selected from the group consisting of —OH, —O-alkyl, -alkylene-OH, —$CO_2H$, -alkylene-$CO_2H$, —C(O)O-alkyl, -alkylene-$CO_2$-alkyl, —C(O)O-aryl, —$CH_2$=$CHCO_2H$, —$CH_2$=CHC(O)O-alkyl, —$CH_2$=CHC(O)O-aryl, —$OPO_2R_{p1}R_{p2}$, —$OPO_3R_{p1}R_{p2}$, —$CH_2PO_3R_{p1}R_{p2}$, —$OPO_2(S)R_{p1}R_{p2}$, and —C(Z')(Z") $PO_3R_{p1}R_{p2}$, any of which may be optionally substituted on carbon with halogen, alkyl, hydroxyl, carboxy, or alkoxy; and wherein Z' is hydroxyl or halogen;

Z" is H or halogen;

$R_{p1}$ and $R_{p2}$ are each independently hydrogen, $C_1$-$C_6$-alkyl, aryl, or one of the following groups:

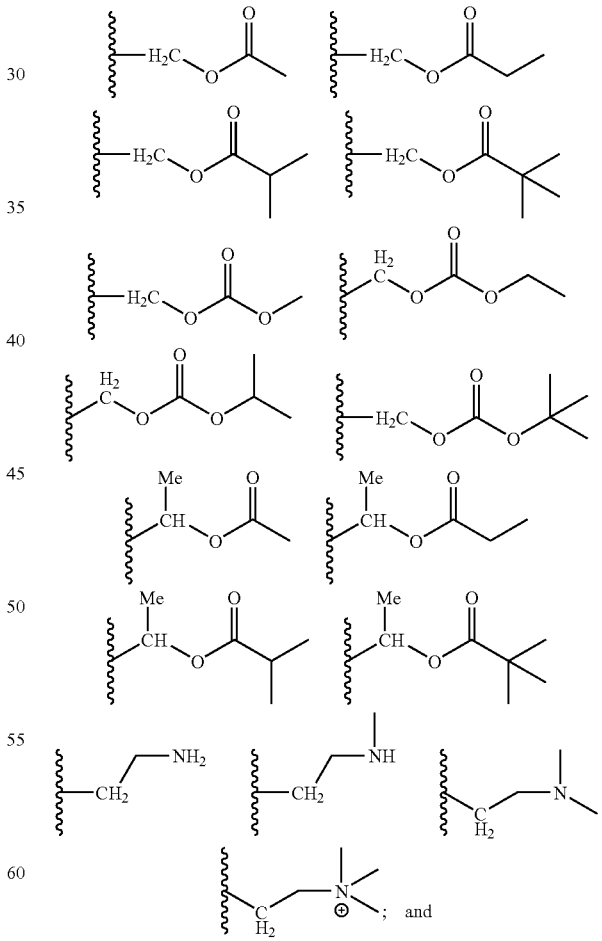

Y is heterocyclo or heteroaryl.

In some embodiments, compounds of the present invention include compounds listed in the following table:

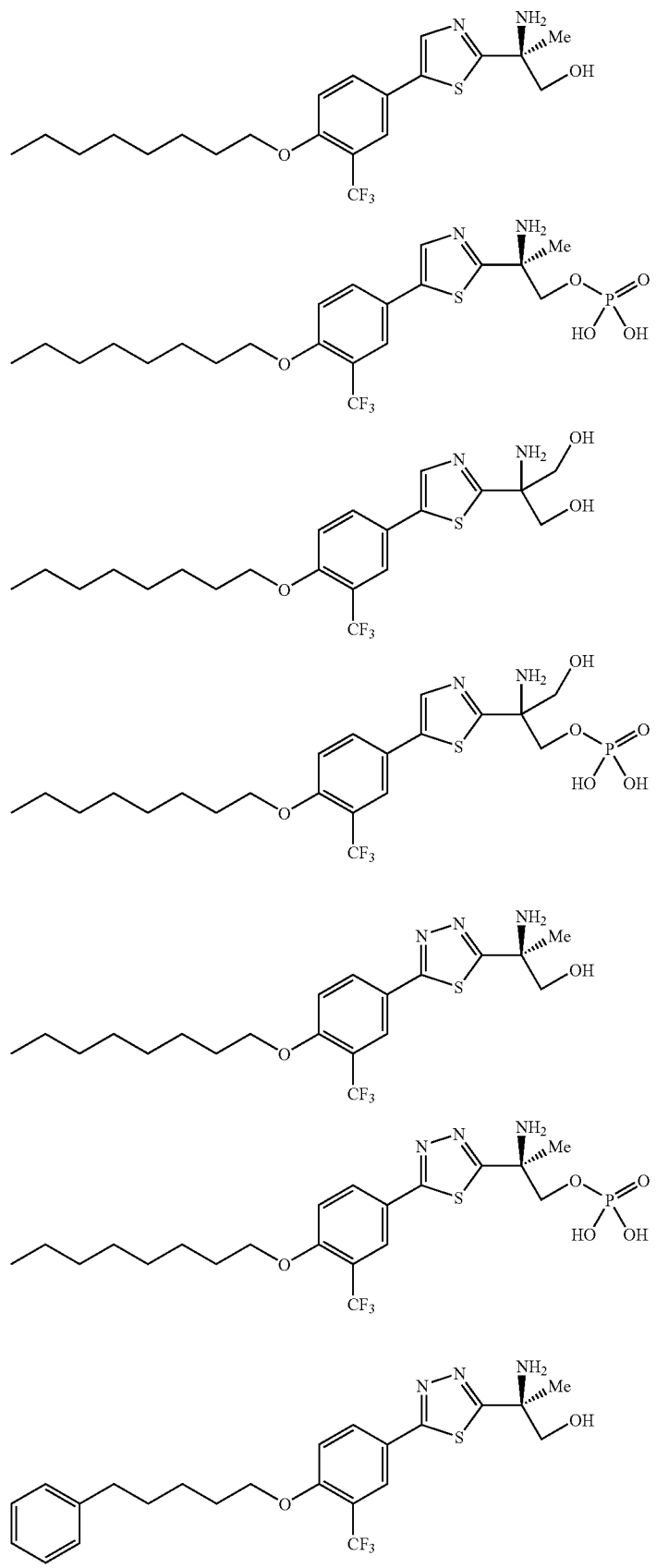

-continued
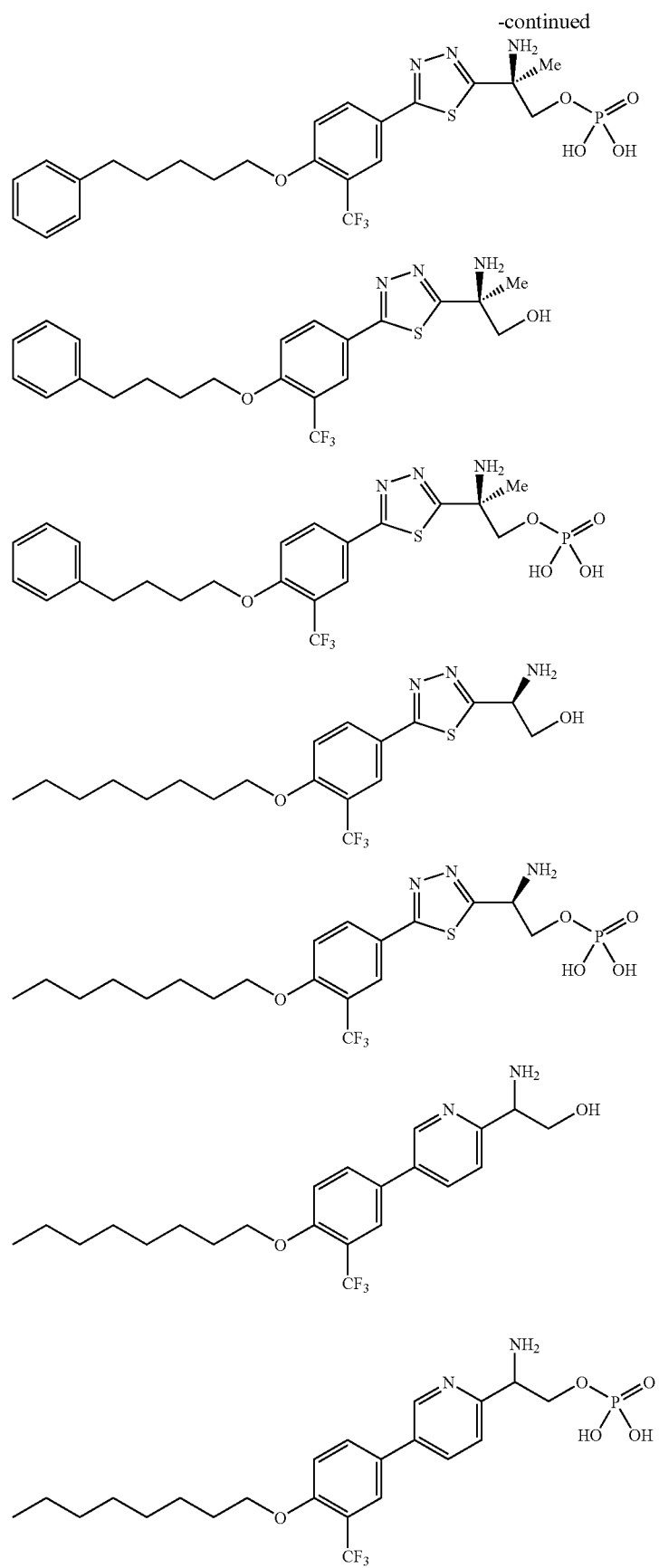

-continued
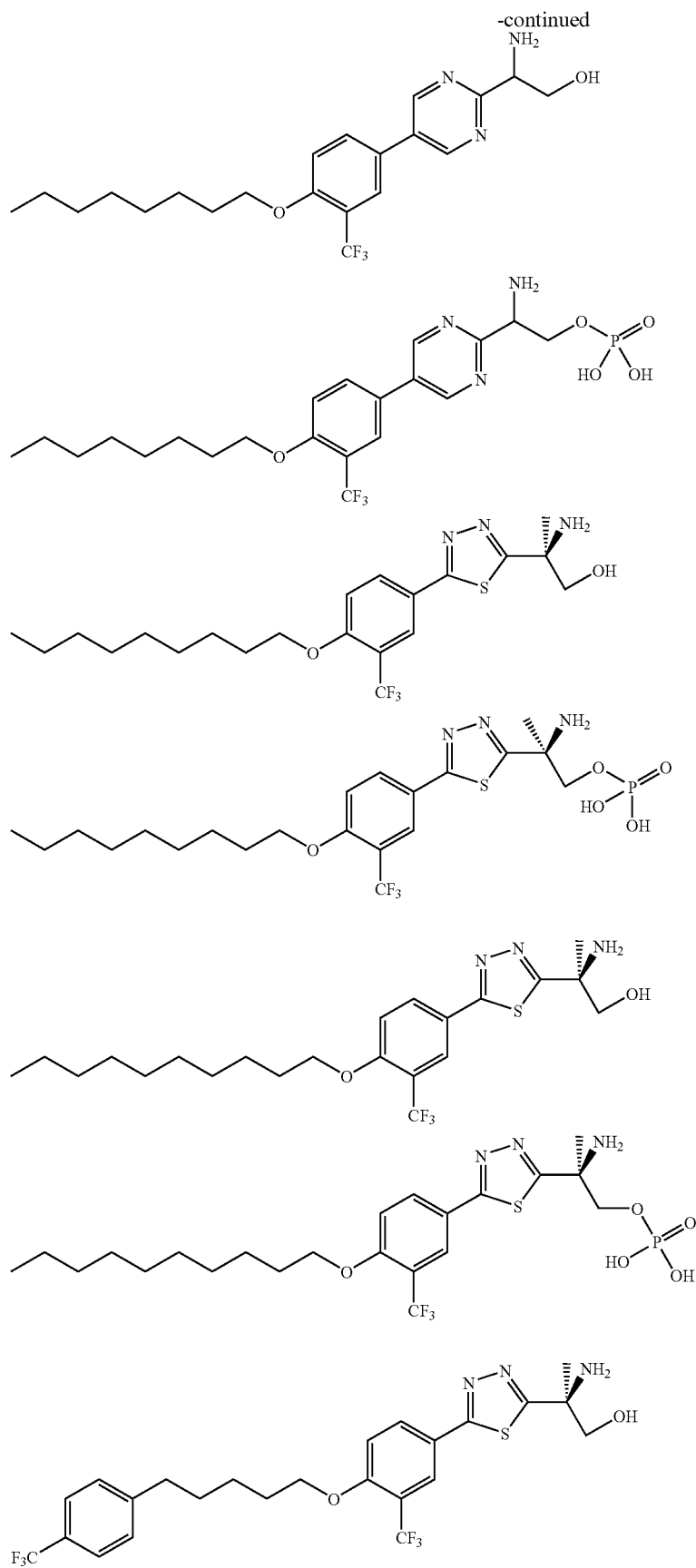

-continued
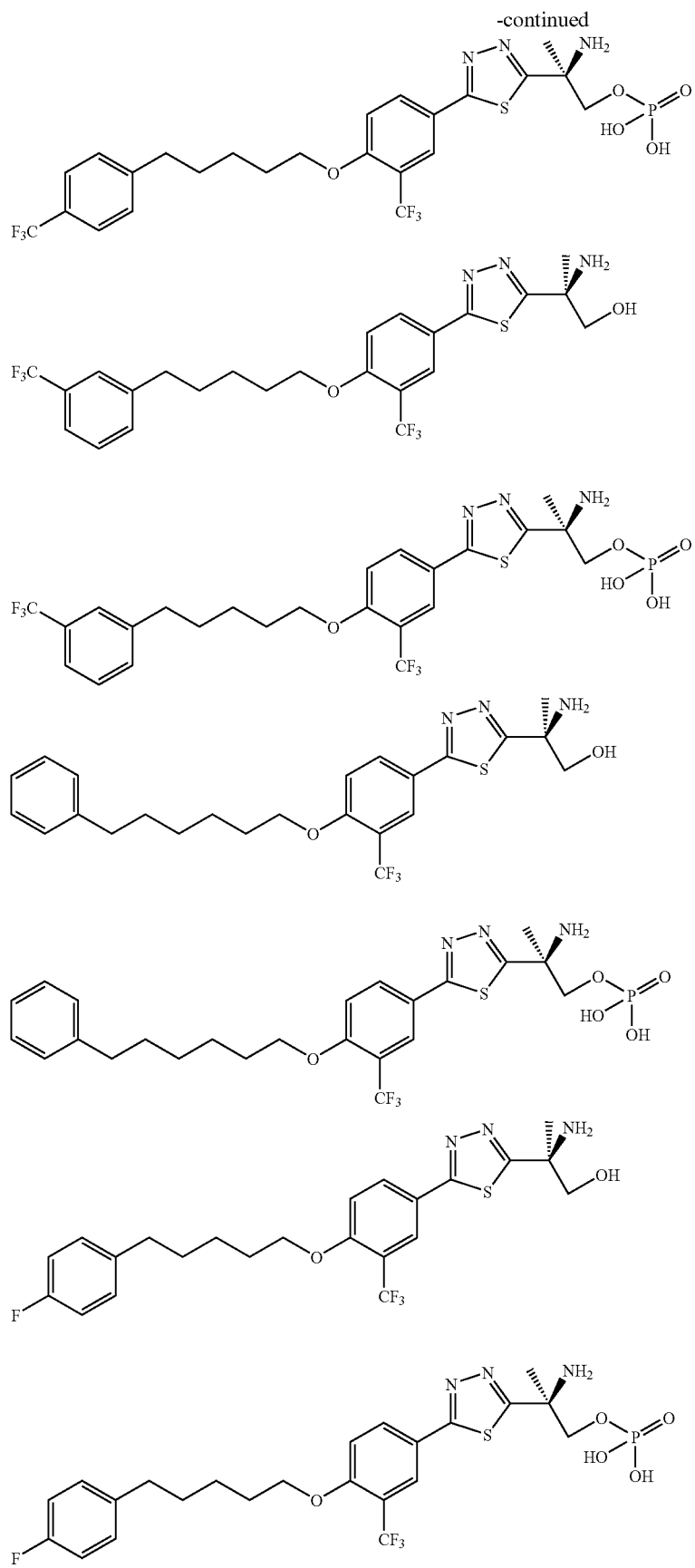

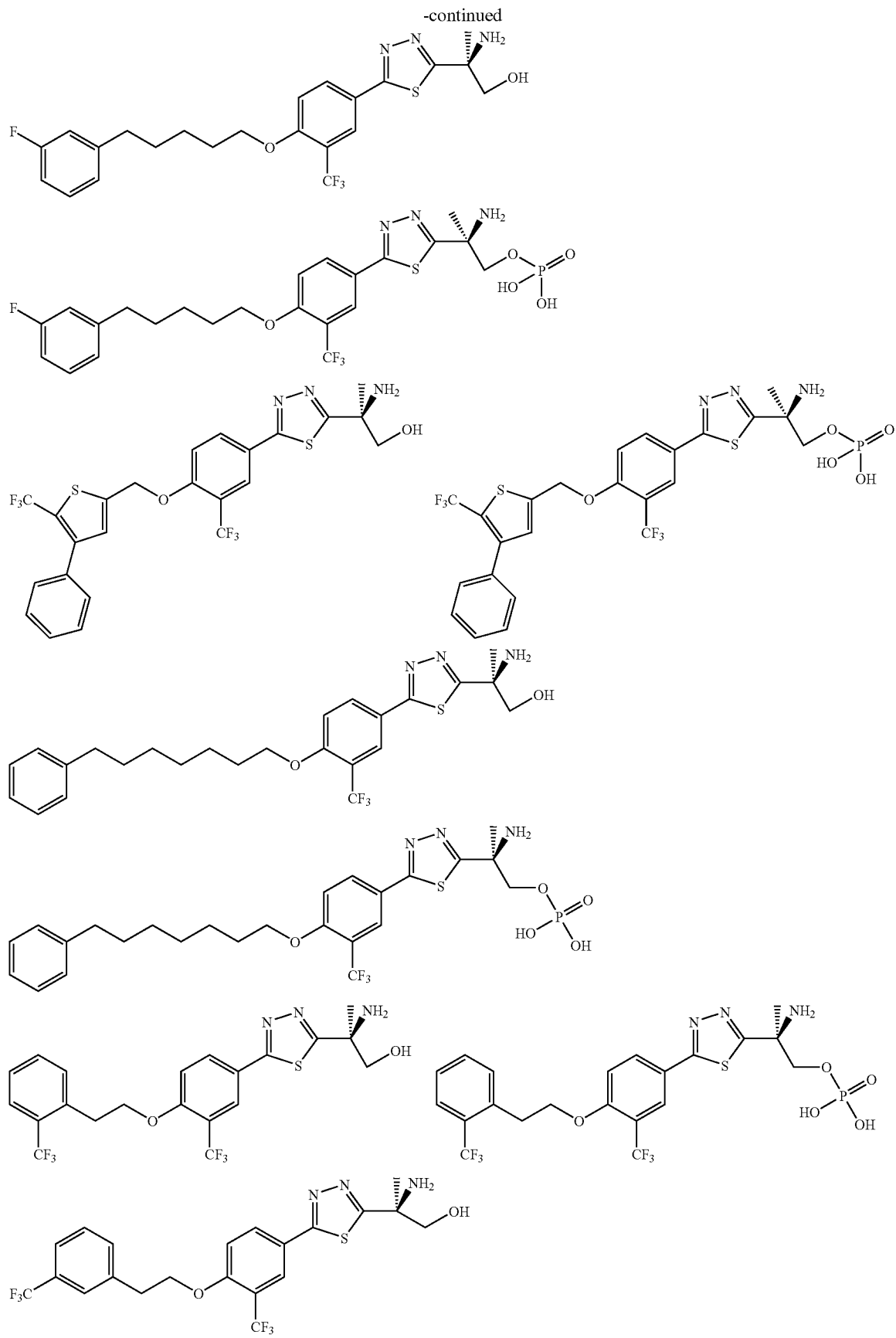

-continued
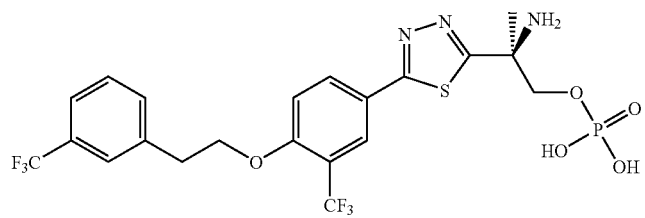
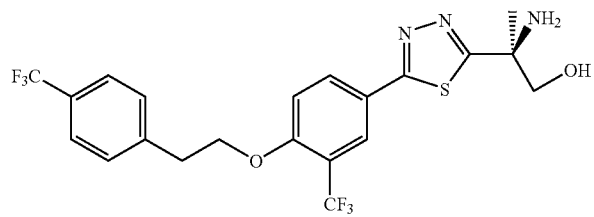
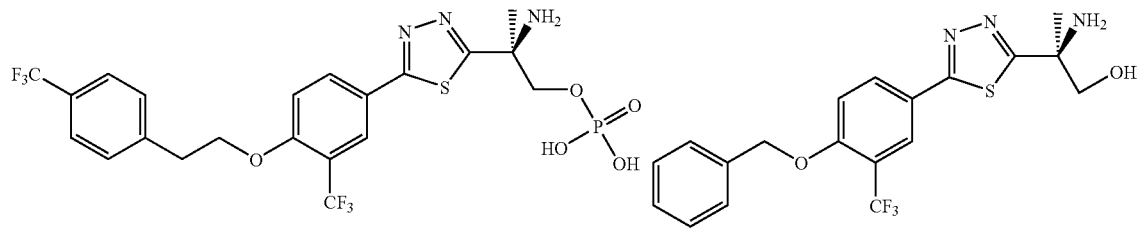
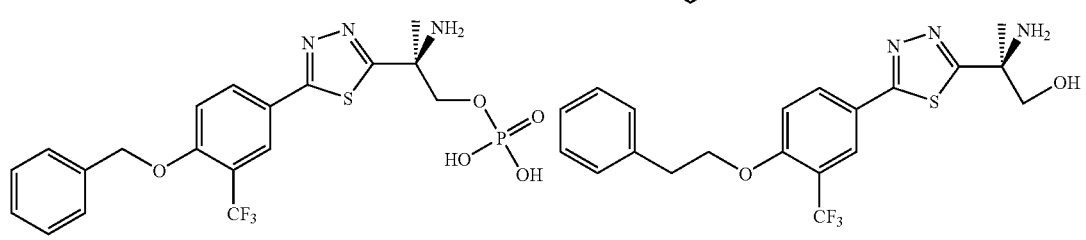
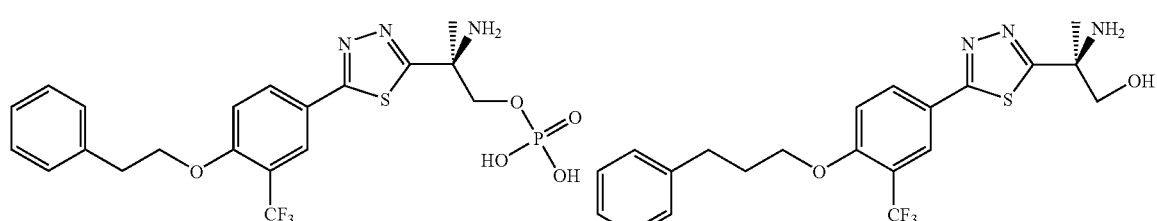
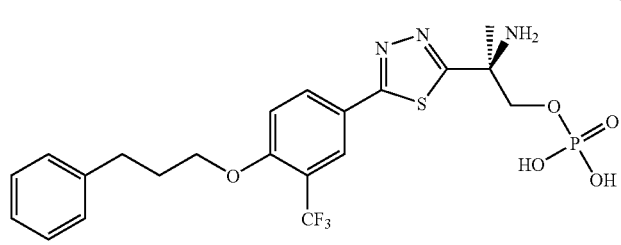
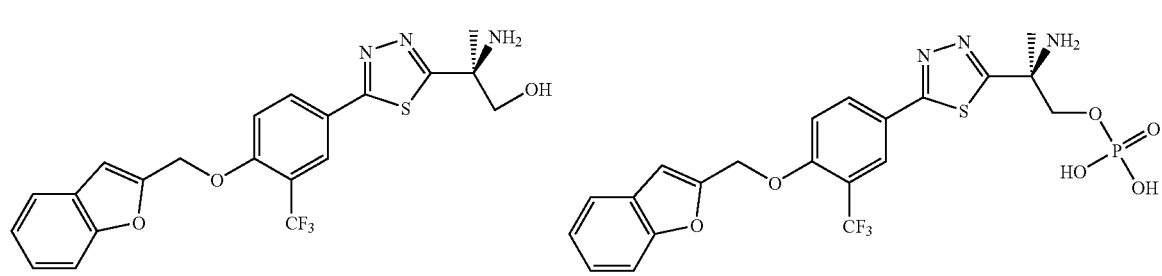

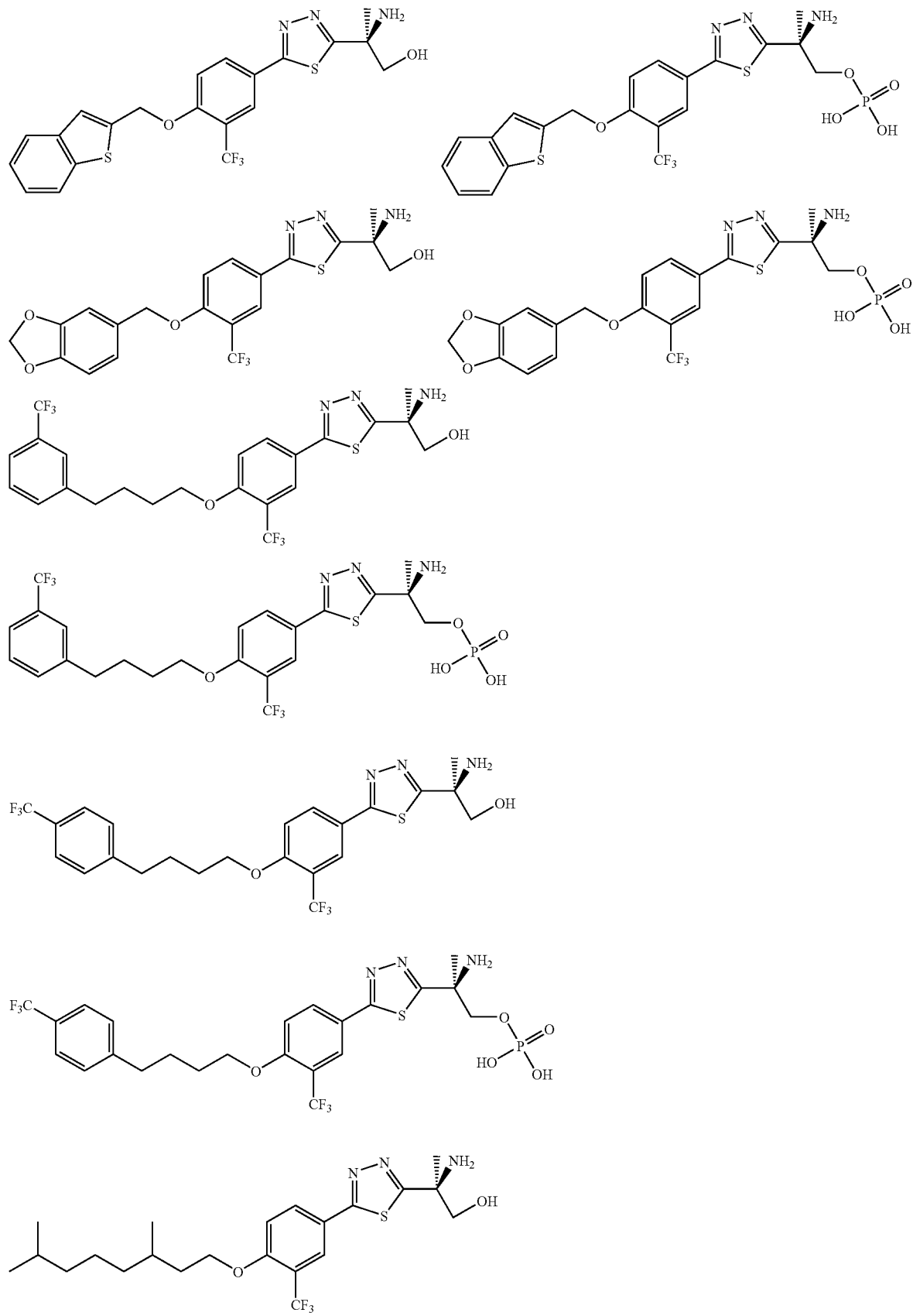

-continued
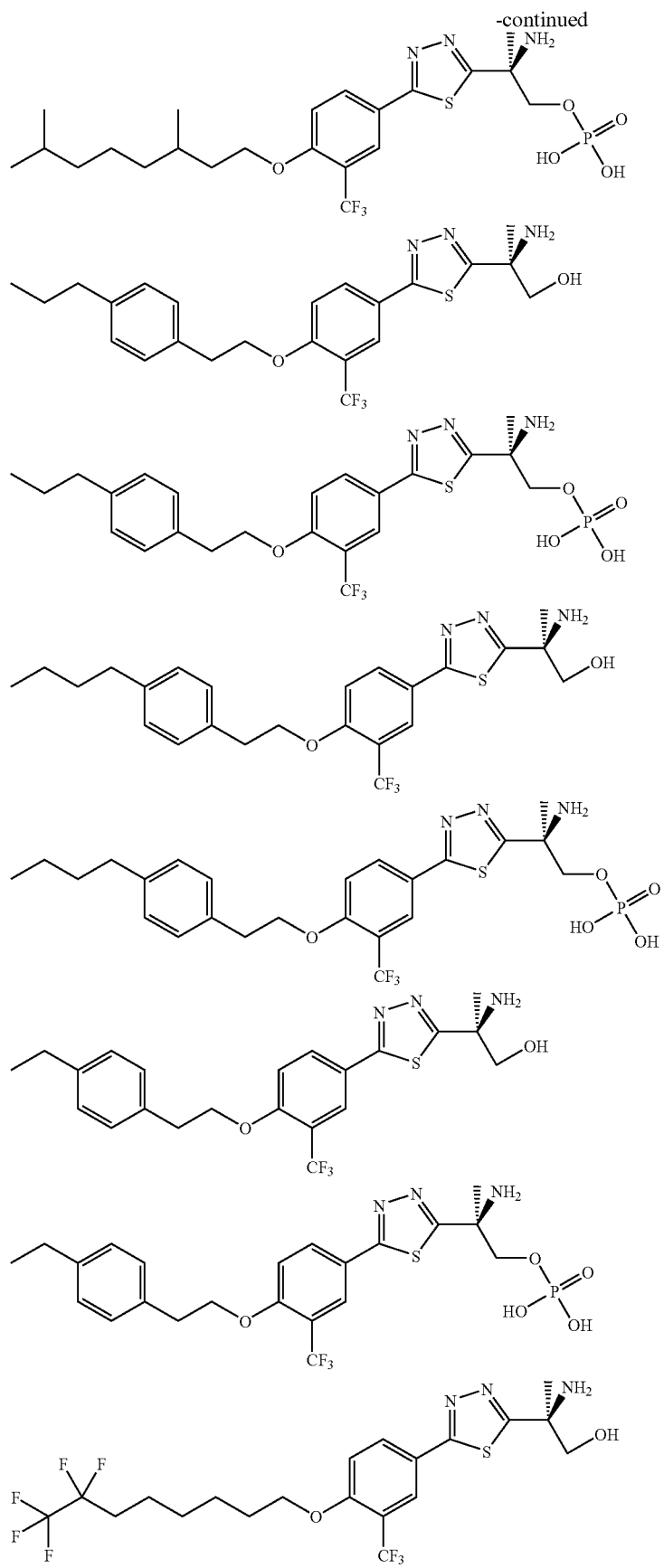

-continued
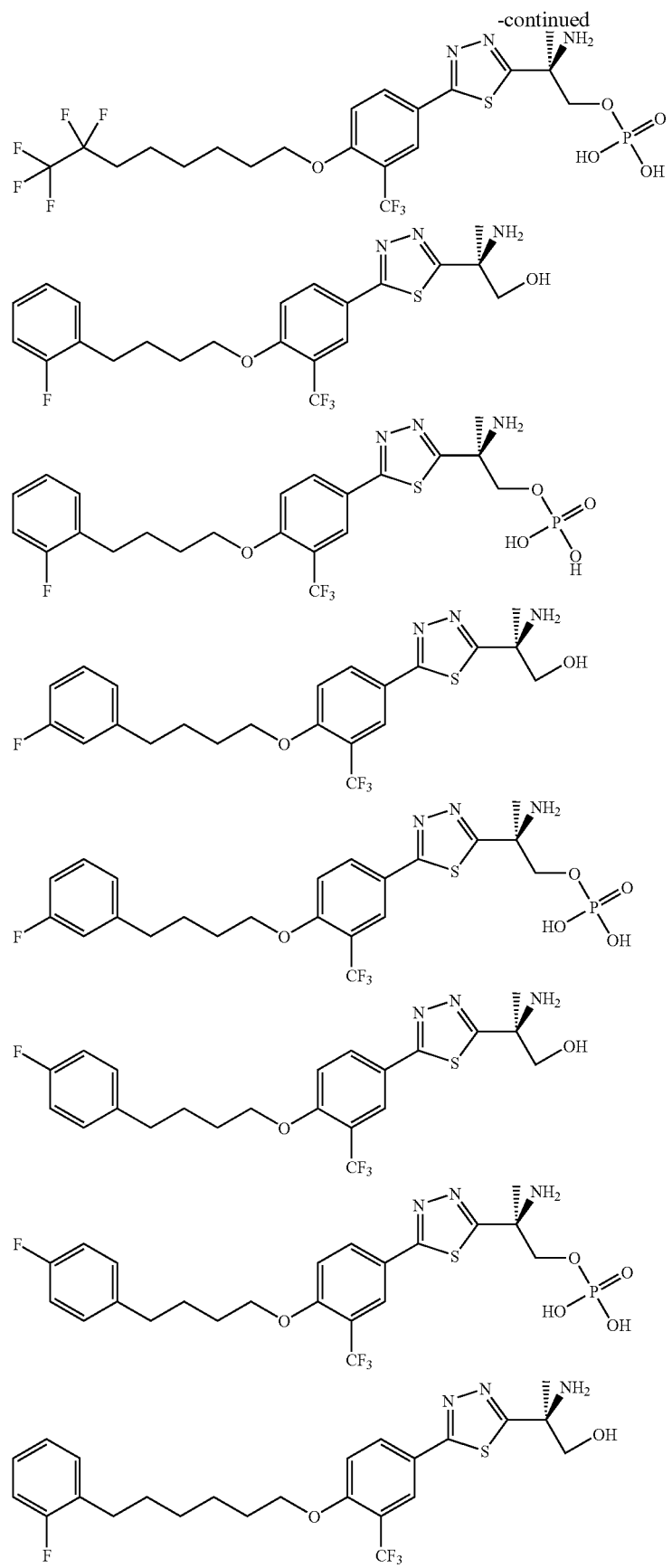

-continued
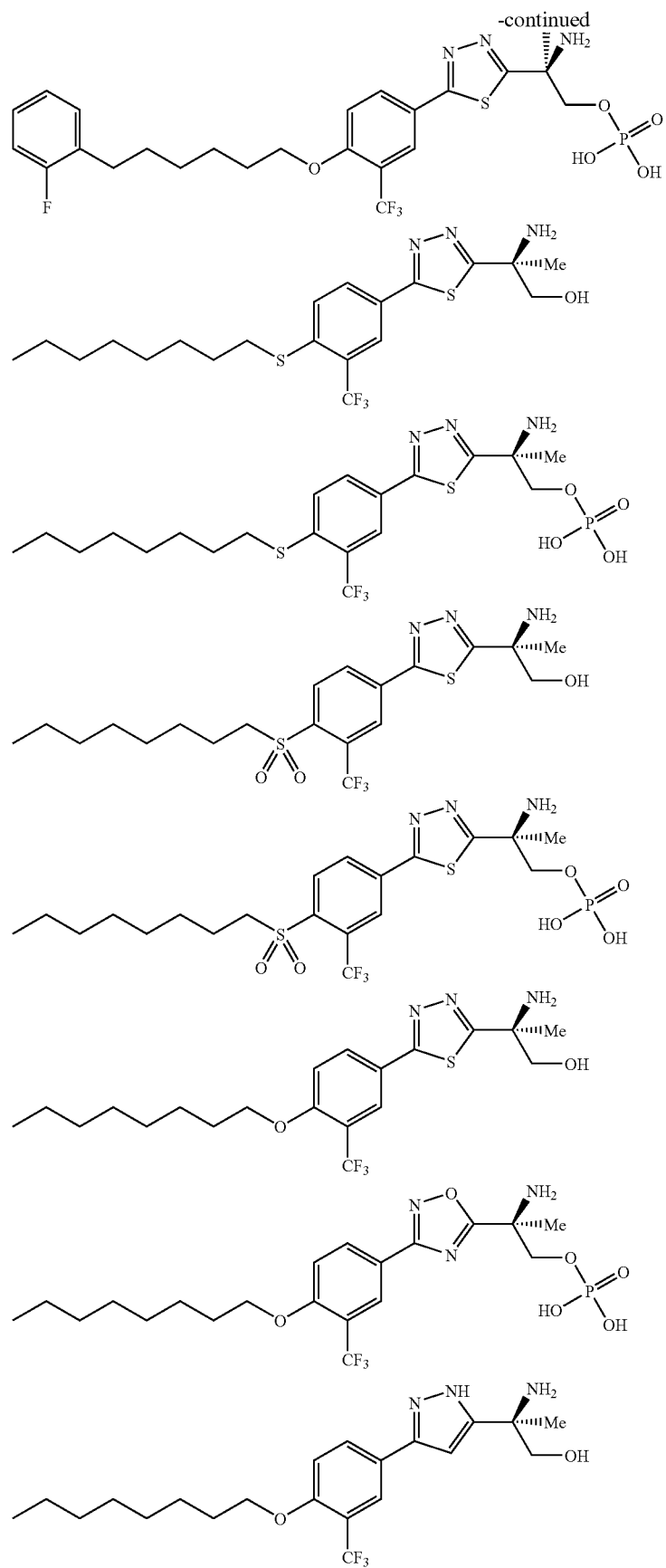

-continued
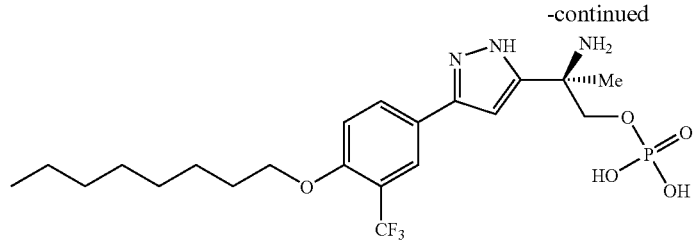
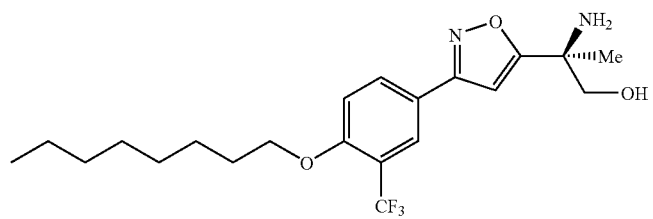
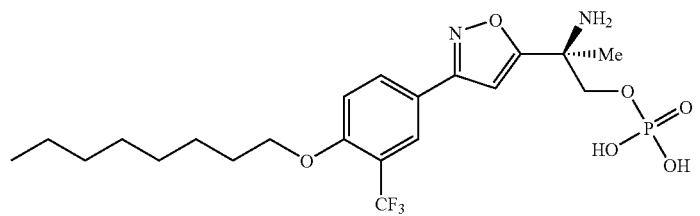
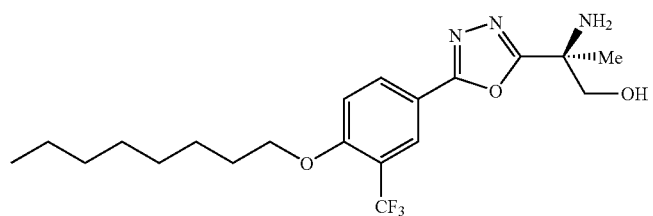
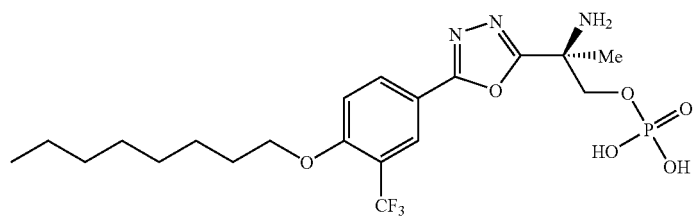
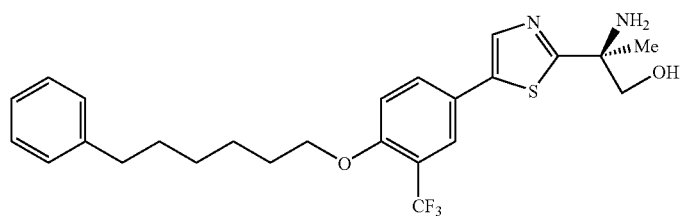
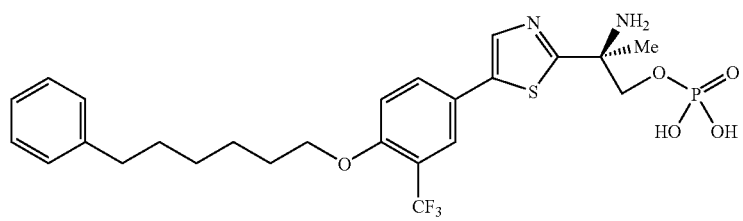

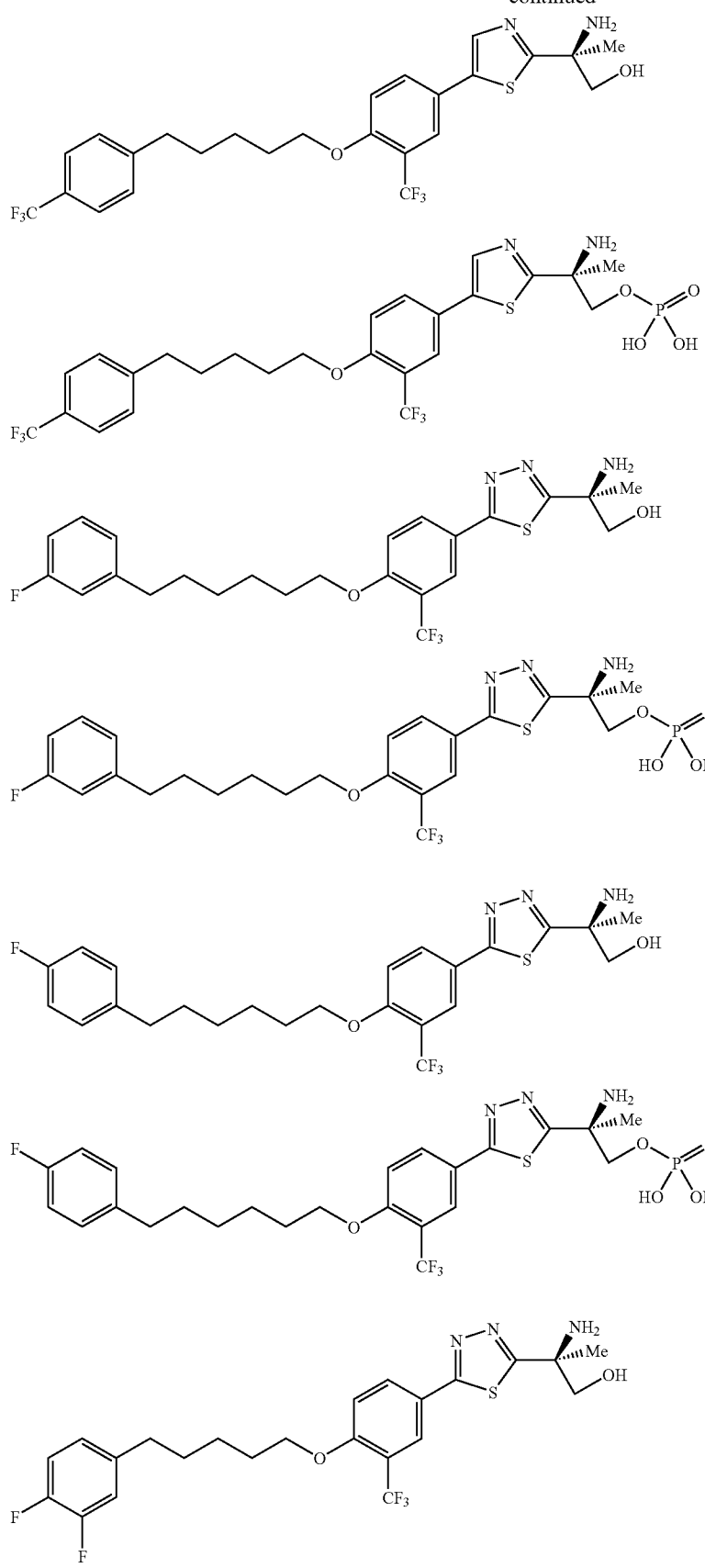

-continued
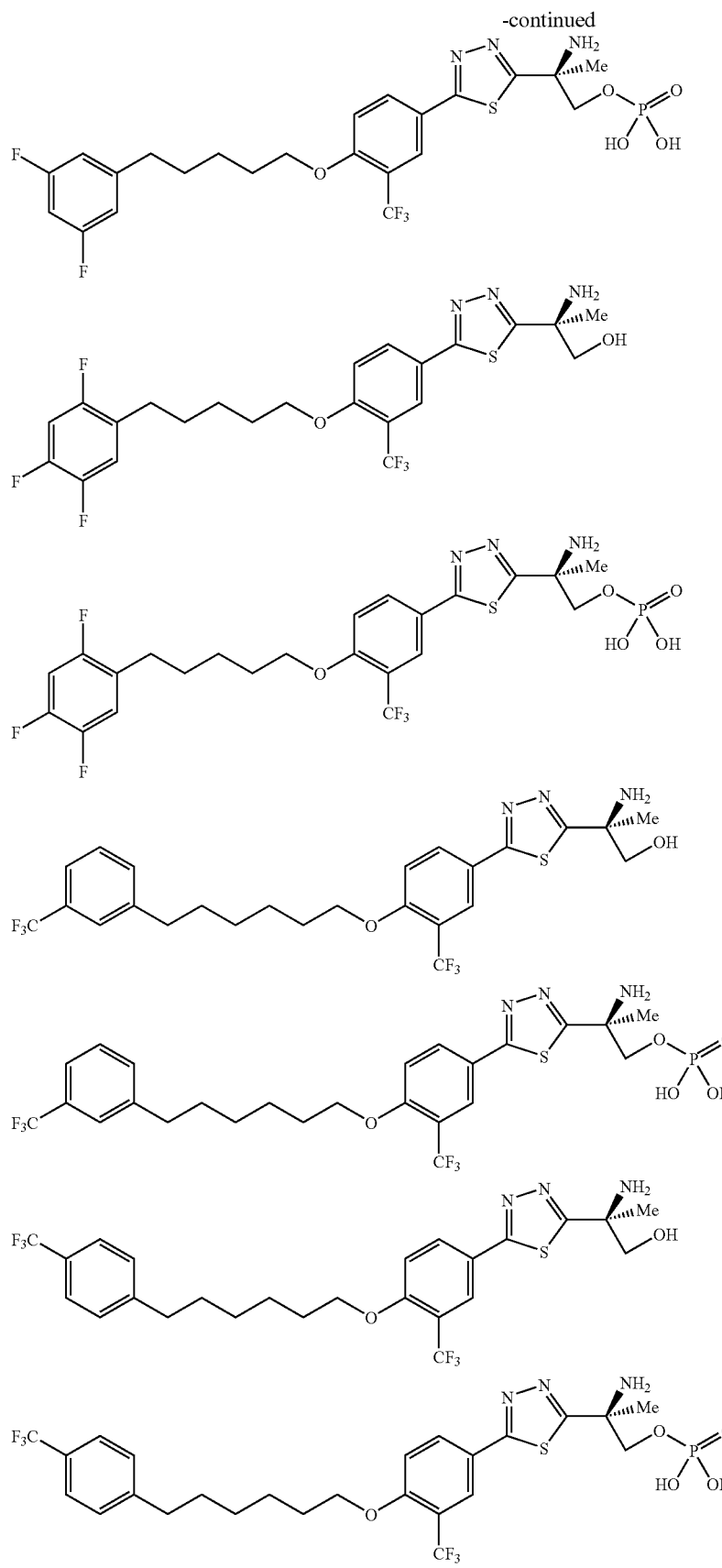

as well as pharmaceutically acceptable salts, phosphate derivatives, phosphate mimics, or phosphate precursor analogs thereof.

In some aspects, the present invention is directed to a compound of formula III:

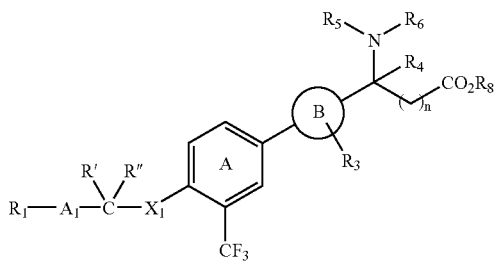

or a pharmaceutically acceptable salt thereof, wherein:

$R_1$ is hydrogen, halogen, cyano, alkyl, aryl, heteroaryl, cycloalkyl, heterocycloalkyl, aralkyl, heteroalkyl, —O-alkyl, —O-aryl, —O-heteroaryl, —S-alkyl, alkylene-O-alkyl, alkylene-$CO_2H$, alkylene-$CO_2$alkyl, alkyl$SO_2$, alkylenesulfonyl, alkylene-CO-amino, alkylene-CO-alkylamino, alkylene-CO-dialkylamino, alkylene-NH—$CO_2H$, alkylene-NH—$CO_2$alkyl —$CO_2$alkyl, —OH, —C(O)-alkyl, —C(O)O-alkyl, —$CONH_2$, —CO-alkylamino, —CO-dialkylamino, amino, alkylamino, or dialkylamino, any of which may be optionally substituted on carbon with 1, 2, or 3 groups selected from halo, alkyl, haloalkyl, —$CF_3$, —CN, —OH, or —O-alkyl;

A is $(C_1-C_{20})$alkylene, $(C_2-C_{20})$alkenylene, or $(C_2-C_{20})$alkynylene, each of which may be optionally substituted on carbon with 1, 2, or 3 groups selected from OH, $CO_2H$, $CO_2$alkyl, halogen, amino, alkylamino, dialkylamino, —O-alkyl, alkylene-O-alkyl, alkylene-OH, or alkylene-$CO_2H$;

$X_1$ is a bond or is $CH_2$, O, —$CH_2O$—, S, —S(O), —$S(O)_2$, —C(O)—, —C(O)O—, or $NR_x$, wherein $R_x$ is H or $(C_1-C_6)$ alkyl;

R' and R" are each independently hydrogen, halogen, alkyl optionally substituted on carbon with halogen, alkyl, or taken together with the carbon to which they are attached form C=O or a 3, 4, 5, or 6-membered ring, optionally containing 1 or 2 heteroatoms selected from 0 NH, N-alkyl, SO, or $SO_2$, any of which may be optionally substituted on carbon with alkyl or halogen $R_3$ is absent, hydrogen, halogen, cyano, alkyl, aryl, heteroaryl, cycloalkyl, heterocycloalkyl, aralkyl, heteroalkyl, —O-alkyl, —O-aryl, —O-heteroaryl, aralkoxy, heteroaralkoxy, —S-alkyl, alkylene-O-alkyl, alkylene-$CO_2H$, alkylene-$CO_2$alkyl, alkyl$SO_2$, alkylenesulfonyl, alkylene-CO-amino, alkylene-CO-alkylamino, alkylene-CO-dialkylamino, alkylene-NH—$CO_2H$, alkylene-NH—$CO_2$alkyl —$CO_2$alkyl, —OH, —C(O)-alkyl, —C(O)O-alkyl, —$CONH_2$, —CO-alkylamino, —CO-dialkylamino, amino, alkylamino, and dialkylamino, any of which may be optionally substituted on carbon with 1, 2, or 3 groups selected from halo, alkyl, OH, or —O-alkyl;

is phenyl or pyridyl;

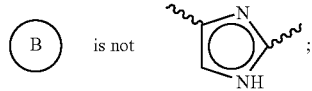

is aryl, heteroaryl, heterocyclo, or cycloalkyl, any of which may be optionally substituted on carbon with 1, 2, or 3 groups selected form halogen, alkyl, O-alkyl, $CO_2H$, $CO_2$alkyl, halogen, amino, alkylamino, dialkylamino, —O-alkyl, alkylene-O-alkyl, alkylene-OH, or alkylene-$CO_2H$, provided that (B) is not [pyrrole];

$R_4$ is hydrogen, cyano, alkyl, aryl, heteroaryl, alkylene-O-alkyl, alkylene-OH, aryl, alkylene-O-alkyl, —$CO_2H$, —$CO_2$-alkyl, alkylene-$CO_2H$, or alkylene-$CO_2$-alkyl, alkylene-OC(O)R wherein R is hydrogen or alkyl; cycloalkyl, heterocycloalkyl, alkylene-$NH_2$, alkylene-alkylamino, or alkylene-dialkylamino, any of which may be optionally substituted on carbon with 1, 2, or 3 groups selected from OH, $CO_2H$, $CO_2$alkyl, halogen, amino, alkylamino, dialkylamino, —O-alkyl, alkylene-O-alkyl, alkylene-OH, or alkylene-$CO_2H$;

$R_5$ and $R_6$ are each independently selected from the group consisting of hydrogen, alkyl, alkylene-OH, aryl, alkylene-O-alkyl, —$CO_2H$, $CO_2$-alkyl, alkylene-OC(O)alkyl, cycloalkyl, heterocyclo, —C(O)-alkyl, —C(O)-aryl, C(O)-aralkyl, —C(O)—Oalkyl, —C(O)—Oaryl, —C(O)—Oaralkyl, alkylene-amino, alkylene-alkylamino, and alkylene-dialkylamino, any of which may be optionally substituted on carbon with halogen, alkyl, hydroxyl, $CO_2H$, $CO_2$alkyl or alkoxy; or $R_5$ and $R_6$, together with the nitrogen to which they are attached, may form a 3, 4, 5, or 6-membered saturated or unsaturated ring, optionally containing 1 or 2 additional heteroatoms selected from O, S, NH, or N-alkyl, and optionally substituted on carbon with halogen, alkyl, hydroxyl, or alkoxy;

$R_8$ is hydrogen, alkyl or aryl; and n is 0, 1, or 2.

In some embodiments, compounds of the present invention include compounds listed in the following table:

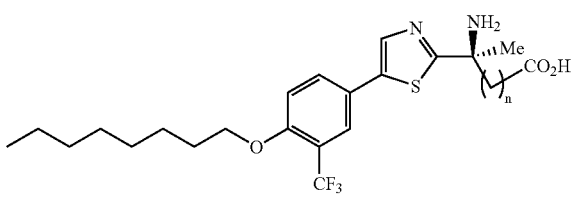

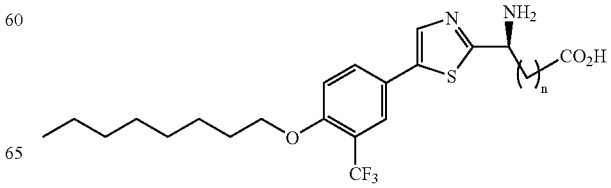

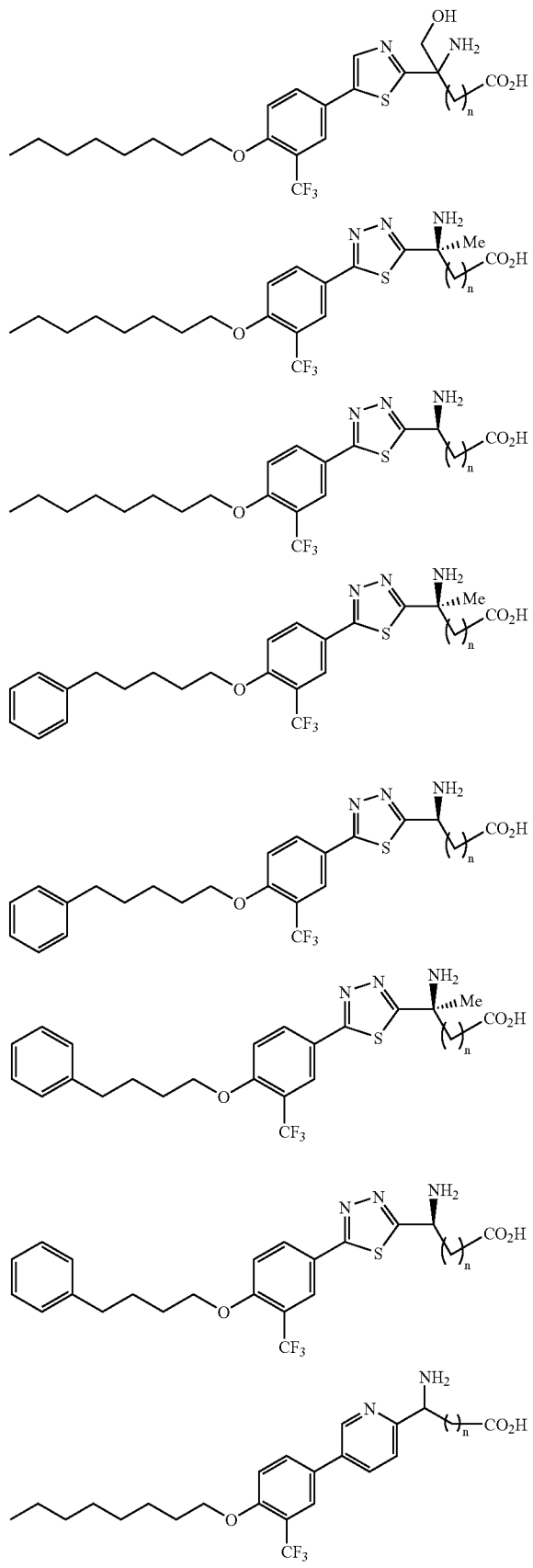
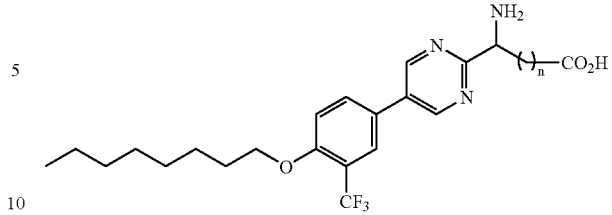

wherein n for each compound is 0, 1 or 2, as well as pharmaceutically acceptable salts, phosphate derivatives, phosphate mimics, or phosphate precursor analogs thereof.

In some aspects, the present invention is directed to compound selected from:

(S)-2-Amino-2-(5-(4-(octyloxy)-3-(trifluoromethyl)phenyl) thiazol-2-yl)propan-1-ol;

2-Amino-2-(5-(4-(octyloxy)-3-(trifluoromethyl)phenyl) thiazol-2-yl)propane-1,3-diol;

(S)-2-Amino-2-(5-(4-(octyloxy)-3-(trifluoromethyl)phenyl)-1,3,4-thiadiazol-2-yl)propan-1-ol;

(S)-2-Amino-2-(5-(4-(5-phenylpentyloxy)-3-(trifluoromethyl)phenyl)-1,3,4-thiadiazol-2-yl)propan-1-ol;

(S)-2-Amino-2-(5-(4-(4-phenylbutoxy)-3-(trifluoromethyl)phenyl)-1,3,4-thiadiazol-2-yl)propan-1-ol;

(S)-2-Amino-2-(5-(4-(nonyloxy)-3-(trifluoromethyl)phenyl)-1,3,4-thiadiazole-2-yl)propan-1-ol;

(S)-2-Amino-2-(5-(4-(decyloxy)-3 (trifluoromethyl)phenyl)-1,3,4-thiadiazol-2-yl)propan-1-ol;

(S)-2-Amino-2-(5-(3-(trifluoromethyl)-4-(5-(4-(trifluoromethyl)phenyl)pentyloxy)phenyl)-1,3,4-thiadiazole-2-yl) propan-1-ol;

(S)-2-Amino-2-(5-(3-(trifluoromethyl)-4-(5-(3-(trifluoromethyl)phenyl)pentyloxy)phenyl)-1,3,4-thiadiazol-2-yl) propan-1-ol;

(S)-2-Amino-2-(5-(4-(6-phenylhexyloxy)-3-(trifluoromethyl)phenyl)-1,3,4-thiadiazol-2-yl)propan-1-ol;

(S)-2-Amino-2-(5-(4-(5-(4-fluorophenyl)pentyloxy)-3-(trifluoromethyl)phenyl)-1,3,4-thiadiazol-2-yl)propan-1-ol;

(S)-2-Amino-2-(5-(4-(5-(3-fluorophenyl)pentyloxy)-3-(trifluoromethyl)phenyl)-1,3,4-thiadiazol-2-yl)propan-1-ol;

(S)-2-Amino-2-(5-(4-((4-phenyl-5-(trifluoromethyl) thiophen-2-yl)methoxy)-3-(trifluoromethyl)phenyl)-1,3,4-thiadiazol-2-yl)propan-1-ol;

(S)-2-Amino-2-(5-(4-(7-phenylheptyloxy)-3-(trifluoromethyl)phenyl)-1,3,4-thiadiazol-2-yl)propan-1-ol;

(S)-2-Amino-2-(5-(3-(trifluoromethyl)-4-(2-(trifluoromethyl)phenethoxy)phenyl)-1,3,4-thiadiazol-2-yl)propan-1-ol;

(S)-2-Amino-2-(5-(3-(trifluoromethyl)-4-(3-(trifluoromethyl)phenethoxy)phenyl)-1,3,4-thiadiazol-2-yl)propan-1-ol;

(S)-2-Amino-2-(5-(3-(trifluoromethyl)-4-(4-(trifluoromethyl)phenethoxy)phenyl)-1,3,4-thiadiazol-2-yl)propan-1-ol;

(S)-2-Amino-2-(5-(4-(benzyloxy)-3-(trifluoromethyl)phenyl)-1,3,4-thiadiazol-2-yl)propan-1-ol;

(S)-2-Amino-2-(5-(4-phenethoxy-3-(trifluoromethyl)phenyl)-1,3,4-thiadiazol-2-yl)propan-1-ol;

(S)-2-Amino-2-(5-(4-(3-phenylpropoxy)-3-(trifluoromethyl)phenyl)-1,3,4-thiadiazol-2-yl)propan-1-ol;

(S)-2-Amino-2-(5-(4-(benzofuran-2-ylmethoxy)-3-(trifluoromethyl)phenyl)-1,3,4-thiadiazol-2-yl)propan-1-ol;

(S)-2-Amino-2-(5-(4-(benzo[b]thiophen-2-ylmethoxy)-3-(trifluoromethyl)phenyl)-1,3,4-thiadiazol-2-yl)propan-1-ol;
(S)-2-Amino-2-(5-(4-(benzo[d][1,3]dioxol-5-ylmethoxy)-3-(trifluoromethyl)phenyl)-1,3,4-thiadiazol-2-yl)propan-1-ol;
(S)-2-Amino-2-(5-(3-(trifluoromethyl)-4-(4-(3-(trifluoromethyl)phenyl)butoxy)phenyl)-1,3,4-thiadiazol-2-yl)propan-1-ol;
(S)-2-Amino-2-(5-(3-(trifluoromethyl)-4-(4-(4-(trifluoromethyl)phenyl)butoxy)phenyl)-1,3,4-thiadiazol-2-yl)propan-1-ol;
(2S)-2-Amino-2-(5-(4-(3,7-dimethyloctyloxy)-3-(trifluoromethyl)phenyl)-1,3,4-thiadiazol-2-yl)propan-1-ol;
(S)-2-Amino-2-(5-(4-(4-propylphenethoxy)-3-(trifluoromethyl)phenyl)-1,3,4-thiadiazol-2-yl)propan-1-ol;
(S)-2-Amino-2-(5-(4-(4-butylphenethoxy)-3-(trifluoromethyl)phenyl)-1,3,4-thiadiazol-2-yl)propan-1-ol;
(S)-2-Amino-2-(5-(4-(4-ethylphenethoxy)-3-(trifluoromethyl)phenyl)-1,3,4-thiadiazol-2-yl)propan-1-ol;
(S)-2-Amino-2-(5-(4-(7,7,8,8,8-pentafluorooctyloxy)-3-(trifluoromethyl)phenyl)-1,3,4-thiadiazol-2-yl)propan-1-ol;
(S)-2-Amino-2-(5-(4-(4-(2-fluorophenyl)butoxy)-3-(trifluoromethyl)phenyl)-1,3,4-thiadiazol-2-yl)propan-1-ol;
(S)-2-Amino-2-(5-(4-(4-(3-fluorophenyl)butoxy)-3-(trifluoromethyl)phenyl)-1,3,4-thiadiazol-2-yl)propan-1-ol;
(S)-2-Amino-2-(5-(4-(4-(4-fluorophenyl)butoxy)-3-(trifluoromethyl)phenyl)-1,3,4-thiadiazol-2-yl)propan-1-ol;
(S)-2-Amino-2-(5-(4-(6-(2-fluorophenyl)hexyloxy)-3-(trifluoromethyl)phenyl)-1,3,4-thiadiazol-2-yl)propan-1-ol;
(S)-2-Amino-2-(5-(4-(6-(3-fluorophenyl)hexyloxy)-3-(trifluoromethyl)phenyl)-1,3,4-thiadiazol-2-yl)propan-1-ol;
(S)-2-Amino-2-(5-(4-(6-(4-fluorophenyl)hexyloxy)-3-(trifluoromethyl)phenyl)-1,3,4-thiadiazol-2-yl)propan-1-ol;
(S)-2-Amino-2-(5-(4-(5-(3,4-difluorophenyl)pentyloxy)-3-(trifluoromethyl)phenyl)-1,3,4-thiadiazol-2-yl)propan-1-ol;
(S)-2-Amino-2-(5-(3-(trifluoromethyl)-4-(5-(2,4,5-trifluorophenyl)pentyloxy)phenyl)-1,3,4-thiadiazol-2-yl)propan-1-ol;
(S)-2-Amino-2-(5-(3-(trifluoromethyl)-4-(6-(3-(trifluoromethyl)phenyl)hexyloxy)phenyl)-1,3,4-thiadiazol-2-yl)propan-1-ol;
(S)-2-Amino-2-(5-(3-(trifluoromethyl)-4-(6-(4-(trifluoromethyl)phenyl)hexyloxy)phenyl)-1,3,4-thiadiazol-2-yl)propan-1-ol;
(S)-2-Amino-2-(5-(4-(octylthio)-3-(trifluoromethyl)phenyl)-1,3,4-thiadiazol-2-yl)propan-1-ol;
(S)-2-Amino-2-(5-(4-(octylsulfonyl)-3-(trifluoromethyl)phenyl)-1,3,4-thiadiazol-2-yl)propan-1-ol;
(S)-2-Amino-2-(3-(4-(octyloxy)-3-(trifluoromethyl)phenyl)-1,2,4-oxadiazol-5-yl)propan-1-ol;
(R)-2-Amino-2-(5-(4-(octyloxy)-3-(trifluoromethyl)phenyl)-1H-pyrazol-3-yl)propan-1-ol;
(S)-2-Amino-2-(3-(4-(octyloxy)-3-(trifluoromethyl)phenyl)isoxazol-5-yl)propan-1-ol;
(S)-2-Amino-2-(5-(4-(octyloxy)-3-(trifluoromethyl)phenyl)-1,3,4-oxadiazol-2-yl)propan-1-ol;
(S)-2-Amino-2-(5-(4-(6-phenylhexyloxy)-3-(trifluoromethyl)phenyl)thiazol-2-yl)propan-1-ol;
(S)-2-Amino-2-(5-(3-(trifluoromethyl)-4-(5-(4-(trifluoromethyl)phenyl)pentyloxy)phenyl)thiazol-2-yl)propan-1-ol;

and pharmaceutically acceptable salts, phosphate derivatives, phosphate mimics, and phosphate precursor analogs thereof.

In some aspects, the present invention is directed to a compound which is (S)-2-Amino-2-(5-(4-(trifluoromethyl)phenyl)thiazol-2-yl)propan-1-ol or a pharmaceutically acceptable salt, phosphate derivative, phosphate mimic, or phosphate precursor analog thereof. In other aspects, the present invention is directed to a compound which is (S)-2-Amino-2-(5-(4-(octyloxy)-3-(trifluoromethyl)phenyl)thiazol-2-yl)propyl dihydrogen phosphate or a pharmaceutically acceptable salt thereof.

In some aspects, the present invention is directed to a compound which is (S)-2-Amino-2-(5-(4-(octyloxy)-3-(trifluoromethyl)phenyl)-1,3,4-thiadiazol-2-yl)propan-1-ol or a pharmaceutically acceptable salt, phosphate derivative, phosphate mimic, or a phosphate precursor analog thereof. In other aspects, the present invention is directed to a compound which is (S)-2-Amino-2-(5-(4-(octyloxy)-3-(trifluoromethyl)phenyl)-1,3,4-thiadiazol-2-yl)propyl dihydrogen phosphate or a pharmaceutically acceptable salt thereof.

In some aspects, the present invention is directed to a method of treating a sphingosine 1-phosphate associated disorder in a subject in need thereof comprising administering to the subject a therapeutically safe and effective amount of a compound of any of formulas I, II or III, or a pharmaceutically acceptable salt, phosphate derivative, phosphate mimic, or phosphate precursor analog thereof, such that the sphingosine 1-phosphate associated disorder is treated.

In some aspects, the present invention is directed to a method of treating an autoimmune disorder comprising administering to a subject in need thereof a pharmaceutically acceptable amount of a compound of any of formulas I, II or III, such that the autoimmune disorder is treated.

In some aspects, the present invention is directed to a method treating transplant rejection comprising administering to a subject in need thereof a pharmaceutically acceptable amount of a compound of any of formulas I, II or III, such that the transplant rejection is treated.

In some aspects, the present invention is directed to a compound of any of formulas I, II or III for use as a therapeutic substance.

In some aspects, the present invention is directed to a compound of any of formulas I, II or III for use in the treatment of sphingosine associated disorders. In some aspects, the present invention is directed to a compound of any of formulas I, II or III for use in the treatment of multiple sclerosis.

In some aspects, the present invention is directed to a compound of any of formulas I, II or III for use in the manufacture of a medicament for use in the treatment of sphingosine associated disorders. In some aspects, the present invention is directed to a compound of any of formulas I, II or III for use in the manufacture of a medicament for the treatment of multiple sclerosis.

In some aspects, the present invention is directed to a pharmaceutical composition comprising a compound of any of formulas I, II or III and a pharmaceutically acceptable carrier.

In some aspects, the present invention is directed to a process for making any of the compounds described herein.

DETAILED DESCRIPTION OF THE INVENTION

Definitions

The following definitions are used, unless otherwise described.

"Halogen" or "halo" means fluoro (F), chloro (Cl), bromo (Br), or iodo (I).

The term "hydrocarbon" used alone or as a suffix or prefix, refers to any structure comprising only carbon and hydrogen atoms up to 14 carbon atoms.

The term "hydrocarbon radical" or "hydrocarbyl" used alone or as a suffix or prefix, refers to any structure as a result of removing one or more hydrogens from a hydrocarbon.

The term "alkyl" used alone or as a suffix or prefix, refers to monovalent straight or branched chain hydrocarbon radicals comprising 1 to about 12 carbon atoms.

The term "alkylene" used alone or as suffix or prefix, refers to divalent straight or branched chain hydrocarbon radicals comprising 1 to about 12 carbon atoms, which serves to links two structures together.

The term "cycloalkyl" used alone or as suffix or prefix, refers to a saturated or partially unsaturated monovalent ring-containing hydrocarbon radical comprising at least 3 up to about 12 carbon atoms.

The term "aryl" used alone or as suffix or prefix, refers to a monovalent hydrocarbon radical having one or more polyunsaturated carbon rings having aromatic character, and comprising 5 up to about 14 carbon atoms.

The term "heterocycle" used alone or as a suffix or prefix, refers to a ring-containing structure or molecule having one or more multivalent heteroatoms, independently selected from N, O and S, as a part of the ring structure and including at least 3 and up to about 20 atoms in the ring(s). Heterocycle may be saturated or unsaturated, containing one or more double bonds, and heterocycle may contain more than one ring. When a heterocycle contains more than one ring, the rings may be fused or unfused. Fused rings generally refer to at least two rings share two atoms therebetween. Heterocycle may have aromatic character or may not have aromatic character.

The terms "heterocyclic group", "heterocyclic moiety", "heterocyclic", or "heterocyclo" used alone or as a suffix or prefix, refers to a radical derived from a heterocycle by removing one or more hydrogens therefrom.

The term "heterocyclyl" used alone or as a suffix or prefix, refers a monovalent radical derived from a heterocycle by removing one hydrogen therefrom.

The term "heteroaryl" used alone or as a suffix or prefix, refers to a heterocyclyl having aromatic character.

Heterocycle includes, for example, monocyclic heterocycles such as: aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide.

In addition, heterocycle includes aromatic heterocycles (heteroaryl groups), for example, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

Additionally, heterocycle encompass polycyclic heterocycles, for example, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine.

In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

Heterocyclyl includes, for example, monocyclic heterocyclyls, such as: aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl.

Additionally, heterocyclyl encompasses polycyclic heterocyclyls (including both aromatic and non-aromatic), for example, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl.

In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include quinuclidinyl, diazabicyclo[2.2.1]heptyl; and 7-oxabicyclo[2.2.1]heptyl.

The term "six-membered" used as prefix refers to a group having a ring that contains six ring atoms.

The term "five-membered" used as prefix refers to a group having a ring that contains five ring atoms.

A five-membered heteroaryl ring is a heteroaryl with a ring having five ring atoms wherein 1, 2 or 3 ring atoms are independently selected from N, O and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein 1, 2 or 3 ring atoms are independently selected from N, O and S. Exemplary six-membered ring heteroaryls are pyridyl, pyrazinyl, pyrimidinyl, triazinyl and pyridazinyl.

The term "aralkyl" refers to an alkyl group substituted with an aryl group.

The term "heteroaralkyl" refers to an alkyl group substituted with an heteroaryl group.

Unless otherwise specified, the term "substituted", when used as a prefix, refers to a structure, molecule or group, wherein one or more hydrogens are replaced with one or more alkyl groups, or one or more chemical groups containing one or more heteroatoms selected from N, O, S, F, Cl, Br, I, and P. Exemplary chemical groups containing one or more heteroatoms include heterocyclyl, —NO$_2$, —O-alkyl, halo, —CF$_3$, —CO$_2$H, —CO$_2$R, —NH$_2$, —SH, —NHR, —NR$_2$, —SR, —SO$_3$H, —SO$_2$R, —S(O)R, —CN, —OH, —C(O)NR$_2$, —NRC(O)R, oxo (=O), imino (=NR), thio (=S), and oximino (=N—OR), wherein each "R" is alkyl as defined above. For example, substituted phenyl may refer to nitrophenyl, pyridylphenyl, methoxyphenyl, chlorophenyl, aminophenyl, an so on, wherein the nitro, pyridyl, methoxy, chloro, and amino groups may replace any suitable hydrogen on the phenyl ring. It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc.

The term "alkoxy" used alone or as a suffix or prefix, refers to radicals of the general —O-alkyl, Exemplary alkoxy groups includes methoxy, ethoxy, propoxy, isopropoxy, butoxy, t-butoxy, isobutoxy, cyclopropylmethoxy, allyloxy, and propargyloxy.

The term "amine" or "amino" used alone or as a suffix or prefix, refers —NH$_2$.

The term "alkylamino" used alone or as a suffix or prefix, refers —NH(alkyl). The term "dialkylamino" used alone or as a suffix or prefix, refers —NH(alkyl)$_2$.

"Acyl" used alone, as a prefix or suffix, means —C(O)—R, wherein R hydrogen, hydroxyl, amino, alkylamino, dialkylamino, or alkoxy, any of which may be substituted as provided by the definition of "substituted" given above. Acyl groups include, for example, acetyl, propionyl, benzoyl, phenyl acetyl, carboethoxy, and dimethylcarbamoyl.

Some of the compounds in the present invention may exist as stereoisomers, including enantiomers, diastereomers, and geometric isomers. All of these forms, including (R), (S), epimers, diastereomers, cis, trans, syn, anti, solvates (including hydrates), tautomers, and mixtures thereof, are contemplated in the compounds of the present invention.

The invention also relates to salts of the compounds of the invention and, in particular, to pharmaceutically acceptable salts. A "pharmaceutically acceptable salt" is a salt that retains the desired biological activity of the parent compound and does not impart any undesired toxicological effects. The salts can be, for example, salts with a suitable acid, such as hydrochloric acid, hydrobromic acid, sulfuric acid, phosphoric acid, nitric acid, and the like; acetic acid, oxalic acid, tartaric acid, succinic acid, malic acid, benzoic acid, pamoic acid, alginic acid, methanesulfonic acid, naphthalenesulfonic acid, and the like. Also included are salts of cations such as ammonium, sodium, potassium, lithium, zinc, copper, barium, bismuth, calcium, and the like; or organic cations such as tetralkylammonium and trialkylammonium cations. Combinations of the above salts are also useful. Salts of other acids and/or cations are also included, such as salts with trifluoroacetic acid, chloroacetic acid, and trichloroacetic acid. The invention also includes different crystal forms, hydrates, and solvates of the compounds of the invention.

The terms "phosphate precursor" and "phosphate precursor analog," as used herein, refer to substituent moieties in invention compounds that may be directly phosphorylated in vivo, or which may be cleaved in vivo to reveal a moiety that may then be phosphorylated in vivo. In certain embodiments, the phosphate precursor may be L$_1$-O—H or L$_1$-O-L$_2$, wherein L$_1$ is a linking moiety and L$_2$ is a labile moiety. Exemplary embodiments of the phosphate precursor, include but are not limited to -alkyl-OH, -halo-alkyl-OH, alkoxy-OH, -alkyl-OCOR$^a$, -halo-alkyl-OCOR$^a$, -alkoxy-OCOR$^a$, -alkyl-OC(O)NR$^a$R$^b$, -halo-alkyl-OC(O)NHR$^a$R$^b$, -alkoxy-OC(O)NR$^a$R$^b$, —(CH$_2$)$_q$CO$_2$R$^c$, and —(CH$_2$)$_n$CH$_2$=CHC(O)OR$^c$, wherein q is an integer between 0 and 4;

R$^a$ and R$^b$ are independently selected from the group consisting of hydrogen, straight chain or branched C$_1$-C$_6$-alkyl, all of which may be optionally substituted with OH, halogen, straight chain or branched C$_1$-C$_6$-alkoxy, straight chain or branched halo-C$_1$-C$_6$-alkyl, straight chain or branched halo-C$_1$-C$_6$-alkoxy, C$_1$-C$_6$-alkoxy-C$_1$-C$_6$-alkyl, hydroxyl-C$_1$-C$_6$-alkyl, carboxy-C$_1$-C$_6$-alkyl, substituted or unsubstituted C$_3$-C$_{10}$ carbocyclic rings, and substituted or unsubstituted C$_3$-C$_{10}$ heterocyclic rings, which may contain one or more heteroatoms and may be saturated or unsaturated; and R$^c$ is selected from the group consisting of hydrogen, straight chain or branched C$_1$-C$_6$-alkyl, straight chain or branched halo-C$_1$-C$_6$-alkyl, substituted or unsubstituted aryl group, or one of the following groups.

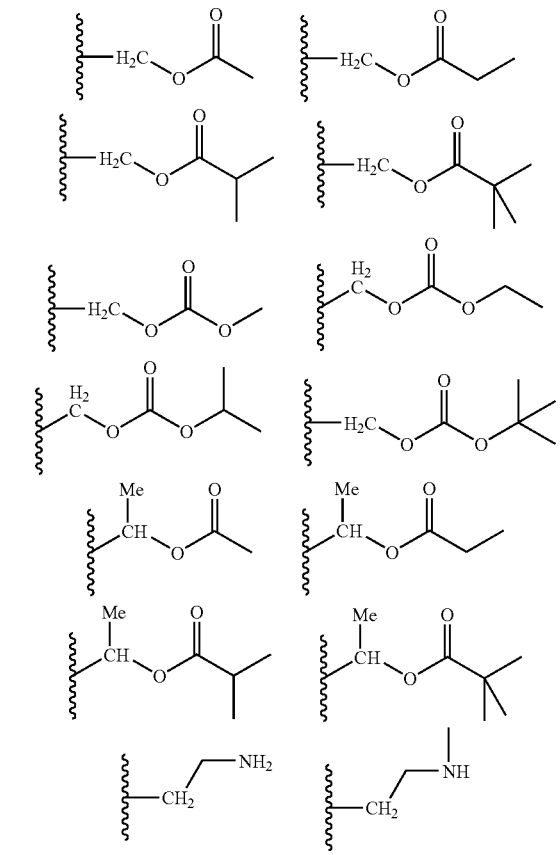

-continued

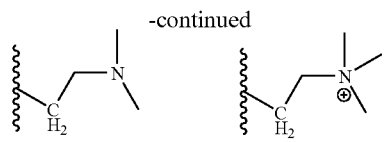

The "linking moiety," may contain 1-8 atoms or may be a bond, and serves as the connection point through which the phosphate mimic, phosphate derivative, or phosphate precursor substituent moieties are linked to the remaining structure of the compounds of the invention. In certain embodiments, the linking moiety may include, but is not limited to, substituted or unsubstituted alkyl (e.g., methylene chains), substituted or unsubstituted alkenyl (e.g., n-alkenes), substituted or unsubstituted alkynyl, substituted or unsubstituted haloalkyl, substituted or unsubstituted alkoxy, and substituted or unsubstituted halo-alkoxy. In specific embodiments, the linking moiety may be carbonyl derivatized.

The language "labile moiety" refers to a moiety that is subject to cleavage, for instance, by hydrolysis or enzymatic degradation. In certain embodiments, the labile moiety is an ester moiety, which may result in a carboxylate or hydroxyl derivative, depending on the orientation of the ester functionality in the molecule prior to cleavage.

The term "phosphate derivative" refers to substituent moieties in invention compounds that contain a phosphate or phosphate ester group. When a compound of the invention containing a phosphate derivative is administered to a subject, the compound may act as is in vivo or the phosphate derivative (within the compound) may be cleaved and then re-phosphorylated in vivo leading to an active compound. In certain embodiments, the phosphate derivative may be selected from the group consisting of $-(CH_2)_q OPO_2 R^d R^e$, $-(CH_2)_q OPO_3 R^d R^e$, and $-(CH_2)_q OPO_2(S) R^d R^e$, wherein q is an integer between 0 and 4; and $R^d$ and $R^e$ are each independently selected from the group consisting of hydrogen, straight chain or branched $C_1$-$C_6$-alkyl, straight chain or branched halo-$C_1$-$C_6$-alkyl, substituted or unsubstituted aryl group, and a prodrug derivatizing moiety (PDM).

The term "phosphate mimic" refers to substituent moieties in invention compounds in which a phosphate substrate has been replaced with a non-hydrolyzable functional group, resulting in a moiety that mimics the biological function of a phosphate or phosphate ester moiety. In certain embodiments, the phosphate mimic is -$L_1$-$Z_2$, wherein $L_1$ is a linking moiety and $Z_2$ is a non-hydrolyzable moiety covalently bonded, to $L_1$. In certain embodiments, the phosphate mimic is selected from the group consisting of $-(CH_2)_q CH_2 PO_3 R^d R^e$, and $-(CH_2)_q C(Y_1)(Y_2) PO_3 R^d R^e$, wherein q is an integer between 0 and 4;

$Y_1$ and $Y_2$ are independently selected from the group consisting of hydrogen, straight chain or branched $C_1$-$C_6$-alkyl, all of which may be optionally substituted with OH, halogen, straight chain or branched $C_1$-$C_6$-alkoxy, straight chain or branched halo-$C_1$-$C_6$-alkyl, straight chain or branched halo-$C_1$-$C_6$-alkoxy, $C_1$-$C_6$-alkoxy-$C_1$-$C_6$-alkyl, hydroxyl-$C_1$-$C_6$-alkyl, carboxy-$C_1$-$C_6$-alkyl, substituted or unsubstituted $C_3$-$C_{10}$ carbocyclic rings, and substituted or unsubstituted $C_3$-$C_{10}$ heterocyclic rings, which may contain one or more heteroatoms and may be saturated or unsaturated; and $R^d$ and $R^e$ are each independently selected from the group consisting of hydrogen, straight chain or branched $C_1$-$C_6$-alkyl, straight chain or branched halo-$C_1$-$C_6$-alkyl, substituted or unsubstituted aryl group, and a prodrug derivatizing moiety (PDM).

The language "non-hydrolyzable moiety" is art-recognized, and refers to moieties containing bonds, such as carbon-phosphorous bonds, that are not hydrolyzable in vivo.

Compounds of the Invention

In some aspects, the present invention is directed to a compound of formula I:

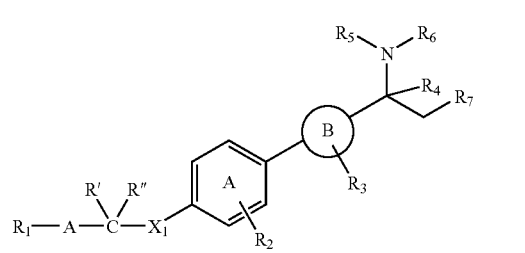

or a pharmaceutically acceptable salt thereof, wherein:

$R_1$ is hydrogen, halogen, cyano, alkyl, aryl, heteroaryl, cycloalkyl, heterocycloalkyl, aralkyl, heteroalkyl, —O-alkyl, —O-aryl, —O-heteroaryl, —S-alkyl, alkylene-O-alkyl, alkylene-$CO_2H$, alkylene-$CO_2$alkyl, alkylSO$_2$, alkylenesulfonyl, alkylene-CO-amino, alkylene-CO-alkylamino, alkylene-CO-dialkylamino, alkylene-NH—$CO_2H$, alkylene-NH—$CO_2$alkyl —$CO_2$alkyl, —OH, —C(O)-alkyl, —C(O)O-alkyl, —CONH$_2$, —CO-alkylamino, —CO-dialkylamino, amino, alkylamino, or dialkylamino, any of which may be optionally substituted on carbon with 1, 2, or 3 groups selected from halo, alkyl, haloalkyl, —CF$_3$, aryl, —CN, —OH, or —O-alkyl;

A is $(C_1$-$C_{20})$alkylene, $(C_2$-$C_{20})$alkenylene, or $(C_2$-$C_{20})$alkynylene, each of which may be optionally substituted on carbon with 1, 2, o3 groups selected from OH, $CO_2H$, $CO_2$alkyl, halogen, amino, alkylamino, dialkylamino, —O-alkyl, alkylene-O-alkyl, alkylene-OH, or alkylene-$CO_2H$;

$X_1$ is a bond or is $CH_2$, O, —$CH_2$O—, S, —S(O), —S(O)$_2$, —C(O)—, —C(O)O—, or NR, wherein $R_x$ is H or $(C_1$-$C_6)$ alkyl;

R' and R" are each independently hydrogen, halogen, alkyl optionally substituted on carbon with halogen, alkyl, or taken together with the carbon to which they are attached form C=O or a 3, 4, 5, or 6-membered ring, optionally containing 1 or 2 heteroatoms selected from 0 NH, N-alkyl, SO, or SO$_2$, any of which may be optionally substituted on carbon with alkyl or halogen $R_2$ is cyano, alkyl, aryl, heteroaryl, cycloalkyl, heterocycloalkyl, aralkyl, heteroalkyl, —O-alkyl, —O-aryl, —O-heteroaryl, aralkoxy, heteroaralkoxy, —S-alkyl, alkylene-O-alkyl, alkylene-$CO_2H$, alkylene-$CO_2$alkyl, alkylSO$_2$, alkylenesulfonyl, alkylene-CO-amino, alkylene-CO-alkylamino, alkylene-CO-dialkylamino, alkylene-NH—$CO_2H$, alkylene-NH—$CO_2$alkyl —$CO_2$alkyl, —OH, —C(O)-alkyl, —C(O)O-alkyl, —CONH$_2$, —CO-alkylamino, —CO-dialkylamino, amino, alkylamino, and dialkylamino, any of which may be optionally substituted on carbon with 1, 2, or 3 groups selected from halo, alkyl, OH, or —O-alkyl;

$R_3$ is absent, hydrogen, halogen, cyano, alkyl, aryl, heteroaryl, cycloalkyl, heterocycloalkyl, aralkyl, heteroalkyl, —O-alkyl, —O-aryl, —O-heteroaryl, aralkoxy, heteroaralkoxy, —S-alkyl, alkylene-O-alkyl, alkylene-$CO_2H$, alkylene-$CO_2$alkyl, alkylSO$_2$, alkylenesulfonyl, alkylene- CO-amino, alkylene-CO-alkylamino, alkylene-CO-dialkylamino, alkylene-NH—CO₂H, alkylene-NH—CO₂alkyl —CO₂alkyl, —OH, —C(O)-alkyl, —C(O)O-alkyl, —CONH₂, —CO-alkylamino, —CO-dialkylamino, amino, alkylamino, and dialkylamino, any of which may be optionally substituted on carbon with 1, 2, or 3 groups selected from halo, alkyl, OH, or —O-alkyl;

is phenyl or pyridyl;

is aryl, heteroaryl, heterocyclo, or cycloalkyl, any of which may be optionally substituted on carbon with 1, 2, or 3 groups selected form halogen, alkyl, O-alkyl, CO₂H, CO₂alkyl, halogen, amino, alkylamino, dialkylamino, —O-alkyl, alkylene-O-alkyl, alkylene-OH, or alkylene-CO₂H, provided that

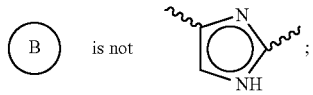

R₄ is hydrogen, cyano, alkyl, aryl, heteroaryl, alkylene-O-alkyl, alkylene-OH, aryl, alkylene-O-alkyl, —CO₂H, —CO₂-alkyl, alkylene-CO₂H, or alkylene-CO₂-alkyl, alkylene-OC(O)R wherein R is hydrogen or alkyl; cycloalkyl, heterocycloalkyl, alkylene-NH₂, alkylene-alkylamino, or alkylene-dialkylamino, any of which may be optionally substituted on carbon with 1, 2, or 3 groups selected from OH, CO₂H, CO₂alkyl, halogen, amino, alkylamino, dialkylamino, —O-alkyl, alkylene-O-alkyl, alkylene-OH, or alkylene-CO₂H;

R₅ and R₆ are each independently selected from the group consisting of hydrogen, alkyl, alkylene-OH, aryl, alkylene-O-alkyl, —CO₂H, CO₂-alkyl, alkylene-OC(O)alkyl, cycloalkyl, heterocyclo, —C(O)-alkyl, —C(O)-aryl, C(O)-aralkyl, —C(O)—Oalkyl, —C(O)—Oaryl, —C(O)—Oaralkyl, alkylene-amino, alkylene-alkylamino, and alkylene-dialkylamino, any of which may be optionally substituted on carbon with halogen, alkyl, hydroxyl, CO₂H, CO₂alkyl or alkoxy; or R₅ and R₆, together with the nitrogen to which they are attached, may form a 3, 4, 5, or 6-membered saturated or unsaturated ring, optionally containing 1 or 2 additional heteroatoms selected from O, S, NH, or N-alkyl, and optionally substituted on carbon with halogen, alkyl, hydroxyl, or alkoxy;

R₇ is selected from the group consisting of —OH, —O-alkyl, alkylene-OH, —CO₂H, alkylene-CO₂H, —C(O)O-alkyl, -alkylene-CO₂-alkyl, —C(O)O-aryl, —CH₂=CHCO₂H, —CH₂=CHC(O)O-alkyl, —CH₂=CHC(O)O-aryl, —OPO₂R$_{p1}$R$_{p2}$, —OPO₃R$_{p1}$R$_{p2}$, —CH₂PO₃R$_{p1}$R$_{p2}$, —OPO₂(S)R$_{p1}$R$_{p2}$, and —C(Z')(Z")PO₃R$_{p1}$R$_{p2}$, any of which may be optionally substituted on carbon with halogen, alkyl, hydroxyl, carboxy, or alkoxy; and wherein Z' is hydroxyl or halogen;

Z" is H or halogen;

R$_{p1}$ and R$_{p2}$ are each independently hydrogen, C₁-C₆-alkyl, aryl, or one of the following groups:

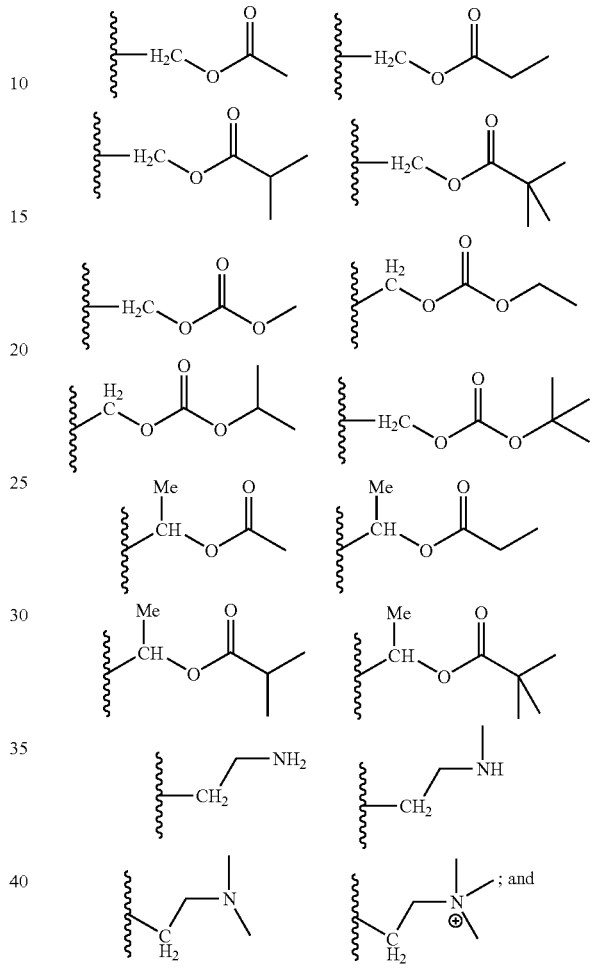

Y is heterocyclo or heteroaryl.

In some embodiments, R₁ is aryl or heteroaryl, optionally substituted with 1, 2, or 3 groups selected from halo, alkyl, haloalkyl, -aryl, —CF₃, —CN, —OH, or —O-alkyl. In some embodiments, R₁ is aryl, e.g., phenyl, optionally substituted with 1 or 2 groups selected from —CF₃, —CN, —OMe, —Cl or —F. In some embodiments, R₁ is heteroaryl, e.g., thiophene or benzothiophene, optionally substituted with 1 or 2 groups selected from phenyl, —CF₃, —CN, —OMe, —Cl or —F. In some embodiments, R₁ is hydrogen. In other embodiments, R₁ is phenyl. In some embodiments, R₁ is pyridyl. In other embodiments, R₁ is thiophenyl. In still other embodiments, R₁ is cyclohexyl. In some embodiments, R₁ is cyclopentyl.

In some embodiments, A is a C₁-C₁₀ alkylene. In some embodiments, A is a branched C₁-C₁₀ alkylene. In other embodiments, A is n-octyl. In other embodiments, A is n-heptyl. In other embodiments, A is n-hexyl. In some embodiments, A is a C₁-C₅ alkylene. In some embodiments, A is n-pentyl. In other embodiments, A is n-butyl. In still other embodiments, A is n-propyl. In other embodiments, A is ethyl. In still other embodiments, A is methyl.

In some embodiments, $X_1$ is O. In other embodiments, $X_1$ is S. In still other embodiments, $X_1$ is $SO_2$. In some embodiments, $X_1$ is $CH_2$. In other embodiments, $X_1$ is C=O. In still other embodiments, $CH_2O$, wherein either the oxygen or the carbon may be attached to

In some embodiments, R' is hydrogen. In other embodiments, R' is methyl. In some embodiments, R" is hydrogen. In other embodiments, R" is methyl. In some embodiments, R' and R" taken together with the carbon to which they are attached, is C=O, with the provision that only one of $X_1$ or R' and R" taken together with the carbon may form C=O.

The compounds of the present invention include a selectivity enhancing moiety. The term "selectivity enhancing moiety (SEM)" is defined in U.S. application Ser. No. 11/349,069 filed on Feb. 6, 2006 which is assigned to the assignee of the present application, the contents of which are incorporated herein by reference, refers to one or more moieties that provide an enhancement in the selectivity of the compound to which they are attached for the S1P-1 receptor, as compared to the compound not containing the moiety or moieties. The SEM confers selectivity to the compound to which it is attached for the S1P-1 receptor as compared to, for example, the S1P-2 to S1P-5 receptors. The enhancement conferred to a compound by the SEM may be measured by, for example, determining the binding specificity of a compound for the S1P-1 receptor and one or more of the other S1P receptors wherein enhancement conferred to a compound by the SEM may be in the form of increased potency. In some embodiments, at least one of $R_2$ and/or $R_3$ is an SEM. In some embodiments, the SEM is a halo-substituted alkyl group such as $CF_3$, $CF_2CF_3$, $CF_2CF_2CF_3$, $CFHCF_3$, $CH_2CF_3$, $CH_2CH_2CF_3$, $CHCl_2$, or $CH_2Cl$.

In certain embodiments, the SEM may possess a selectivity enhancing orientation (SEQ). The term "selectivity enhancing orientation" or "SEO," is defined in U.S. application Ser. No. 11/349,069 filed on Feb. 6, 2006 which is assigned to the assignee of the present application, the contents of which are incorporated herein by reference and as used herein refers to the relative selectivity enhancement of a compound based on the orientation of the SEM as well as the additional substitutents on the ring, either alone or in combination with each other. In particular, the SEQ may result from the orientation of the SEM on the ring to which it is attached, in relation to any other ring and/or moiety attached to the same ring. In one embodiment, the SEM on

is in the ortho position relative to $X_1$ in Formula I. In another specific embodiment, the SEM is in the meta position relative to $X_1$.

Thus, in some embodiments, $R_2$ is alkyl substituted with 1, 2 or 3 halo groups. In some embodiments, $R_2$ is trifluoromethyl. In still other embodiments, $R_2$ is methyl.

In some embodiments, $R_3$ is absent. For example, in the case of compounds where

$R_3$ would be considered absent, because there no substituents on the ring. In other embodiments, $R_3$ is halogen.

In some embodiments, $R_4$ is hydrogen. In other embodiments, $R_4$ is an alkyl, e.g., a $C_1$-$C_4$ alkyl. For example, in some embodiments, $R_4$ is methyl. In some embodiments, $R_4$ is hydroxymethyl.

In some embodiments, $R_5$ is hydrogen. In some embodiments, $R_6$ is hydrogen. In some embodiments, $R_5$ is an alkyl, e.g., a $C_1$-$C_4$ alkyl. In some embodiments, $R_6$ is an alkyl, e.g., a $C_1$-$C_4$ alkyl.

In some embodiments, $R_7$ is OH. In other embodiments, $R_7$ is $CO_2H$. In still other embodiments, $R_7$ is $CO_2Me$ or $CO_2Et$. In other embodiments, $R_7$ is $CO_2$-phenyl. In still other embodiments, $R_7$ is —OP(O)$_3$H$_2$. In other embodiments, $R_7$ is —CH$_2$P(O)$_3$H$_2$.

In some embodiments,

is phenyl. In other embodiments,

is pyridyl.

In some embodiments,

In some embodiments,

is

In some embodiments, 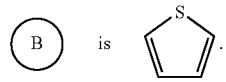 is .
In some embodiments,
is
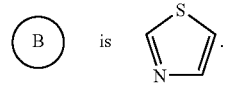
In some embodiments,  is .
In some embodiments,
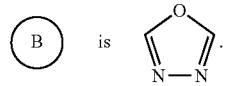
is
In some embodiments,  is 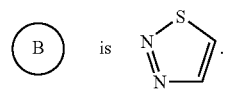.
In some embodiments,
is
In some embodiments, 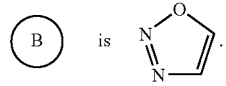 is .
In some embodiments,
is
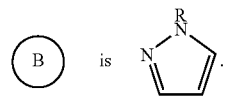

In some embodiments,

is

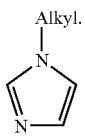

In some embodiments,

 is 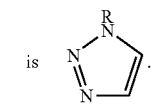

In some embodiments,

In some embodiments,

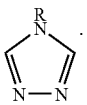

In some embodiments,

 is 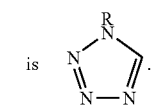

In some embodiments,

 is 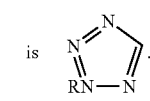

In each of the above structures, R can be hydrogen or alkyl.
In some embodiments,

is pyridyl. In some embodiments,

 is 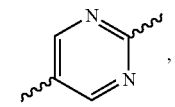, wherein "〰" indicates the points of attachment of the B ring to the remainder of the compound.

In some embodiments, compounds of the invention are compounds wherein $R_1$ is hydrogen, aryl, cycloalkyl, or heteroaryl.
$R_4$ is hydrogen, alkyl, alkylene-OH, aryl, -alkylene-O-alkyl, alkylene-CO$_2$H, or -alkylene-CO$_2$-alkyl;
$R_5$ and $R_6$ are each independently hydrogen or alkyl, or alkylene-OH;
$R_7$ is selected from the group consisting of OH, alkylene-OH, —CO$_2$H, alkylene-CO$_2$H, -alkylene-CO$_2$-alkyl, C(O)O-alkyl, —C(O)O-aryl, —CH$_2$=CHCO$_2$H, —CH$_2$=CHC(O)O-alkyl, —CH$_2$=CHC(O)O-aryl, —OPO$_2$R$_{p1}$R$_{p2}$, —OPO$_3$R$_{p1}$R$_{p2}$, —CH$_2$PO$_3$R$_{p1}$R$_{p2}$, —OPO$_2$(S)R$_{p1}$R$_{p2}$, or —C(Z')(Z")PO$_3$R$_{p1}$R$_{p2}$.

In some embodiments, compounds of the invention are compounds wherein $R_1$ is hydrogen or aryl;
$R_4$ is hydrogen or alkyl;
$R_5$ and $R_6$ are each independently hydrogen or alkyl, or alkylene-OH;
$R_7$ is selected from the group consisting of —OH, alkylene-OH, —CO$_2$H, alkylene-CO$_2$H, -alkylene-CO$_2$-alkyl, C(O)O-alkyl, —C(O)O-aryl, —CH$_2$=CHCO$_2$H, —CH$_2$=CHC(O)O-alkyl, —CH$_2$=CHC(O)O-aryl, —OPO$_2$R$_{p1}$R$_{p2}$, —OPO$_3$R$_{p1}$R$_{p2}$, —CH$_2$PO$_3$R$_{p1}$R$_{p2}$, —OPO$_2$(S)R$_{p1}$R$_{p2}$, and —C(Z')(Z")PO$_3$R$_{p1}$R$_{p2}$.

In other embodiments, compounds of the invention are compounds wherein

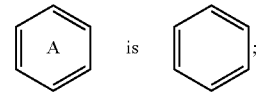

 is 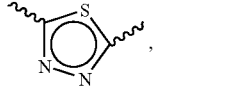, , or

, $R_1$ is phenyl;
A is (C$_1$-C$_{10}$)alkyl;
R' and R" are hydrogen;
$X_1$ is O;
$R_4$ is hydrogen, alkyl, or alkylene-OH;
$R_5$ and $R_6$ are each independently hydrogen, alkyl;
$R_7$ is selected from the group consisting of —OH, alkylene-OH, —CO$_2$H, alkylene-CO$_2$H, —C(O)O-alkyl, —C(O)O-aryl, —CH$_2$=CHCO$_2$H, —CH$_2$=CHC(O)O-alkyl, —CH$_2$=CHC(O)O-aryl, —OPO$_2$R$_{p1}$R$_{p2}$, —OPO$_3$R$_{p1}$R$_{p2}$, —CH$_2$PO$_3$R$_{p1}$R$_{p2}$, —OPO$_2$(S)R$_{p1}$R$_{p2}$, and —C(Z')(Z")PO$_3$R$_{p1}$R$_{p2}$;

In some embodiments, compounds of the invention are compounds of formula I-1.

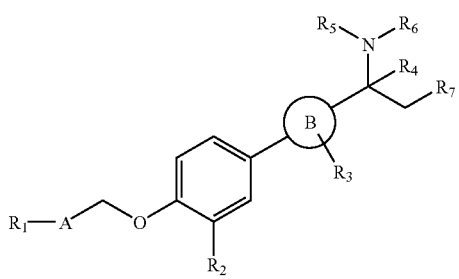

Another specific group of compounds of the invention are compounds of formula I-2.

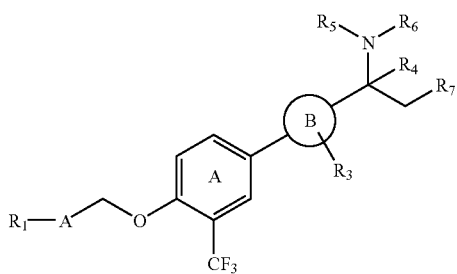

In other aspects, the present invention is directed to a compound of formula II:

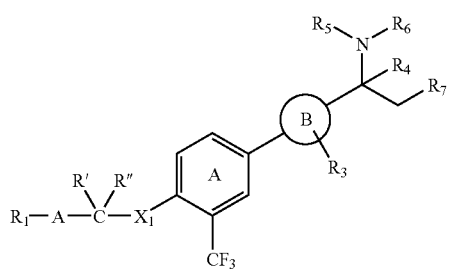

or a pharmaceutically acceptable salt thereof, wherein:

R$_1$ is hydrogen, halogen, cyano, alkyl, aryl, heteroaryl, cycloalkyl, heterocycloalkyl, aralkyl, heteroalkyl, —O-alkyl, —O-aryl, —O-heteroaryl, —S-alkyl, alkylene-O-alkyl, alkylene-CO$_2$H, alkylene-CO$_2$alkyl, alkylSO$_2$, alkylenesulfonyl, alkylene-CO-amino, alkylene-CO-alkylamino, alkylene-CO-dialkylamino, alkylene-NH—CO$_2$H, alkylene-NH—CO$_2$alkyl —CO$_2$alkyl, —OH, —C(O)-alkyl, —C(O)O-alkyl, —CON—H$_2$, —CO-alkylamino, —CO-dialkylamino, amino, alkylamino, or dialkylamino, any of which may be optionally substituted on carbon with 1, 2, or 3 groups selected from halo, alkyl, haloalkyl, —CF$_3$, —CN, —OH, or —O-alkyl;

A is (C$_1$-C$_{20}$)alkylene, (C$_2$-C$_{20}$)alkenylene, or (C$_2$-C$_{20}$)alkynylene, each of which may be optionally substituted on carbon with 1, 2, or 3 groups selected from OH, CO$_2$H, CO$_2$alkyl, halogen, amino, alkylamino, dialkylamino, —O-alkyl, alkylene-O-alkyl, alkylene-OH, or alkylene-CO$_2$H;

X$_1$ is a bond or is CH$_2$, O, —CH$_2$O—, S, —S(O), —S(O)$_2$, —C(O)—, —C(O)O—, or NR$_x$, wherein R$_x$ is H or (C$_1$-C$_6$) alkyl;

R' and R" are each independently hydrogen, halogen, alkyl optionally substituted on carbon with halogen, alkyl, or taken together with the carbon to which they are attached form C=O or a 3, 4, 5, or 6-membered ring, optionally containing 1 or 2 heteroatoms selected from 0 NH, N-alkyl, SO, or SO$_2$, any of which may be optionally substituted on carbon with alkyl or halogen R$_3$ is absent, hydrogen, halogen, cyano, alkyl, aryl, heteroaryl, cycloalkyl, heterocycloalkyl, aralkyl, heteroalkyl, —O-alkyl, —O-aryl, —O-heteroaryl, aralkoxy, heteroaralkoxy, —S-alkyl, alkylene-O-alkyl, alkylene-CO$_2$H, alkylene-CO$_2$alkyl, alkylSO$_2$, alkylenesulfonyl, alkylene-CO-amino, alkylene-CO-alkylamino, alkylene-CO-dialkylamino, alkylene-NH—CO$_2$H, alkylene-NH—CO$_2$alkyl —CO$_2$alkyl, —OH, —C(O)-alkyl, —C(O)O-alkyl, —CONH$_2$, —CO-alkylamino, —CO-dialkylamino, amino, alkylamino, and dialkylamino, any of which may be optionally substituted on carbon with 1, 2, or 3 groups selected from halo, alkyl, OH, or —O-alkyl;

is phenyl or pyridyl;

is aryl, heteroaryl, heterocyclo, or cycloalkyl, any of which may be optionally substituted on carbon with 1, 2, or 3 groups selected form halogen, alkyl, O-alkyl, CO$_2$H, CO$_2$alkyl, halogen, amino, alkylamino, dialkylamino, —O-alkyl, alkylene-O-alkyl, alkylene-OH, or alkylene-CO$_2$H, provided that

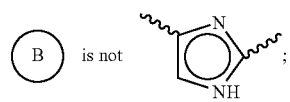

R$_4$ is hydrogen, cyano, alkyl, aryl, heteroaryl, alkylene-O-alkyl, alkylene-OH, aryl, alkylene-O-alkyl, —CO$_2$H, —CO$_2$-alkyl, alkylene-CO$_2$H, or alkylene-CO$_2$-alkyl, alkylene-OC(O)R wherein R is hydrogen or alkyl; cycloalkyl, heterocycloalkyl, alkylene-NH$_2$, alkylene-alkylamino, or alkylene-dialkylamino, any of which may be optionally substituted on carbon with 1, 2, or 3 groups selected from OH, CO$_2$H, CO$_2$alkyl, halogen, amino, alkylamino, dialkylamino, —O-alkyl, alkylene-O-alkyl, alkylene-OH, or alkylene-CO$_2$H;

R$_5$ and R$_6$ are each independently selected from the group consisting of hydrogen, alkyl, alkylene-OH, aryl, alkylene-O-alkyl, —CO$_2$H, CO$_2$-alkyl, alkylene-OC(O)alkyl, cycloalkyl, heterocyclo, —C(O)-alkyl, —C(O)-aryl, C(O)-aralkyl, —C(O)—Oalkyl, —C(O)—Oaryl, —C(O)—

Oaralkyl, alkylene-amino, alkylene-alkylamino, and alkylene-dialkylamino, any of which may be optionally substituted on carbon with halogen, alkyl, hydroxyl, $CO_2H$, $CO_2$alkyl or alkoxy; or $R_5$ and $R_6$, together with the nitrogen to which they are attached, may form a 3, 4, 5, or 6-membered saturated or unsaturated ring, optionally containing 1 or 2 additional heteroatoms selected from O, S, NH, or N-alkyl, and optionally substituted on carbon with halogen, alkyl, hydroxyl, or alkoxy;

$R_7$ is selected from the group consisting of —OH, —O-alkyl, -alkylene-OH, —$CO_2H$, -alkylene-$CO_2H$, —C(O)O-alkyl, -alkylene-$CO_2$-alkyl, —C(O)O-aryl, —$CH_2$=$CHCO_2H$, —$CH_2$=CHC(O)O-alkyl, —$CH_2$=CHC(O)O-aryl, —$OPO_2R_{p1}R_{p2}$, —$OPO_3R_{p1}R_{p2}$, —$CH_2PO_3R_{p1}R_{p2}$, —$OPO_2(S)R_{p1}R_{p2}$, and —C(Z')(Z'')$PO_3R_{p1}R_{p2}$, any of which may be optionally substituted on carbon with halogen, alkyl, hydroxyl, carboxy, or alkoxy; and wherein Z' is hydroxyl or halogen;

Z'' is H or halogen;

$R_{p1}$ and $R_{p2}$ are each independently hydrogen, $C_1$-$C_6$-alkyl, aryl, or one of the following groups:

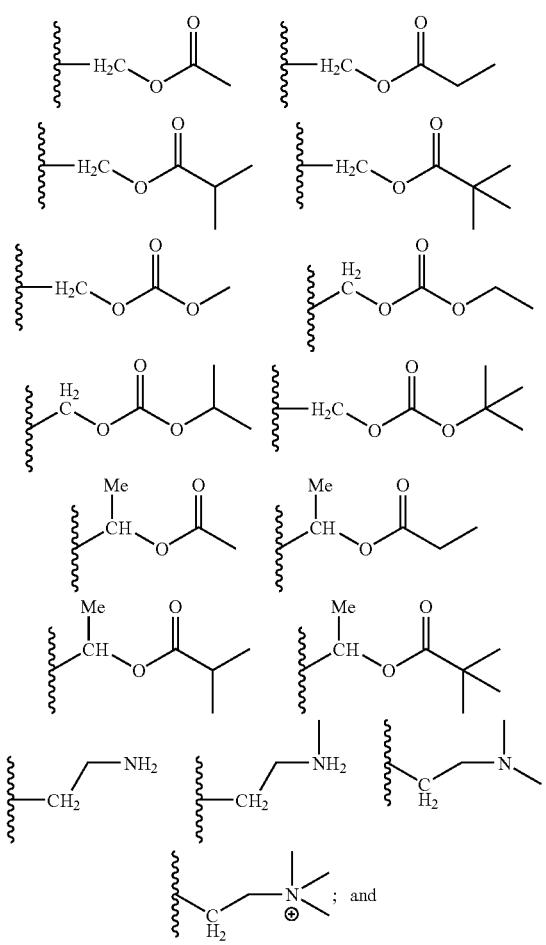

Y is heterocyclo or heteroaryl.

In some embodiments, $R_1$ is aryl or heteroaryl, optionally substituted with 1, 2, or 3 groups selected from halo, alkyl, haloalkyl, -aryl, —$CF_3$, —CN, —OH, or —O-alkyl. In some embodiments, $R_1$ is aryl, e.g., phenyl, optionally substituted with 1 or 2 groups selected from —$CF_3$, —CN, —OMe, —Cl or —F. In some embodiments, $R_1$ is heteroaryl, e.g., thiophene or benzothiophene, optionally substituted with 1 or 2 groups selected from phenyl, —$CF_3$, —CN, —OMe, —Cl or —F. In some embodiments, $R_1$ is hydrogen. In other embodiments, $R_1$ is phenyl. In some embodiments, $R_1$ is pyridyl. In other embodiments, $R_1$ is thiophenyl. In still other embodiments, $R_1$ is cyclohexyl. In some embodiments, $R_1$ is cyclopentyl.

In some embodiments, A is a $C_1$-$C_{10}$ alkylene. In some embodiments, A is a branched $C_1$-$C_{10}$ alkylene. In other embodiments, A is n-octyl. In other embodiments, A is n-heptyl. In other embodiments, A is n-hexyl. In some embodiments, A is a $C_1$-$C_5$ alkylene. In some embodiments, A is n-pentyl. In other embodiments, A is n-butyl. In still other embodiments, A is n-propyl. In other embodiments, A is ethyl. In still other embodiments, A is methyl.

In some embodiments, $X_1$ is O. In other embodiments, $X_1$ is S. In still other embodiments, $X_1$ is $SO_2$. In some embodiments, $X_1$ is $CH_2$. In other embodiments, $X_1$ is C=O. In still other embodiments, $CH_2O$, wherein either the oxygen or the carbon may be attached to

In some embodiments, R' is hydrogen. In other embodiments, R' is methyl. In some embodiments, R'' is hydrogen. In other embodiments, R'' is methyl. In some embodiments, R' and R'' taken together with the carbon to which they are attached, is C=O, with the provision that only one of $X_1$ or R' and R'' taken together with the carbon may form C=O.

In some embodiments, $R_3$ is absent. For example, in the case of compounds where

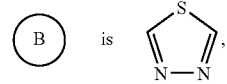

$R_3$ would be considered absent, because there no substituents on the ring. In other embodiments, $R_3$ is halogen.

In some embodiments, $R_4$ is hydrogen. In other embodiments, $R_4$ is an alkyl, e.g., a $C_1$-$C_4$ alkyl. For example, in some embodiments, $R_4$ is methyl. In some embodiments, $R_4$ is hydroxymethyl.

In some embodiments, $R_5$ is hydrogen. In some embodiments, $R_6$ is hydrogen. In some embodiments, $R_5$ is an alkyl, e.g., a $C_1$-$C_4$ alkyl. In some embodiments, $R_6$ is an alkyl, e.g., a $C_1$-$C_4$ alkyl.

In some embodiments, $R_7$ is OH. In other embodiments, $R_7$ is $CO_2H$. In still other embodiments, $R_7$ is $CO_2Me$ or $CO_2Et$. In other embodiments, $R_7$ is $CO_2$-phenyl. In still other embodiments, $R_7$ is —OP(O)$_3H_2$. In other embodiments, $R_7$ is —$CH_2P(O)_3H_2$. In some embodiments,

is phenyl. In other embodiments,
is pyridyl.
In some embodiments,
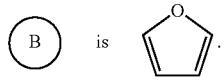
In some embodiments,
In some embodiments,
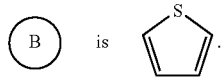
In some embodiments,
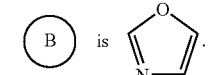
In some embodiments,
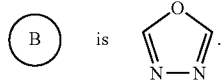
In some embodiments,
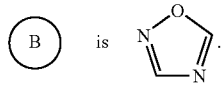
In some embodiments,
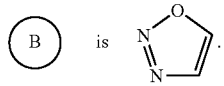
In some embodiments,
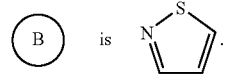
In some embodiments,
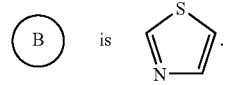
In some embodiments,
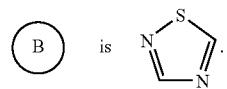
In some embodiments,
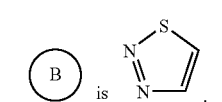
In some embodiments,
In some embodiments,
In some embodiments,
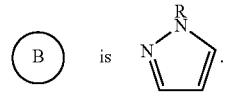
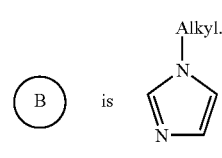

In some embodiments,

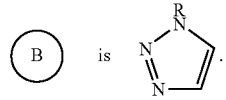

In some embodiments,

In some embodiments,

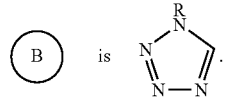

In some embodiments,

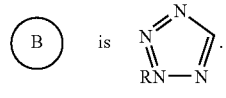

In each of the above structures, R can be hydrogen or alkyl.

In some embodiments,

is pyridyl. In some embodiments,

wherein "⁓" indicates the points of attachment of the B ring to the remainder of the compound.

In some embodiments, compounds of formula II are compounds of formula II-1.

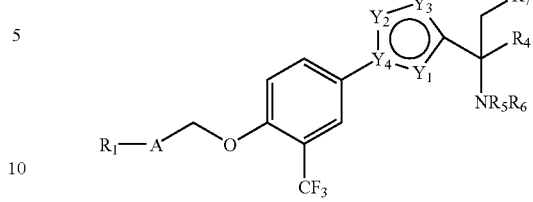

wherein

is a heteroaryl ring containing up to four heteroatoms selected from N, O, or S, optionally substituted on carbon with halogen or alkyl, wherein $Y_1$ is CH, N, S, or O;

$Y_2$ and $Y_3$ are each independently CH, N, O, or S; provided that when

contains an N—H, that hydrogen may be replaced with alkyl; and $Y_4$ is C or N.

In some embodiments, compounds of formula II are compounds of formula II-2,

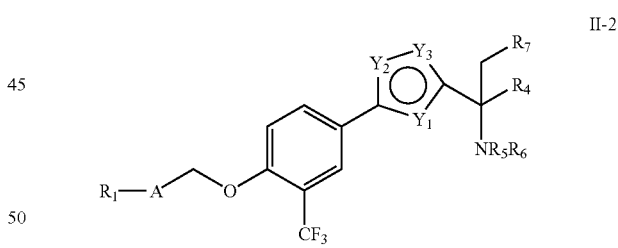

In other embodiments, compounds of formula II are compounds of formula II-3,

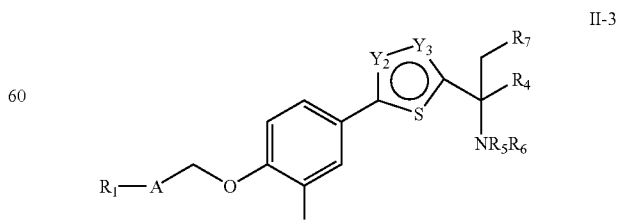

In some embodiments, compounds of formula II are compounds of formula II-4,
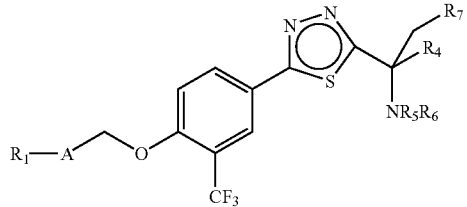
In some embodiments, compounds of the present invention include compounds listed in the following table:
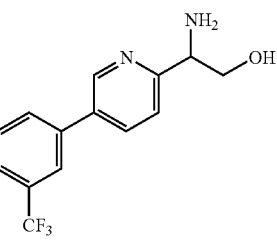
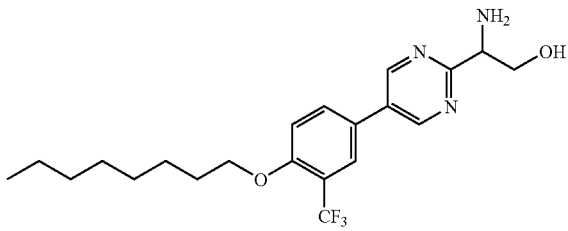
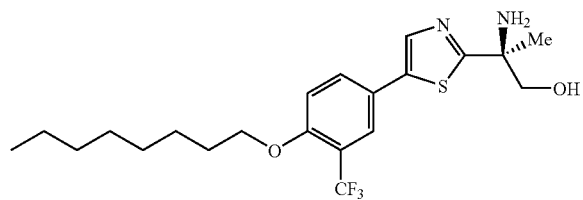
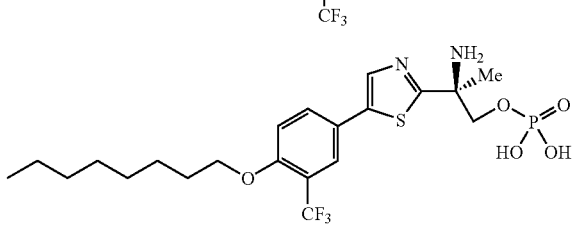
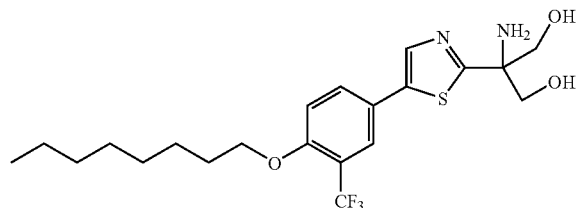
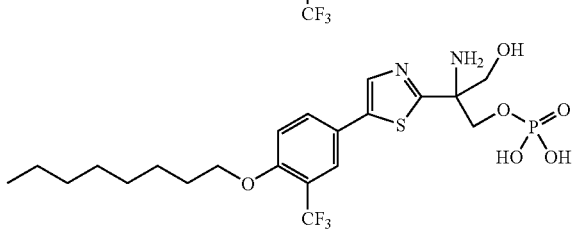
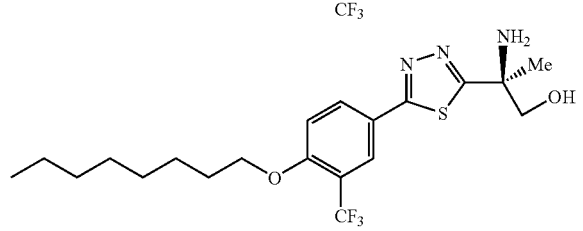
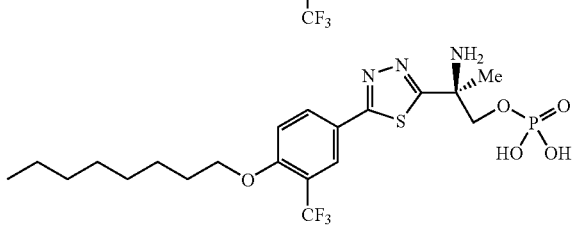
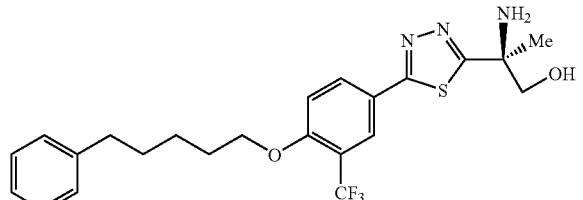
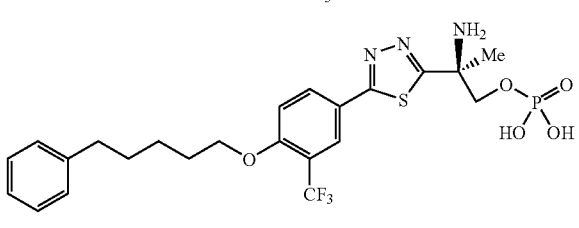
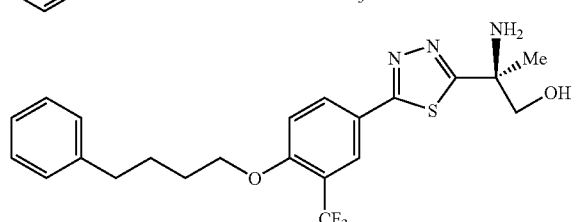
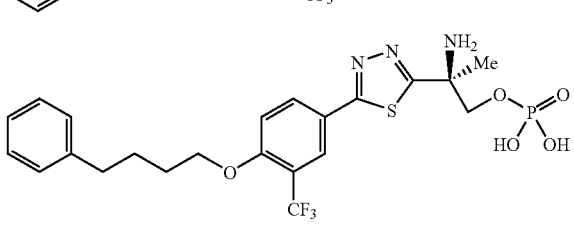
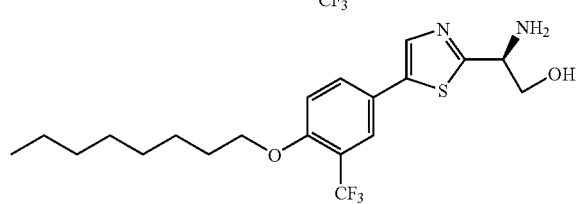

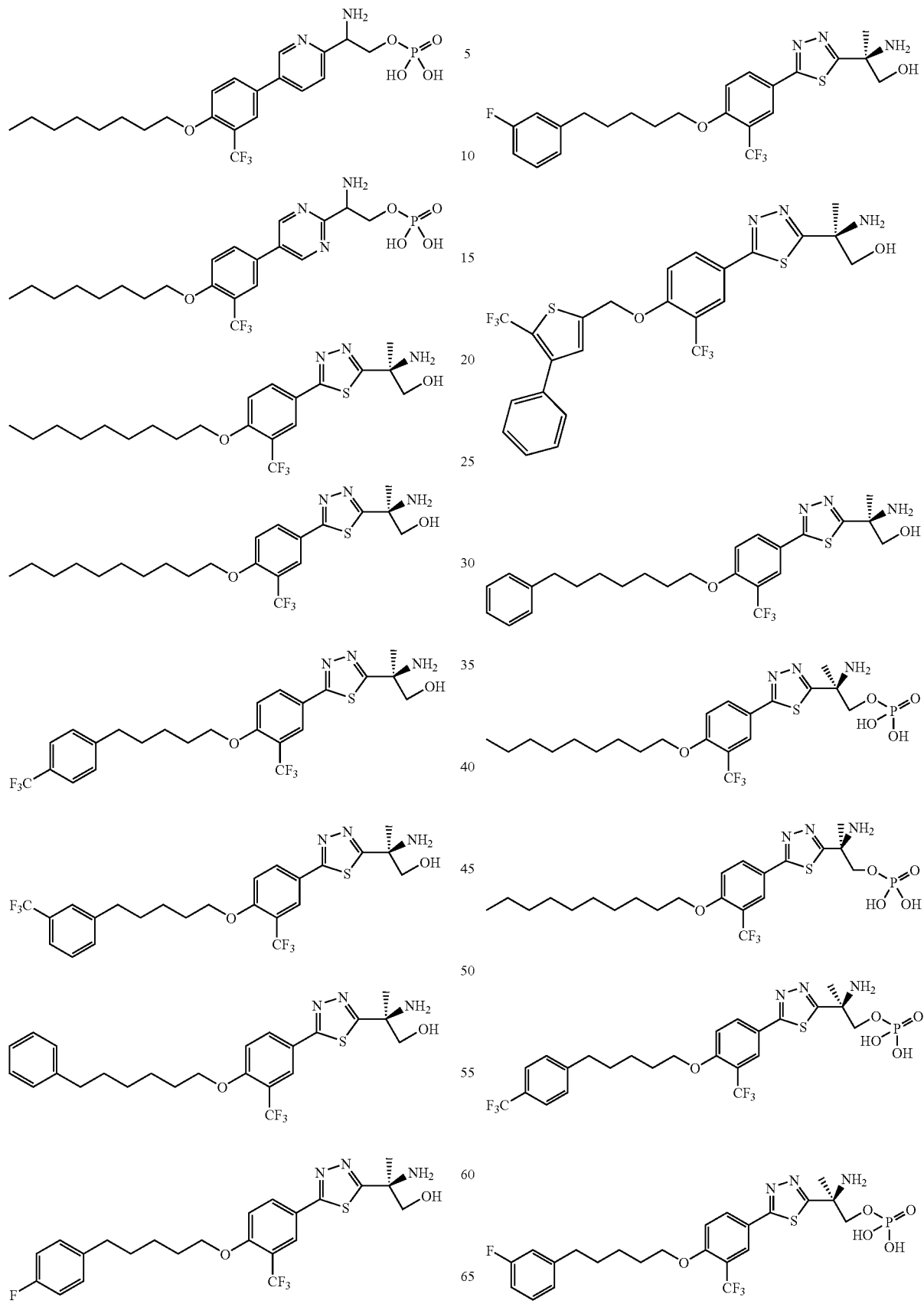

-continued
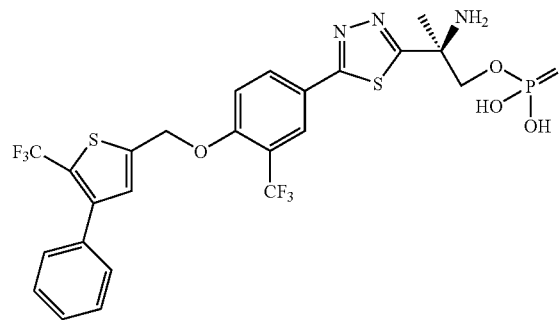
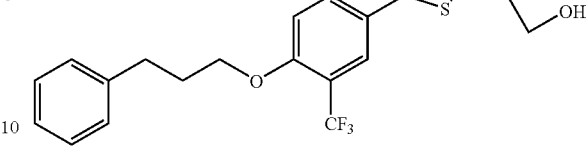
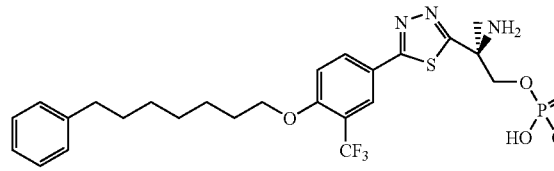
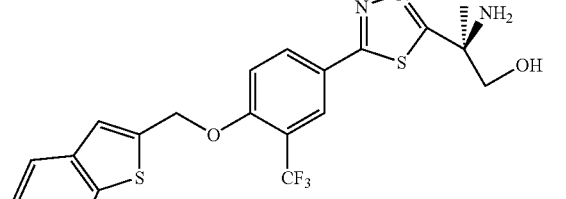
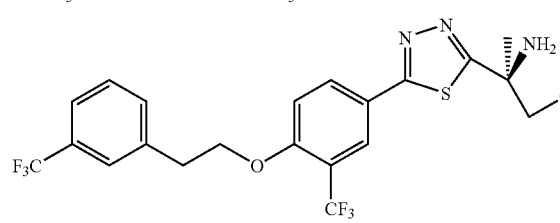
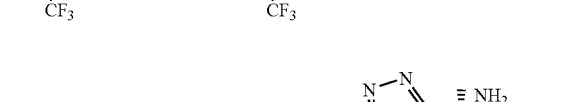
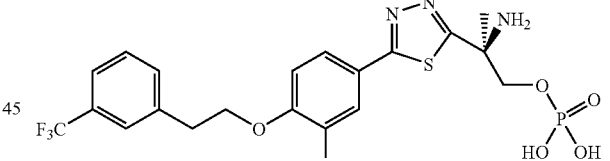
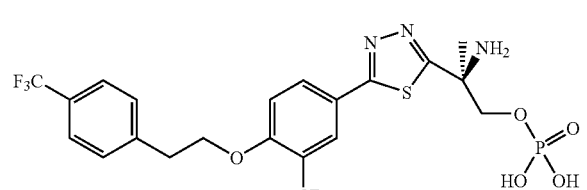
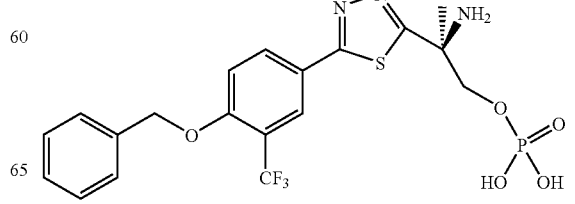

-continued
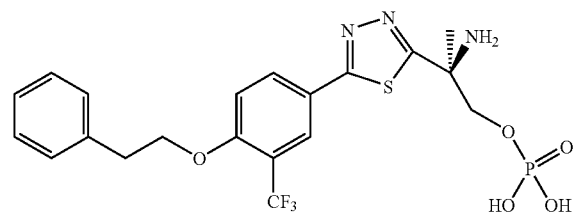
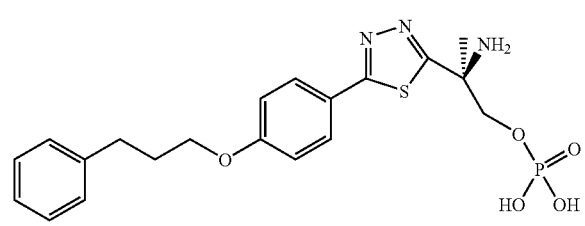
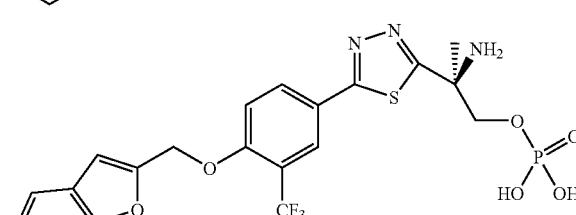
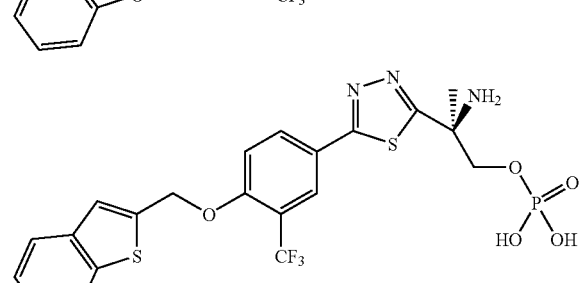
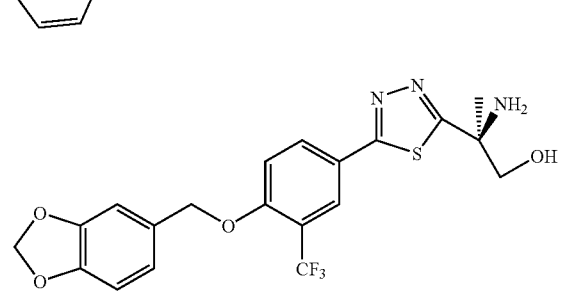
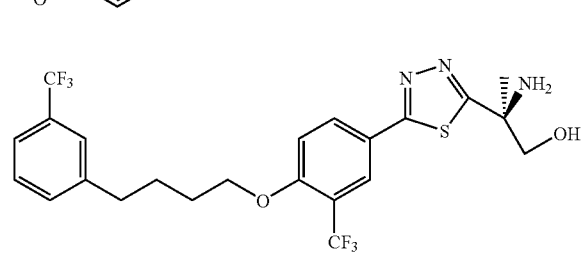
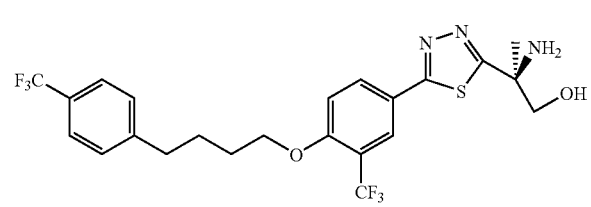
-continued
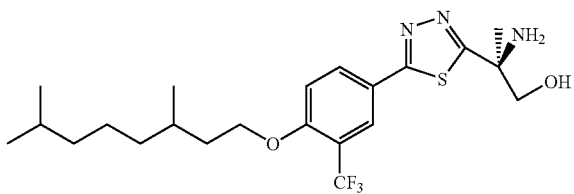
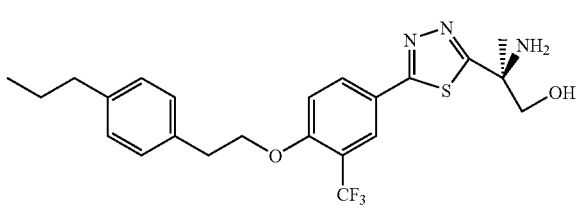
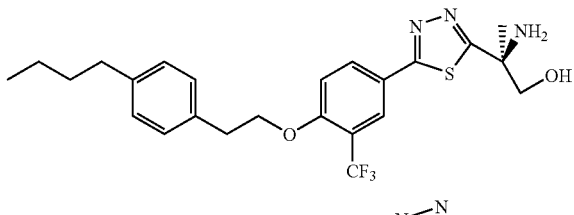
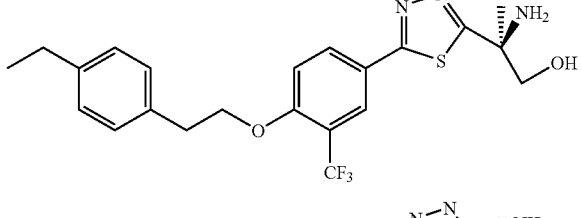
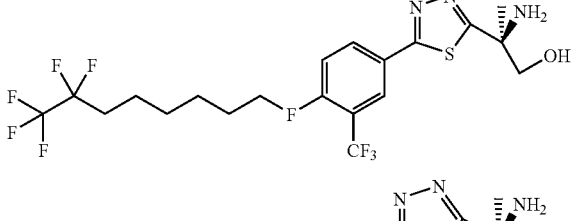
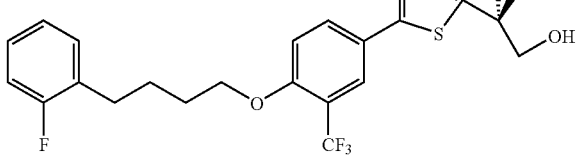
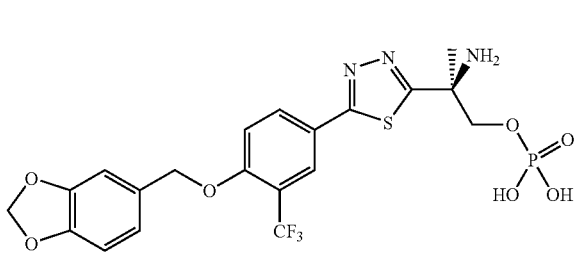
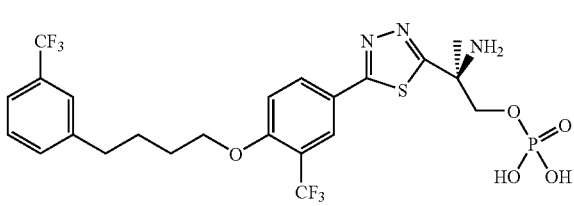

-continued
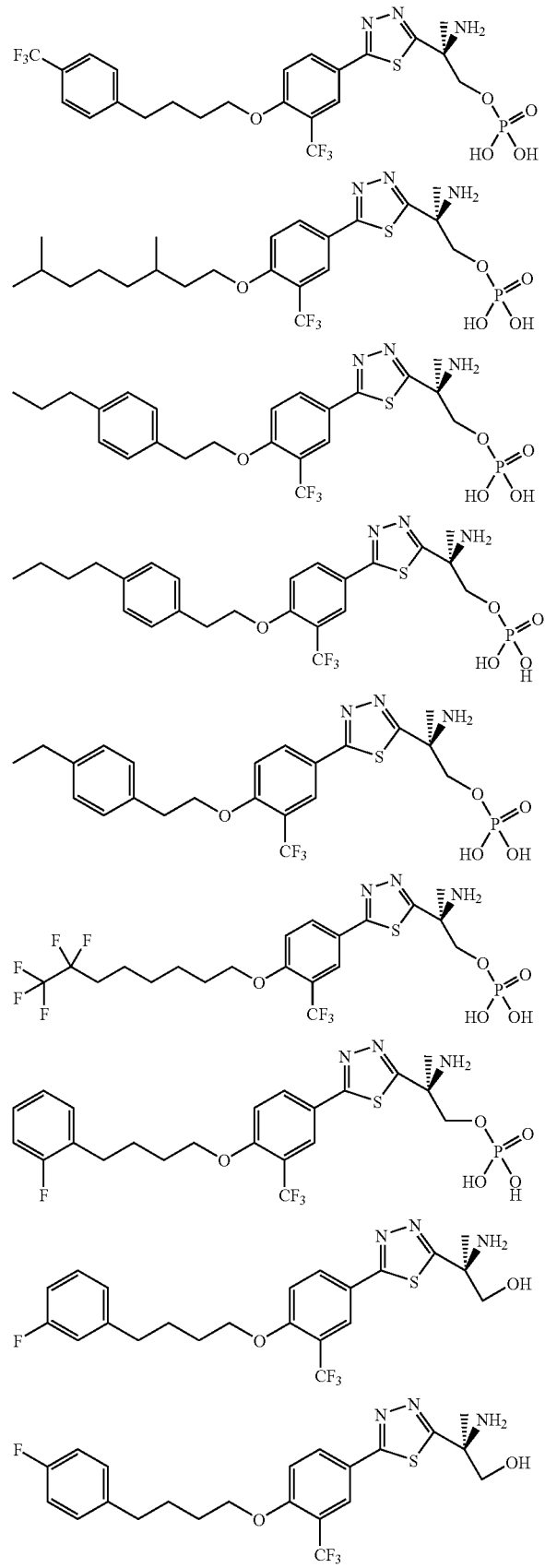
-continued
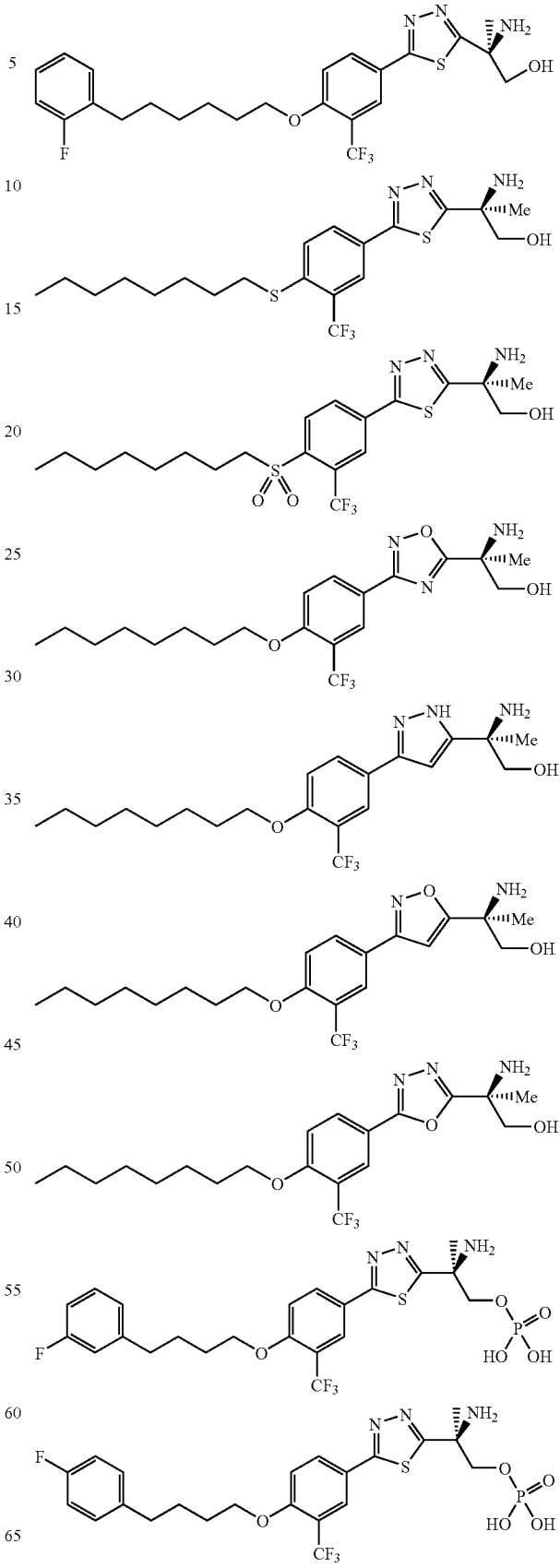

71
-continued
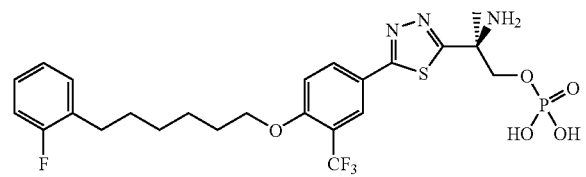
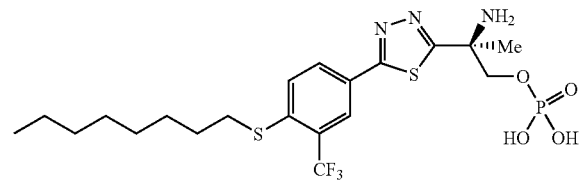
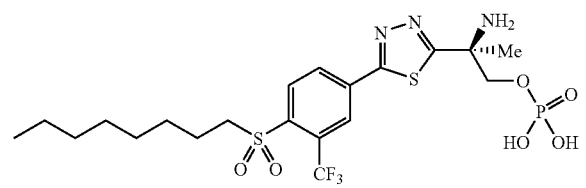
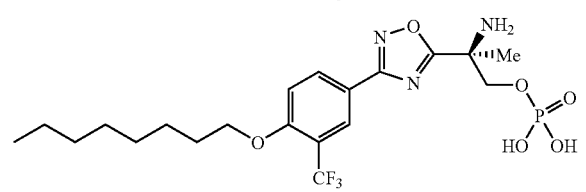
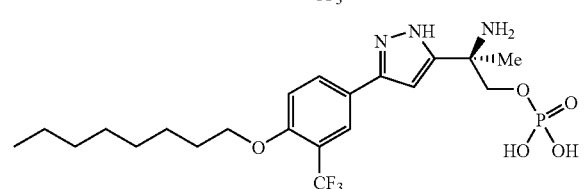
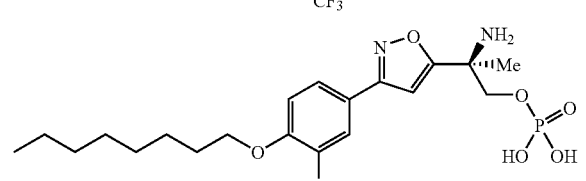
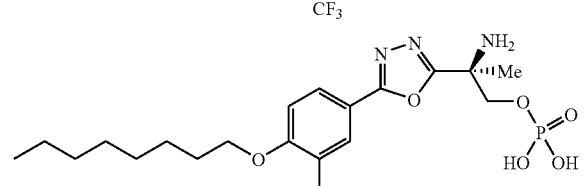
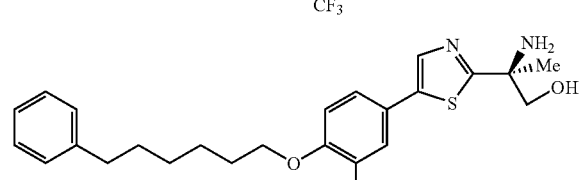
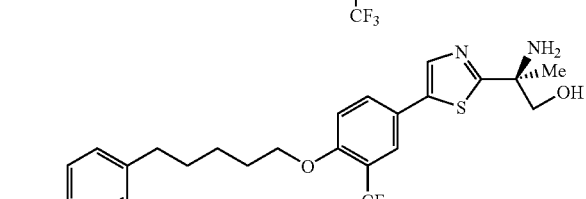
72
-continued
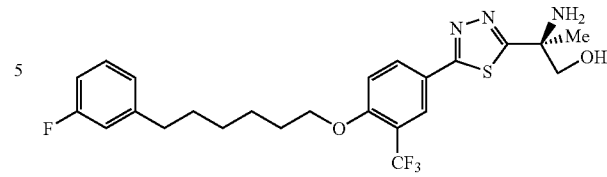
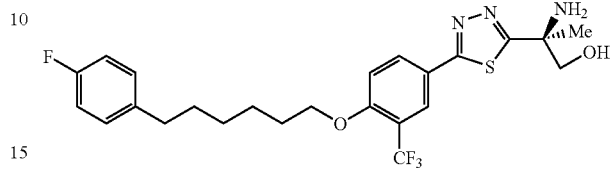
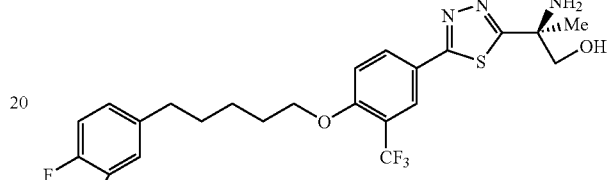
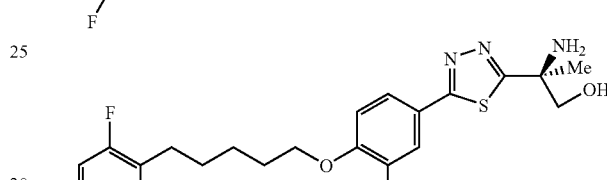
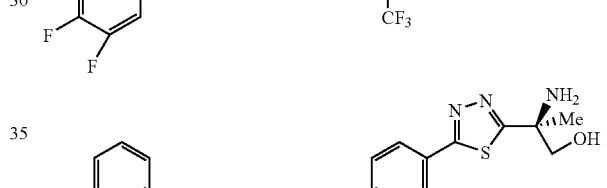
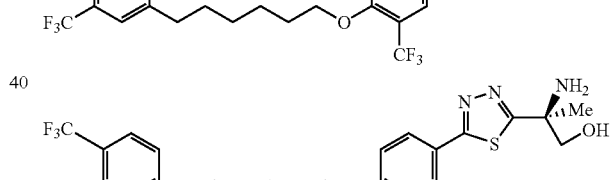
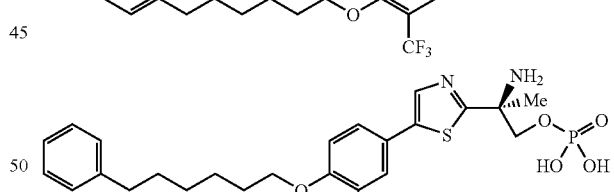
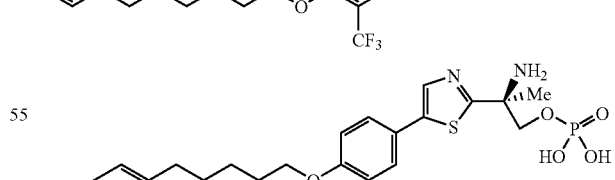
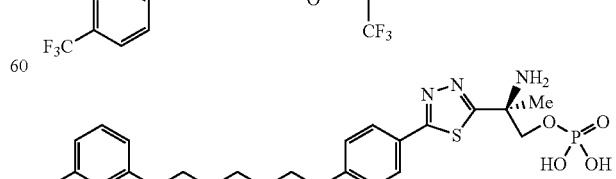

-continued

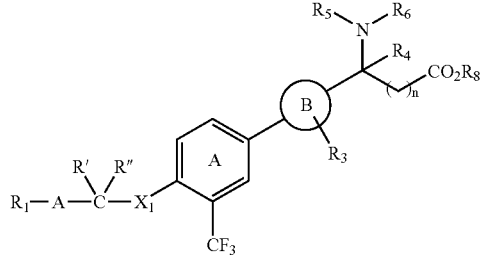

as well as pharmaceutically acceptable salts, phosphate derivatives, phosphate mimics, or phosphate precursor analogs thereof.

In some aspects, the present invention is directed to a compound of formula III:

III or a pharmaceutically acceptable salt thereof, wherein:

$R_1$ is hydrogen, halogen, cyano, alkyl, aryl, heteroaryl, cycloalkyl, heterocycloalkyl, aralkyl, heteroalkyl, —O-alkyl, —O-aryl, —O-heteroaryl, —S-alkyl, alkylene-O-alkyl, alkylene-$CO_2H$, alkylene-$CO_2$alkyl, alkyl$SO_2$, alkylenesulfonyl, alkylene-CO-amino, alkylene-CO-alkylamino, alkylene-CO-dialkylamino, alkylene-NH—$CO_2H$, alkylene-NH—$CO_2$alkyl —$CO_2$alkyl, —OH, —C(O)-alkyl, —C(O)O-alkyl, —$CONH_2$, —CO-alkylamino, —CO-dialkylamino, amino, alkylamino, or dialkylamino, any of which may be optionally substituted on carbon with 1, 2, or 3 groups selected from halo, alkyl, haloalkyl, —$CF_3$, —CN, —OH, or —O-alkyl;

A is ($C_1$-$C_{20}$)alkylene, ($C_2$-$C_{20}$)alkenylene, or ($C_2$-$C_{20}$) alkynylene, each of which may be optionally substituted on carbon with 1, 2, or 3 groups selected from OH, $CO_2H$, $CO_2$alkyl, halogen, amino, alkylamino, dialkylamino, —O-alkyl, alkylene-O-alkyl, alkylene-OH, or alkylene-$CO_2H$;

$X_1$ is a bond or is $CH_2$, O, —$CH_2O$—, S, —S(O), —S(O)$_2$, —C(O)—, —C(O)O—, or $NR_x$, wherein $R_x$ is H or ($C_1$-$C_6$) alkyl;

R' and R" are each independently hydrogen, halogen, alkyl optionally substituted on carbon with halogen, alkyl, or taken together with the carbon to which they are attached form C=O or a 3, 4, 5, or 6-membered ring, optionally containing 1 or 2 heteroatoms selected from 0 NH, N-alkyl, SO, or $SO_2$, any of which may be optionally substituted on carbon with alkyl or halogen $R_3$ is absent, hydrogen, halogen, cyano, alkyl, aryl, heteroaryl, cycloalkyl, heterocycloalkyl, aralkyl, heteroalkyl, —O-alkyl, —O-aryl, —O-heteroaryl, aralkoxy, heteroaralkoxy, —S-alkyl, alkylene-O-alkyl, alkylene-$CO_2H$, alkylene-$CO_2$alkyl, alkyl$SO_2$, alkylenesulfonyl, alkylene-CO-amino, alkylene-CO-alkylamino, alkylene-CO-dialkylamino, alkylene-NH—$CO_2H$, alkylene-NH—$CO_2$alkyl —$CO_2$alkyl, —OH, —C(O)-alkyl, —C(O)O-alkyl, —$CONH_2$, —CO-alkylamino, —CO-dialkylamino, amino, alkylamino, and dialkylamino, any of which may be optionally substituted on carbon with 1, 2, or 3 groups selected from halo, alkyl, OH, or —O-alkyl;

[A]

is phenyl or pyridyl;

[B]

is aryl, heteroaryl, heterocyclo, or cycloalkyl, any of which may be optionally substituted on carbon with 1, 2, or 3 groups selected form halogen, alkyl, O-alkyl, $CO_2H$, $CO_2$alkyl, halogen, amino, alkylamino, dialkylamino, —O-alkyl, alkylene-O-alkyl, alkylene-OH, or alkylene-$CO_2H$, provided that

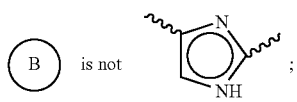 is not ;

R₄ is hydrogen, cyano, alkyl, aryl, heteroaryl, alkylene-O-alkyl, alkylene-OH, aryl, alkylene-O-alkyl, —CO₂H, —CO₂-alkyl, alkylene-CO₂H, or alkylene-CO₂-alkyl, alkylene-OC(O)R wherein R is hydrogen or alkyl; cycloalkyl, heterocycloalkyl, alkylene-NH₂, alkylene-alkylamino, or alkylene-dialkylamino, any of which may be optionally substituted on carbon with 1, 2, or 3 groups selected from OH, CO₂H, CO₂alkyl, halogen, amino, alkylamino, dialkylamino, —O-alkyl, alkylene-O-alkyl, alkylene-OH, or alkylene-CO₂H;

R₅ and R₆ are each independently selected from the group consisting of hydrogen, alkyl, alkylene-OH, aryl, alkylene-O-alkyl, —CO₂H, CO₂-alkyl, alkylene-OC(O)alkyl, cycloalkyl, heterocyclo, —C(O)-alkyl, —C(O)-aryl, C(O)-aralkyl, —C(O)—Oalkyl, —C(O)—Oaryl, —C(O)—Oaralkyl, alkylene-amino, alkylene-alkylamino, and alkylene-dialkylamino, any of which may be optionally substituted on carbon with halogen, alkyl, hydroxyl, CO₂H, CO₂alkyl or alkoxy; or R₅ and R₆, together with the nitrogen to which they are attached, may form a 3, 4, 5, or 6-membered saturated or unsaturated ring, optionally containing 1 or 2 additional heteroatoms selected from O, S, NH, or N-alkyl, and optionally substituted on carbon with halogen, alkyl, hydroxyl, or alkoxy;

R₈ is hydrogen, alkyl or aryl; and n is 0, 1, or 2.

In some embodiments, R₁ is aryl or heteroaryl, optionally substituted with 1, 2, or 3 groups selected from halo, alkyl, haloalkyl, -aryl, —CF₃, —CN, —OH, or —O-alkyl. In some embodiments, R₁ is aryl, e.g., phenyl, optionally substituted with 1 or 2 groups selected from —CF₃, —CN, —OMe, —Cl or —F. In some embodiments, R₁ is heteroaryl, e.g., thiophene or benzothiophene, optionally substituted with 1 or 2 groups selected from phenyl, —CF₃, —CN, —OMe, —Cl or —F. In some embodiments, R₁ is hydrogen. In other embodiments, R₁ is phenyl. In some embodiments, R₁ is pyridyl. In other embodiments, R₁ is thiophenyl. In still other embodiments, R₁ is cyclohexyl. In some embodiments, R₁ is cyclopentyl.

In some embodiments, A is a C₁-C₁₀ alkylene. In some embodiments, A is a branched C₁-C₁₀ alkylene. In other embodiments, A is n-octyl. In other embodiments, A is n-heptyl. In other embodiments, A is n-hexyl. In some embodiments, A is a C₁-C₅ alkylene. In some embodiments, A is n-pentyl. In other embodiments, A is n-butyl. In still other embodiments, A is n-propyl. In other embodiments, A is ethyl. In still other embodiments, A is methyl.

In some embodiments, X₁ is O. In other embodiments, X₁ is S. In still other embodiments, X₁ is SO₂. In some embodiments, X₁ is CH₂. In other embodiments, X₁ is C=O. In still other embodiments, CH₂O, wherein either the oxygen or the carbon may be attached to

In some embodiments, R' is hydrogen. In other embodiments, R' is methyl. In some embodiments, R" is hydrogen. In other embodiments, R" is methyl. In some embodiments, R' and R" taken together with the carbon to which they are attached, is C=O, with the provision that only one of X₁ or R' and R" taken together with the carbon may form C=O.

In some embodiments, R₃ is absent. For example, in the case of compounds where

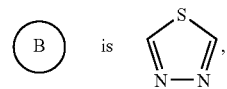

would be considered absent, because there no substituents on the ring. In other embodiments, R₃ is halogen.

In some embodiments, R₄ is hydrogen. In other embodiments, R₄ is an alkyl, e.g., a C₁-C₄ alkyl. For example, in some embodiments, R₄ is methyl. In some embodiments, R₄ is hydroxymethyl.

In some embodiments, R₅ is hydrogen. In some embodiments, R₆ is hydrogen. In some embodiments, R₅ is an alkyl, e.g., a C₁-C₄ alkyl. In some embodiments, R₆ is an alkyl, e.g., a C₁-C₄ alkyl.

In some embodiments,

is phenyl. In other embodiments,

is pyridyl.

In some embodiments,

In some embodiments,

In some embodiments,
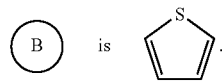
In some embodiments,
In some embodiments,
In some embodiments,
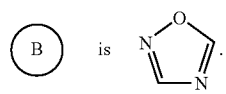
In some embodiments,
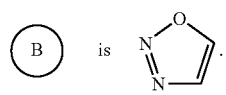
In some embodiments,
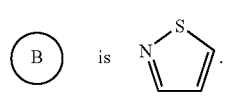
In some embodiments,
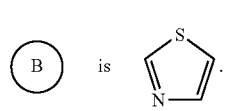
In some embodiments,
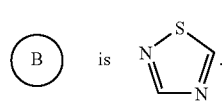
In some embodiments,
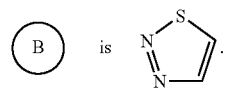
In some embodiments,
In some embodiments,
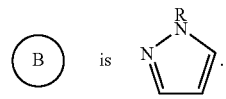
In some embodiments,
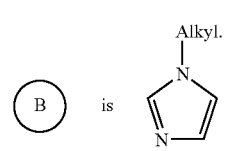
In some embodiments,
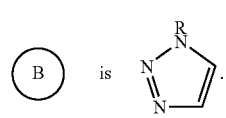
In some embodiments,
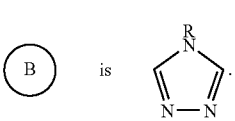
In some embodiments,
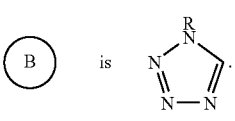

In some embodiments,

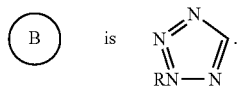

In each of the above structures, R can be hydrogen or alkyl.
In some embodiments,

is pyridyl. In some embodiments,

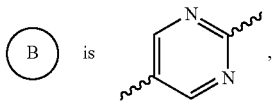

wherein

"⁓"

indicates the points of attachment of the B ring to the remainder of the compound.

In some embodiments, compounds of the present invention include compounds listed in the following table:

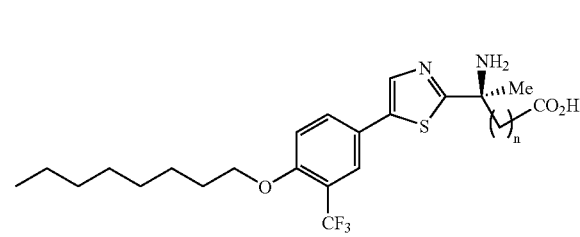

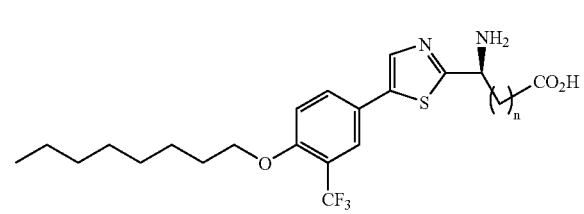

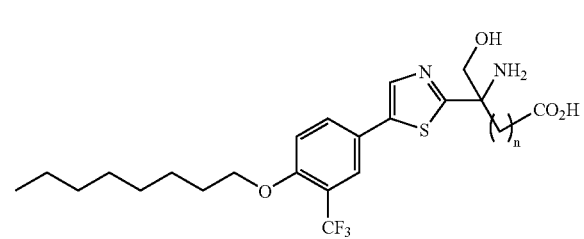

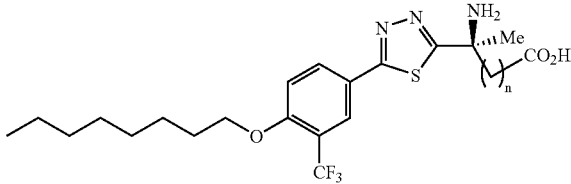

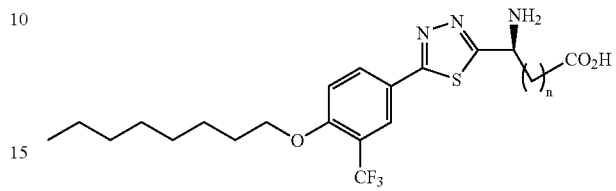

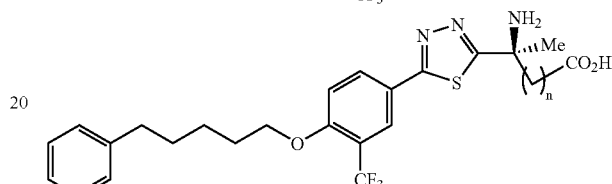

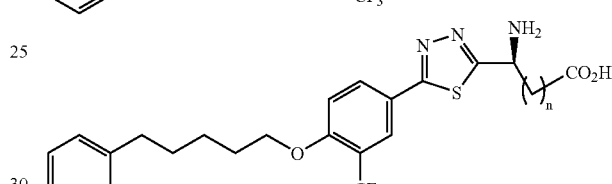

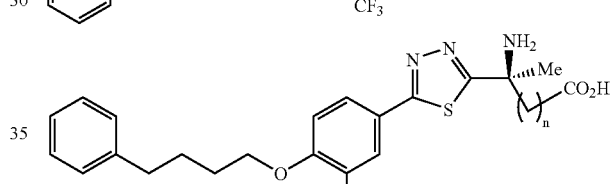

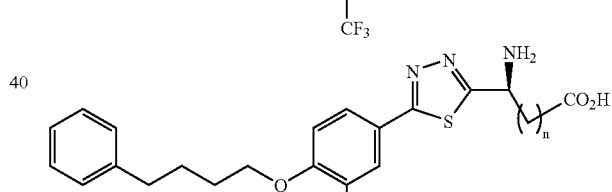

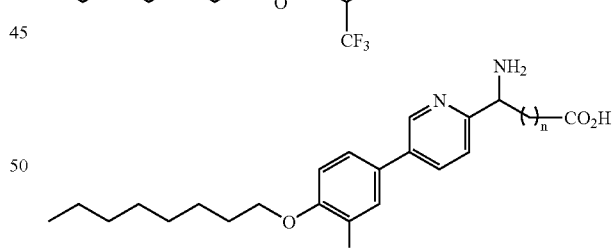

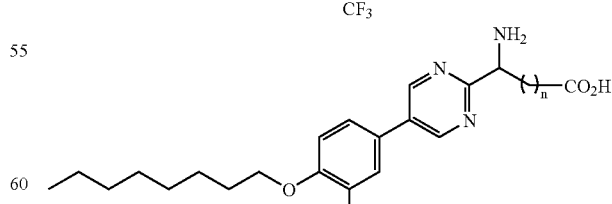

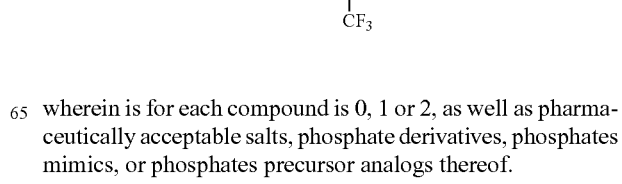

wherein is for each compound is 0, 1 or 2, as well as pharmaceutically acceptable salts, phosphate derivatives, phosphates mimics, or phosphates precursor analogs thereof.

Compounds of the present invention include the following compounds:

(S)-2-Amino-2-(5-(4-(octyloxy)-3-(trifluoromethyl)phenyl)thiazol-2-yl)propan-1-ol;

2-Amino-2-(5-(4-(octyloxy)-3-(trifluoromethyl)phenyl)thiazol-2-yl)propan-1,3-diol;

(S)-2-Amino-2-(5-(4-(octyloxy)-3-(trifluoromethyl)phenyl)-1,3,4-thiadiazol-2-yl)propan-1-ol;

(S)-2-Amino-2-(5-(4-(5-phenylpentyloxy)-3-(trifluoromethyl)phenyl)-1,3,4-thiadiazol-2-yl)propan-1-ol;

(S)-2-Amino-2-(5-(4-(4-phenylbutoxy)-3-(trifluoromethyl)phenyl)-1,3,4-thiadiazol-2-yl)propan-1-ol;

(S)-2-Amino-2-(5-(4-(nonyloxy)-3-(trifluoromethyl)phenyl)-1,3,4-thiadiazole-2-yl)propan-1-ol;

(S)-2-Amino-2-(5-(4-(decyloxy)-3(trifluoromethyl)phenyl)-1,3,4-thiadiazol-2-yl)propan-1-ol;

(S)-2-Amino-2-(5-(3-(trifluoromethyl)-4-(5-(4-(trifluoromethyl)phenyl)pentyloxy)phenyl)-1,3,4-thiadiazole-2-yl)propan-1-ol;

(S)-2-Amino-2-(5-(3-(trifluoromethyl)-4-(5-(3-(trifluoromethyl)phenyl)pentyloxy)phenyl)-1,3,4-thiadiazol-2-yl)propan-1-ol;

(S)-2-Amino-2-(5-(4-(6-phenylhexyloxy)-3-(trifluoromethyl)phenyl)-1,3,4-thiadiazol-2-yl)propan-1-ol;

(S)-2-Amino-2-(5-(4-(5-(4-fluorophenyl)pentyloxy)-3-(trifluoromethyl)phenyl)-1,3,4-thiadiazol-2-yl)propan-1-ol;

(S)-2-Amino-2-(5-(4-(5-(3-fluorophenyl)pentyloxy)-3-(trifluoromethyl)phenyl)-1,3,4-thiadiazol-2-yl)propan-1-ol;

(S)-2-Amino-2-(5-(4-((4-phenyl-5-(trifluoromethyl)thiophen-2-yl)methoxy)-3-(trifluoromethyl)phenyl)-1,3,4-thiadiazol-2-yl)propan-1-ol;

(S)-2-Amino-2-(5-(4-(7-phenylheptyloxy)-3-(trifluoromethyl)phenyl)-1,3,4-thiadiazol-2-yl)propan-1-ol;

(S)-2-Amino-2-(5-(3-(trifluoromethyl)-4-(2-(trifluoromethyl)phenethoxy)phenyl)-1,3,4-thiadiazol-2-yl)propan-1-ol;

(S)-2-Amino-2-(5-(3-(trifluoromethyl)-4-(3-(trifluoromethyl)phenethoxy)phenyl)-1,3,4-thiadiazol-2-yl)propan-1-ol;

(S)-2-Amino-2-(5-(3-(trifluoromethyl)-4-(4-(trifluoromethyl)phenethoxy)phenyl)-1,3,4-thiadiazol-2-yl)propan-1-ol;

(S)-2-Amino-2-(5-(4-(benzyloxy)-3-(trifluoromethyl)phenyl)-1,3,4-thiadiazol-2-yl)propan-1-ol;

(S)-2-Amino-2-(5-(4-phenethoxy-3-(trifluoromethyl)phenyl)-1,3,4-thiadiazol-2-yl)propan-1-ol;

(S)-2-Amino-2-(5-(4-(3-phenylpropoxy)-3-(trifluoromethyl)phenyl)-1,3,4-thiadiazol-2-yl)propan-1-ol;

(S)-2-Amino-2-(5-(4-(benzofuran-2-ylmethoxy)-3-(trifluoromethyl)phenyl)-1,3,4-thiadiazol-2-yl)propan-1-ol;

(S)-2-Amino-2-(5-(4-(benzo[b]thiophen-2-ylmethoxy)-3-(trifluoromethyl)phenyl)-1,3,4-thiadiazol-2-yl)propan-1-ol;

(S)-2-Amino-2-(5-(4-(benzo[d][1,3]dioxol-5-ylmethoxy)-3-(trifluoromethyl)phenyl)-1,3,4-thiadiazol-2-yl)propan-1-ol (S)-2-Amino-2-(5-(3-(trifluoromethyl)-4-(4-(3-(trifluoromethyl)phenyl)butoxy)phenyl)-1,3,4-thiadiazol-2-yl)propan-1-ol;

(S)-2-Amino-2-(5-(3-(trifluoromethyl)-4-(4-(4-(trifluoromethyl)phenyl)butoxy)phenyl)-1,3,4-thiadiazol-2-yl)propan-1-ol;

(2S)-2-Amino-2-(5-(4-(3,7-dimethyloctyloxy)-3-(trifluoromethyl)phenyl)-1,3,4-thiadiazol-2-yl)propan-1-ol;

(S)-2-Amino-2-(5-(4-(4-propylphenethoxy)-3-(trifluoromethyl)phenyl)-1,3,4-thiadiazol-2-yl)propan-1-ol;

(S)-2-Amino-2-(5-(4-(4-butylphenethoxy)-3-(trifluoromethyl)phenyl)-1,3,4-thiadiazol-2-yl)propan-1-ol;

(S)-2-Amino-2-(5-(4-(4-ethylphenethoxy)-3-(trifluoromethyl)phenyl)-1,3,4-thiadiazol-2-yl)propan-1-ol;

(S)-2-Amino-2-(5-(4-(7,7,8,8,8-pentafluorooctyloxy)-3-(trifluoromethyl)phenyl)-4,3,4-thiadiazol-2-yl)propan-1-ol;

(S)-2-Amino-2-(5-(4-(4-(2-fluorophenyl)butoxy)-3-(trifluoromethyl)phenyl)-1,3,4-thiadiazol-2-yl)propan-1-ol;

(S)-2-Amino-2-(5-(4-(4-(3-fluorophenyl)butoxy)-3-(trifluoromethyl)phenyl)-1,3,4-thiadiazol-2-yl)propan-1-ol;

(S)-2-Amino-2-(5-(4-(4-(4-fluorophenyl)butoxy)-3-(trifluoromethyl)phenyl)-1,3,4-thiadiazol-2-yl)propan-1-ol;

(S)-2-Amino-2-(5-(4-(6-(2-fluorophenyl)hexyloxy)-3-(trifluoromethyl)phenyl)-1,3,4-thiadiazol-2-yl)propan-1-ol;

(S)-2-Amino-2-(5-(4-(6-(3-fluorophenyl)hexyloxy)-3-(trifluoromethyl)phenyl)-1,3,4-thiadiazol-2-yl)propan-1-ol;

(S)-2-Amino-2-(5-(4-(6-(4-fluorophenyl)hexyloxy)-3-(trifluoromethyl)phenyl)-1,3,4-thiadiazol-2-yl)propan-1-ol;

(S)-2-Amino-2-(5-(4-(5-(3,4-difluorophenyl)pentyloxy)-3-(trifluoromethyl)phenyl)-1,3,4-thiadiazol-2-yl)propan-1-ol;

(S)-2-Amino-2-(5-(3-(trifluoromethyl)-4-(5-(2,4,5-trifluorophenyl)pentyloxy)phenyl)-1,3,4-thiadiazol-2-yl)propan-1-ol;

(S)-2-Amino-2-(5-(3-(trifluoromethyl)-4-(6-(3-(trifluoromethyl)phenyl)hexyloxy)phenyl)-1,3,4-thiadiazol-2-yl)propan-1-ol;

(S)-2-Amino-2-(5-(3-(trifluoromethyl)-4-(6-(4-(trifluoromethyl)phenyl)hexyloxy)phenyl)-1,3,4-thiadiazol-2-yl)propan-1-ol;

(S)-2-Amino-2-(5-(4-(octylthio)-3-(trifluoromethyl)phenyl)-1,3,4-thiadiazol-2-yl)propan-1-ol;

(S)-2-Amino-2-(5-(4-(octylsulfonyl)-3-(trifluoromethyl)phenyl)-1,3,4-thiadiazol-2-yl)propan-1-ol;

(S)-2-Amino-2-(3-(4-(octyloxy)-3-(trifluoromethyl)phenyl)-1,2,4-oxadiazol-5-yl)propan-1-ol;

(R)-2-Amino-2-(5-(4-(octyloxy)-3-(trifluoromethyl)phenyl)-1H-pyrazol-3-yl)propan-1-ol;

(S)-2-Amino-2-(3-(4-(octyloxy)-3-(trifluoromethyl)phenyl)isoxazol-5-yl)propan-1-ol;

(S)-2-Amino-2-(5-(4-(octyloxy)-3-(trifluoromethyl)phenyl)-1,3,4-oxadiazol-2-yl)propan-1-ol;

(S)-2-Amino-2-(5-(4-(6-phenylhexyloxy)-3-(trifluoromethyl)phenyl)thiazol-2-yl)propan-1-ol;

(S)-2-Amino-2-(5-(3-(trifluoromethyl)-4-(5-(4-(trifluoromethyl)phenyl)pentyloxy)phenyl)thiazol-2-yl)propan-1-ol;

and pharmaceutically acceptable salts, phosphate derivatives, phosphate mimics, or phosphate precursor analogs thereof.

Compounds of the present invention further include the following compounds:

(S)-2-amino-2-(5-(4-(octyloxy)-3-(trifluoromethyl)phenyl)thiazol-2-yl)propyl dihydrogen phosphate;

(S)-2-Amino-2-(5-(4-(octyloxy)-3-(trifluoromethyl)phenyl)-1,3,4-thiadiazol-2-yl)propyl dihydrogen phosphate;

(S)-2-Amino-2-(5-(4-(5-phenylpentyloxy)-3-(trifluoromethyl)phenyl)-1,3,4-thiadiazol-2-yl)propyl dihydrogen phosphate;

(S)-2-Amino-2-(5-(4-(4-phenylbutoxy)-3-(trifluoromethyl)phenyl)-1,3,4-thiadiazol-2-yl)propyl dihydrogen phosphate;

(S)-2-Amino-2-(5-(4-(octylthio)-3-(trifluoromethyl)phenyl)-1,3,4-thiadiazol-2-yl)propyl dihydrogen phosphate;

(S)-2-Amino-2-(5-(4-(nonyloxy)-3-(trifluoromethyl)phenyl)-1,3,4-thiadiazol-2-yl)propyl dihydrogen phosphate;

(S)-2-Amino-2-(5-(3-(trifluoromethyl)-4-(5-(3-(trifluoromethyl)phenyl)pentyloxy)phenyl)-1,3,4-thiadiazol-2-yl) propyl dihydrogen phosphate;
(S)-2-Amino-2-(5-(3-(trifluoromethyl)-4-(5-(4-(trifluoromethyl)phenyl)pentyloxy)phenyl)-1,3,4-thiadiazol-2-yl) propyl dihydrogen phosphate;
(S)-2-Amino-2-(5-(4-((4-phenyl-5-(trifluoromethyl) thiophen-2-yl)methoxy)-3-(trifluoromethyl)phenyl)-1,3,4-thiadiazol-2-yl)propyl dihydrogen phosphate;
(S)-2-Amino-2-(5-(4-(6-phenylhexyloxy)-3-(trifluoromethyl)phenyl)-1,3,4-thiadiazol-2-yl)propyl dihydrogen phosphate;
(S)-2-Amino-2-(5-(4-(5-(3-fluorophenyl)pentyloxy)-3-(trifluoromethyl)phenyl)-1,3,4-thiadiazol-2-yl)propyl dihydrogen phosphate;
(S)-2-Amino-2-(5-(4-(5-(4-fluorophenyl)pentyloxy)-3-(trifluoromethyl)phenyl)-1,3,4-thiadiazol-2-yl)propyl dihydrogen phosphate;
(S)-2-Amino-2-(5-(3-(trifluoromethyl)-4-(4-(3-(trifluoromethyl)phenyl)butoxy)phenyl)-1,3,4-thiadiazol-2-yl)propyl dihydrogen phosphate;
(S)-2-Amino-2-(5-(4-(4-(4-fluorophenyl)butoxy)-3-(trifluoromethyl)phenyl)-1,3,4-thiadiazol-2-yl)propyl dihydrogen phosphate;
(S)-2-Amino-2-(5-(4-(6-(3-fluorophenyl)hexyloxy)-3-(trifluoromethyl)phenyl)-1,3,4-thiadiazol-2-yl)propyl dihydrogen phosphate;
(S)-2-Amino-2-(5-(4-(6-(4-fluorophenyl)hexyloxy)-3-(trifluoromethyl)phenyl)-1,3,4-thiadiazol-2-yl)propyl dihydrogen phosphate;
(S)-2-Amino-2-(5-(4-(5-(3,4-difluorophenyl)pentyloxy)-3-(trifluoromethyl)phenyl)-1,3,4-thiadiazol-2-yl)propyl dihydrogen phosphate;
(S)-2-Amino-2-(5-(3-(trifluoromethyl)-4-(5-(2,4,5-trifluorophenyl)pentyloxy)phenyl)-1,3,4-thiadiazol-2-yl)propyl dihydrogen phosphate;
(S)-2-Amino-2-(3-(4-(octyloxy)-3-(trifluoromethyl)phenyl)-1,2,4-oxadiazol-5-yl)propyl dihydrogen phosphate;
(R)-2-Amino-2-(3-(4-(octyloxy)-3-(trifluoromethyl)phenyl)-1H-pyrazol-5-yl)propyl dihydrogen phosphate;
(S)-2-Amino-2-(3-(4-(octyloxy)-3-(trifluoromethyl)phenyl) isoxazol-5-yl)propyl dihydrogen phosphate;
(S)-2-Amino-2-(5-(4-(octyloxy)-3-(trifluoromethyl)phenyl)-1,3,4-oxadiazol-2-yl)propyl dihydrogen phosphate;
(S)-2-Amino-2-(5-(4-(6-phenylhexyloxy)-3-(trifluoromethyl)phenyl)thiazol-2-yl)propyl dihydrogen phosphate; and
(S)-2-Amino-2-(5-(3-(trifluoromethyl)-4-(5-(4-(trifluoromethyl)phenyl)pentyloxy)phenyl)thiazol-2-yl)propyl dihydrogen phosphate.

Biological Activity of Invention Compounds

Lymphopenia Assay

Several of the compounds described herein were evaluated for the ability to induce lymphopenia in mice. Male C57Bl/6 mice were divided into groups of three. A control group received the 3% BSA vehicle only. The other groups received a single dose of either a specified dose of test compound in vehicle administered orally (PO) and intravenously (IV). After 6 hours, the mice were anesthesized with isoflurane and approximately 250 μL of blood was removed from the retroorbital sinus and collected in an EDTA microtainer, mixed with an anticoagulant and placed on a tilt table until complete blood count (CBC) analysis. Oral administration (10 mg/K) of these compounds induced increased lymphopenia versus the vehicle.

A 10 mg/Kg oral dose of (S)-2-amino-2-(5-(4-(octyloxy)-3-(trifluoromethyl)phenyl)thiazol-2-yl)propan-1-ol produced a lymphopenia of 75% in this assay.
A 10 mg/Kg oral dose of (S)-2-amino-2-(5-(4-(octyloxy)-3-(trifluoromethyl)phenyl)-1,3,4-thiadiazol-2-yl)propan-1-ol produced a lymphopenia of 77% in this assay.

Binding to S1P-1 or S1P-3 Receptors

In certain embodiments, the compounds of the invention selective for the S1P-1 receptor as compared to one or more of the other S1P receptors. For example, one set of compounds includes compounds which are selective for the S1P-1 receptor relative to the S1P-3 receptor. Compounds selective for the S1P-1 receptor can be agonists of the S1P-1 receptor, significantly weaker agonists of one or more other receptors and/or antagonists of one or more other receptors. A compound is "selective" for the S1P-1 receptor relative to a second receptor, if the $EC_{50}$ of the compound for the second receptor is at least two-fold greater than the $EC_{50}$ for the S1P-1 receptor. The $EC_{50}$ of a compound is determined using the $^{35}$S-GTPγS binding assay, as described in WO 03/061567, the entire contents of which are incorporated herein by reference. Additionally or alternatively, a compound is "selective" for the S1P-1 receptor relative to a second receptor, if the $IC_{50}$ of the compound for the second receptor is at least two-fold greater than the $IC_{50}$ for the S1P-1 receptor. The $IC_{50}$ of a compound is determined using the [$^{33}$P]sphingosine 1-phosphate binding assay, as described in Davis, M. D. et al., Sphingosine 1-Phosphate Analogs as Receptor Antagonists. *J. Biol. Chem.* (2005) 280:9833-9841, the entire contents of which are incorporated herein by this reference.

The terms "agonist" or "S1P-1 receptor agonist" as used herein include the compounds described herein which bind to and/or agonize the S1P-1 receptor. In one embodiment, the S1P receptor agonists have an $IC_{50}$ for the S1-1 receptor of about 100 nM-0.25 nM, about 50 nM-0.25 nM, about 25 nM-0.5 nM, about 100 nM or less, about 75 nM or less, about 50 nM or less, about 40 nM or less, about 30 nM or less, about 20 nM or less, about 10 nM or less, about 5 nM or less, about 1 nM or less, about 0.5 nM or less, or about 0.25 nM or less. The compounds' $IC_{50}$ for the S1P-1 receptor can be measured using the binding assays described in Example 13 or those described in WO 03/061567. Compounds of the invention generally had an $IC_{50}$ in the range of 100 μM (picomolar) to 100 M.

For example,

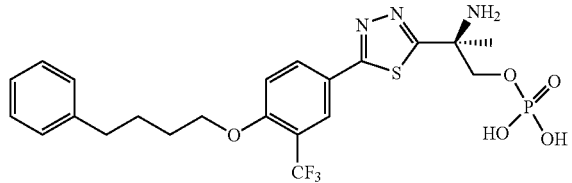

had an $IC_{50}$ 3.23 nM

Ranges intermediate to the above recited values are also intended to be part of this invention. For example, ranges using a combination of any of the above recited values as upper and/or lower limits are intended to be included.

In a further embodiment, the S1P receptor agonist has an $IC_{50}$ value for the S1P-3 receptor of about 10 nM-10,000 nM, about 100 nM-5000 nM, about 100 nM-3000 nM, about 10 nM or greater, about 20 nM or greater, about 40 nM or greater, about 50 nM or greater, about 75 nM or greater, or about 100 nM or greater. In another embodiment, the S1P compound of the invention binds the S1P-3 receptor with an $IC_{50}$ of 1000 nM or greater, 2000 nM or greater, 3000 nM or greater, 5000 nM or greater, 10,000 nM or greater. The $IC_{50}$ for of S1P-3 receptor can be measured using the binding assays described herein or those described in WO 03/061567.

In addition, it should be understood that the ranges intermediate to the above recited values are also intended to be part of this invention. For example, ranges using a combination of any of the above recited values as upper and/or lower limits are intended to be included.

In yet another embodiment, the S1P receptor agonists described herein have an $IC_{50}$ value for the S1P-1 receptor that is about 5-fold lower, about 10-fold lower, about 20-fold lower, about 50-fold lower, about 100-fold lower, about 200-fold lower, about 500-fold lower or about 1000-fold lower than their $IC_{50}$ value for the S1P-3 receptor.

Ranges intermediate to the above recited values are also intended to be part of this invention. For example, ranges using a combination of any of the above recited values as upper and/or lower limits are intended to be included.

The ability of several of the compounds described herein to bind to the S1P-1 or S1P-3 receptor was also tested as follows.

For the membrane preparation, plasmid DNA was transfected into HEK 293 T cells using the FuGENE 6 transfection protocol (publicly available from Roche). Briefly, subconfluent monolayers of HEK 293 T cells were transfected with the DNA mixture containing FuGENE 6 (using a 1:3 ratio). The dishes containing the cells were then placed in a tissue culture incubator (5% $CO_2$, 37° C.). The cells were harvested 48 hours after addition of the DNA by scraping in HME buffer (in mM: 20 HEPES, 5 $MgCl_2$, 1 EDTA, pH 7.4, 1 mM PMSF) containing 10% sucrose on ice, and disrupted using a Dounce homogenizer. After centrifugation at 800×g, the supernatant was diluted with HME without sucrose and centrifuged at 17,000×g for 1 hour. This crude membrane pellet was resuspended in HME with sucrose, aliquoted, and snap-frozen by immersion in liquid nitrogen. The membranes were stored at −70 C. Protein concentration was determined spectroscopically by Bradford protein assay.

For the binding assay, [$^{33}$P]sphingosine 1-phosphate (obtained from American Radiolabeled Chemicals, Inc) was added to membranes in 200 µl in 96-well plates with assay concentrations of 2.5 µM [$^{33}$P]sphingosine 1-phosphate, 4 mg/ml BSA, 50 mM HEPES, pH 7.5, 100 mM NaCl, 5 mM $MgCl_2$, and 5 µg of protein. Binding was performed for 60 minutes at room temperature with gentle mixing and terminated by collecting the membranes onto GF/B filter plates. After drying the filter plates for 10 minutes, 50 µl of Microscint 40 was added to each well, and filter-bound radionuclide was measured on a Packard Top Count. Nonspecific binding was defined as the amount of radioactivity remaining in the presence of excess of unlabeled S1P.

GTPgS Assay Protocol
Membrane Preparation

For membrane preparations all steps were performed at 4° C. Rat hepatoma cells stably expressing the human S1P1 receptor or Rat Basophilic Leukaemia cells (RBL) stably expressing human S1P3 receptor were grown to 80% confluency before being harvested into 10 ml Phospho-Buffered Saline (PBS) and centrifuged at 1200 rpm for 5 minutes. After removal of the supernatant, the pellet was re-suspended and cells were homogenised within a glass Waring blender for 2 bursts of 15 secs in 200 mls of buffer (50 mM HEPES, 1 mM leupeptin, 25 ug/ml bacitracin, 1 mM EDTA, 1 mM PMSF, 2 uM pepstatin A). The blender was plunged into ice for 5 mins after the first burst and 10-40 mins after the final burst to allow foam to dissipate. The material was then spun at 500 g for 20 mins and the supernatant spun for 36 mins at 48,000 g. The pellet was resuspended in the same buffer as above but without PMSF and pepstatin A. The material was then forced through a 0.6 mm needle, made up to the required volume, (usually ×4 the volume of the original cell pellet), aliquoted and stored frozen at −80° C.

GTPgS Assay

Human S1P1 rat hepatoma or S1P3 expressing RBL membranes (1.5 ug/well) were adhered to WGA-coated SPA beads (0.125 mg/well) in assay buffer (HEPES 20 mM, $MgCl_2$ 3 mM, NaCl 100 mM and pH adjusted to 7.4 using KOH 5M, GDP 10 uM FAC and saponin 90 ug/well FAC was also added).

After 30 minutes pre-coupling at 4° C. the bead and membrane suspension was dispensed into a white Greiner polypropylene LV384-well plate (5 ul/well), containing 0.1 ul of test compound or S1P. 5 ul/well [$^{35}$S]-GTP☐S (0.5 nM final radio-ligand conc) made up in assay buffer was then added to the plates. The final assay cocktail (10.1 ul) was centrifuged at 1000 rpm for 5 minutes then read immediately on a Viewlux.

All test compounds were dissolved in DMSO at a concentration of 10 mM and were prepared in 100% DMSO using a 1 in 4 dilution step to provide 11 point dose response curves. The dilutions were transferred to the assay plates ensuring that the DMSO concentration was constant across the plate for all assays.

All data was normalized to the mean of 16 high and 16 low control wells on each plate. A four parameter curve fit was then applied.

The trifluoracetic acid salt of (S)-2-amino-2-(5-(4-(octyloxy)-3-(trifluoromethyl)phenyl)thiazol-2-yl)propyl dihydrogen phosphate had a pEC50 of 8.5 in the S1P1 assay and pEC50 of 6.5 in the S1P3 assay.

The trifluoracetic acid salt of (S)-2-Amino-2-(5-(4-(octyloxy)-3-(trifluoromethyl)phenyl)-1,3,4-thiadiazol-2-yl)propyl dihydrogen phosphate had a pEC50 of 9.2 in the S1P1 assay and pEC50 of 6.1 in the S1P3 assay.

Methods of Using Invention Compounds

The compounds of the invention have been determined to be useful in the treatment of sphingosine 1-phosphate associated disorders. Accordingly, in one embodiment, the invention relates to a method for treating a subject suffering from a sphingosine 1-phosphate associated disorder, comprising administering to a subject an effective amount of a compound of the invention; that is, a compound of formula I or compounds otherwise described herein, such that the subject is treated for a sphingosine 1-phosphate associated disorder.

The term "sphingosine 1-phosphate associated disorder" includes disorders, diseases or conditions which are associated with or caused by a misregulation in S1P receptor function and/or signaling or S1P receptor ligand function. The term also includes diseases, disorders or conditions which can be treated by administering to a subject an effective amount of a sphingosine 1-phosphate receptor agonist. Such disorders include disorders that are associated with an inappropriate immune response and conditions associated with an overactive immune response, e.g., autoimmune diseases. In some embodiments, sphingosine 1-phosphate associated disorders include autoimmune diseases. In other embodiments, sphingosine 1-phosphate associated disorders include inflammation. In further embodiments, sphingosine 1-phosphate associated disorders include transplant rejection. In still other embodiments, sphingosine 1-phosphate associated disorders include acute respiratory distress syndrome (ARDS). In other embodiments, sphingosine 1-phosphate associated disorders include asthma. In yet other embodiments, sphingosine 1-phosphate associated disorders include any combination of the disorders listed herein.

"Treatment", or "treating" as used herein, is defined as the application or administration of a therapeutic agent such as a compound of formula I to a subject who has a shingosine 1-phosphate associated disorder as described herein, with the purpose to cure, heal, alleviate, delay, relieve, alter, remedy, ameliorate, improve or affect the disease or disorder, or symptoms of the disease or disorder. The term "treatment" or "treating" is also used herein in the context of administering agents prophylactically.

In some embodiments, the efficacy of the compounds of the present invention can be measured by comparing a value, level, feature, characteristic, property, etc. to a "suitable control". A "suitable control" is any control or standard familiar to one of ordinary skill in the art useful for comparison purposes. In one embodiment, a "suitable control" is a value, level, feature, characteristic, property, etc. determined prior to administering a composition of the present invention. For example, the immune response, etc. can be determined prior to introducing a compound of the invention into a cell or subject. In another embodiment, a "suitable control" is a value, level, feature, characteristic, property, etc. determined in a cell or organism, e.g., a control or normal cell or organism, exhibiting, for example, normal traits. In yet another embodiment, a "suitable control" is a predefined value, level, feature, characteristic, property, etc. For example a "suitable control" can be a pre-defined level of binding to a specified S1P receptor.

An additional embodiment of the invention pertains to a method for treating a subject suffering from a sphingosine 1-phosphate associated disorder, comprising administering to a subject a compound, such that the subject is treated for a sphingosine 1-phosphate associated disorder by a compound of the invention; that is, a compound of formulae I or compounds otherwise described herein.

The present invention is also directed to a method of selectively treating a sphingosine 1-phosphate associated disorder, comprising administering to a subject an effective amount of a compound of the invention, e.g., compounds of any of Formulae I-VIII or compounds otherwise described herein, such that the subject is selectively treated for a sphingosine 1-phosphate associated disorder. In certain embodiments, the sphingosine 1-phosphate associated disorder is a sphingosine 1-phosphate-(1) associated disorder. In a particular embodiment, the sphingosine 1-phosphate-(1) associated disorder is selectively treated as compared with a sphingosine 1-phosphate-(3) associated disorder.

Another embodiment of the invention is a method of selectively treating a sphingosine 1-phosphate associated disorder, comprising administering to a subject a compound, such that the subject is selectively treated for a sphingosine 1-phosphate associated disorder by a compound of the invention, e.g., compounds of any of Formulae I-VIII or compounds otherwise described herein. In certain embodiments, the sphingosine 1-phosphate associated disorder is a sphingosine 1-phosphate-(1) associated disorder. In a particular embodiment, the sphingosine 1-phosphate-(1) associated disorder is selectively treated as compared with a sphingosine 1-phosphate-(3) associated disorder.

In another embodiment, the present invention provides a method of treating a condition associated with an activated immune system. Such diseases or disorders include multiple sclerosis as well as rejection of transplanted organs, tissue or cells; graft-versus-host diseases brought about by transplantation; autoimmune syndromes including rheumatoid arthritis; systemic lupus erythematosus; antiphospholipid syndrome; Hashimoto's thyroiditis; lymphocytic thyroiditis; myasthenia gravis; type I diabetes; uveitis; episcleritis; scleritis; Kawasaki's disease, uveo-retinitis; posterior uveitis; uveitis associated with Behcet's disease; uveomeningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; psoriatic arthritis; atopic dermatitis; myopathy; myositis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; scleroderma; alopecia greata; keratoconjunctivitis; vernal conjunctivitis; keratitis; herpetic keratitis; dystrophia epithelialis corneas; corneal leukoma; ocular pemphigus; Mooren's ulcer; ulcerative keratitis; scleritis; Graves' opthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchiolitis; bronchitis; endometriosis; orchitis; gastric ulcers; ischemic bowel diseases; inflammatory bowel diseases; necrotizing enterocolitis; intestinal lesions associated with thermal burns; coeliac disease; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; tubulointerstitial nephritis; interstitial cystitis; multiple myositis; Guillain-Barre syndrome; Meniere's disease; polyneuritis; multiple neuritis; myelitis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; autoimmune thrombocytopenia; agranulocytosis; pernicious anemia; megaloblastic anemia; aneryth-roplasia; osteoporosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; myocarditis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; hypophysitis; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung solid cancer; malignancy of lymphoid origin; acute or chronic lymphocytic leukemias; lymphoma; psoriasis; pulmonary emphysema; cataracts; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; peripheral artery disease; carcinogenesis; solid cancer tumors; metastasis of carcinoma; hypobaropathy; autoimmune hepatitis; primary biliary cirrhosis; sclerosing cholangitis; partial liver resection; acute liver necrosis; cirrhosis; alcoholic cirrhosis;

hepatic failure; fulminant hepatic failure; late-onset hepatic failure; "acute-on-chronic" liver failure.

As used herein, the term "subject" includes warm-blooded animals, e.g., mammals, including humans, cats, dogs, horses, bears, lions, tigers, ferrets, rabbits, mice, cows, sheep, pigs, etc. In a particular embodiment, the subject is a primate. In a specific embodiment, the primate is a human.

As used herein, the term "administering" to a subject includes dispensing, delivering or applying a compound of the invention in a pharmaceutical formulation (as described herein), to a subject by any suitable route for delivery of the compound to the desired location in the subject, including delivery by either the parenteral or oral route, intramuscular injection, subcutaneous/intradermal injection, intravenous injection, buccal administration, topical delivery, transdermal delivery and administration by the rectal, colonic, vaginal, intranasal or respiratory tract route.

As used herein, the term "effective amount" includes an amount effective, at dosages and for periods of time necessary, to achieve the desired result, e.g., sufficient to treat the condition in a subject. An effective amount of a compound of the invention, as defined herein, may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the compound are outweighed by the therapeutically beneficial effects.

A therapeutically effective amount of a compound of the invention (i.e., an effective dosage) may range from about 0.001 to 30 mg/kg body weight, for example, about 0.01 to 25 mg/kg body weight, for example, about 0.1 to 20 mg/kg body weight. It is to be understood that all values and ranges between those listed are intended to be encompassed by the present invention. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the invention can include a single treatment or, for example, can include a series of treatments. It will also be appreciated that the effective dosage of the compound used for treatment may increase or decrease over the course of a particular treatment.

The methods of the invention further include administering to a subject a therapeutically effective amount of a compound of the invention in combination with another pharmaceutically active compound known to treat the disease or condition, e.g., an immunomodulatory agent or an anti-inflammatory agent. Pharmaceutically active compounds that may be used depend upon the condition to be treated, but include as examples cyclosporin, rapamycin, FK506, methotrexate, etanercept, infliximab, adalimumab, non-steroidal anti-inflammatory agents, cyclooxygenase-2-inhibitors, such as celecoxib and rofecoxib, and corticosteroids. Other suitable compounds can be found in Harrison's Principles of Internal Medicine, Thirteenth Edition, Eds. T. R. Harrison et al. McGraw-Hill N.Y., N.Y.; and the Physicians Desk Reference 50th Edition 1997, Oradell New Jersey, Medical Economics Co., the complete contents of which are expressly incorporated herein by reference. The compound of the invention and the additional pharmaceutically active compound may be administered to the subject in the same pharmaceutical composition or in different pharmaceutical compositions (at the same time or at different times).

Pharmaceutical Compositions Comprising Invention Compounds

The present invention also provides pharmaceutically acceptable formulations and compositions comprising one or more compounds of the invention; that is, compounds of formula I or compounds otherwise described herein. In certain embodiments, the compound of the invention is present in the formulation in a therapeutically effective amount; that is, an amount effective to treat a sphingosine 1-phosphate associated disorder.

Accordingly, in one embodiment, the invention pertains to a pharmaceutical composition comprising a therapeutically effective amount of a compound of the invention; that is, compounds of formula I or compounds otherwise described herein, and a pharmaceutically acceptable carrier.

In another embodiment, the invention is directed to a packaged pharmaceutical composition comprising a container holding a therapeutically effective amount of a compound of the invention; that is, compounds of formula I or compounds otherwise described herein; and instructions for using the compound to treat a sphingosine 1-phosphate associated disorder in a subject.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions can contain information pertaining to the compound's ability to perform its intended function, e.g., treating, preventing, or reducing a sphingosine 1-phosphate associated disorder in a subject.

Another embodiment of the invention relates to a packaged pharmaceutical composition comprising a container holding a therapeutically effective amount of a compound of the invention; that is, a compound of formula I or compounds otherwise described herein, and instructions for using the compound to selectively treat a sphingosine 1-phosphate associated disorder in a subject.

Such pharmaceutically acceptable formulations typically include one or more compounds of the invention as well as one or more pharmaceutically acceptable carriers and/or excipients. As used herein, "pharmaceutically acceptable carrier" includes any and all solvents, dispersion media, coatings, antibacterial and antifungal agents, isotonic and absorption delaying agents, and the like that are physiologically compatible. The use of such media and agents for pharmaceutically active substances is well known in the art. Except insofar as any conventional media or agent is incompatible with the compounds of the invention, use thereof in the pharmaceutical compositions is contemplated.

Supplementary pharmaceutically active compounds known to treat transplant or autoimmune disease, i.e., immunomodulatory agents and anti-inflammatory agents, as described above, can also be incorporated into the compositions of the invention. Suitable pharmaceutically active compounds that may be used can be found in Harrison's Principles of Internal Medicine.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injection include sterile aqueous solutions (where water soluble) or dispersions, or sterile powders for the extemporaneous preparation of sterile injectable solutions or dispersions. For intravenous administration, suitable carriers include physiological saline, bacteriostatic water, Cremophor EI™ (BASF, Parsippany, N.J.) or phosphate buffered saline (PBS). In all cases, the pharmaceutical composition must be sterile and should be fluid to the extent that easy syringability exists. It must also be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the compound of the invention in the required amount in an appropriate solvent with one or a combination of the ingredients enumerated above, as needed, followed by filtered sterilization. Generally, dispersions are prepared by incorporating the compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the compound plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the compound of the invention can be incorporated with excipients and used in the form of tablets, troches, or capsules. Oral compositions can also include an enteric coating. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds of the invention are delivered in the form of an aerosol spray from a pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compounds of the invention are formulated into ointments, salves, gels, or creams as generally known in the art.

The present pharmaceutical compositions can also be prepared in the form of suppositories (e.g., with conventional suppository bases such as cocoa butter and other glycerides) or retention enemas for rectal delivery.

In one embodiment, the compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811, U.S. Pat. No. 5,455,044 and U.S. Pat. No. 5,576,018, and U.S. Pat. No. 4,883,666, the contents of all of which are incorporated herein by reference.

The compounds of the invention can also be incorporated into pharmaceutical compositions which allow for the sustained delivery of the compounds to a subject for a period of at least several weeks to a month or more. Such formulations are described in published PCT application no. WO 02/74247, incorporated herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of a compound of the invention calculated to produce the desired therapeutic effect in association with the required pharmaceutical carrier. The specification for the unit dosage forms of the invention are dictated by and directly dependent on the unique characteristics of the compound and the particular therapeutic effect to be achieved, and the limitations inherent in the art of compounding such compounds for the treatment of individuals.

This invention is further illustrated by the following examples, which should not be construed as limiting. The contents of all references, patents, patent applications cited throughout this application are incorporated herein by reference. It should be understood that the use of any of the compounds described herein are within the scope of the present invention and are intended to be encompassed by the present invention and are expressly incorporated herein for all purposes.

EXAMPLES

General Approach to the Synthesis of 2,5-Disubstituted Thiazoles

The synthesis of 2,5-substituted thiazoles is described in Scheme 1. Reaction of alcohol $R^1$—OH wherein $R^1$ alkyl, aralkyl, heteroaryl, heterocyclo, or cycloalkyl with substituted 4-fluoroacetophenone 1 afforded the ether-acetophenone intermediate 2. Ether-acetophenone intermediate 2 was then converted to the corresponding bromo-acetophenone using $Bu_4NBr_3$, which, upon reaction with $NaN_3$, provided the azido-acetophenone intermediate. Hydrogenation of the azido-acetophenone intermediate afforded amine 3, followed by coupling with orthogonally protected amino acid 4 or amino diol-carboxylic acid 5 gave amide 6. As a note, compound 4 was synthesized from (S)-2-(tert-butoxycarbonylamino)-3-hydroxy-2-methylpropanoic acid in three steps in overall 52-64% yield. A synthesis of (R)-3-(tert-butoxycarbonyl)-2,2,4-trimethyloxazolidine-4-carboxylic acid is described in Clemens, J. J.; Davis, M. D.; Lynch, K. R.; Macdonald, T. L. *Bioorg. Med. Chem. Lett.* 2005, 15, 3568-3572. Compound 5 was synthesized from 2-amino-2-(hydroxymethyl)propane-1,3-diol in five steps in overall 30% yield, also as described in Clemens, J. J.; Davis, M. D.; Lynch, K. R.; Macdonald, T. L. *Bioorg. Med. Chem. Lett.* 2005, 15, 3568-3572. Under conditions using Lawesson's reagent, amide 6 was converted to thiazole 7 in good yield. Removal of the protecting groups afforded the final alcohol 8, which upon reaction with diethyl chlorophosphate and subsequent deprotection with TMSBr gave the phosphate 9.

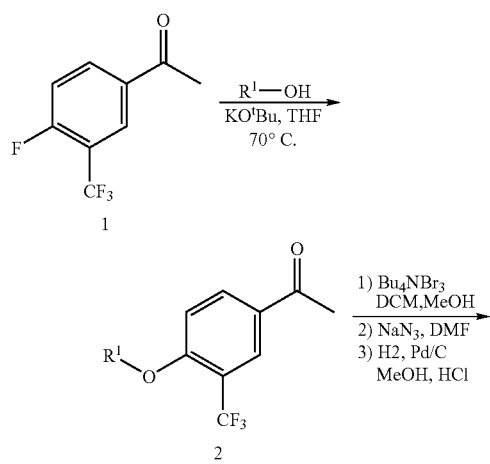

Scheme 1

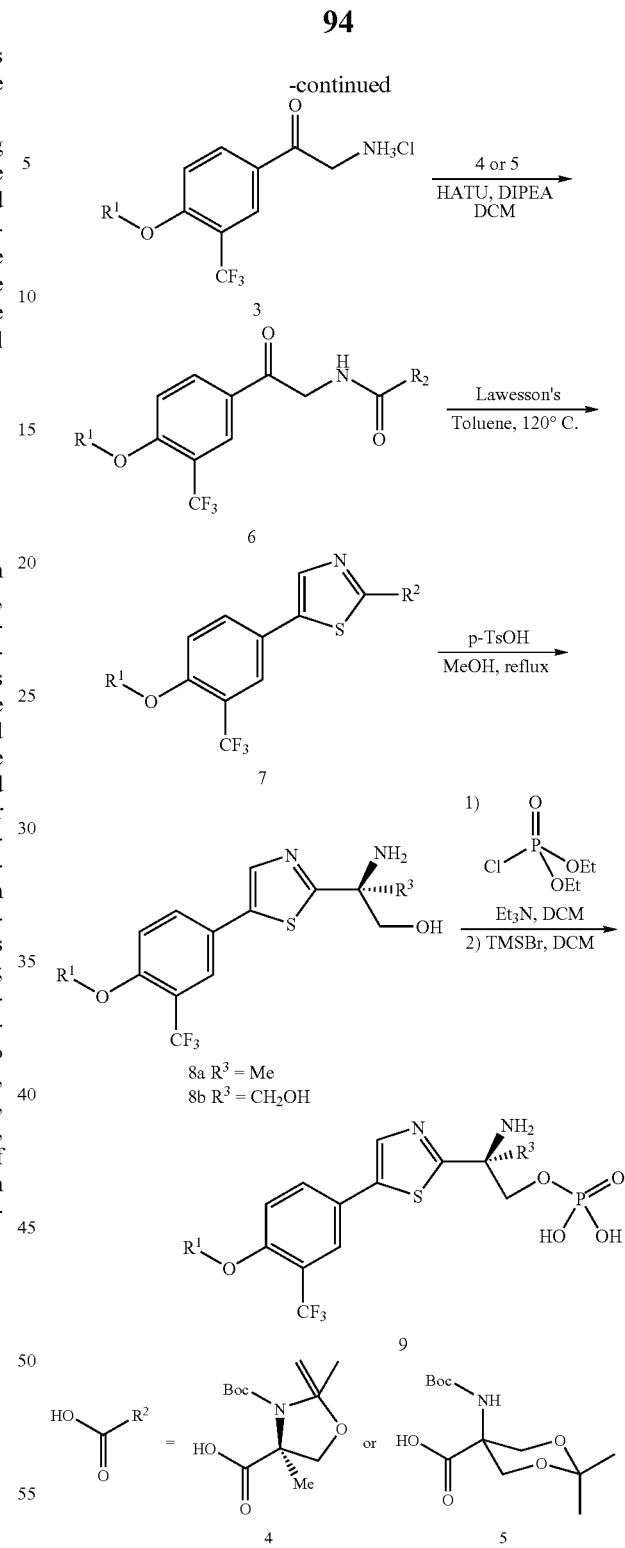

General Protocol for Synthesis of Substituted Acetophenones (Williamson Ether Synthesis) (2)

To a solution of the desired alcohol (1.0 equivalent) in dry THF under nitrogen atmosphere was added KO$^t$Bu (either 1.0 M solution in THF or solid, 1.1 equivalent). The reaction mixture was heated at 60-70° C. for 10 minutes, then substituted 4-fluoroacetophenone 1 (1.0 equivalent) was added. The reaction was then stirred for 1 to 3 hours before cooling to room temperature (RT). The solvent removed in vacuo. The product was purified by silica gel column chromatography using the Combi-Flash system (Hex:EtOAc).

1-(4-(Octyloxy)-3-(trifluoromethyl)phenyl)ethanone (2)

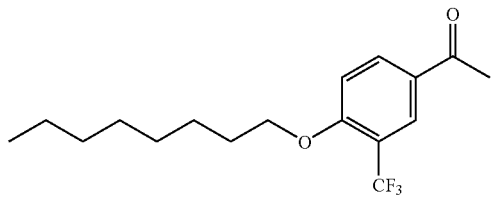

The product was purified by silica gel column chromatography using the Combi-Flash system (Hex:EtOAc) as white solid in 60% (1.20 g). TLC (1:5 EtOAc:Hex), $R_f$=0.4; $^1$H NMR (400 MHz, CDCl$_3$) δ 8.18 (d, 1H, J=2.0 Hz), 8.10 (dd, 1H, J=8.8 Hz, J=2.3 Hz), 7.02 (d, 1H, J=8.8 Hz), 4.12 (t, 2H, J=6.4 Hz), 2.58 (m, 3H), 1.80-1.89 (m, 2H), 1.42-1.54 (m, 2H), 1.22-1.40 (m, 8H), 0.89 (t, 3H, J=6.7 Hz).

2-Amino-1-(4-(octyloxy)-3-(trifluoromethyl)phenyl) ethanone hydrochloride (3)

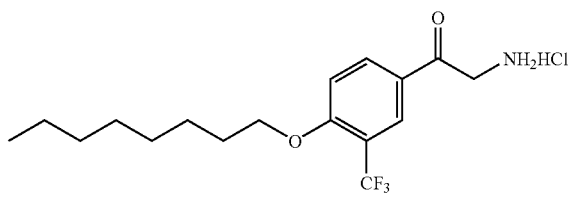

To a solution of the substituted acetophenone 2 (390 mg, 1.0 equivalent) in dry CH$_2$Cl$_2$ (9 mL) under nitrogen atmosphere was added Bu$_4$NBr$_3$ (0.60 g, 1.0 equiv). To the solution was added anhydrous MeOH (1.0 mL). The reaction mixture was stirred at room temperature overnight. The solvent was removed in vacuo, and the bromo-acetophenone product was used as is in the next step. TLC (4:1, Hex/EtOAc), $R_f$=0.6.

To the desired bromo-acetophenone (from last step, 1.0 equivalents), in DMF (10 mL) was added NaN$_3$ (0.24 g, 3.0 equiv). The resulting mixture was then stirred in DMF for 1 hour. The reaction mixture was diluted with EtOAc (50 mL) and washed with H$_2$O (2×50). The solvent removed in vacuo and the product was purified by silica gel column chromatography using the Combi-Flash system (Hex:EtOAc) to give the azido-acetophenone product as a white solid in 99% (0.44 g) yield. TLC (4:1, Hex/EtOAc), $R_f$=0.4.

To a solution of the azido-acetophenone (0.44 g, 1.0 equivalent) in MeOH (10 mL) was added concentrated HCl (1.5 mL), and 10% Pd/C (44 mg). The reaction mixture was stirred under an atmosphere of H$_2$ (g) for 2 hours. The reaction mixture was then filtered through a thin layer of Celite and the solvent was removed in vacuo. The amino-acetophenone 3 was obtained a white solid in quantitative yield (0.46 mg) with 90% purity. TLC (1:5 EtOAc:Hex), $R_f$=0.4; $^1$H NMR (400 MHz, CDCl$_3$) δ 8.18 (d, 1H, J=2.0 Hz), 8.10 (dd, 1H, J=8.8 Hz, J=2.3 Hz), 7.02 (d, 1H, J=8.8 Hz), 4.52 (s, 2H), 4.12 (t, 2H, J=6.4 Hz), 1.80-1.89 (m, 2H), 1.42-1.54 (m, 2H), 1.22-1.40 (m, 8H), 0.89 (t, 3H, J=6.7 Hz).

(R)-3-(tert-Butoxycarbonyl)-2,2,4-trimethyloxazolidine-4-carboxylic acid (4)

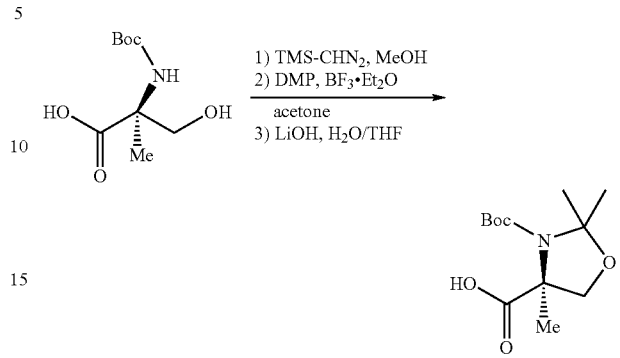

To a solution of the (S)-2-(tert-butoxycarbonylamino)-3-hydroxy-2-methylpropanoic acid (5.0 g, 1.0 equivalent) in CH$_2$Cl$_2$/MeOH (4:1, 50 mL) at 0° C. was added a solution of TMS-CHN$_2$ (2.0 M in diethyl ether or hexanes, 12.5 mL, 1.1 equivalents) drop-wise until the colourless solution turned a light yellow color. The reaction mixture was stirred for 20 minutes then a few drops of acetic acid were added to quench the last unreacted TMS-CHN$_2$ (the solution turns colorless from light yellow). The solvent was removed in vacuo. TLC (2:1, Hex/EtOAc), $R_f$=0.4.

The residue was dissolved in acetone (30 mL). To the resulting solution was then added 2,2-dimethoxypropane (DMP) (15 mL). To the mixture was added BF$_3$.OEt$_2$ (2 mL) drop-wise and the solution was stirred at RT for 4-18 hours. The solvent was removed in vacuo and the product was purified by silica gel column chromatography using the Combi-Flash system (Hex:EtOAc). TLC (3:1, Hex/EtOAc), $R_f$=0.6; $^1$H NMR (400 MHz, CDCl$_3$) δ 4.06-4.12 (m, 1H), 3.73-3.83 (m, 4H), 1.55-1.64 (m, 9H), 1.48 (br s, 3H), 1.41 (br s, 6H).

The purified residue was dissolved in THF (40 mL) and to the solution was added LiOH (1.15 g, 1.20 equiv) in H$_2$O (20 mL). The solution was heated at reflux for 6-18 hours, then concentrated in vacuo to remove most of the THF. The solution was diluted with H$_2$O (150 mL) and washed with Et$_2$O (2×150 mL). The aqueous layer was cooled to 0° C. then acidified to a pH of approximately 3 using concentrated HCl, then extracted with EtOAc (2×200 mL). The EtOAc layers were combined, dried (MgSO$_4$), filtered, and the solvent was removed in vacuo to afford carboxylate 4 as a white solid in 52-64% yield (3.78 g) yield. TLC (1:1 EtOAc:Hex), $R_f$=0.2; $^1$H NMR (400 MHz, CDCl$_3$) 6 (rotamers) 4.47 (br d, 0.5H, J=8.8 Hz), 4.17 (br d, 0.5H, J=8.8 Hz), 3.85 (br d, 0.5H, J=8.8 Hz), 3.78 (br d, 0.5H, J=8.8 Hz), 1.38-1.67 (m, 18H).

5-(tert-butoxycarbonylamino)-2,2-dimethyl-1,3-dioxane-5-carboxylic acid (5)

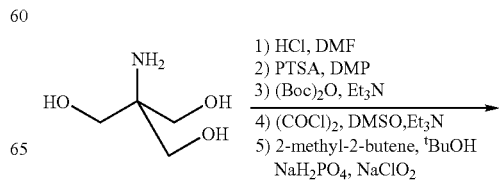

-continued

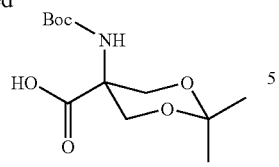

To a solution of the 2-amino-2-(hydroxymethyl)propane-1,3-diol (2.0 g, 1.0 equivalent) in DMF (20 mL) at RT was added 1M HCl (16.5 mL, 1.0 equiv) in diethyl ether. The resulting mixture was stirred for 20 minutes, then para-toluenesulfonic acid (PTSA) (157 mg, 0.05 equivalent) and 2,2-dimethoxypropane or (2.23 mL, 1.1 equivalents) were added. The reaction mixture was stirred for 24 hours, then Et$_3$N (3.0 equivalent, 6.90 mL) and (Boc)$_2$O (1.0 equiv, 3.60 g) were added and the mixture was stirred overnight. The reaction mixture was diluted with EtOAc (50 mL) and washed with H$_2$O (2×50 mL). The solvent removed in vacuo and the product was purified by silica gel column chromatography using the Combi-Flash system (Hex:EtOAc) as a white solid in 58% (2.49 g) yield. TLC (2:1, Hex/EtOAc), R$_f$=0.3; $^1$H NMR (400 MHz, CDCl$_3$) δ 5.33 (br s, 1H), 4.27 (br s, 1H), 3.79-3.84 (m, 4H), 3.72 (d, 2H, J=6.4 Hz), 1.46 (s, 12H), 1.44 (s, 3H).

To a solution of oxalyl chloride (2.0 M in CH$_2$Cl$_2$, 5.74 mL, 3.0 equivalents) in dry CH$_2$Cl$_2$ (10 mL) at −78° C. was added DMSO (1.36 ml, 5.0 equivalents). The resulting mixture was stirred for 15 minutes, then a solution of the desired alcohol (from last step, 1.0 g) in dry CH$_2$Cl$_2$ (10 mL) was added drop-wise. The mixture was stirred for 2 hours, then Et$_3$N (5.33 mL, 10 equivalents) was added. The reaction mixture was stirred for 10 minutes then the cooling bath was removed and the mixture was allowed to warm to RT. The reaction mixture was then diluted with EtOAc (50 mL) and washed with 10% NH$_4$Cl (2×50 mL). The organic layer was dried over MgSO$_4$, filtered, and the solvent was removed in vacuo to afford aldehyde intermediate as a white solid in >99% yield (1.00 g). For more detailed Swern oxidatrion conditions see: a) Blaskovich, M. A.; Evindar, G.; Rose, N. G. W.; Wilkinson, S.; Luo, Y.; Lajoie, G. A. J. Org. Chem. 1998, 63, 3631-3646. and b) Rose, N. G. W.; Blaskovich, M. A.; Evindar, G.; Wilkinson, S.; Luo, Y.; Fishlock, D.; Reid, C.; Lajoie, G. A. Organic Syntheses 2002, 79, 216-227. TLC (2:1, Hex/EtOAc), R$_f$=0.7; $^1$H NMR (400 MHz, CDCl$_3$) δ 9.63 (s, 1H), 5.55 (br s, 1H), 4.07 (d, 2H, J=12.0 Hz), 3.95 (d, 2H, J=12.0 Hz), 1.47 (s, 18H).

To a solution of the aldehyde (from last step, 1.0 g) in t-BuOH (20 mL) and 2-methyl-2-butene (10 mL) at room temperature was added a solution of NaH$_2$PO$_4$ (1.06 g, 2.0 equivalents), and NaClO$_2$ (1.40 g, 4.0 equivalents) in H$_2$O (10 mL). The reaction was stirred for 3 hours and then was diluted with H$_2$O (10 mL). The mixture was extracted with EtOAc (30 mL). The organic layer was dried over MgSO$_4$, filtered, and the solvent was removed in vacuo to afford carboxylate 5 as a white solid in 52% yield (550 mg). For more detailed procedure for oxidation of aldehyde to carboxylate see: Taylor, R. E.; Galvin, G. M.; Hilfiker, K. A.; Chen, Y. J. Org. Chem. 1998, 63, 9580-9583. TLC (1:1 EtOAc:Hex), R$_f$=0.2; $^1$H NMR (400 MHz, CDCl$_3$) δ 5.50 (br s, 1H), 4.18 (d, 2H, J=11.8 Hz), 4.10 (d, 2H, J=11.8 Hz), 1.47 (br s, 18H).

(R)-tert-Butyl 2,2,4-trimethyl-4-(2-(4-(octyloxy)-3-(trifluoromethyl)phenyl)-2-oxoethylcarbamoyl)oxazolidine-3-carboxylate (6)

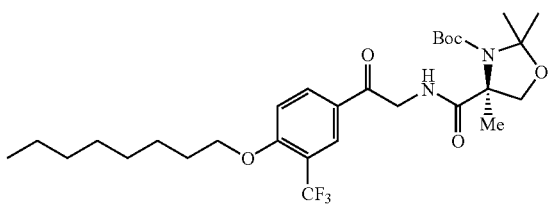

To a solution of protected oxazolidine-4-carboxylic acid 4 (176 mg, 1 equivalents), HATU (310 mg, 1.2 equivalents), and DIEA (1.2 mL, 10 equivalents) in CH2CL2/DMF (1:1, 10 mL) was added amino-acetophenone 3 (250 mg, 1.0 equivalents). The resultant mixture was stirred at room temperature overnight. The reaction mixture was diluted with EtOAc (50 mL) and washed with 10% NH$_4$Cl (2×50 mL) and saturated NaCl (1×50 mL). The solvent removed in vacuo and the product was obtained, silica gel column chromatography using the Combi-Flash system (Hex:EtOAc), as a white solid in 40% yield (185 mg). TLC (1:2 EtOAc:Hex), R$_f$=0.3; MS (ESI, M+Na)=572.99; $^1$H NMR (400 MHz, CDCl$_3$) δ 8.21 (s, 1H), 8.11 (d, 1H, J=8.4 Hz), 7.05 (d, 1H, J=8.4 Hz), 4.62-4.79 (m, 2H), 4.13 (t, 2H, J=6.4 Hz), 3.28 (br s, 1H), 1.22-1.90 (m, 30H), 0.89 (t, 3H, J=6.4 Hz).

(R)-tert-Butyl 2,2,4-trimethyl-4-(5-(4-(octyloxy)-3-(trifluoromethyl)phenyl)thiazol-2-yl)oxazolidine-3-carboxylate (7)

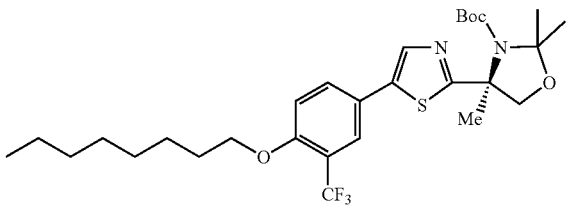

A suspension of protected oxazolidine-amide 6 (180 mg, 1.0 equivalent) and Lawesson's Reagent (390 mg, 3.0 equivalents) in toluene (5 mL) was sealed and heated at 100° C. for 1 hour. After cooling to room temperature, the reaction mixture was purified by silica gel column chromatography using the Combi-Flash system (Hex:EtOAc) as a thick colourless oil in 67% yield (120 mg). TLC (1:2 EtOAc:Hex), R$_f$=0.8; MS (ESI, M+H$^+$)=571.11; $^1$H NMR (400 MHz, CDCl$_3$) δ 7.73 (br s, 1H), 7.70 (s, 1H), 7.61 (d, 1H, J=6.8 Hz), 7.01 (d, 1H, J=6.8 Hz), 3.96-4.28 (m, 4H), 1.21-1.99 (m, 30H), 0.89 (t, 3H, J=7.6 Hz).

(S)-2-Amino-2-(5-(4-(octyloxy)-3-(trifluoromethyl) phenyl)thiazol-2-yl)propan-1-ol (8a)

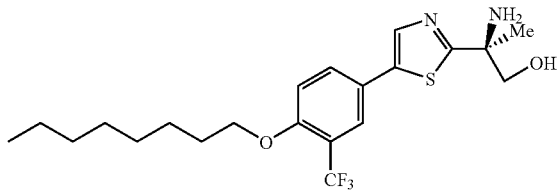

A solution of thiazole 7 (120 mg) and para toluenesulfonic acid (PTSA, 400 mg, 10 equivalents) in MeOH (6 mL) was refluxed for 6 hours. The solvent was removed in vacuo and the product was purified by reverse phase preparative HPLC, then lyophilized to dryness to obtain the trifluoroacetate salt of the product as a white solid in 79% yield (90.5 mg). MS (ESI, M+H$^+$)=431.01; $^1$H NMR (400 MHz, DMSO-d$_6$) δ 8.27 (s, 1H), 7.88 (dd, 1H, J=8.8 Hz, J=2.4 Hz), 7.85 (d, 1H, J=2.4 Hz), 7.34 (d, 1H, J=8.4 Hz), 5.77 (br s, 1H), 4.14 (t, 2H, J=6.4 Hz), 3.76 (dd, 1H, J=11.2, Hz, J=1.2 Hz), 3.66 (dd, 1H, J=11.2 Hz, J=1.2 Hz), 1.73 (q, 2H, J=6.8 Hz), 1.58 (s, 3H), 1.36-1.48 (m, 2H), 1.20-1.36 (m, 8H), 0.85 (t, 3H, J=6.4 Hz).

2-Amino-2-(5-(4-(octyloxy)-3-(trifluoromethyl)phenyl)thiazol-2-yl)propane-1,3-diol (8b)

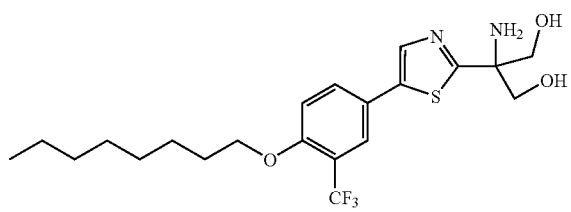

The diol 8b was prepared from carboxylate 5 and aminoacetophenone 3 analogously to thiazole 8a in 35% yield over three steps. MS (ESI, M+H$^+$)=447.01; $^1$H NMR (400 MHz, DMSO-d$_6$) δ 8.27 (s, 1H), 7.87 (dd, 1H, J=8.8 Hz, J=2.4 Hz), 7.84 (d, 1H, J=2.4 Hz), 7.32 (d, 1H, J=8.4 Hz), 5.71 (br s, 1H), 4.13 (t, 2H, J=6.4 Hz), 3.71-3.85 (m, 4H), 1.72 (q, 2H, J=6.4 Hz), 1.36-1.46 (m, 2H), 1.19-1.35 (m, 8H), 0.84 (t, 3H, J=6.4 Hz).

General Approach to the Synthesis of 2,5-Disubstituted-1,3,4-Thiadizoles

The synthesis of 2,5-substituted thiadizoles is described in Scheme 2. Reaction of alcohol ROH with substituted 4-fluorobezoic acid 10 afforded ether-benzoate intermediate 11. The ether-benzoate intermediate 11 was then coupled with hydrazine to afford benzohydrazide 13. Reaction of benzohydrazide 13 with orthogonally protected amino Note, this phrase used here and elsewhere in the application is new to me acid 4 under using N,N,N',N'-Tetramethyl-O-(7-azabenzotriazol-1-yl)uronium hexafluorophosphate (HATU) followed by cyclization with Lawesson's reagent provided thiadizole 14 in good yield. Removal of the protecting groups afforded final alcohol 15. Alcohol 15 was then converted to corresponding phosphate as reported in scheme 1.

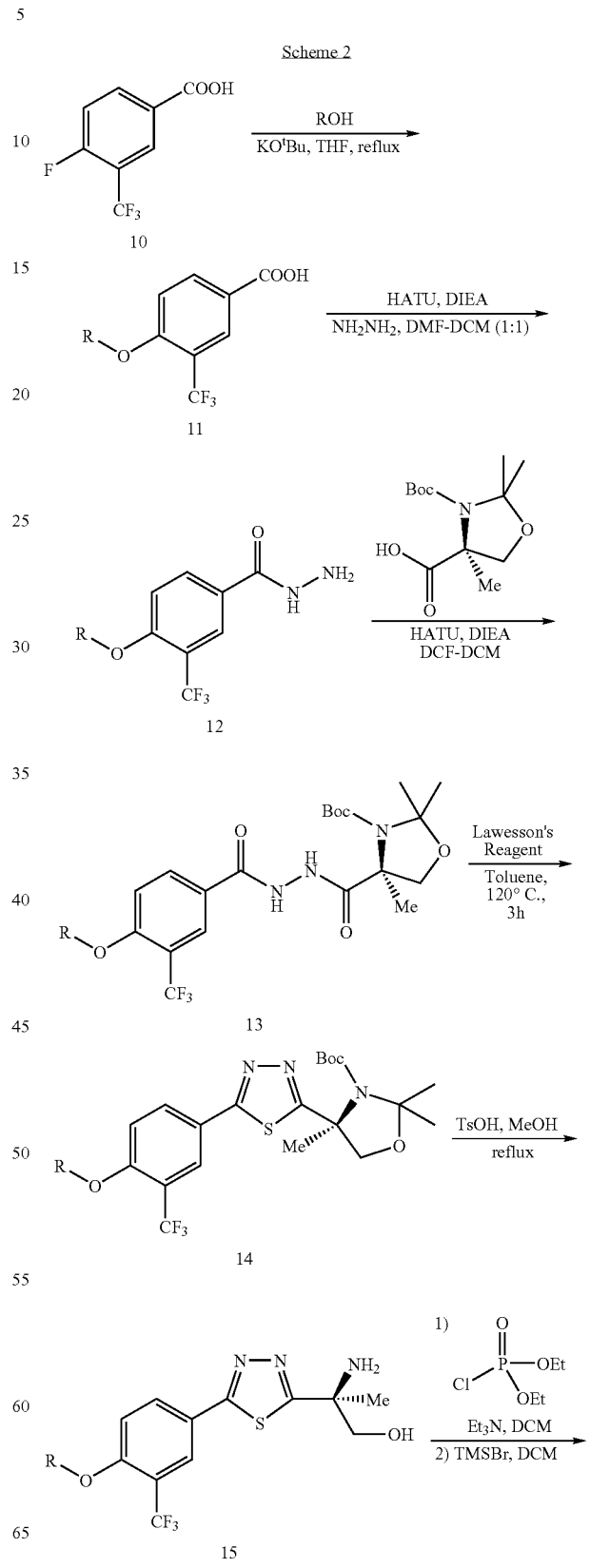

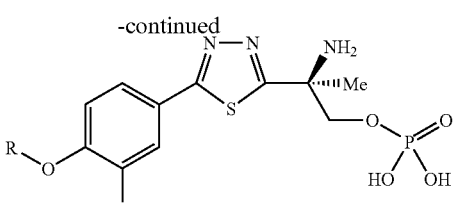

4-(Octyloxy)-3-(trifluoromethyl)benzoic acid (11a)

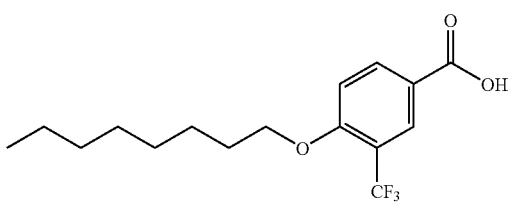

To a solution of 1-octanol (315 µL, 2.0 mmol) in anhydrous THF (5 mL) was added potassium t-butoxide (5 mL, 1M solution in THF). The mixture was heated at 70° C. for 15 min then cooled down to room temperature. 4-Fluoro-3-trifluoromethylbenzoid acid (10) (417 mg, 2.0 mmol) in THF (5 mL) was added and the resultant was heated at 75° C. overnight. After cooling down to room temperature, the reaction mixture was diluted with ethyl acetate and washed with water. The water layer was acidified to a pH of approximately 3 with HCl (2M) and extracted with ethyl acetate. The combined organic layers were washed with brine, dried over $Na_2SO_4$ and concentrated in vacuo to afford the title compound (632 mg, HPLC purity >95%), which was used for next reaction without further purification. HPLC retention time on a C8(2) column (30×3.00 mm, 3µ) was 3.28 min with gradient 50-98% acetonitrile-$H_2O$ (0.1% trifluoroacetic acid (TFA)) in 3.5 min as mobile phase.

4-(5-Phenylpentyloxy)-3-(trifluoromethyl)benzoic acid (11b)

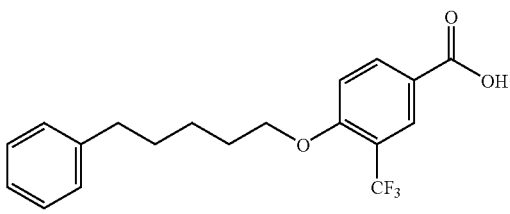

The title compound was prepared analogously to 4-(octyloxy)-3-(trifluoromethyl)benzoic acid (11a) in >95% yield. HPLC retention time on a C8(2) column (30×3.00 mm, 3µ) is 3.31 min with gradient 20-98% acetonitrile-$H_2O$ (0.1% TFA) in 3.5 min as mobile phase.

4-(4-Phenylbutoxy)-3-(trifluoromethyl)benzoic acid (11c)

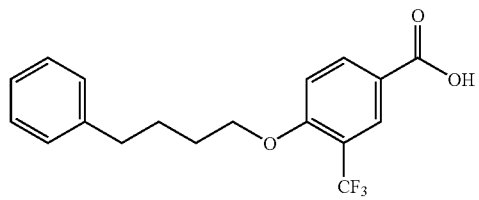

The title compound was prepared analogously to 4-(octyloxy)-3-(trifluoromethyl)benzoic acid (11a) in >95% yield. HPLC retention time on a C8(2) column (30×3.00 mm, 3µ) is 3.14 min with gradient 20-98% acetonitrile-$H_2O$ (0.1% TFA) in 3.5 min as mobile phase.

4-(Octyloxy)-3-(trifluoromethyl)benzohydrazide (12a)

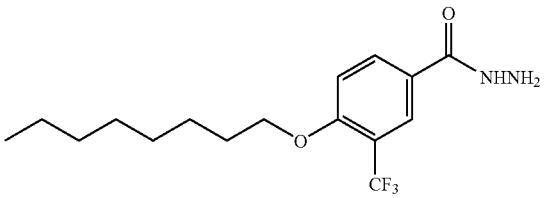

4-(Octyloxy)-3-(trifluoromethyl)benzoic acid (11a) (632 mg, crude, approximately 1.89 mmol) was stirred with HATU (905 mg) and DIEA (1.7 mL) in $CH_2Cl_2$-DMF (10 mL, 4:1) for 10 min followed by addition of hydrazine (297 µL) dropwise. The reaction mixture was continuously stirred for another hour, then was diluted with ethyl acetate (30 mL) and washed with water (10 mL) and brine (3×15 mL). The organic layer was dried over $Na_2SO_4$ and concentrated in vacuo to afford the title compound (661 mg, HPLC purity >90%), which was used for next reaction without further purification. MS (ESI): 333.08 ($MH^+$); HPLC retention time on a C8(2) column (30×3.00 mm, 3µ) is 1.61 min with gradient 50-98% acetonitrile-$H_2O$ (0.1% TFA) in 3.5 min as mobile phase.

4-(5-Phenylpentyloxy)-3-(trifluoromethyl)benzohydrazide (12b)

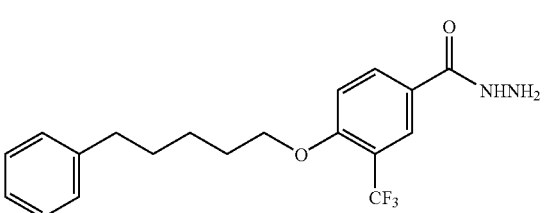

The title compound was prepared analogously to 4-(octyloxy)-3-(trifluoromethyl)-benzo-hydrazide (12a) in >95% yield. MS (ESI): 367.14 (MH⁺); HPLC retention time on a C8(2) column (30×3.00 mm, 3µ) is 2.44 min with gradient 20-98% acetonitrile-H$_2$O (0.1% TFA) in 3.5 min as mobile phase.

4-(4-Phenylbutoxy)-3-(trifluoromethyl)benzohydrazide (12c)

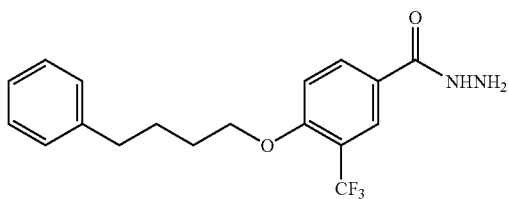

The title compound was prepared analogously to 4-(octyloxy)-3-(trifluoromethyl)-benzo-hydrazide (12a) in >95% yield. MS (ESI): 353.11 (MH⁺); HPLC retention time on a C8(2) column (30×3.00 mm, 3µ) is 2.30 min with gradient 20-98% acetonitrile-H$_2$O (0.1% TFA) in 3.5 min as mobile phase.

(S)-tert-Butyl 2,2,4-trimethyl-4-(2-(4-(octyloxy)-3-(trifluoromethyl)benzoyl)-hydrazinecarbonyl)oxazolidine-3-carboxylate (13a)

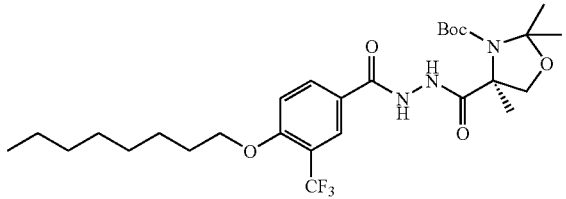

(R)-3-(tert-Butoxycarbonyl)-2,2,4-trimethyloxazolidine-4-carboxylic acid (4) (210 mg, 0.81 mmol) was stirred with HATU (372 mg, 0.98 mmol) and diisopropylethyl amine (DIEA) (0.705 mL, 4.1 mmol) in CH$_2$Cl$_2$-DMF (2:1, 6 mL) for 10 min followed by addition of 4-(octyloxy)-3-(trifluoromethyl)benzohydrazide (12a) (270 mg, 0.81 mmol) in CH$_2$Cl$_2$ (2 mL). The reaction was stirred at room temperature for 1 hour and then was concentrated under vacuum. The residue was diluted with ethyl acetate (20 mL) and washed with water (5 mL), brine (2×10 mL) and dried over Na$_2$SO$_4$. The organic layer was concentrated in vacuo and chromatographed on a silica gel column (ethyl acetate-hexane, 0-33%, as eluent) to afford the title compound (428 mg, 82% yield). MS (ESI): 573.84 (MH⁺); ¹H NMR (400 MHz, CDCl$_3$) δ 9.43 (br, 2H), 8.06 (d, 1H, J=2.0 Hz), 7.94 (dd, 1H, J=8.8 Hz, J=2.0 Hz), 6.96 (d, 1H, J=8.8 Hz), 4.52 (br, 1H), 4.07 (t, 2H, J=6.4 Hz), 3.76 (br, 1H), 1.82 (m, 2H), 1.67 (s, 6H), 1.57 (s, 3H), 1.51 (s, 9H), 1.51-1.43 (m, 4H), 1.38-1.24 (m, 6H), 0.88 (t, 3H, J=7.2 Hz).

(S)-tert-Butyl 2,2,4-trimethyl-4-(2-(4-(5-phenylpentyloxy)-3-(trifluoromethyl)-benzoyl)hydrazinecarbonyl)oxazolidine-3-carboxylate (13b)

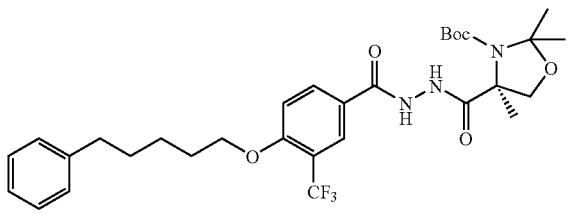

The title compound was prepared analogously to (S)-tert-butyl 2,2,4-trimethyl-4-(2-(4-(octyloxy)-3-(trifluoromethyl)benzoyl)-hydrazinecarbonyl)oxazolidine-3-carboxylate (13a) in 95% yield. MS (ESI): 607.81 (MH⁺); ¹H NMR (400 MHz, CDCl$_3$) δ 9.94 (br, 1H), 9.04 (br, 1H), 8.05 (d, 1H, J=2.4 Hz), 7.93 (dd, 1H, J=8.8 Hz, J=2.4 Hz), 7.29-7.25 (m, 2H), 7.18-7.15 (m, 3H), 6.97 (d, 1H, J=8.8 Hz), 4.55 (br, 1H), 4.07 (t, 2H, J=6.4 Hz), 3.77 (br, 1H), 2.64 (d, 2H, J=7.6 Hz), 1.86 (m, 2H), 1.73-1.65 (m, 9H), 1.58-1.52 (m, 13H).

(S)-tert-Butyl 2,2,4-trimethyl-4-(2-(4-(4-phenylbutoxy)-3-(trifluoromethyl)benzoyl)-hydrazinecarbonyl)oxazolidine-3-carboxylate (13c)

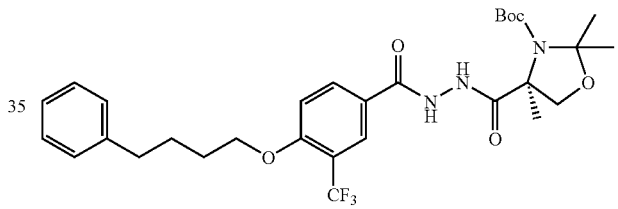

The title compound was prepared analogously to (S)-tert-butyl 2,2,4-trimethyl-4-(2-(4-(octyloxy)-3-(trifluoromethyl)benzoyl)-hydrazinecarbonyl)oxazolidine-3-carboxylate (13a) in 97% yield. MS (ESI): 593.87 (MH⁺); ¹H NMR (400 MHz, CDCl$_3$) δ 9.94 (br, 1H), 8.79 (br s, 1H), 8.05 (d, 1H, J=2.4 Hz), 7.93 (dd, 1H, J=8.8 Hz, J=2.4 Hz), 7.30-7.25 (m, 2H), 7.20-7.16 (m, 3H), 6.98 (d, 1H, J=8.8 Hz), 4.55 (br, 1H), 4.10 (t, 2H, J=6.4 Hz), 3.78 (br s, 1H), 2.69 (d, 2H, J=7.6 Hz), 1.86 (m, 4H), 1.68 (s, 6H), 1.58 (s, 3H), 1.52 (s, 9H).

(R)-tert-Butyl 2,2,4-trimethyl-4-(5-(4-(octyloxy)-3-(trifluoromethyl)phenyl)-1,3,4-thiadiazol-2-yl)oxazolidine-3-carboxylate (14a)

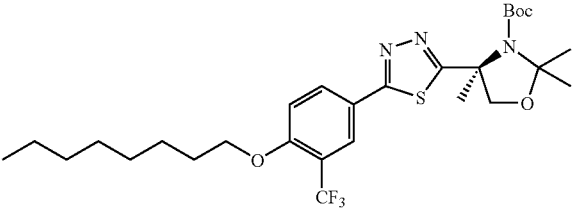

A solution of (S)-tert-butyl 2,2,4-trimethyl-4-(2-(4-(octyloxy)-3-(trifluoromethyl)-benzoyl)hydrazinecarbonyl)oxazolidine-3-carboxylate (13a) (228 mg, 0.39 mmol) in toluene (5 mL) was treated with Lawesson's reagent (473 mg, 1.17 mmol) at 85° C. for 2 hours. The reaction was cooled down to room temperature and the supernatant was chromatographed on a silica gel column eluted with ethyl acetate-hexane (0-30%, v/v) to afford the title compound (156 mg, 70% yield). MS (ESI): 572.17 (MH$^+$), $^1$H NMR (400 MHz, CDCl$_3$) δ 8.10 (d, 1H, J=8.8 Hz), 8.08 (d, 1H, J=6.8 Hz), 7.06 (d, 1H, J=8.0 Hz), 4.41 (d, 1H, J=8.0 Hz), 4.18 (d, 1H, J=9.6 Hz), 4.13-4.07 (m, 3H), 2.00 (s, 3H), 1.85 (m, 2H), 1.78 (s, 3H), 1.68 (m, 4H), 1.51 (s, 3H), 1.47 (m, 2H), 1.39-1.28 (m, 13H), 0.89 (t, 3H, J=7.2 Hz).

(R)-tert-Butyl 2,2,4-trimethyl-4-(5-(4-(5-phenylpentyloxy)-3-(trifluoromethyl)-phenyl)-1,3,4-thiadiazol-2-yl)oxazolidine-3-carboxylate (14b)

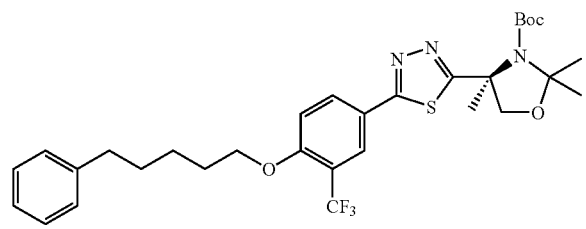

The title compound was prepared analogously to (R)-tert-butyl 2,2,4-trimethyl-4-(5-(4-(octyloxy)-3-(trifluoromethyl) phenyl)-1,3,4-thiadiazol-2-yl)oxazolidine-3-carboxylate (14a) in 80% yield. MS (ESI): 606.19 (MH$^+$), HPLC retention time on a C8(2) column (30×3.00 mm, 3µ) is 3.78 min with gradient 50-98% acetonitrile-H$_2$O (0.1% TFA) in 3.5 min as mobile phase.

(R)-tert-Butyl 2,2,4-trimethyl-4-(5-(4-(4-phenylbutoxy)-3-(trifluoromethyl)phenyl)-1,3,4-thiadiazol-2-yl)oxazolidine-3-carboxylate (14c)

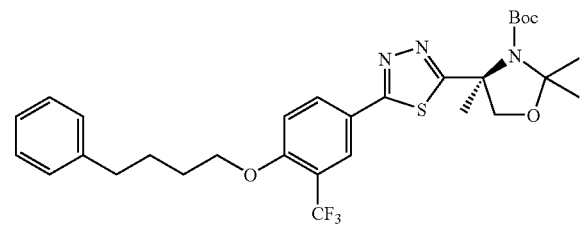

The title compound was prepared analogously to (R)-tert-butyl 2,2,4-trimethyl-4-(5-(4-(octyloxy)-3-(trifluoromethyl) phenyl)-1,3,4-thiadiazol-2-yl)oxazolidine-3-carboxylate (14a) in 75% yield. MS (ESI): 592.14 (MH$^+$), HPLC retention time on a C8(2) column (30×3.00 mm, 3µ) is 3.55 min with gradient 50-98% acetonitrile-H$_2$O (0.1% TFA) in 3.5 min as mobile phase (S)-2-Amino-2-(5-(4-(octyloxy)-3-(trifluoromethyl) phenyl)-1,3,4-thiadiazol-2-yl)propan-1-ol (15a)

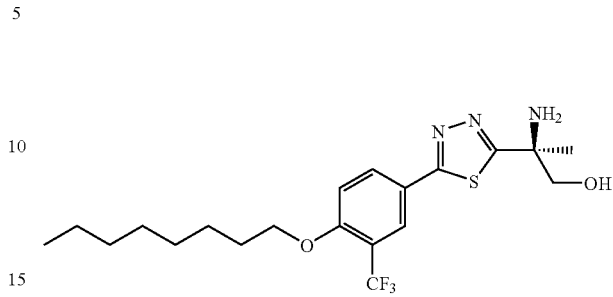

A solution of (S)-tert-butyl 2,2,4-trimethyl-4-(2-(4-(octyloxy)-3-(trifluoromethyl)-benzoyl)hydrazinecarbonyl)oxazolidine-3-carboxylate (14a) (156 mg, 0.27 mmol) in methanol (5 mL) was treated with p-toluenesulfonic acid monohydrate (259 mg, 1.36 mmol) at 70° C. for 2 hours. The reaction mixture was then cooled to room temperature and purified by prep HPLC on a C8(2) column ((Luna, 5µ, 100× 21.10 mm) with acetonitrile-H$_2$O (0.1% TFA) as mobile phase and gradient 30-98% in 20 min. The title compound was obtained as the bis-TFA salt (36 mg, 20%). MS (ESI): 432.00 (MH$^+$); $^1$H NMR (400 MHz, DMSO-d$_6$) δ 8.21 (dd, 1H, J=2.0 Hz, J=8.8 Hz), 8.15 (d, 1H, J=2.0 Hz), 8.09 (br s, 2H), 7.45 (d, 1H, J=8.8 Hz), 5.96 (t, 1H, J=4.8 Hz), 4.21 (t, 2H, J=6.4 Hz), 3.81 (dd, 1H, J=11.2 Hz, J=5.2 Hz), 3.73 (dd, 1H, J=11.2 Hz, J=5.2 Hz), 1.76 (m, 2H), 1.66 (s, 3H), 1.44 (m, 2H), 1.28 (m, 8H), 0.86 (t, 3H, J=6.8 Hz).

(S)-2-Amino-2-(5-(4-(5-phenylpentyloxy)-3-(trifluoromethyl)phenyl)-1,3,4-thiadiazol-2-yl)propan-1-ol (15b)

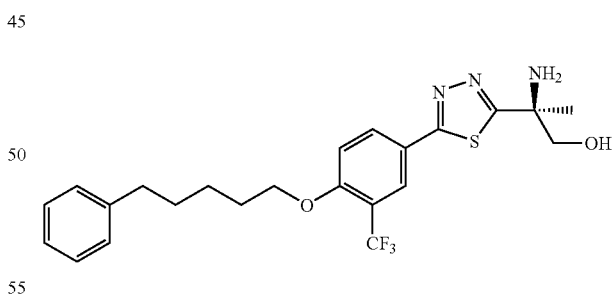

The title compound was prepared analogously to (S)-2-amino-2-(5-(4-(octyloxy)-3-(trifluoromethyl)phenyl)-1,3,4-thiadiazol-2-yl)propan-1-ol (15a) in 67% yield. MS (ESI): 466.05 (MH$^+$); $^1$H NMR (400 MHz, DMSO-d$_6$) δ 8.87 (br s, 2H), 8.22 (dd, 1H, J=8.8 Hz, J=2.0 Hz), 8.16 (d, 1H, J=2.0 Hz), 7.45 (d, 1H, J=8.8 Hz), 7.26 (t, 2H, J=7.6 Hz), 7.20-7.14 (m, 3H), 6.10 (br, 1H), 4.22 (t, 2H, J=6.4 Hz), 3.83 (d, 1H, J=11.2 Hz), 3.77 (d, 1H, J=11.2 Hz), 2.59 (t, 2H, J=7.2 Hz), 1.80 (m, 2H), 1.70 (s, 3H), 1.46 (m, 2H), 1.46 (m, 2H).

(S)-2-Amino-2-(5-(4-(4-phenylbutoxy)-3-(trifluoromethyl)phenyl)-1,3,4-thiadiazol-2-yl)propan-1-ol (15c)

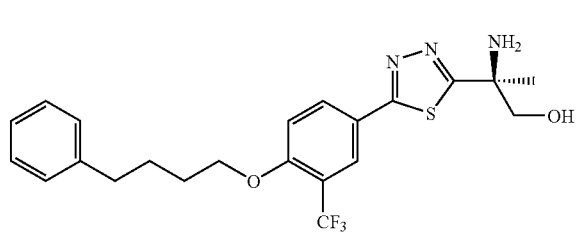

The title compound was prepared analogously to (S)-2-amino-2-(5-(4-(octyloxy)-3-(trifluoromethyl)phenyl)-1,3,4-thiadiazol-2-yl)propan-1-ol (15a) in 70% yield. MS (ESI): 452.06 (MH$^+$); $^1$H NMR (400 MHz, DMSO-d$_6$) δ 8.60 (br s, 2H), 8.23 (dd, 1H, J=8.8 Hz, J=2.4 Hz), 8.16 (d, 1H, J=2.4 Hz), 7.45 (d, 1H, J=8.8 Hz), 7.28 (t, 2H, J=7.2 Hz), 7.21-7.15 (m, 3H), 4.25, 4.22 (t, 2H, J=5.6 Hz), 3.82 (d, 1H, J=9.6 Hz), 3.75 (d, 1H, J=9.6 Hz), 2.65 (t, 2H, J=7.2 Hz), 1.80-172 (m, 4H), 1.68 (s, 3H).

General Method for Phosphate Synthesis

Synthetic strategy for synthesis of desired phosphates is illustrated in Scheme 1 above. To a solution of unprotected amino alcohol (1.0 equiv) in dry CH$_2$Cl$_2$ at room temperature was added excess diethyl chlorophosphate (10.0 equiv) and triethylamine (20.0 equivalents) and the reaction stirred for 12-18 hours. The reaction was monitored by LC-MS. The crude reaction mixture was then evaporated to dryness in vacuo. The obtained phospho-diester intermediate was reacted with excess bromotrimethylsilane (10.0-20.0 equiv) in dry CH$_2$Cl$_2$ at room temperature over a period of 6-10 hours to afford the final phosphate which was purified by reverse-phase preparative HPLC after evaporation of the solvent and excess reagent.

(S)-2-amino-2-(5-(4-(octyloxy)-3-(trifluoromethyl)phenyl)thiazol-2-yl)propyl dihydrogen phosphate (9a)

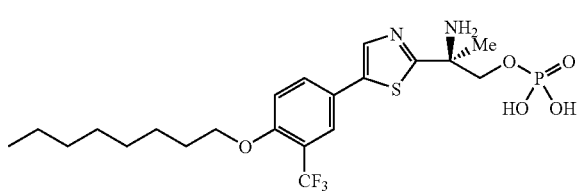

The product was obtained as a white solid in 28% (10 mg) yield from the alcohol precursor. MS (ESI, M+H$^+$)=511.1.

(S)-2-Amino-2-(5-(4-(octyloxy)-3-(trifluoromethyl)phenyl)-1,3,4-thiadiazol-2-yl)propyl dihydrogen phosphate (16a)

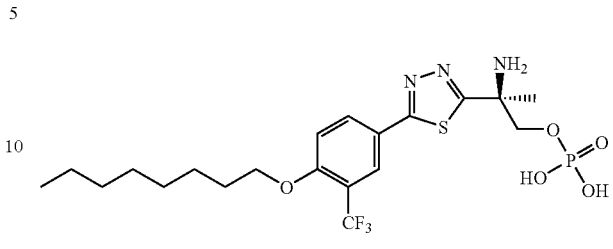

MS (ESI): 511.98 (MH$^+$), HPLC retention time on a C8(2) column (30×3.00 mm, 3μ) is 1.88 min with gradient 40-98% acetonitrile-H$_2$O (0.1% TFA) in 3.5 min as mobile phase.

(S)-2-Amino-2-(5-(4-(5-phenylpentyloxy)-3-(trifluoromethyl)phenyl)-1,3,4-thiadiazol-2-yl)propyl dihydrogen phosphate (16b)

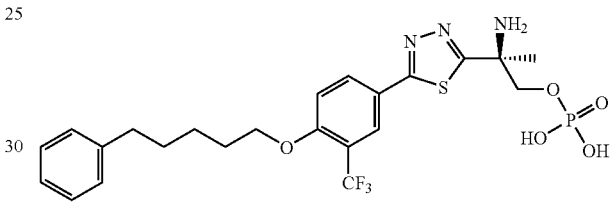

MS (ESI): 546.01 (MH$^+$), HPLC retention time on a C8(2) column (30×3.00 mm, 3μ) is 2.06 min with gradient 30-98% acetonitrile-H$_2$O (0.1% TFA) in 3.5 min as mobile phase.

(S)-2-Amino-2-(5-(4-(4-phenylbutoxy)-3-(trifluoromethyl)phenyl)-1,3,4-thiadiazol-2-yl)propyl dihydrogen phosphate (16c)

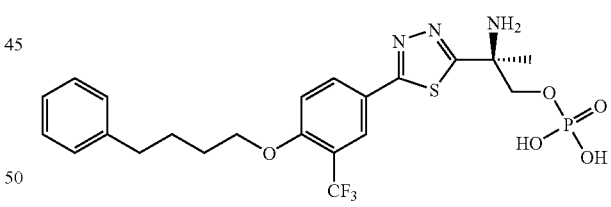

MS (EST): 532.01 (MH$^+$), HPLC retention time on a C8(2) column (30×3.00 mm, 3μ) is 1.96 min with gradient 30-98% acetonitrile-H$_2$O (0.1% TFA) in 3.5 min as mobile phase.

General Approach to Synthesis of Compounds of Formula III

The synthesis of compounds of formula III is described in Scheme 3. Synthesis of compounds 1a and 1b in strategy A and compound 3 in strategy B were described in schemes 1 and 2. Oxidation of the compounds 1a and 1b in strategy A followed by deprotection afforded compounds 2a and 2b. In strategy B, coupling of the free amine in compound 3 with the desired protected-amino acid gave compound 4 which upon cyclization under Lawesson's reagent conditions provided the desired azole 5. Removal of the protecting groups afforded the final carboxylate 6.

Scheme 3

Strategy A:

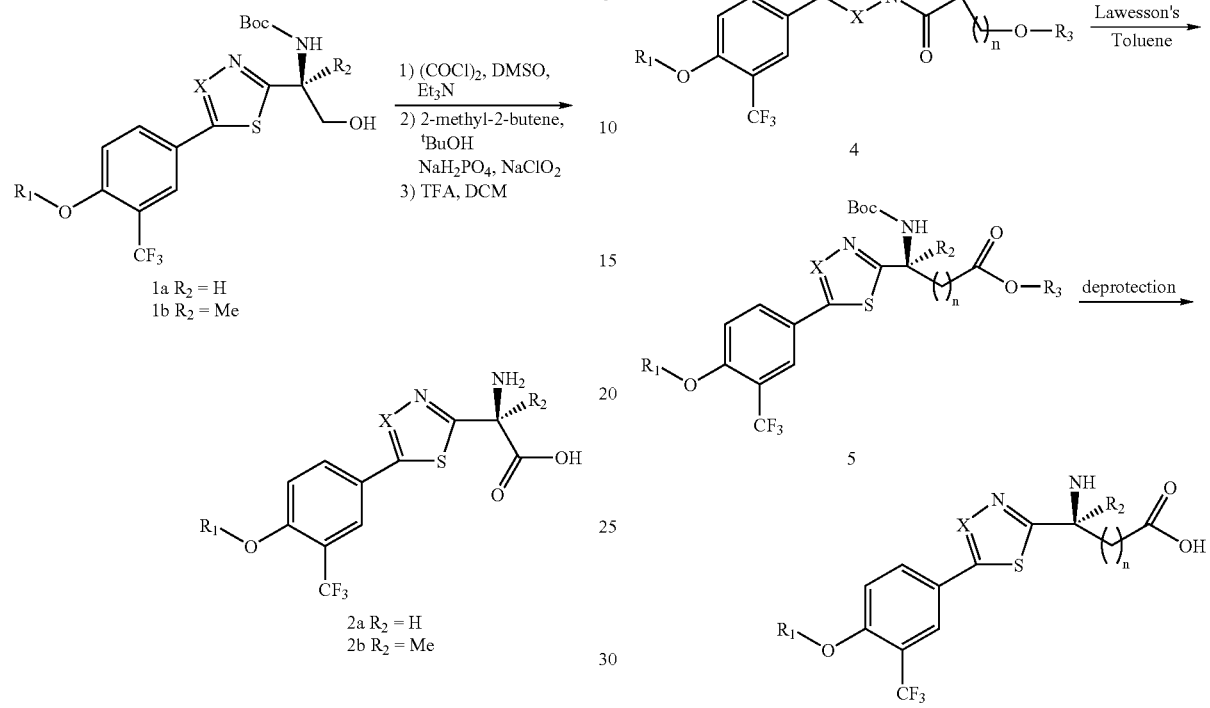

Strategy B:

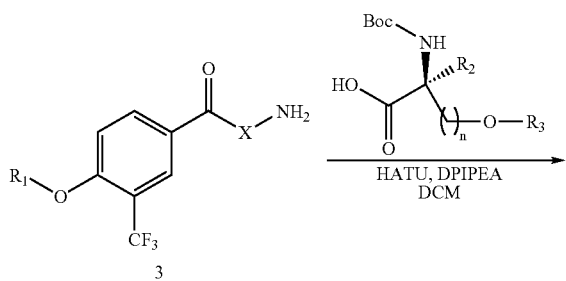

General Approach to Synthesis of Ether-Phenyl-Thiadiazoles

Synthesis of phenyl-thiazoles is described in Scheme 4. Reaction of benzyl or allyl alcohol with substituted 4-fluorobenzoic acid 1 afforded the substituted ether-benzoate 2. The substituted ether-benzoate 2 was then coupled with hydrazine to afford benzohydrazide 3. Reaction of benzohydrazide 3 with orthogonally protected amino acid 4 under HATU conditions followed by cyclization and deprotection (or vis versa) provided phenol 6 in good yield. Mitsunobu reaction of phenol 6 with desired alcohol followed by deprotection afforded the desired final compound 8. Reaction of the alcohol 8 with diethyl chlorophosphate followed by deprotection with TMSBr gave the corresponding phosphate.

Scheme 4:

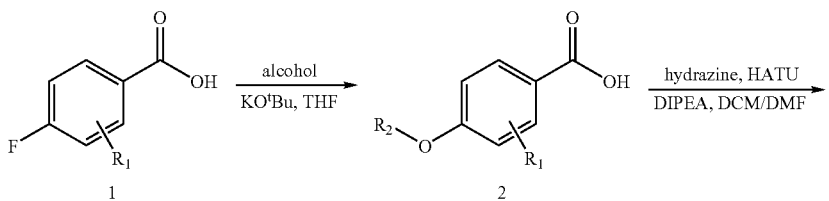

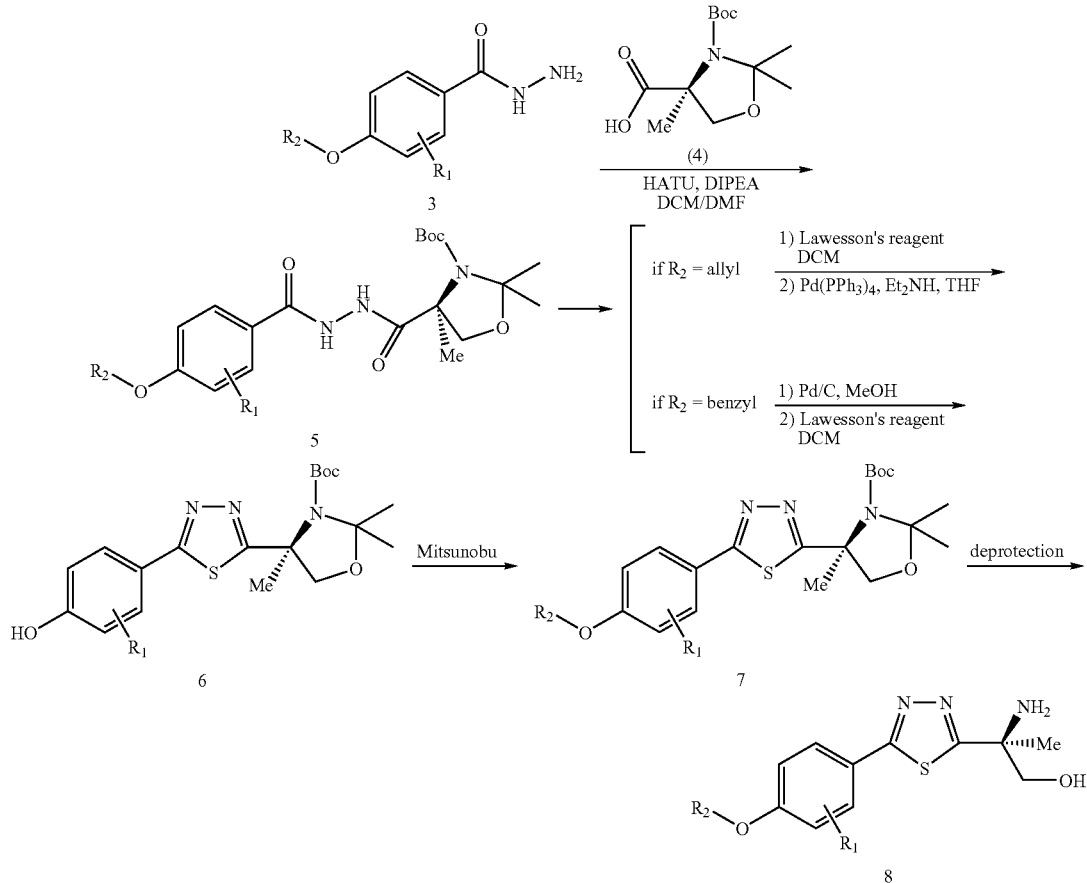

General Procedure for Preparation of Substituted Phenyl Alcohols

Various starting material alcohols for Mitsunobu reaction were prepared as described below.

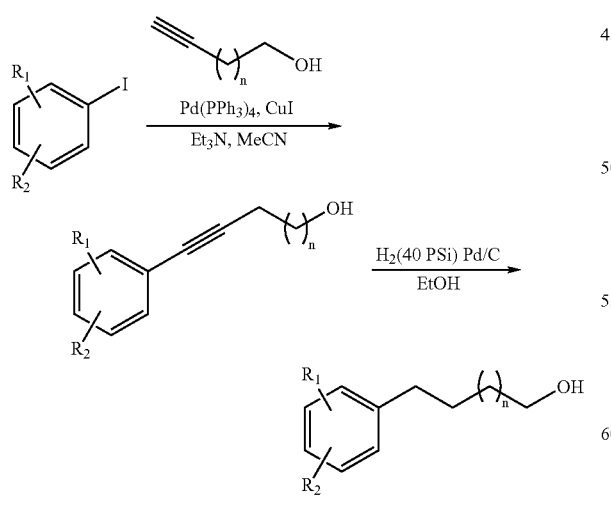

General Procedure for Sonogashira Cross-Coupling

To a mixture of a substituted 4-iodobenzene (1.0 equiv), Pd(PPh$_3$)$_4$ (0.02 equiv) and CuI (0.04 equiv) in MeCN was added the alkynol (1.5 equiv) and Et$_3$N (1.5 equiv). The reaction mixture was stirred for 2-16 hours at reflux, then the solvent removed in vacuo. The crude product was purified by silica gel column chromatography using the Combi-Flash system (Hex:EtOAc) as needed.

General Method for Hydrogenation of Alkyne

The desired alkyne is dissolved in ethanol and a heterogeneous mixture of palladium on carbon is added. The reaction is shaken for 2 hours under 40 psi of H$_2$. Filtration through celite and removal of the solvent in vacuo gives the desired product.

6-Phenylhexan-1-ol

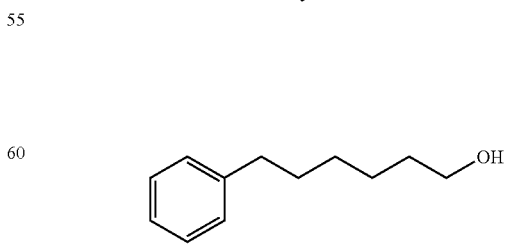

The title compound was prepared from 6-phenylhex-5-yn-1-ol in 70% (241 mg) yield. $^1$H NMR (400 MHz, CDCl$_3$) δ

7.18-7.27 (m, 2H), 7.16-7.18 (m, 3H) 3.63 (t, 2H, J=6.4 Hz), 2.61 (t, 2H, J=8.0 Hz), 1.56-1.69 (m, 4H), 1.37-1.40 (m, 5H).

5-(3-(Trifluoromethyl)phenyl)pentan-1-ol

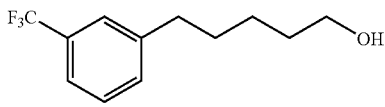

The title compound was prepared from 5-(3-(trifluoromethyl)phenyl)pent-4-yn-1-ol in 85% (241 mg) yield. $^1$H NMR (400 MHz, CDCl$_3$) δ 7.36-7.42 (m, 4H), 3.65 (t, 2H, J=6.8 Hz), 2.68 (t, 2H, J=6.0 Hz), 1.59-1.68 (m, 4H), 1.37-1.44 (m, 3H).

5-(4-(Trifluoromethyl)phenyl)pentan-1-ol

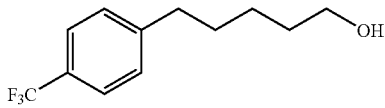

The title compound was prepared from 5-(4-(trifluoromethyl)phenyl)pent-4-yn-1-ol in 60% (140 mg) yield. $^1$H NMR (400 MHz, CDCl$_3$) δ 7.52 (d, 2H, J=8.4 Hz), 7.27 (d, 2H, J=7.3 Hz), 3.64 (t, 2H, J=6.8 Hz), 2.68 (t, 2H, J=8.0 Hz), 1.57-1.70 (m, 4H), 1.39-1.45 (m, 3H).

4-(4-(Trifluoromethyl)phenyl)butan-1-ol

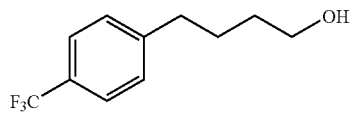

The title compound was prepared from 4-(4-(trifluoromethyl)phenyl)but-3-yn-1-ol in 28% (183 mg) yield. $^1$H NMR (400 MHz, CDCl$_3$) δ 7.53 (d, 2H, J=8.0 Hz), 7.29 (d, 2H, J=7.6 Hz), 3.67 (t, 2H, J=6.4 Hz), 2.71 (t, 2H, J=7.6 Hz), 1.69-1.76 (m, 2H), 1.59-1.64 (m, 3H).

4-(3-(Trifluoromethyl)phenyl)butan-1-ol

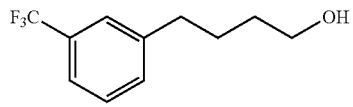

The title compound was prepared from 4-(3-(trifluoromethyl)phenyl)but-3-yn-1-ol in 70% (453 mg) yield. $^1$H NMR (400 MHz, CDCl$_3$) δ 7.26-7.67 (m, 4H), 3.67 (t, 2H, J=6.4 Hz), 2.70 (t, 2H, J=6.4 Hz), 1.71-1.92 (m, 2H), 1.57-1.70 (m, 3H).

5-(3-Fluorophenyl)pentan-1-ol

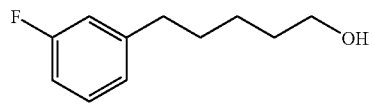

The title compound was prepared from 5-(3-fluorophenyl)pent-4-yn-1-ol in 73% (405 mg) yield. $^1$H NMR (400 MHz, CDCl$_3$) δ 7.19-7.26 (m, 1H), 6.94 (d, 1H, J=7.6 Hz), 6.84-6.88 (m, 2H), 3.64 (t, 2H, J=6.8 Hz), 2.62 (t, 2H, J=7.6 Hz), 1.56-1.69 (m, 4H), 1.36-1.46 (m, 5H).

5-(4-Fluorophenyl)pentan-1-ol

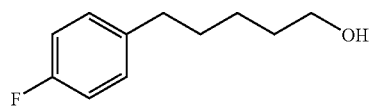

The title compound was prepared from 5-(4-fluorophenyl)pent-4-yn-1-ol in 60% (325 mg) yield. $^1$H NMR (400 MHz, CDCl$_3$) δ 7.10-7.13 (m, 2H), 6.93-6.97 (m, 2H), 3.64 (t, 2H, J=6.8 Hz), 2.59 (t, 2H, J=7.2 Hz), 1.56-1.66 (m, 5H), 1.37-1.43 (m, 4H).

4-(2-Fluorophenyl)butan-1-ol

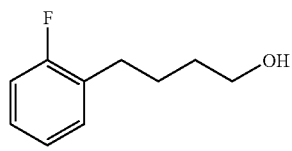

The title compound was prepared from 4-(2-fluorophenyl)but-3-yn-1-ol in 50% (246 mg) yield. $^1$H NMR (400 MHz, CDCl$_3$) δ 7.13-7.25 (m, 2H), 6.97-7.03 (m, 2H), 3.66 (t, 2H, J=6.0 Hz), 2.68 (t, 2H, J=6.8 Hz), 1.59-1.73 (m, 4H), 1.37 (br s, 1H).

4-(3-Fluorophenyl)butan-1-ol

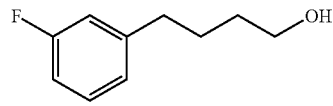

The title compound was prepared from 4-(3-fluorophenyl)but-3-yn-1-ol in 60% (295 mg) yield. $^1$H NMR (400 MHz, CDCl$_3$) δ 7.19-7.29 (m, 1H), 6.95 (d, 1H, J=7.2 Hz), 6.83-

6.89 (m, 2H), 3.66 (t, 2H, J=6.4 Hz), 2.64 (t, 2H, J=7.6 Hz), 1.56-1.74 (m, 4H), 1.39 (br s, 1H).

4-(4-Fluorophenyl)butan-1-ol

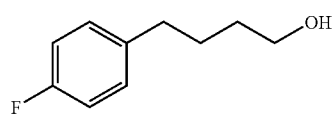

The title compound was prepared from 4-(4-fluorophenyl)but-3-yn-1-ol in 47% (233 mg) yield. ¹H NMR (400 MHz, CDCl₃) δ 7.10-7.15 (m, 2H), 6.93-6.98 (m, 2H), 3.66 (t, 2H, J=6.4 Hz), 2.61 (t, 2H, J=7.6 Hz), 1.56-1.72 (m, 4H), 1.35 (s, 1H).

6-(4-Fluorophenyl)hexan-1-ol

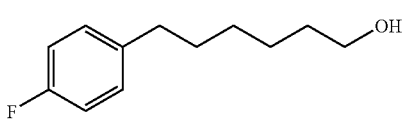

The title compound was prepared from 6-(4-fluorophenyl)hex-5-yn-1-ol in 17% (95 mg) yield. ¹H NMR (400 MHz, CDCl₃) δ 7.15-7.18 (m, 2H), 6.98-7.07 (m, 2H), 3.65 (t, 2H, 6.8 Hz), 2.65 (t, 2H, J=7.6 Hz), 1.57-1.65 (m, 4H), 1.38-1.42 (m, 4H), 1.31 (s, 1H).

6-(3-fluorophenyl)hexan-1-ol

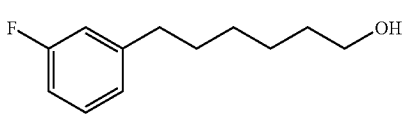

The title compound was prepared from 6-(3-(trifluoromethyl)phenyl)hex-5-yn-1-ol in 17% (100 mg) yield. ¹H NMR (400 MHz, CDCl₃) δ 7.19-7.25 (m, 1H), 6.93 (d, 1H, J=8.0 Hz), 6.83-6.88 (m, 2H), 3.63 (t, 2H, J=6.4 Hz), 2.60 (t, 2H, J=7.6 Hz), 1.53-1.66 (m, 4H), 1.31-1.43 (m, 5H)

6-(4-fluorophenyl)hexan-1-ol

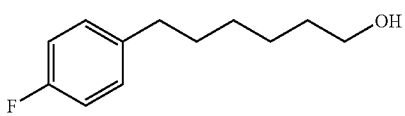

The title compound was prepared from 6-(3-(trifluoromethyl)phenyl)hex-5-yn-1-ol in 27% (162 mg) yield. ¹H NMR (400 MHz, CDCl₃) δ 7.19-7.27 (m, 1H), 7.09-7.13 (m, 1H), 6.92-7.04 (m, 2H), 3.63 (t, 2H, J=6.4 Hz), 2.57 (t, 2H, J=7.6 Hz), 1.49-1.66 (m, 5H), 1.34-1.42 (m, 4H).

5-(3,4-difluorophenyl)pentan-1-ol

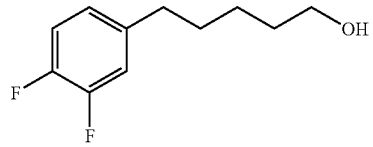

The title compound was prepared from 6-(3-(trifluoromethyl)phenyl)hex-5-yn-1-ol in 67% (404 mg) yield. ¹H NMR (400 MHz, CDCl₃) δ 6.93-7.05 (m, 2H), 6.84-6.87 (m, 1H), 3.64 (t, 2H, J=6.8 Hz), 2.58 (t, 2H, J=7.6 Hz), 1.56-1.66 (m, 4H), 1.35-1.43 (m, 3H)

5-(2,4,5-trifluorophenyl)pentan-1-ol

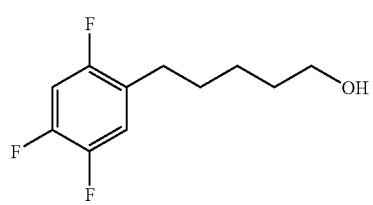

The title compound was prepared from 6-(3-(trifluoromethyl)phenyl)hex-5-yn-1-ol in 57% (0.376 g) yield. ¹H NMR (400 MHz, CDCl₃) δ 6.96-7.01 (m, 1H), 6.83-6.89 (m, 1H), 3.64 (t, 2H, J=6.8 Hz), 2.59 (t, 2H, J=7.2 Hz), 1.56-1.65 (m, 4H), 1.34-1.44 (m, 3H)

6-(3-(trifluoromethyl)phenyl)hexan-1-ol

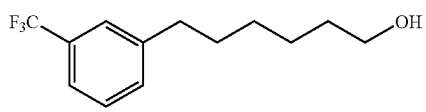

The title compound was prepared from 6-(3-(trifluoromethyl)phenyl)hex-5-yn-1-ol in 50% (362 mg) yield. ¹H NMR (400 MHz, CDCl₃) δ 7.33-7.44 (m, 4H), 3.64 (t, 2H, J=6.8 Hz), 2.67 (t, 2H, J=7.2 Hz), 1.54-1.69 (m, 4H), 1.24-1.44 (m, 5H).

6-(4-(trifluoromethyl)phenyl)hexan-1-ol

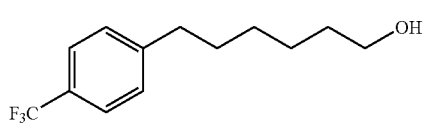

The title compound was prepared from 6-(4-(trifluoromethyl)phenyl)hex-5-yn-1-ol in 72% (534 mg) yield. ¹H NMR (400 MHz, CDCl₃) δ 7.52 (d, 2H, J=8.0 Hz), 7.27 (d, 2H, J=8.0 Hz), 3.64 (t, 2H, J=6.4 Hz), 2.66 (t, 2H, J=7.2 Hz), 1.53-1.68 (m, 4H), 1.35-1.42 (m, 5H).

General Protocol for Synthesis of Substituted 4-(allyloxy) benzoic acid (2)

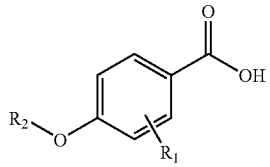

To a solution of the desired alcohol (1.05 equiv) in anhydrous THF was added potassium t-butyloxide (2.05 equiv). The mixture was heated at 65° C. for 10 minutes then added substituted 4-fluorobenzoic acid (1) (1.00 equiv) in THF. The resultant solution was heated at 65° C. 1 to 3 hours. After cooling down to room temperature, the reaction was diluted with ethyl acetate and washed with 10% $KHSO_4$ or 1N HCl (1×), and saturated NaCl (1×). The organic layer was dried over $MgSO_4$, filtered, and the solvent was removed in vacuo to afford intermediate 2.

4-(Allyloxy)-3-(trifluoromethyl)benzoic acid (2a)

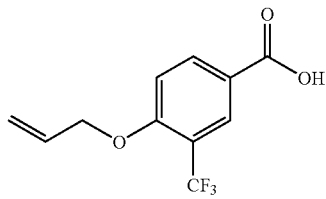

The title compound was prepared from 4-fluoro-3-(trifluoromethyl)benzoic acid (1a) in >99% (5.65 g) yield. HPLC retention time on a C8(2) column (30×3.00 mm, 3 i) was 2.53 min with gradient 20-98% acetonitrile-$H_2O$ (0.1% TFA) in 4.0 min as mobile phase. $^1$H NMR (400 MHz, DMSO-$d_6$) δ 13.10 (br s, 1H), 8.15 (dd, 1H, J=8.8 Hz, J=2.4 Hz), 8.08 (d, 1H, J=2.4 Hz), 7.35 (d, 1H, J=8.8 Hz), 5.95-6.80 (m, 1H), 5.38-5.45 (m, 1H), 5.26-5.32 (m, 1H), 4.77-4.82 (m, 2H).

4-(Benzyloxy)-3-(trifluoromethyl)benzoic acid (2b)

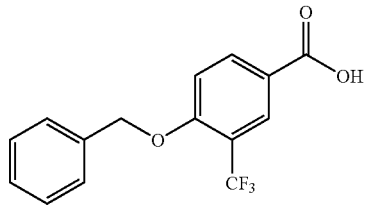

The title compound was prepared from 4-fluoro-3-(trifluoromethyl)benzoic acid (1a) in >99% (7.22 g) yield.

General Protocol for Synthesis of Substituted Benzohydrazide (3)

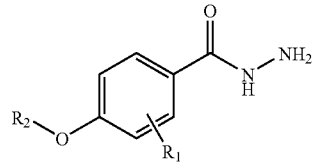

Benzoic acid 2 (1.0 equiv) was stirred with HATU (1.1 equiv) and DIEA (3.0 equiv) in DCM-DMF (2:1) for 20 minutes. The solution was then added to a solution of hydrazine mono-hydrate (3.0-5.0) in DCM-DMF (2:1). The reaction mixture was stirred at rt for 1 hour, then diluted with ethyl acetate and washed with 10% $NH_4Cl$ (2×) and saturated NaCl (1×). The organic layer was dried over $MgSO_4$, filtered, and the solvent was removed in vacuo to afford benzohydrazide 3.

4-(Allyloxy)-3-(trifluoromethyl)benzohydrazide (3a)

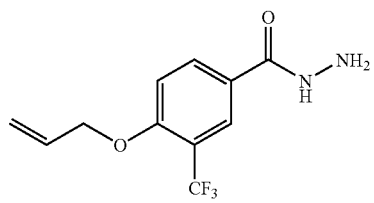

The title compound was prepared from 4-(allyloxy)-3-(trifluoromethyl)benzoic acid (1a) in >99% (6.00 g) yield. HPLC retention time on a C8(2) column (30×3.00 mm, 3μ) was 1.79 min with gradient 20-98% acetonitrile-$H_2O$ (0.1% TFA) in 4.0 min as mobile phase. MS (ESI, M+H$^+$)=261.09

4-(Benzyloxy)-3-(trifluoromethyl)benzohydrazide (3b)

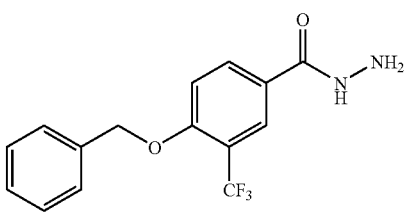

The title compound was prepared from 4-(Benzyloxy)-3-(trifluoromethyl)benzoic acid 2b in >99% (14.7 g) yield. MS (ESI, M+H$^+$)=311.1.

General Protocol for Synthesis of Acyl-Benzohydrazide (5)

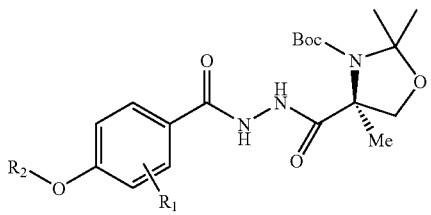

(R)-3-(tert-Butoxycarbonyl)-2,2,4-trimethyloxazolidine-4-carboxylic acid 4 (1.0 equiv) was stirred with HATU (1.1 equiv) and DIEA (3.0 equiv) in DCM-DMF (2:1) for 10 min followed by addition of substituted benzohydrazide 3 (1.0 equiv). The reaction mixture was stirred at rt for 1 hour, then diluted with ethyl acetate and washed with 10% NH$_4$Cl (2×) and saturated NaCl (1×). The organic layer was dried over MgSO$_4$, filtered, and the solvent was removed in vacuo to afford acyl-benzohydrazide 5.

(R)-tert-Butyl 4-(2-(4-(allyloxy)-3-(trifluoromethyl)benzoyl)hydrazinecarbonyl)-2,2,4-trimethyloxazolidine-3-carboxylate (5a)

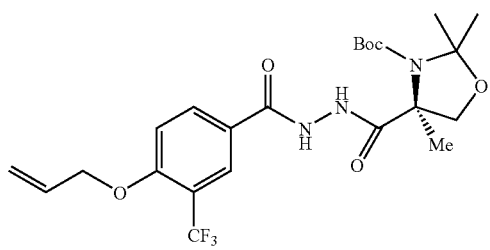

The title compound was prepared from 4-(allyloxy)-3-(trifluoromethyl)benzohydrazide 3a in >99% (11.51 g) yield. HPLC retention time on a C8(2) column (30×3.00 mm, 3μ) was 2.92 min with gradient 20-98% acetonitrile-H$_2$O (0.1% TFA) in 4.0 min as mobile phase. MS (ESI, M+Na$^+$)=524.1

(R)-tert-Butyl 4-(2-(4-(benzyloxy)-3-(trifluoromethyl)benzoyl)hydrazinecarbonyl)-2,2,4-trimethyloxazolidine-3-carboxylate (5b)

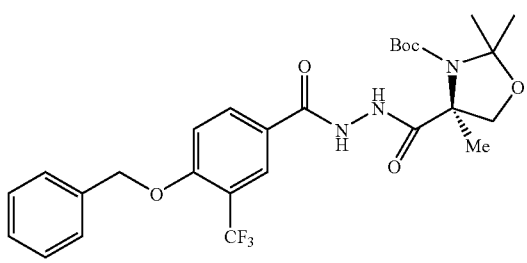

The title compound was prepared from 4-(benzyloxy)-3-(trifluoromethyl)benzohydrazide 3b in 83% (13.1 g) yield. MS (ESI, M+Na$^+$)=574.1; TLC (2:1, Hex/EtOAc), R$_f$=0.34.

General Protocol for Synthesis of Phenyl-Thiadiazole from Allyl Protected Precursor (6)

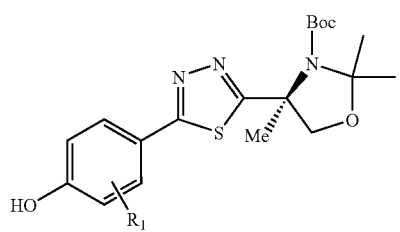

A solution of allyl protected acyl-benzohydrazide 5a (1.0 equiv) in DCM was treated with Lawesson's reagent (1.0 equiv) at 50° C. overnight. The reaction was cooled down to room temperature and the supernatant was chromatographed on a silica gel column eluted with ethyl acetate in hexanes (0-40%, v/v) to afford phenyl-thiadiazole.

A solution of phenyl-thiadiazole (1.0 equiv) and Et$_2$NH (1.5 equiv) in THF was treated with Pd(PPh$_3$)$_4$ (0.02 to 0.05 equiv) at rt for 1-3 hours. The solvent removed in vacuo and the product was purified by silica gel column chromatography using the Combi-Flash system (Hex:EtOAc).

(R)-tert-Butyl 4-(5-(4-(allyloxy)-3-(trifluoromethyl)phenyl)-1,3,4-thiadiazol-2-yl)-2,2,4-trimethyloxazolidine-3-carboxylate

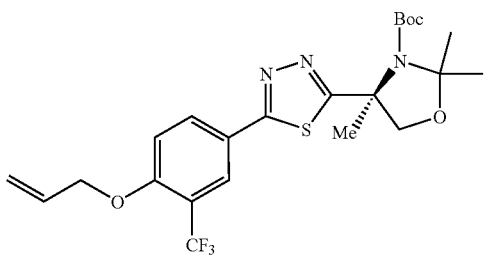

The title compound was prepared from acyl-benzohydrazide 5a in 88% (8.35 g) yield. HPLC retention time on a C8(2) column (30×3.00 mm, 3 f) was 2.84 min with gradient 50-98% acetonitrile-H$_2$O (0.1% TFA) in 4.0 min as mobile phase. MS (ESI, M+H$^+$)=500.0; $^1$H NMR (400 MHz, DMSO-d$_6$) δ 8.13-8.24 (m, 2H), 7.42 (d, 1H, J=8.4 Hz), 5.98-6.10 (m, 1H), 5.40-5.50 (m, 1H), 5.25-5.34 (m, 1H), 4.80-4.84 (m, 2H), 4.10-4.40 (m, 2H), 1.88 (s, 3H), 1.66 (s, 3H), 1.56 (s, 3H), 1.41 (s, 3H), 1.18 (s, 6H).

(R)-tert-Butyl 4-(5-(4-hydroxy-3-(trifluoromethyl) phenyl)-1,3,4-thiadiazol-2-yl)-2,2,4-trimethyloxazolidine-3-carboxylate (6a)

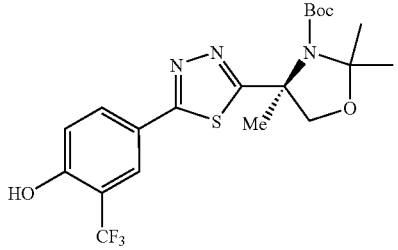

The title compound was prepared from allyl protected phenyl-thiadiazole 6a in 64% (4.86 g) yield. HPLC retention time on a C8(2) column (30×3.00 mm, 3μ) was 2.06 min with gradient 50-98% acetonitrile-$H_2O$ (0.1% TFA) in 4.0 min as mobile phase. MS (ESI, M+H$^+$)=460.0; $^1$H NMR (400 MHz, DMSO-$d_6$) δ 11.40 (s, 1H), 8.00-8.10 (m, 2H), 7.18 (d, 1H, J=8.8 Hz), 4.07-4.21 (m, 2H), 1.88 (s, 3H), 1.67 (s, 3H), 1.57 (s, 3H), 1.42 (s, 3H), 1.19 (s, 6H).

(R)-tert-Butyl 4-(2-(4-hydroxy-3-(trifluoromethyl) benzoyl)hydrazinecarbonyl)-2,2,4-trimethyloxazolidine-3-carboxylate (5c)

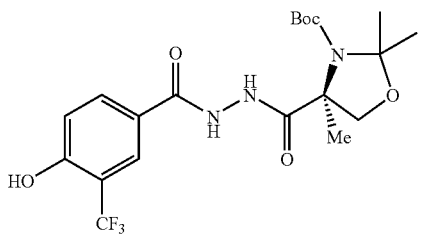

A solution of benzyl protected acyl-benzohydrazide 5b (1.0 equiv) in MeOH was subjected to hydrogenation in the presence of Pd/C (10% w) for 1 h. The reaction mixture was filtered through celite and concentrated to give compound 5c (6.86 g, 99% yield). MS (ESI, M+Na$^+$): 484.0; TLC (2:1, Hex/EtOAc), $R_f$=0.20; $^1$H NMR (400 MHz, CD$_3$OD) δ 8.11 (s, 1H,), 7.95 (d, 1H, J=8.8 Hz), 7.01 (d, 1H, J=8.8 Hz), 4.28 (br s, 1H), 3.91 (br s, 1H), 1.69 (s, 3H,), 1.64 (s, 3H), 1.58 (s, 3H), 1.49 (s, 9H).

(R)-tert-Butyl 4-(5-(4-hydroxy-3-(trifluoromethyl) phenyl)-1,3,4-thiadiazol-2-yl)-2,2,4-trimethyloxazolidine-3-carboxylate (6a)

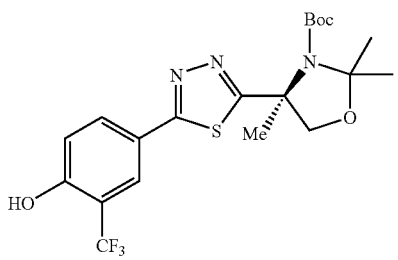

The phenyl-thiazole 6a was prepared through two different protocols (A and B) from 5c:

Protocol A:

A solution of acyl-benzohydrazide 5c (1 equiv) in DCM was treated with Lawesson's reagent (3.0 equiv) at 50° C. overnight. The reaction was cooled down to room temperature and the supernatant was chromatographed on a silica gel column eluted with ethyl acetate in hexanes (0-40%, v/v) to afford phenyl-thiadiazole 6 in 37% (670 mg) yield.

Protocol B:

A solution of acyl-benzohydrazide 5c (1 equiv) in DCM was added acetyl anhydride (1.1 equiv) and pyridine (1.1 equiv). The mixture was stirred at rt for 4 h. The solvent was removed under vacuum and the residue was dissolved in ethyl acetate, washed with brine (3×), dried over MgSO$_4$ and concentrated to afford crude acylated 5c in quantitative (5.46 g) yield. TLC (4:1, Hex/EtOAc), $R_f$=0.40; MS (ESI, M+H$^+$)=504.1.

To a solution of acylated intermediate 5c (1.0 equiv) in toluene was added Lawesson's reagent (1.1 equiv). The mixture was heated at 85° C. for 3 h. The reaction was cooled down to room temperature and the supernatant was chromatographed on a silica gel column eluted with ethyl acetate in hexanes (15%-30%, v/v) to afford acylated 6a in 82% (5.1 g) yield. MS (ESI, M+H$^+$)=502.0.

Acylated 6a was dissolved in a mixture of methanol and saturated NaHCO$_3$ (2:1, v/v) and stirred at rt overnight. The methanol was removed and the aqueous phase was extracted with ethyl acetate (3×). The combined organic phase was washed with brine, dried over MgSO$_4$ and concentrated to afford 6a in 76% (3.1 g) yield.

General Protocol for Mitsunobu Reaction (7)

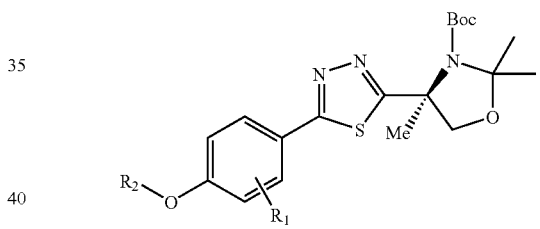

To a suspension of triphenyl phosphine, polymer bound [3 mmol/g loading] (1.2-6.0 equiv) in DCM or PPh$_3$ (1.0 equiv) in DCM or THF, was added a phenol 6 (1.0 equiv) and the desired alcohol (1.0 equiv). The reaction was then cooled to 0° C. in an ice bath and added diisopropyl azodicarboxylate (DIAD) (1.0 equiv). The reaction was then allowed to warm to rt and stirred for 4-12 hours. The reaction mixture was filtered and the filtrate was concentrated under reduced pressure to give a crude product, which was taken on to the next step without any further purification.

General Protocol for One Pot Deprotection of both Boc and Oxazolidine (8)

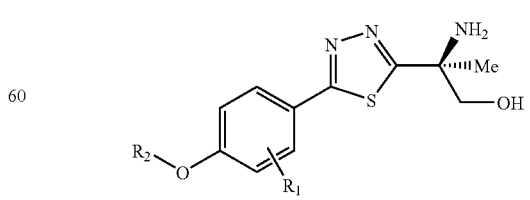

To a solution of compound 8 in DCM added TFA (10-50% v/v) and 1% anisole or triisopropyl silane (TIPS) as scavenger. The reaction mixture was allowed to stir at rt for 0.5-2 hours, dried under vacuum and was subjected directly to prep HPLC purification. The product was purified by prep HPLC on a C8(2) column ((Luna, 5p, 100×21.10 mm) with acetonitrile-H$_2$O (0.1% TFA) as mobile phase and gradient 30-98% in 20 min.

(S)-2-Amino-2-(5-(4-(nonyloxy)-3-(trifluoromethyl)phenyl)-1,3,4-thiadiazole-2-yl)propan-1-ol (8a)

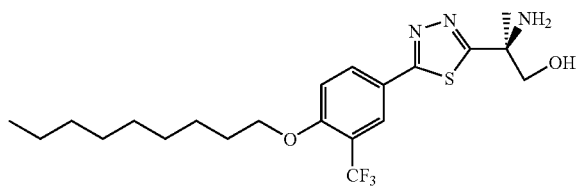

The title compound was prepared from protected phenylthiadiazole 6a in 90% (579 mg) yield. HPLC retention time on a C8(2) column (30×50 mm, 3 μL) is 1.68 min with gradient 50-98% acetonitrile-H$_2$O (0.1% TFA) in 3.5 min as mobile phase. MS (ESI, M+H$^+$)=446.2; $^1$H NMR (400 MHz, DMSO-d$_6$) δ 8.21 (dd, 1H, J=9.0 Hz, J=2.0 Hz), 8.15 (d, 1H, J=2.0 Hz), 7.45 (d, 1H, J=8.4), 4.21 (t, 2H, J=6.2 Hz), 3.74-3.85 (m, 3H), 1.68-1.77 (m, 5H), 1.25-1.45 (m, 12H), 0.849 (t, 3H, J=6.4).

(S)-2-Amino-2-(5-(4-(decyloxy)-3(trifluoromethyl)phenyl)-1,3,4-thiadiazol-2-yl)propan-1-ol (8b)

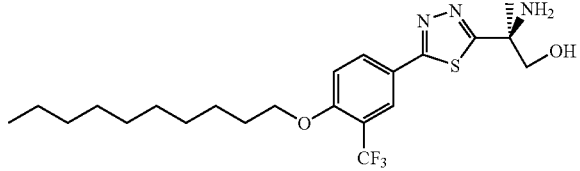

The title compound was prepared from protected phenylthiadiazole 6a in 50% (208 mg) yield. HPLC retention time on a C8(2) column (30×50 mm, 3 μL) is 1.95 min with gradient 50-98% acetonitrile-H$_2$O (0.1% TFA) in 3.5 min as mobile phase. MS (ESI, M+H$^+$)=460.2; $^1$H NMR (400 MHz, DMSO-d$_6$) δ 8.2 (d, 1H, J=8.8 Hz), 8.15 (s, 1H), 7.44 (d, 1H, J=8.8 Hz), 4.21 (t, 2H, J=4.8 Hz), 3.74-3.78 (m, 3H), 1.75 (t, 3H, J=6.8 Hz), 1.65 (s, 3H), 1.25-1.43 (m, 14H), 0.83-0.86 (m, 3H).

(S)-2-Amino-2-(5-(3-(trifluoromethyl)-4-(5-(4-(trifluoromethyl)phenyl)pentyloxy)phenyl)-1,3,4-thiadiazole-2-yl)propan-1-ol (8c)

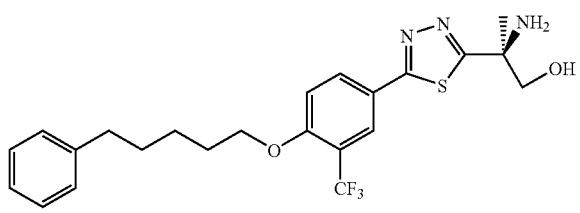

The title compound was prepared from protected phenylthiadiazole 6a in 20% (149 mg) yield. HPLC retention time on a C8(2) column (30×50 mm, 3 μL) is 1.66 min with gradient 50-98% acetonitrile-H$_2$O (0.1% TFA) in 3.5 min as mobile phase. MS (ESI, M+H$^+$)=534.1; $^1$H NMR (400 MHz, DMSO-d$_6$) δ 8.87 (br s, 2H), 8.22 (d, 1H, J=8 Hz), 8.16 (s, 1H), 7.44-7.55 (m, 5H), 4.22 (t, 2H, J=6 Hz), 3.77-3.83 (m, 3H), 2.71 (t, 2H, J=7.6 Hz), 1.68-1.82 (m, 7H), 1.46-1.48 (m, 2H).

(S)-2-Amino-2-(5-(3-(trifluoromethyl)-4-(5-(3-(trifluoromethyl)phenyl)pentyloxy)phenyl)-1,3,4-thiadiazol-2-yl)propan-1-ol (8d)

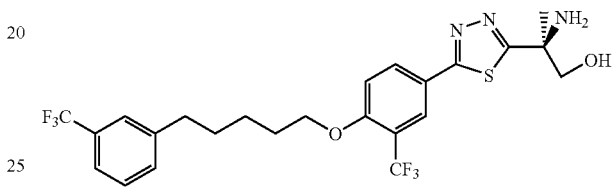

The title compound was prepared from protected phenylthiadiazole 6a in 50% (379 mg) yield. HPLC retention time on a C8(2) column (30×50 mm, 3 μL) is 2.52 min with gradient 30-98% acetonitrile-H$_2$O (0.1% TFA) in 3.5 min as mobile phase. MS (ESI, M+H$^+$)=534.1; $^1$H NMR (400 MHz, DMSO-d$_6$) δ 8.22 (d, 1H, J=8 Hz), 8.15 (d, 1H, J=2.0 Hz), 7.43-7.55 (m, 4H), 7.44 (d, 1H, J=8.8 Hz), 4.22 (t, 2H, J=6.0 Hz), 3.75-3.80 (m, 3H), 2.70 (t, 2H, J=7.6 Hz), 1.78-1.82 (m, 2H), 1.67-1.70 (m, 5H), 1.45-1.47 (m, 2H).

(S)-2-Amino-2-(5-(4-(6-phenylhexyloxy)-3-(trifluoromethyl)phenyl)-1,3,4-thiadiazol-2-yl)propan-1-ol (8e)

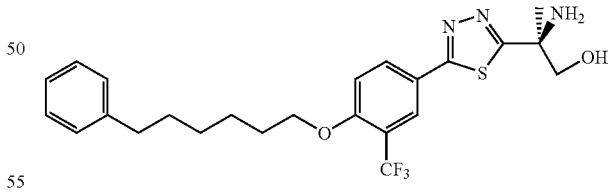

The title compound was prepared from protected phenylthiadiazole 6a in 40% (271 mg) yield. HPLC retention time on a C8(2) column (30×50 mm, 3 μL) is 2.48 min with gradient 30-98% acetonitrile-H$_2$O (0.1% TFA) in 3.5 min as mobile phase. MS (ESI, M+H$^+$)=480.1; $^1$H NMR (400 MHz, DMSO-d$_6$) δ 8.21 (d, 1H, J=9.6 Hz), 8.16 (s, 1H), 7.44 (d, 1H, J=8.8 Hz), 7.13-7.27 (m, 5H), 4.21 (t, 2H, J=6.4 Hz), 3.74-3.84 (m, 3H), 2.57 (t, 2H, J=7.6 Hz), 1.69-1.79 (m, 5H), 1.55-1.62 (m, 2H), 1.44-1.51 (m, 2H), 1.33-1.39 (m, 2H).

(S)-2-Amino-2-(5-(4-(5-(4-fluorophenyl)pentyloxy)-3-(trifluoromethyl)phenyl)-1,3,4-thiadiazol-2-yl)propan-1-ol (8f)

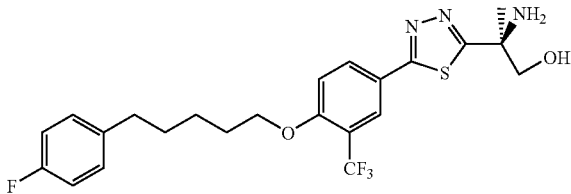

The title compound was prepared from protected phenyl-thiadiazole 6a in 25% (155 mg) yield. HPLC retention time on a C8(2) column (30×50 mm, 3 µL) is 1.92 min with gradient 40-98% acetonitrile-$H_2O$ (0.1% TFA) in 3.5 min as mobile phase. MS (ESI, M+H$^+$)=484.1; $^1$H NMR (400 MHz, DMSO-$d_6$) δ 8.19 (d, 1H, J=9.6 Hz), 8.13 (s, 1H), 7.43 (d, 1H, J=8.8 Hz), 7.19-7.22 (m, 2H), 7.03-7.08 (m, 2H), 4.20 (t, 2H, J=6.0 Hz), 3.74-3.79 (m, 3H), 2.57 (t, 2H, J=7.6 Hz), 1.76-1.79 (m, 2H), 1.60-1.67 (m, 5H), 1.42-1.45 (m, 2H).

(S)-2-Amino-2-(5-(4-(5-(3-fluorophenyl)pentyloxy)-3-(trifluoromethyl)phenyl)-1,3,4-thiadiazol-2-yl)propan-1-ol (8g)

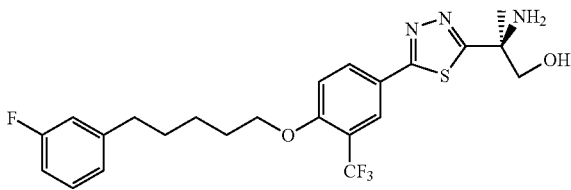

The title compound was prepared from protected phenyl-thiadiazole 6a in 35% (304 mg) yield. HPLC retention time on a C8(2) column (30×50 mm, 3 µL) is 2.71 min with gradient 20-95% acetonitrile-$H_2O$ (0.1% TFA) in 3.5 min as mobile phase. MS (ESI, M+H$^+$)=484.1; $^1$H NMR (400 MHz, DMSO-$d_6$) δ 8.21 (dd, 1H, J=8.4 Hz, J=2.0 Hz), 8.15 (s, 1H), 7.44 (d, 1H, J=8.8 Hz), 7.26-7.31 (m, 1H), 6.94-7.09 (m, 3H), 4.21 (t, 2H, J=6.0 Hz), 3.74-3.83 (m, 3H), 2.61 (t, 2H, J=7.6 Hz), 1.75-1.82 (m, 2H), 1.60-1.68 (m, 5H), 1.38-1.48 (m, 4H).

(S)-2-Amino-2-(5-(4-((4-phenyl-5-(trifluoromethyl)thiophen-2-yl)methoxy)-3-(trifluoromethyl)phenyl)-1,3,4-thiadiazol-2-yl)propan-1-ol (8h)

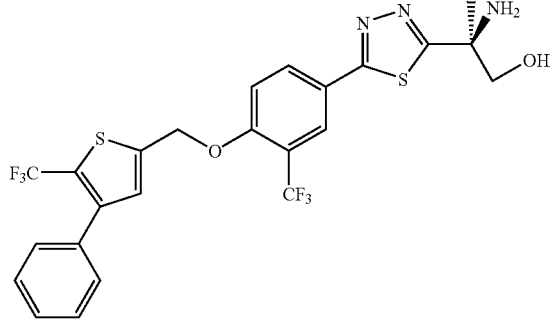

The title compound was prepared from 4-(5-(4-hydroxy-3-(trifluoromethyl)phenyl)-1,3,4-thiadiazol-2-yl)-2,2,4-trimethyoxyazolidine-3-carboxylate 6a in 38% (254 mg) yield. HPLC retention time on a Synergi-Max RP column (2×20 mm, 2 µL) is 1.47 min with gradient 30-99% acetonitrile-$H_2O$ (0.1% TFA) in 2 min as mobile phase. MS (ESI, M+H$^+$)=560.0; $^1$H NMR (400 MHz, DMSO-$d_6$) δ 8.88 (br s, 2H), 8.31 (dd, 1H, J=9.2 Hz, J=2.4 Hz), 8.23 (d, 1H, J=2.0 Hz), 7.44-7.51 (m, 6H), 6.11 (s, 1H), 5.72 (s, 2H), 3.79-3.85 (m, 3H), 1.72 (s, 3H).

(S)-2-Amino-2-(5-(4-(7-phenylheptyloxy)-3-(trifluoromethyl)phenyl)-1,3,4-thiadiazol-2-yl)propan-1-ol (8I)

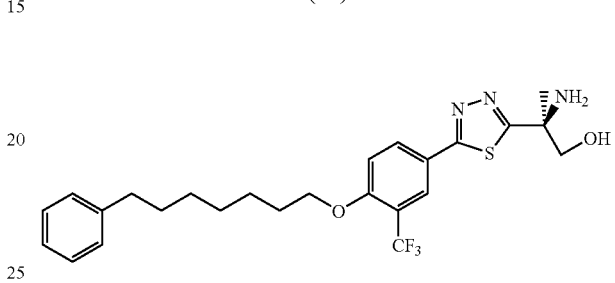

The title compound was prepared from 4-(5-(4-hydroxy-3-(trifluoromethyl)phenyl)-1,3,4-thiadiazol-2-yl)-2,2,4-trimethyoxyazolidine-3-carboxylate 6a in 50% (306 mg) yield. HPLC retention time on a Synergi-Max RP column (2×20 mm, 2 µL) is 1.32 min with gradient 40-99% acetonitrile-$H_2O$ (0.1% TFA) in 2 min as mobile phase. MS (ESI, M+H$^+$)=494.2; $^1$H NMR (400 MHz, DMSO-$d_6$) δ 8.87 (br s, 2H), 8.22 (dd, 1H, J=8.8, J=2.4), 8.16 (d, 1H, J=2.0 Hz), 7.45 (d, 1H, J=8.4 Hz), 7.24-7.25 (m, 4H), 7.13-7.17 (m, 2H), 7.04 (s, 1H), 4.21 (t, 2H, J=6.0 Hz), 3.78-3.85 (m, 3H), 2.56 (t. 2H, J=7.6 Hz), 1.67-1.78 (m, 4H), 1.53-1.61 (m, 2H), 1.27-1.47 (m, 5H).

(S)-2-Amino-2-(5-(3-(trifluoromethyl)-4-(2-(trifluoromethyl)phenethoxy)phenyl)-1,3,4-thiadiazol-2-yl)propan-1-ol (8j)

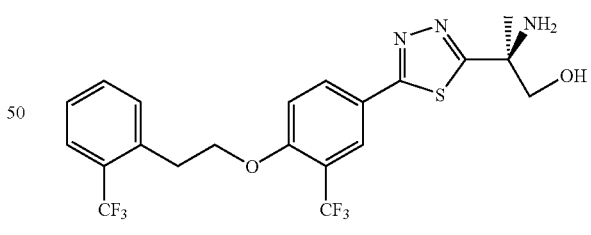

The title compound was prepared from 4-(5-(4-hydroxy-3-(trifluoromethyl)phenyl)-1,3,4-thiadiazol-2-yl)-2,2,4-trimethyoxyazolidine-3-carboxylate 6a in 58% (35 mg) yield. HPLC retention time on a Synergi-Max RP column (2×20 mm, 2 µL) is 0.70 min with gradient 40-99% acetonitrile-$H_2O$ (0.1% TFA) in 2 min as mobile phase. MS (ESI, M+H$^+$)=492.0; $^1$H NMR (400 MHz, DMSO-$d_6$) δ 8.79 (br s, 2H), 8.22 (dd, 1H, J=9.0 Hz, J=2.0 Hz), 8.15 (d, 1H, J=2.4 Hz), 7.73 (d, 1H, J=8 Hz), 7.45-7.52 (m, 4H), 4.49 (t, 2H, J=6.4 Hz), 3.75-3.85 (m, 3H), 3.28 (t, 2H, J=6.4 Hz), 1.70 (s, 3H).

(S)-2-Amino-2-(5-(3-(trifluoromethyl)-4-(3-(trifluoromethyl)phenethoxy)phenyl)-1,3,4-thiadiazol-2-yl)propan-1-ol (8k)

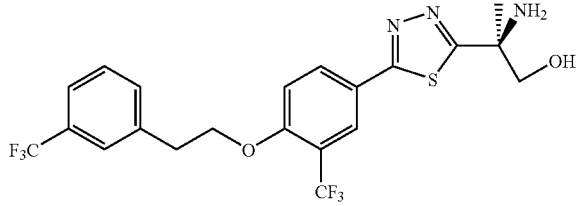

The title compound was prepared from 4-(5-(4-hydroxy-3-(trifluoromethyl)phenyl)-1,3,4-thiadiazol-2-yl)-2,2,4-trimethyoxyazolidine-3-carboxylate 6a in 51% (30.7 mg) yield. HPLC retention time on a Synergi-Max RP column (2×20 mm, 2 μL) is 0.68 min with gradient 40-99% acetonitrile-H$_2$O (0.1% TFA) in 2 min as mobile phase. MS (ESI, M+H$^+$)=491.9; $^1$H NMR (400 MHz, DMSO-d$_6$) δ 8.88 (br s, 2H), 8.21 (dd, 1H, J=8.6 Hz, J=2.0 Hz), 8.14 (d, 1H, J=2.4 Hz), 7.49-7.70 (m, 5H), 4.48 (t, 2H, J=6.4 Hz), 3.77-3.85 (m, 3H), 3.20 (t, 2H, J=6.0 Hz), 1.71 (s, 3H).

(S)-2-Amino-2-(5-(3-(trifluoromethyl)-4-(4-(trifluoromethyl)phenethoxy)phenyl)-1,3,4-thiadiazol-2-yl)propan-1-ol (8l)

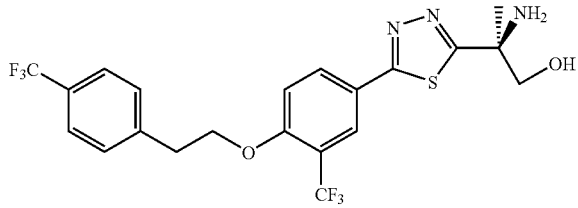

The title compound was prepared from 4-(5-(4-hydroxy-3-(trifluoromethyl)phenyl)-1,3,4-thiadiazol-2-yl)-2,2,4-trimethyoxyazolidine-3-carboxylate 6a in 64% (39 mg) yield. HPLC retention time on a Synergi-Max RP column (2×20 mm, 2 μL) is 0.77 min with gradient 50-98% acetonitrile-H$_2$O (0.1% TFA) in 2 min as mobile phase. MS (ESI, M+H$^+$)=491.9; $^1$H NMR (400 MHz, DMSO-d$_6$) δ 8.91 (br s, 2H), 8.22 (dd, 1H, J=9.0 Hz, J=2.0 Hz), 8.15 (d, 1H, J=2.4 Hz), 7.44-7.68 (m, 5H), 4.49 (t, 2H, J=6.0 Hz), 3.74-3.86 (m, 3H), 3.20 (t, 2H, J=6.4 Hz), 1.71 (s, 3H).

(S)-2-Amino-2-(5-(4-(benzyloxy)-3-(trifluoromethyl)phenyl)-1,3,4-thiadiazol-2-yl)propan-1-ol (8m)

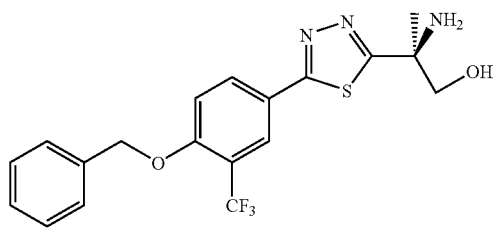

The title compound was prepared from 4-(5-(4-hydroxy-3-(trifluoromethyl)phenyl)-1,3,4-thiadiazol-2-yl)-2,2,4-trimethyoxyazolidine-3-carboxylate 6a in 19% (10 mg) yield. HPLC retention time on a Synergi-Max RP column (2×20 mm, 2 μL) is 1.37 min with gradient 20-95% acetonitrile-H$_2$O (0.1% TFA) in 2 min as mobile phase. MS (ESI, M+H$^+$)=409.9; $^1$H NMR (400 MHz, CD$_3$OD) δ 8.25 (d, 1H, J=2.4 Hz), 8.16 (dd, 1H, J=8.4 Hz, J=2.4 Hz), 7.32-7.48 (m, 6H), 5.34 (s, 2H), 3.89-3.96 (m, 2H, 1.83 (s, 3H).

(S)-2-Amino-2-(5-(4-phenethoxy-3-(trifluoromethyl)phenyl)-1,3,4-thiadiazol-2-yl)propan-1-ol (8n)

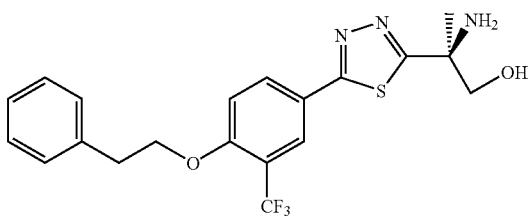

The title compound was prepared from 4-(5-(4-hydroxy-3-(trifluoromethyl)phenyl)-1,3,4-thiadiazol-2-yl)-2,2,4-trimethyoxyazolidine-3-carboxylate 6a in 12% (6.2 mg) yield. HPLC retention time on a Synergi-Max RP column (2×20 mm, 2 μL) is 1.45 min with gradient 20-95% acetonitrile-H$_2$O (0.1% TFA) in 2 min as mobile phase. MS (ESI, M+H$^+$)=423.9; $^1$H NMR (400 MHz, CD$_3$OD) δ 8.25 (d, 1H, J=2.4 Hz), 8.16 (dd, 1H, J=8.4 Hz, J=2.4 Hz), 7.26-7.35 (m, 6H), 4.40 (t, 2H, J=6.8 Hz), 3.89-3.96 (m, 2H), 3.14 (t, 2H, J=6.8 Hz), 1.82 (s, 3H).

(S)-2-Amino-2-(5-(4-(3-phenylpropoxy)-3-(trifluoromethyl)phenyl)-1,3,4-thiadiazol-2-yl)propan-1-ol (8o)

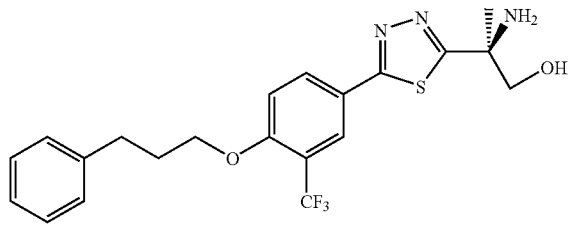

The title compound was prepared from 4-(5-(4-hydroxy-3-(trifluoromethyl)phenyl)-1,3,4-thiadiazol-2-yl)-2,2,4-trimethyoxyazolidine-3-carboxylate 6a in 12% (6.0 mg) yield. HPLC retention time on a Synergi-Max RP column (2×20 mm, 2 μL) is 1.26 min with gradient 30-99% acetonitrile-H$_2$O (0.1% TFA) in 2 min as mobile phase. MS (ESI, M+H$^+$)=437.9; $^1$H NMR (400 MHz, CD$_3$OD) δ 8.25 (d, 1H, J=2.4 Hz), 8.16 (dd, 1H, J=8.4 Hz, J=2.4 Hz), 7.16-7.31 (m, 6H), 4.16 (t, 2H, J=6.0 Hz), 3.89-3.96 (m, 2H), 2.85 (t, 2H, J=7.6 Hz), 2.13-2.17 (m, 2H), 1.83 (s, 3H).

(S)-2-Amino-2-(5-(4-(benzofuran-2-ylmethoxy)-3-(trifluoromethyl)phenyl)-1,3,4-thiadiazol-2-yl)propan-1-ol (8p)

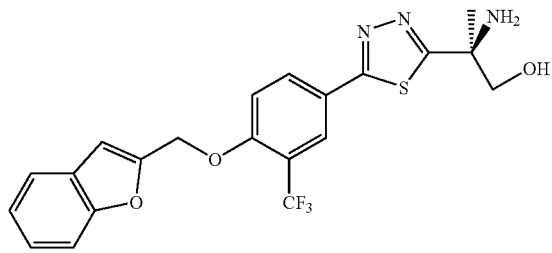

The title compound was prepared from 4-(5-(4-hydroxy-3-(trifluoromethyl)phenyl)-1,3,4-thiadiazol-2-yl)-2,2,4-trimethyoxyazolidine-3-carboxylate 6a in 29% (16 mg) yield. HPLC retention time on a C8(2) column (30×50 mm, 3 µL) is 2.12 min with gradient 20-98% acetonitrile-H$_2$O (0.1% TFA) in 2 min as mobile phase. MS (ESI, M+H$^+$)=450.0; $^1$H NMR (400 MHz, DMSO-d$_6$) δ 8.85 (br s, 2H), 8.28 (dd, 1H, J=8.4 Hz, J=2.4 Hz), 8.20 (d, 1H, J=2.0 Hz), 7.89-7.74 (m, 3H), 7.25-7.37 (m, 2H), 6.97-7.23 (m, 1H), 5.59 (s, 3H), 3.75-3.85 (m, 3H), 1.71 (s, 3H).

(S)-2-Amino-2-(5-(4-(benzo[b]thiophen-2-ylmethoxy)-3-(trifluoromethyl)phenyl)-1,3,4-thiadiazol-2-yl)propan-1-ol (8q)

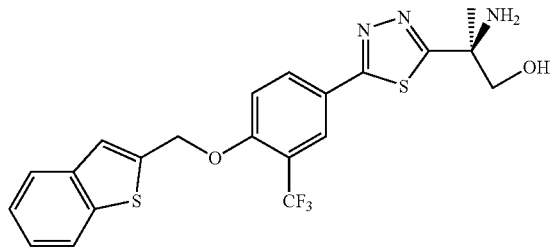

The title compound was prepared from 4-(5-(4-hydroxy-3-(trifluoromethyl)phenyl)-1,3,4-thiadiazol-2-yl)-2,2,4-trimethyoxyazolidine-3-carboxylate 6a in 16% (9 mg) yield. HPLC retention time on a Synergi-Max RP column (2×20 mm, 2 µL) is 1.49 min with gradient 20-95% acetonitrile-H$_2$O (0.1% TFA) in 2 min as mobile phase. MS (ESI, M+H$^+$)=465.9; $^1$H NMR (400 MHz, DMSO-d$_6$) δ 8.82 (br s, 2H), 8.28 (dd, 1H, J=8.6 Hz, J=2.0 Hz), 8.19 (d, 1H, J=2.4 Hz), 8.02-8.04 (m, 1H), 7.91-7.93 (m, 1H), 7.74 (d, 1H, J=8.8 Hz), 7.40-7.46 (m, 2H), 6.95-7.21 (m, 1H), 5.66 (s, 2H), 3.75-3.85 (m, 3H), 1.70 (s, 3H).

(S)-2-Amino-2-(5-(4-(benzo[d][1,3]dioxol-5-ylmethoxy)-3-(trifluoromethyl)phenyl)-1,3,4-thiadiazol-2-yl)propan-1-ol (8r)

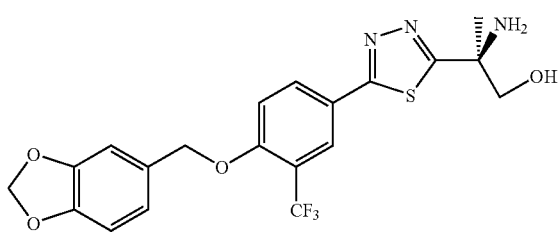

The title compound was prepared from 4-(5-(4-hydroxy-3-(trifluoromethyl)phenyl)-1,3,4-thiadiazol-2-yl)-2,2,4-trimethyoxyazolidine-3-carboxylate 6a in 41% (232 mg) yield. HPLC retention time on a Synergi-Max RP column (2×20 mm, 2 µL) is 1.38 min with gradient 20-95% acetonitrile-H$_2$O (0.1% TFA) in 2 min as mobile phase. MS (ESI, M+H$^+$)=453.9; $^1$H NMR (400 MHz, DMSO-d$_6$) δ 8.87 (br s, 2H), 8.26 (dd, 1H, J=9.2 Hz, J=2.4 Hz), 8.19 (d, 1H, J=2.4 Hz), 7.58 (d, 1H, J=8.8 Hz), 6.87-7.12 (m, 3H), 6.07 (s, 2H), 5.34 (s, 2H), 3.76-3.85 (m, 2H), 1.71 (s, 3H).

(S)-2-Amino-2-(5-(3-(trifluoromethyl)-4-(4-(3-(trifluoromethyl)phenyl)butoxy)phenyl)-1,3,4-thiadiazol-2-yl)propan-1-ol (8s)

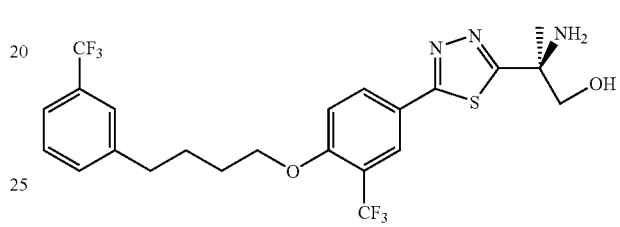

The title compound was prepared from 4-(5-(4-hydroxy-3-(trifluoromethyl)phenyl)-1,3,4-thiadiazol-2-yl)-2,2,4-trimethyoxyazolidine-3-carboxylate 6a in 29% (184 mg) yield. HPLC retention time on a Synergi-Max RP column (2×20 mm, 2 mL) is 1.67 min with gradient 20-95% acetonitrile-H$_2$O (0.1% TFA) in 2 min as mobile phase. MS (ESI, M+H$^+$)=519.9; $^1$H NMR (400 MHz, CD$_3$OD) δ 8.22 (d, 1H, J=2.4 Hz), 8.16 (dd, 1H, J=8.6 Hz, J=2.4 Hz), 7.56 (d, 2H, J=8.4 Hz), 7.4 (d, 2H, J=8.0 Hz), 7.33 (d, 1H, J=8.8 Hz), 4.23 (t, 2H, J=5.2 Hz), 3.92-4.00 (m, 2H), 2.80 (t, 2H, J=6.8 Hz), 1.88-1.92 (m, 4H), 1.84 (s, 3H).

(S)-2-Amino-2-(5-(3-(trifluoromethyl)-4-(4-(4-(trifluoromethyl)phenyl)butoxy)phenyl)-1,3,4-thiadiazol-2-yl)propan-1-ol (8t)

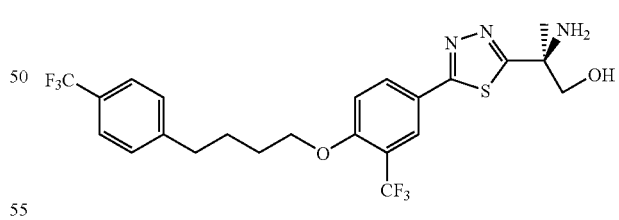

The title compound was prepared from 4-(5-(4-hydroxy-3-(trifluoromethyl)phenyl)-1,3,4-thiadiazol-2-yl)-2,2,4-trimethyoxyazolidine-3-carboxylate 6a in 12% (7.8 mg) yield. HPLC retention time on a Synergi-Max RP column (2×20 mm, 2 µL) is 1.64 min with gradient 20-95% acetonitrile-H$_2$O (0.1% TFA) in 2 min as mobile phase. MS (ESI, M+H$^+$)=519.9; $^1$H NMR (400 MHz, CD$_3$OD) δ 8.22 (d, 1H, J=2.0 Hz), 8.16 (dd, 1H, J=8.6 Hz, J=2.0 Hz), 7.46-7.51 (m, 4H), 7.34 (d, 1H, J=9.2 Hz), 4.24 (s, 2H), 3.90-3.98 (m, 2H), 2.80 (t, 2H, J=6.8 Hz), 1.88-1.91 (m, 4H), 1.83 (s, 3H).

(2S)-2-Amino-2-(5-(4-(3,7-dimethyloctyloxy)-3-(trifluoromethyl)phenyl)-1,3,4-thiadiazol-2-yl)propan-1-ol (8u)

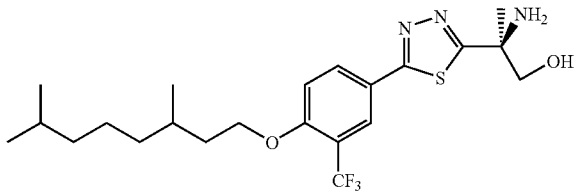

The title compound was prepared from 4-(5-(4-hydroxy-3-(trifluoromethyl)phenyl)-1,3,4-thiadiazol-2-yl)-2,2,4-trimethyoxyazolidine-3-carboxylate 6a in 41% (19 mg) yield. HPLC retention time on a Synergi-Max RP column (2×20 mm, 2 μL) is 1.79 min with gradient 50-98% acetonitrile-$H_2O$ (0.1% TFA) in 2 min as mobile phase. MS (ESI, M+H$^+$)=460.0; $^1$H NMR (400 MHz, $CD_3OD$) δ 8.21 (d, 1H, J=2.4 Hz), 8.17 (dd, 1H, J=8.8 Hz, J=2.4 Hz), 7.36 (d, 1H, J=8.4 Hz), 4.86 (s, 5H), 4.22-4.27 (m, 2H), 3.90-3.98 (m, 2H), 1.87-1.90 (m, 1H), 1.83 (s, 3H), 1.74-1.78 (m, 1H), 1.61-1.65 (m, 1H), 1.50-1.55 (m, 1H), 1.30-1.40 (m, 3H), 1.16-1.22 (m, 3H), 0.97 (d, 3H, J=6.4 Hz), 0.88 (d, 6H, J=6.8 Hz)

(S)-2-Amino-2-(5-(4-(4-propylphenethoxy)-3-(trifluoromethyl)phenyl)-1,3,4-thiadiazol-2-yl)propan-1-ol (8v)

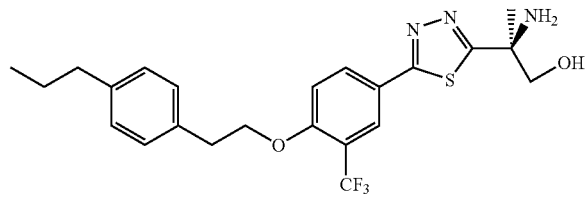

The title compound was prepared from 4-(5-(4-hydroxy-3-(trifluoromethyl)phenyl)-1,3,4-thiadiazol-2-yl)-2,2,4-trimethyoxyazolidine-3-carboxylate 6a in 47% (27 mg) yield. HPLC retention time on a Synergi-Max RP column (2×20 mm, 2 μL) is 1.66 min with gradient 50-98% acetonitrile-$H_2O$ (0.1% TFA) in 2 min as mobile phase. MS (ESI, M+H$^+$)=466.0; $^1$H NMR (400 MHz, $CD_3OD$) δ 8.20 (d, 1H, J=1.6 Hz), 8.13 (dd, 1H, J=8.8 Hz, J=2.4 Hz), 7.32 (d, 1H, J=8.8 Hz), 7.22 (d, 2H, J=8.4 Hz), 7.10 (d, 2H, J=8.4 Hz), 4.44 (t, 2H, J=6.6 Hz), 3.90-3.98 (m, 2H), 3.10 (t, 2H, J=6.6 Hz), 2.55 (t, 2H, J=7.6 Hz), 1.83 (s, 3H), 1.58-1.64 (m, 2H), 1.25 (d, 5H, J=6.4), 0.91 (t, 3H, J=7.6).

(S)-2-Amino-2-(5-(4-(4-butylphenethoxy)-3-(trifluoromethyl)phenyl)-1,3,4-thiadiazol-2-yl)propan-1-ol (8w)

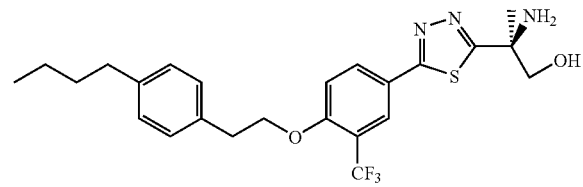

The title compound was prepared from 4-(5-(4-hydroxy-3-(trifluoromethyl)phenyl)-1,3,4-thiadiazol-2-yl)-2,2,4-trimethyoxyazolidine-3-carboxylate 6a in 38% (23 mg) yield. HPLC retention time on a Synergi-Max RP column (2×20 mm, 2 μL) is 1.73 min with gradient 20-95% acetonitrile-$H_2O$ (0.1% TFA) in 2 min as mobile phase. MS (ESI, M+H$^+$)=479.9; $^1$H NMR (400 MHz, $CD_3OD$) δ 8.20 (d, 1H, J=1.6 Hz), 8.13 (dd, 1H, J=2.4 Hz, J=8.8 Hz), 7.32 (d, 1H, J=8.8 Hz), 7.22 (d, 2H, J=8 Hz), 7.10 (d, 2H, J=8 Hz), 4.36 (t, 2H, J=6.4), 3.90-3.98 (m, 2H), 3.10 (t, 2H, J=6.8 Hz), 2.57 (t, 2H, J=7.6 Hz), 1.83 (s, 3H), 1.53-1.61 (m, 2H), 1.31-1.36 (m, 2H), 0.917 (t, 3H, J=7.2 Hz).

(S)-2-Amino-2-(5-(4-(4-ethylphenethoxy)-3-(trifluoromethyl)phenyl)-1,3,4-thiadiazol-2-yl)propan-1-ol (8x)

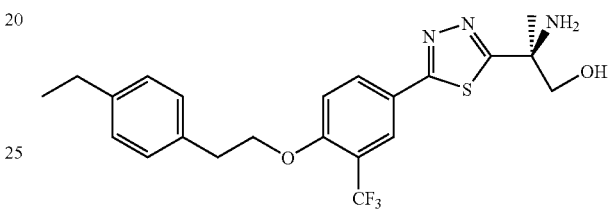

The title compound was prepared from 4-(5-(4-hydroxy-3-(trifluoromethyl)phenyl)-1,3,4-thiadiazol-2-yl)-2,2,4-trimethyoxyazolidine-3-carboxylate 6a in 63% (36 mg) yield. HPLC retention time on a Synergi-Max RP column (2×20 mm, 2 μL) is 1.59 min with gradient 20-95% acetonitrile-$H_2O$ (0.1% TFA) in 2 min as mobile phase. MS (ESI, M+H$^+$)=451.9; $^1$H NMR (400 MHz, $CD_3OD$) δ 8.20 (d, 1H, J=1.6 Hz), 8.14 (dd, 1H, J=8.8 Hz, J=2.4 Hz), 7.32 (d, 1H, J=8.4 Hz), 7.23 (d, 2H, J=8.4 Hz), 7.12 (d, 2H, J=8.0 Hz), 4.36 (t, 2H, J=6.8 Hz), 3.90-3.98 (m, 2H), 3.10 (t, 2H, J=6.8 Hz), 2.55-2.65 (m, 2H), 1.83 (s, 3H), 1.20 (t, 3H, J=7.6 Hz).

(S)-2-Amino-2-(5-(4-(7,7,8,8,8-pentafluoroocty-loxy)-3-(trifluoromethyl)phenyl)-1,3,4-thiadiazol-2-yl)propan-1-ol (8y)

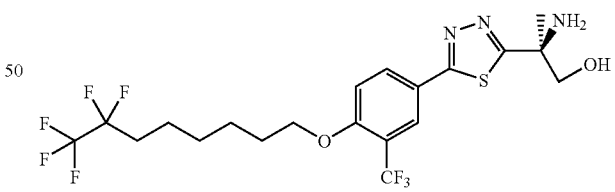

The title compound was prepared from 4-(5-(4-hydroxy-3-(trifluoromethyl)phenyl)-1,3,4-thiadiazol-2-yl)-2,2,4-trimethyoxyazolidine-3-carboxylate 6a in 35% (22 mg) yield. HPLC retention time on a Synergi-Max RP column (2×20 mm, 2 μL) is 1.68 min with gradient 20-95% acetonitrile-$H_2O$ (0.1% TFA) in 2 min as mobile phase. MS (ESI, M+H$^+$)=522.0; $^1$H NMR (400 MHz, $CD_3OD$) δ 8.21 (d, 1H, J=2.4 Hz), 8.16 (dd, 1H, J=8.6 Hz, J=2.4 Hz), 7.34 (d, 1H, J=9.2 Hz), 4.21 (t, 2H, J=6.0 Hz), 3.90-3.96 (m, 2H), 2.05-2.19 (m, 2H), 1.84-1.91 (m, 2H), 1.81 (s, 3H), 1.48-1.67 (m, 6H).

(S)-2-Amino-2-(5-(4-(4-(2-fluorophenyl)butoxy)-3-(trifluoromethyl)phenyl)-1,3,4-thiadiazol-2-yl)propan-1-ol (8z)

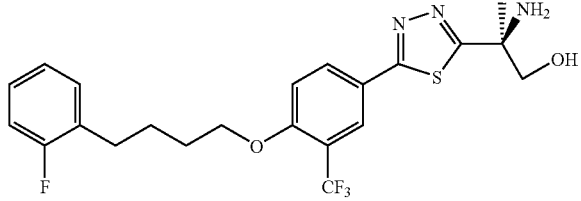

The title compound was prepared from 4-(5-(4-hydroxy-3-(trifluoromethyl)phenyl)-1,3,4-thiadiazol-2-yl)-2,2,4-trimethyoxyazolidine-3-carboxylate 6a in 8% (5 mg) yield. HPLC retention time on a Synergi-Max RP column (2×20 mm, 2 μL) is 1.59 min with gradient 20-95% acetonitrile-H$_2$O (0.1% TFA) in 2 min as mobile phase. MS (ESI, M+H$^+$)=469.9; $^1$H NMR (400 MHz, CD$_3$OD) δ 8.21 (d, 1H, J=1.6 Hz), 8.16 (dd, 1H, J=8.4 Hz, J=2.4 Hz), 7.34 (d, 1H, J=8.4 Hz), 7.16-7.27 (m, 2H), 6.99-7.10 (m, 2H), 4.22 (t, 2H, J=5.6 Hz), 3.90-3.97 (m, 2H), 2.74 (t, 2H, J=7.2 Hz), 1.82-1.90 (m, 4H), 1.82 (s, 2H).

(S)-2-Amino-2-(5-(4-(4-(3-fluorophenyl)butoxy)-3-(trifluoromethyl)phenyl)-1,3,4-thiadiazol-2-yl)propan-1-ol (8aa)

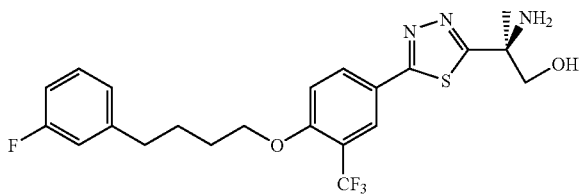

The title compound was prepared from 4-(5-(4-hydroxy-3-(trifluoromethyl)phenyl)-1,3,4-thiadiazol-2-yl)-2,2,4-trimethyoxyazolidine-3-carboxylate 6a in 16% (9 mg) yield. HPLC retention time on a Synergi-Max RP column (2×20 mm, 2 μL) is 1.60 min with gradient 20-95% acetonitrile-H$_2$O (0.1% TFA) in 2 min as mobile phase. MS (ESI, M+H$^+$)=469.9; $^1$H NMR (400 MHz, CD$_3$OD) δ 8.21 (d, 1H, J=2.4 Hz), 8.16 (dd, 1H, J=8.4 Hz, J=2.4 Hz), 7.34 (d, 1H, J=8.4 Hz), 7.23-7.29 (m, 1H), 7.02 (d, 1H, J=5.0 Hz), 6.85-6.96 (m, 2H), 4.22, (t, 2H, J=5.6 Hz), 3.91-3.97 (m, 2H), 2.70-2.74 (m, 2H), 1.83-1.88 (m, 4H), 1.83 (s, 3H).

(S)-2-Amino-2-(5-(4-(4-(4-fluorophenyl)butoxy)-3-(trifluoromethyl)phenyl)-1,3,4-thiadiazol-2-yl)propan-1-ol (8ab)

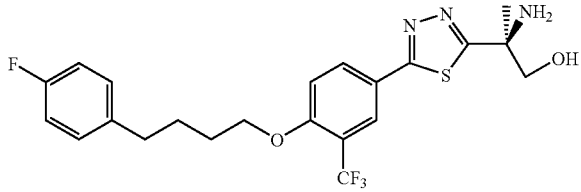

The title compound was prepared from 4-(5-(4-hydroxy-3-(trifluoromethyl)phenyl)-1,3,4-thiadiazol-2-yl)-2,2,4-trimethyoxyazolidine-3-carboxylate 6a in 16% (9 mg) yield. HPLC retention time on a Synergi-Max RP column (2×20 mm, 2 μL) is 1.91 min with gradient 20-95% acetonitrile-H$_2$O (0.1% TFA) in 2 min as mobile phase. MS (ESI, M+H$^+$)=469.9; $^1$H NMR (400 MHz, CD$_3$OD) δ 8.21 (d, 1H, J=2.4 Hz), 8.16 (dd, 1H, J=8.6 Hz, J=2.4 Hz), 7.34 (d, 1H, J=8.0 Hz), 7.2 (m, 2H), 6.95-6.70 (m, 2H), 4.21 (t, 2H, J=5.5 Hz), 3.90-3.98 (m, 2H), 2.69 (t, 2H, J=6.8 Hz), 1.83-1.86 (m, 4H), 1.82 (s, 3H).

(S)-2-Amino-2-(5-(4-(6-(2-fluorophenyl)hexyloxy)-3-(trifluoromethyl)phenyl)-1,3,4-thiadiazol-2-yl)propan-1-ol (8ac)

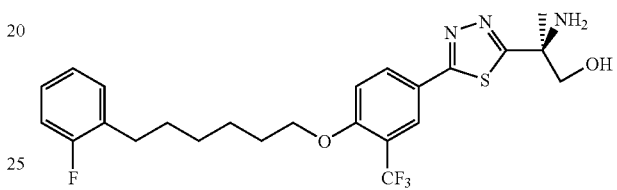

The title compound was prepared from 4-(5-(4-hydroxy-3-(trifluoromethyl)phenyl)-1,3,4-thiadiazol-2-yl)-2,2,4-trimethyoxyazolidine-3-carboxylate 6a in 15% (9 mg) yield. HPLC retention time on a Synergi-Max RP column (2×20 mm, 2 μL) is 1.73 min with gradient 20-95% acetonitrile-H$_2$O (0.1% TFA) in 2 min as mobile phase. MS (ESI, M+H$^+$)=498.1; $^1$H NMR (400 MHz, CD$_3$OD) δ 8.21 (d, 1H, J=2.4 Hz), 8.16 (dd, 1H, J=8.4 Hz, J=2.4 Hz), 7.34 (d, 1H, J=8.4 Hz), 7.14-7.23 (m, 2H), 6.87-7.07 (m, 2H), 4.19 (t, 2H, J=6.0 Hz), 3.90-3.97 (m, 2H), 3.79 (s, 2H), 2.66 (t, 2H, J=8.0 Hz), 1.83-1.88 (m, 1H), 1.82 (s, 3H), 1.53-1.69 (m, 3H), 1.41-1.47 (m, 2H), 1.25-1.27 (m, 3H).

(S)-2-Amino-2-(5-(4-(6-(3-fluorophenyl)hexyloxy)-3-(trifluoromethyl)phenyl)-1,3,4-thiadiazol-2-yl)propan-1-ol (8ad)

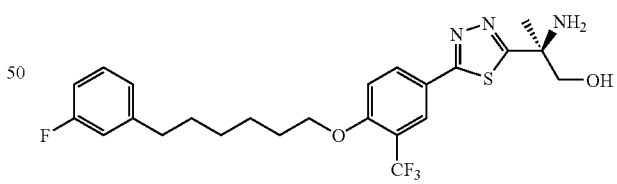

The title compound was prepared from deprotected acylbenzohydrazide 5b in 23% (11.3 mg) yield. HPLC retention time on a Synergi-Max RP column (2×20 mm, 2 μL) is 1.69 min with gradient 20-95% acetonitrile-H$_2$O (0.1% TFA) in 2 min as mobile phase. MS (ESI): 497.98 (MH$^+$); $^1$H NMR (400 MHz, CD$_3$OD) δ 8.21 (d, 1H, J=2.4 Hz), 8.16 (dd, 1H, J=8.6 Hz, J=2.4 Hz), 7.34 (d, 1H, J=8.4 Hz), 7.20-7.24 (m, 1H), 6.98 (d, 1H, J=7.6 Hz), 6.85-6.91 (m, 2H), 4.19 (t, 2H, J=6.4 Hz), 3.90-3.96 (m, 2H), 2.64 (t, 1H, J=7.6 Hz), 1.85-2.01 (m, 2H), 1.83 (s, 3H), 1.63-1.68 (m, 2H), 1.55-1.59 (m, 2H), 1.40-1.46 (m, 2H).

(S)-2-Amino-2-(5-(4-(6-(4-fluorophenyl)hexyloxy)-3-(trifluoromethyl)phenyl)-1,3,4-thiadiazol-2-yl)propan-1-ol (8ae)

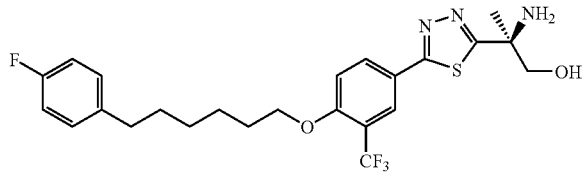

The title compound was prepared from deprotected acyl-benzohydrazide 5b in 35% (17.4 mg) yield. HPLC retention time on a Synergi-Max RP column (2×20 mm, 2 μL) is 1.69 min with gradient 20-95% acetonitrile-H$_2$O (0.1% TFA) in 2 min as mobile phase. MS (ESI): 497.98 (MH$^+$); $^1$H NMR (400 MHz, CD$_3$OD) δ 8.21 (d, 1H, J=2.0 Hz), 8.16 (dd, 1H, J=8.4 Hz, J=2.0 Hz), 7.32 (d, 1H, J=8.4 Hz), 7.14-7.17 (m, 2H), 6.92-6.96 (m, 2H), 4.18 (t, 2H, J=6.4 Hz), 3.90-3.98 (m, 2H), 2.60 (t, 1H, J=8.0 Hz), 1.85-2.01 (m, 2H), 1.83 (s, 3H), 1.60-1.68 (m, 2H), 1.52-1.58 (m, 2H), 1.38-1.44 (m, 2H).

(S)-2-Amino-2-(5-(4-(5-(3,4-difluorophenyl)pentyloxy)-3-(trifluoromethyl)phenyl)-1,3,4-thiadiazol-2-yl)propan-1-ol (8af)

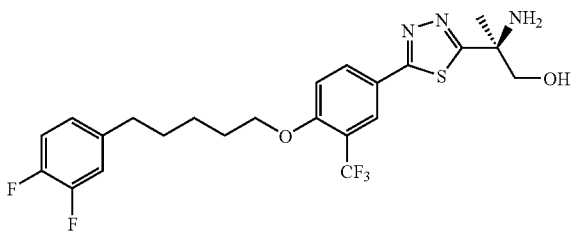

The title compound was prepared from deprotected acyl-benzohydrazide 5b in 44% (22.0 mg). HPLC retention time on a Synergi-Max RP column (2×20 mm, 2 μL) is 1.46 min with gradient 30-99% acetonitrile-H$_2$O (0.1% TFA) in 2 min as mobile phase. MS (ESI): 501.86 (MH$^+$); $^1$H NMR (400 MHz, CD$_3$OD) δ 8.21 (d, 1H, J=2.4 Hz), 8.16 (dd, 1H, J=8.4 Hz, J=2.4 Hz), 7.34 (d, 1H, J=8.4 Hz), 7.05-7.14 (m, 2H), 6.94-6.98 (m, 1H), 4.20 (t, 2H, J=6.0 Hz), 3.89-3.96 (m, 2H), 2.64 (t, 2H, J=7.2 Hz), 1.85-1.91 (m, 2H), 1.83 (s, 3H), 1.66-1.74 (m, 2H), 1.52-1.58 (m, 2H).

(S)-2-Amino-2-(5-(3-(trifluoromethyl)-4-(5-(2,4,5-trifluorophenyl)pentyloxy)phenyl)-1,3,4-thiadiazol-2-yl)propan-1-ol (8ag)

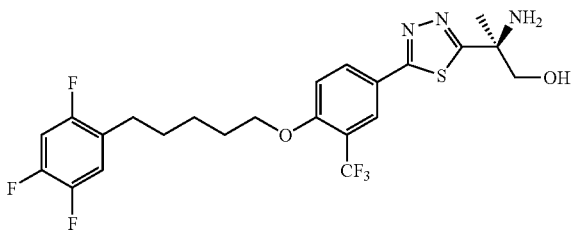

The title compound was prepared from deprotected acyl-benzohydrazide 5b in 28% (14.7 mg). HPLC retention time on a Synergi-Max RP column (2×20 mm, 2 μL) is 1.69 min with gradient 20-95% acetonitrile-H$_2$O (0.1% TFA) in 2 min as mobile phase. MS (ESI): 497.98 (MH$^+$); $^1$H NMR (400 MHz, CD$_3$OD) δ 8.21 (d, 1H, J=2 Hz), 8.16 (dd, 1H, J=8.4 Hz, J=2.0 Hz), 7.34 (d, 1H, J=9.2 Hz), 7.14-7.21 (m, 1H), 7.02-7.08 (m, 1H), 4.20 (t, 2H, J=6.0 Hz), 3.89-3.98 (m, 2H), 2.65 (t, 2H, J=7.2 Hz), 1.83-1.90 (m, 5H), 1.65-1.71 (m, 2H), 1.53-1.59 (m, 2H).

(S)-2-Amino-2-(5-(3-(trifluoromethyl)-4-(6-(3-(trifluoromethyl)phenyl)hexyloxy)phenyl)-1,3,4-thiadiazol-2-yl)propan-1-ol (8ah)

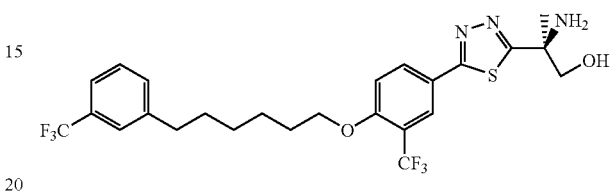

The title compound was prepared from deprotected acyl-benzohydrazide 5b in 60% (33.1 mg). HPLC retention time on a Synergi-Max RP column (2×20 mm, 2 μL) is 1.73 min with gradient 20-95% acetonitrile-H$_2$O (0.1% TFA) in 2 min as mobile phase. MS (ESI): 548.00 (MH$^+$); $^1$H NMR (400 MHz, CD$_3$OD) δ 8.21 (d, 1H, J=1.6 Hz), 8.16 (dd, 1H, J=8.4 Hz, J=2.4 Hz), 7.44-7.46 (m, 4H), 7.33 (d, 1H, J=8.4 Hz), 4.19 (t, 2H, J=6.4 Hz), 3.90-3.99 (m, 2H), 2.71 (t, 2H, J=7.6 Hz), 1.81-1.88 (m, 2H), 1.65-1.73 (m, 2H), 1.54-1.61 (m, 2H), 1.39-1.47 (m, 2H), 1.24-1.28 (m, 3H).

(S)-2-Amino-2-(5-(3-(trifluoromethyl)-4-(6-(4-(trifluoromethyl)phenyl)hexyloxy)phenyl)-1,3,4-thiadiazol-2-yl)propan-1-ol (8ai)

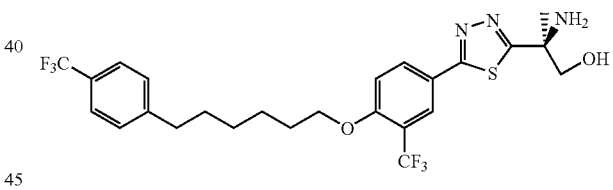

The title compound was prepared from deprotected acyl-benzohydrazide 5b in 59% (32.0 mg). HPLC retention time on a Synergi-Max RP column (2×20 mm, 2 μL) is 1.74 min with gradient 20-95% acetonitrile-H$_2$O (0.1% TFA) in 2 min as mobile phase. MS (ESI): 547.92 (MH$^+$); $^1$H NMR (400 MHz, CD$_3$OD) δ 8.22 (d, 1H, J=2.0 Hz), 8.16 (dd, 1H, J=8.6 Hz, J=2.0 Hz), 7.53 (d, 2H, J=8.0 Hz), 7.32-7.37 (m, 3H), 4.19 (t, 2H, J=6.4 Hz), 3.90-3.98 (m, 2H), 2.72 (t, 2H, J=7.6 Hz), 1.81-1.88 (m, 2H), 1.66-1.73 (m, 2H), 1.54-1.61 (m, 2H), 1.41-1.47 (m, 2H), 1.24-1.27 (m, 3H).

General Approach to Synthesis of Thio-Ether-Phenyl-Thiadiazoles

Synthesis of thio-ether-phenyl-thiazoles is described in Scheme 5. Treatment of substituted 4-fluorobenzoic acid 1 with TMS-CHN$_2$ afforded corresponding methyl ester with upon reaction with various thiols afforded the substituted thio-ether 2. The substituted thio-ether 2 was then condensed with hydrazine to afford benzohydrazide 3. Reaction of benzohydrazide 3 with orthogonally protected amino acid 4 under HATU conditions to give acyl-benzohydrazide 5 which upon treatment with Lawesson's reagent provided phenol 6 in good yield. Mitsunobu reaction of phenol 6 with desired alcohol followed by deprotection afforded the desired final compound 7. Acyl-benzohydrazide could also be oxidized with mCPBA to afford acyl-benzohydrazide 8 before treatment with Lawesson's reagent and deprotection. Reaction of the alcohol 7 with diethyl chlorophosphate followed by deprotection with TMSBr gave the corresponding phosphate.

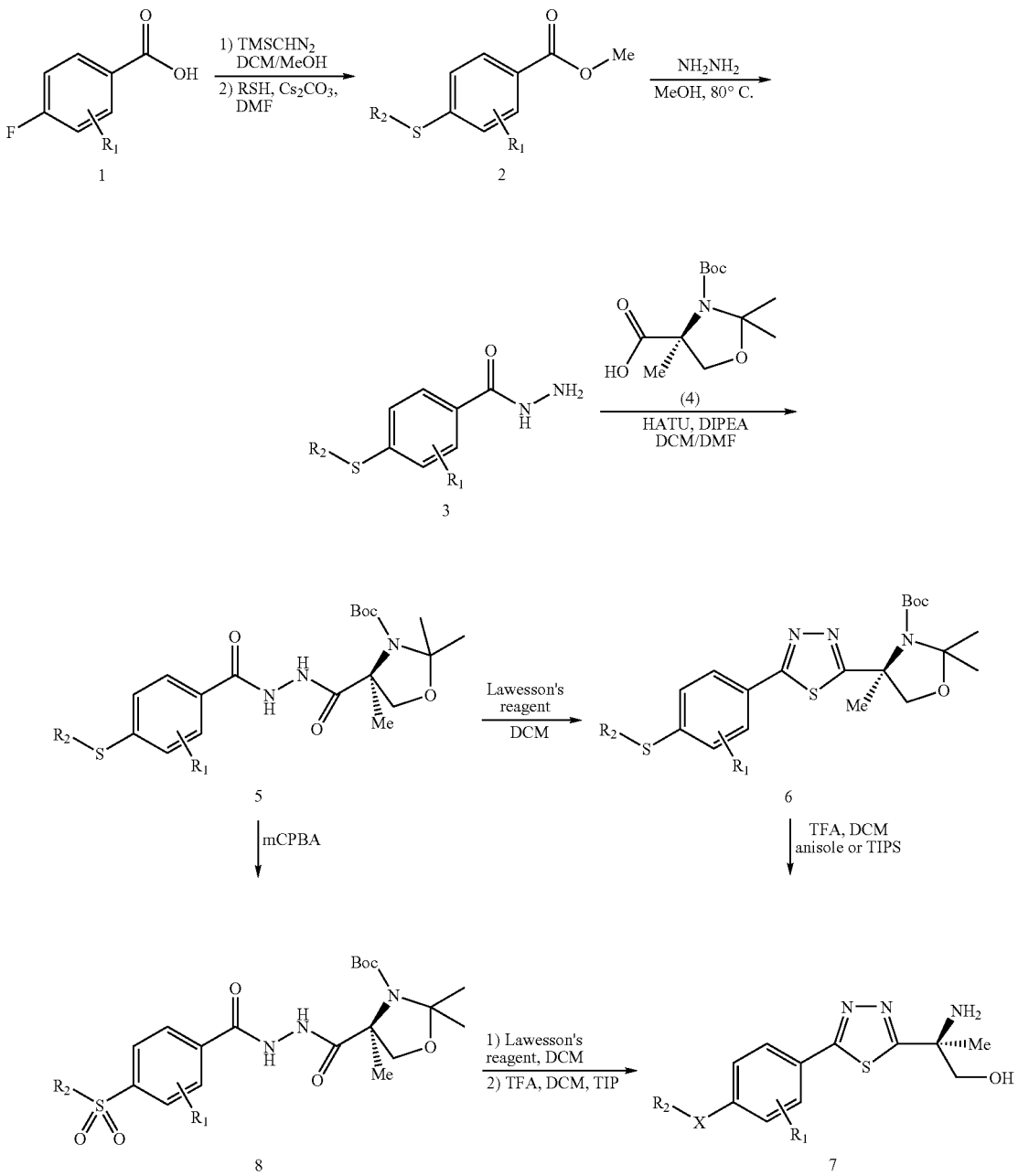

4-(Octylthio)-3-(trifluoromethyl)benzohydrazide (3a)

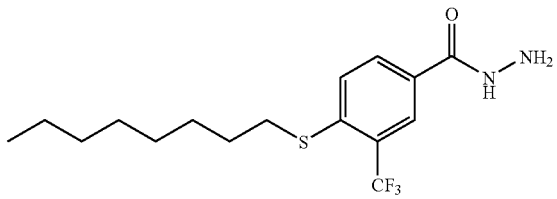

To a solution of 4-fluoro-3-(trifluoromethyl)benzoic acid 1a (1.04 g, 5 mmol) in DCM/MeOH (4:1, 10 mL) at 0° C. was added drop-wise a solution of TMSCHN$_2$ (2.0 M in ether, 2.6 mL, 5.1 mmol). The reaction mixture was stirred at 0° C. until the colorless solution started to turn light yellow and maintained its light yellow color. The reaction was stirred for an additional 20 minutes then a few drops of acetic acid was added to quench the last few drops of TMS-CHN$_2$ (the solution turns colorless from light yellow). The solvent was removed in vacuo to give a crude product which was used directly for next step. MS (ESI, M+H$^+$)=223.0

To a solution of the crude methyl ester in DMF (5 mL) was added octane-1-thiol (0.87 mL, 5 mmol) and Cs$_2$CO$_3$ (2.44 g, 7.5 mmol). The reaction mixture was stirred at 60° C. for 1 h, concentrated, quenched with NH$_4$Cl, extracted with EtOAc. The organics was dried over Na$_2$SO$_4$, concentrated under reduced pressure to leave the crude methyl 4-(octylthio)-3-(trifluoromethyl)benzoate 2a. MS (ESI, M+H$^+$)=349.0

The crude methyl 4-(octylthio)-3-(trifluoromethyl)benzoate was dissolved in 2 mL of MeOH and treated with 2 mL of hydrazine hydrate. The reaction mixture was left to stir at 80° C. for 1 hour, poured into ice-water. The solid was filtered, washed with H$_2$O and dried under vacuum to provide the 4-(octylthio)-3-(trifluoromethyl)benzohydrazide 3a as a yellow solid. HPLC retention time on a C18 column (30×4.6 mm, 3.5µ) was 2.69 min with gradient 10-95% acetonitrile-H$_2$O (0.1% TFA) in 3.5 min as mobile phase. MS (ESI, M+H$^+$)=349.3; $^1$H NMR (400 MHz, CDCl$_3$) δ 9.99 (s, 1H), 8.13 (d, 1H, J=1.6 Hz), 8.03 (dd, 1H, J=8.2 Hz, J=1.6 Hz), 7.67 (d, 1H, J=8.8 Hz), 4.59 (s, 2H), 3.13 (t, 2H, J=7.2 Hz), 1.61 (pentet, 2H, J=6.8 Hz), 1.44-1.36 (m, 2H), 1.30-1.20 (m, 8H), 0.85 (t, 3H, J=6.8 Hz).

(R)-tert-Butyl 2,2,4-trimethyl-4-(2-(4-(octylthio)-3-(trifluoromethyl)benzoyl)hydrazine carbonyl)oxazolidine-3-carboxylate (5a)

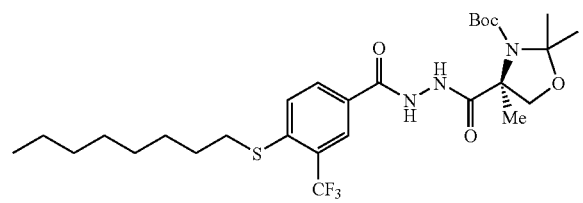

To a solution of (R)-3-(tert-butoxycarbonyl)-2,2,4-trimethyloxazolidine-4-carboxylic acid 4 (129.6 mg, 0.5 mmol) in DMF (1 mL) was added HATU (209 mg, 0.55 mol) and DIPEA (0.436 mL, 2.5 mmol). After being stirred at rt for 10 min, the reaction mixture was treated with 4-(octylthio)-3-(trifluoromethyl)benzohydrazide 3a (174 mg, 0.5 mmol) in THF (2 mL) and was left stirred overnight. Aqueous NaHCO$_3$ solution was added and the mixture was extracted with EtOAc. The organic layer was washed with brine, dried over anhydrous Na$_2$SO$_4$, and evaporated under reduced pressure to give a residue, which was purified by SiO$_2$ column chromatograph (n-hexane/EtOAc=3:7) to give (R)-tert-butyl 2,2,4-trimethyl-4-(2-(4-(octylthio)-3-(trifluoromethyl)benzoyl)hydrazinecarbonyl)oxazolidine-3-carboxylate 5a (247 mg, 84%). HPLC retention time on a C18 column (30×4.6 mm, 3.5µ) was 3.08 min with gradient 10-95% acetonitrile-H$_2$O (0.1% TFA) in 3.5 min as mobile phase. MS (ESI, M+H$^+$)=590.5

(S)-2-Amino-2-(5-(4-(octylthio)-3-(trifluoromethyl)phenyl)-1,3,4-thiadiazol-2-yl)propan-1-ol (7a)

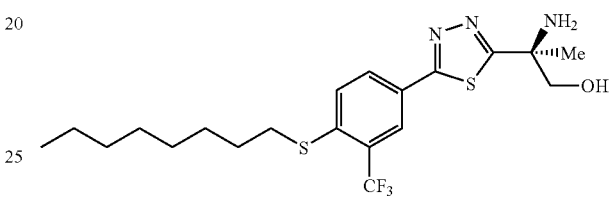

The title product was obtained in 32% yield from (R)-tert-butyl 2,2,4-trimethyl-4-(2-(4-(octylthio)-3-(trifluoromethyl)benzoyl)hydrazinecarbonyl)oxazolidine-3-carboxylate 6a. HPLC retention time on a C18 column (30×4.6 mm, 3.5µ) was 2.46 min with gradient 10-95% acetonitrile-H$_2$O (0.1% TFA) in 3.5 min as mobile phase. MS (ESI, M+H$^+$)=448.4. $^1$H NMR (400 MHz, CD$_3$OD) δ 8.17 (s, 1H), 8.13 (d, 1H, J=8.4 Hz), 7.75 (d, 1H, J=8.4 Hz), 3.80 (AB, 1H, J$_{AB}$=11.2 Hz), 3.73 (AB, 1H, J$_{AB}$=11.2 Hz), 3.14 (t, 2H, J=7.2 Hz), 1.67 (s, 3H), 1.61 (pentet, 2H, J=6.8 Hz), 1.40-1.35 (m, 2H), 1.25-1.20 (m, 8H), 0.81 (t, 3H, J=6.6 Hz).

(R)-tert-Butyl 2,2,4-trimethyl-4-(2-(4-(octylsulfonyl)-3-(trifluoromethyl)benzoyl)hydrazine carbonyl)oxazolidine-3-carboxylate (8a)

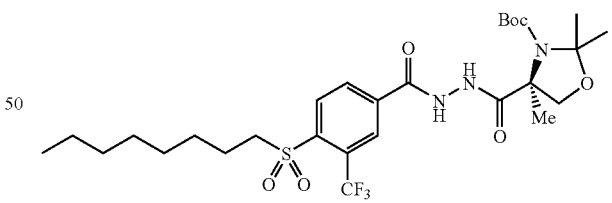

A solution of (R)-tert-butyl 2,2,4-trimethyl-4-(2-(4-(octylthio)-3-(trifluoromethyl)benzoyl)hydrazinecarbonyl)oxazolidine-3-carboxylate 5a (123 mg, 0.21 mmol) in DCM (10 mL) was treated with mCPBA (164 mg, 77%, 722 mmol) at rt. The reaction mixture was stirred at rt overnight, quenched with saturated aqueous NaHCO$_3$, extracted with DCM. The organic layer was washed with saturated aqueous NaHCO$_3$ (3×), dried over Na$_2$SO$_4$, and evaporated under reduced pressure to give a residue, which was purified by SiO$_2$ column chromatograph (n-hexane/EtOAc=3:7) to leave (R)-tert-butyl 2,2,4-trimethyl-4-(2-(4-(octylsulfonyl)-3-(trifluoromethyl)benzoyl)hydrazinecarbonyl)oxazolidine-3-carboxylate 8a (112 mg, 92%). HPLC retention time on a C18 column (30×4.6 mm, 3.5μ) was 3.27 min with gradient 10-95% acetonitrile-H₂O (0.1% TFA) in 3.5 min as mobile phase. MS (ESI, M+H⁺)=622.5.

(S)-2-Amino-2-(5-(4-(octylsulfonyl)-3-(trifluoromethyl)phenyl)-1,3,4-thiadiazol-2-yl)propan-1-ol (7b)

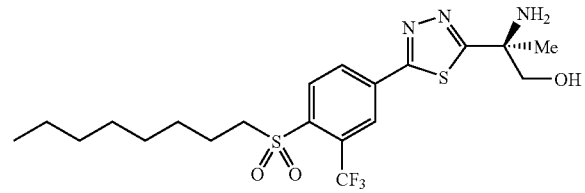

The title compound was prepared according to general procedure from (R)-tert-butyl 2,2,4-trimethyl-4-(2-(4-(octylsulfonyl)-3-(trifluoromethyl)benzoyl)hydrazinecarbonyl)oxazolidine-3-carboxylate 8a. HPLC retention time on a C18 column (30×4.6 mm, 3.5μ) was 2.11 min with gradient 10-95% acetonitrile-H₂O (0.1% TFA) in 3.5 min as mobile phase. MS (ESI, M+H⁺)=480.3; ¹H NMR (400 MHz, DMSO-d6) δ 8.56 (dd, 1H, J=8.2 Hz, J=1.6 Hz), 8.53 (d, 1H, J=1.6 Hz), 8.38 (d, 1H, J=8.8 Hz), 3.87 (AB, 1H, $J_{AB}$=10.8 Hz), 3.80 (AB, 1H, $J_{AB}$=10.8 Hz), 3.44 (t, 1H, J=7.8 Hz), 1.68 (s, 3H), 1.66-1.60 (m, 2H), 1.37-1.31 (m, 2H), 1.25-1.16 (m, 8H), 0.83 (t, 3H, J=7.2 Hz).

General Approach to Synthesis of Phenyl-Oxadiazoles

Synthesis of phenyl-oxadiazoles is described in Scheme 6. Reaction of the desired alcohol with substituted 4-fluorobenzonitrile 1 afforded the substituted benzonitrile 2. The substituted benzonitrile 2 was then condensed with hydroxylamine to afford hydroxybenzimidamide 3. Coupling of the hydroxyamindine intermediate 3 with orthogonally protected amino acid 4 under HATU conditions followed by cyclization provided orthogonally protected oxadiazole 6. Treatment of protected oxadiazole 6 with TFA gave the desired final amino-alcohol 7.

Scheme 6:

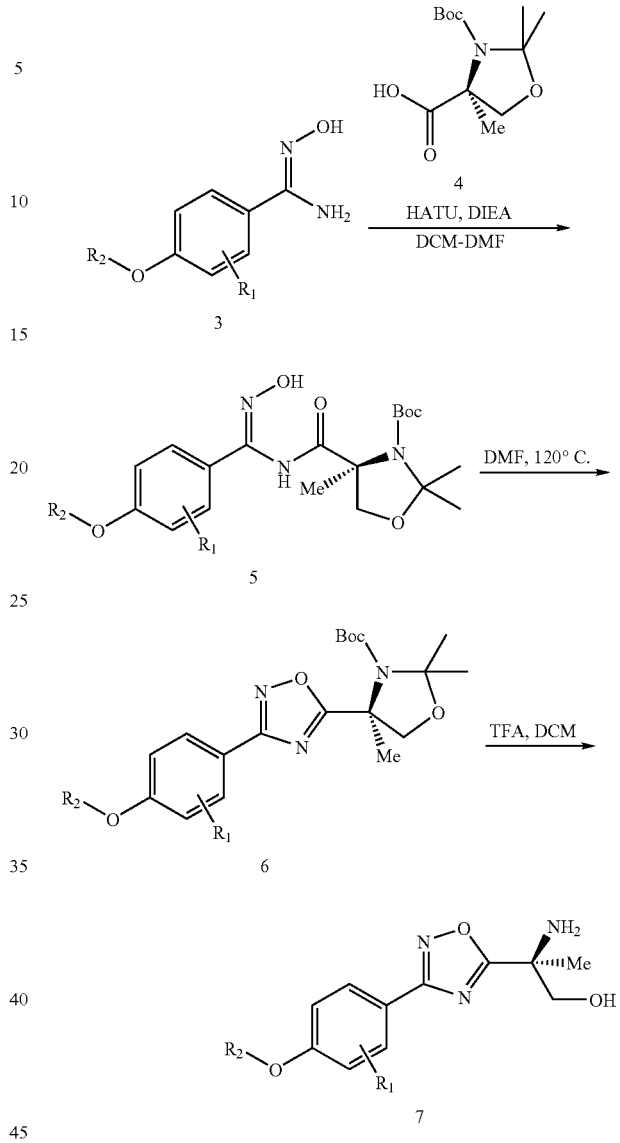

4-(Octyloxy)-3-(trifluoromethyl)benzonitrile (2a)

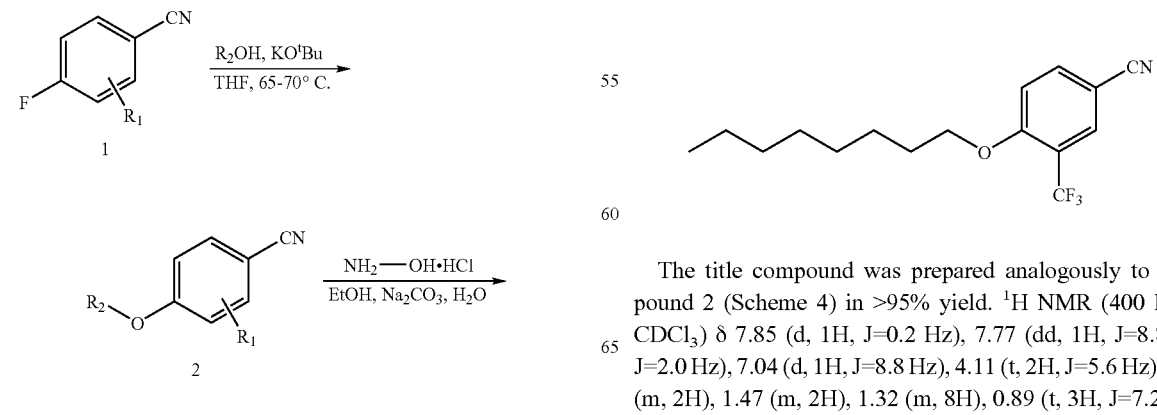

The title compound was prepared analogously to compound 2 (Scheme 4) in >95% yield. ¹H NMR (400 MHz, CDCl₃) δ 7.85 (d, 1H, J=0.2 Hz), 7.77 (dd, 1H, J=8.8 Hz, J=2.0 Hz), 7.04 (d, 1H, J=8.8 Hz), 4.11 (t, 2H, J=5.6 Hz), 1.84 (m, 2H), 1.47 (m, 2H), 1.32 (m, 8H), 0.89 (t, 3H, J=7.2 Hz).

(R)-tert-Butyl 2,2,4-trimethyl-4-(3-(4-(octyloxy)-3-(trifluoromethyl)phenyl)-1,2,4-oxadiazol-5-yl)oxazolidine-3-carboxylate (6a)

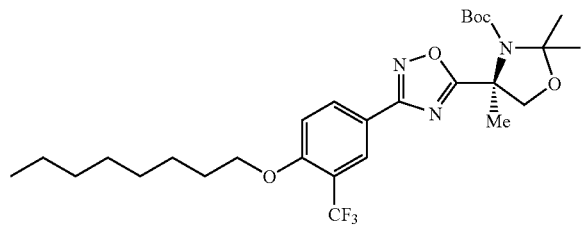

A suspension of 4-(octyloxy)-3-(trifluoromethyl)benzonitrile (600 mg, 1.0 equiv), NH$_2$OH.HCl (280 mg, 2.0 equiv), Na$_2$CO$_3$ (636 mg, 3.0 equiv) in ethanol-water (12 mL, 5:1) was refluxed for 3 h. The reaction was condensed under vacuum and the residue was treated with water followed by extraction with ethyl acetate. The ethyl acetate layer was washed with saturated NaCl (1×), dried over Na$_2$SO$_4$, and condensed to afford hydroxyamindine intermediate (750 mg). Part of the intermediate (166 mg, 1.0 equiv) was treated with HATU (190 mg, 1.0 equiv), DIEA (260 μL, 3.0 equiv) and (R)-3-(tert-butoxycarbonyl)-2,2,4-trimethyloxazolidine-4-carboxylic acid (130 mg, 1.0 equiv) in DMF (1 mL) for 1 hour. The reaction was diluted with ethyl acetate and washed with water followed by saturated NaCl (1×), dried over Na$_2$SO$_4$, and condensed under vacuum. The residue was dissolved in DMF and heated at 120° C. for 2 hours. Aqueous workup followed by Isco system purification provided the title compound in 28% (70 mg) yield over three steps. MS (ESI, M+H$^+$)=558.1 $^1$H NMR (400 MHz, CDCl$_3$) δ 8.28 (d, 1H, J=1.6 Hz), 8.18 (dd, 1H, J=8.4 Hz, J=1.6 Hz), 7.07 (d, 1H, J=8.4 Hz), 4.23, 4.00 (AB, 2H, J=9.2 Hz), 4.11 (t, 2H, J=7.2 Hz), 1.92 (s, 3H), 1.84 (m, 2H), 1.76 (s, 3H), 1.70 (s, 3H), 1.51-1.46 (m, 4H), 1.25 (m, 9H), 1.25 (s, 6H), 0.89 (t, 3H, J=7.2 Hz).

(S)-2-Amino-2-(3-(4-(octyloxy)-3-(trifluoromethyl)phenyl)-1,2,4-oxadiazol-5-yl)propan-1-ol (7a)

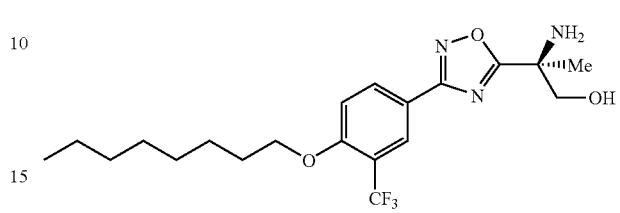

The title compound was prepared analogously to compound 8 (Scheme 4) from compound 7a. MS (ESI, M+H$^+$)=416.0; $^1$H NMR (400 MHz, CD$_3$OD) δ 8.28 (m 2H), 7.34 (d, 1H, J=9.6 Hz), 4.19 (t, 2H, J=5.6 Hz), 4.11, 3.89 (AB, 2H, J=11.6 Hz), 1.84 (m, 2H), 1.77 (s, 3H), 1.53 (m, 2H), 1.40-1.32 (m, 8H), 0.91 (t, 3H, J=7.2 Hz).

General Approach to Synthesis of Phenyl-Isoxazoles and Phenyl-Pyrazoles

Synthesis of phenyl-isoxazoles and phenyl-pyrazoles are described in Scheme 7. Reaction of the desired benzoic acid with oxalyl chloride and trapping the acid chloride with enolate of oxazolidine-ketone 2 afforded 1,3-dione 3. Oxazolidine-ketone 2 was synthesized from oxazolidine-carboxylate 8 after conversion of 8 to corresponding Weinreb amide followed by addition of methyl lithium. Reaction of the 1,3-dione 3 with either hydrazine or hydroxylamine followed by deprotection afforded the desired final compound 6 and 7 respectively.

Scheme 7:

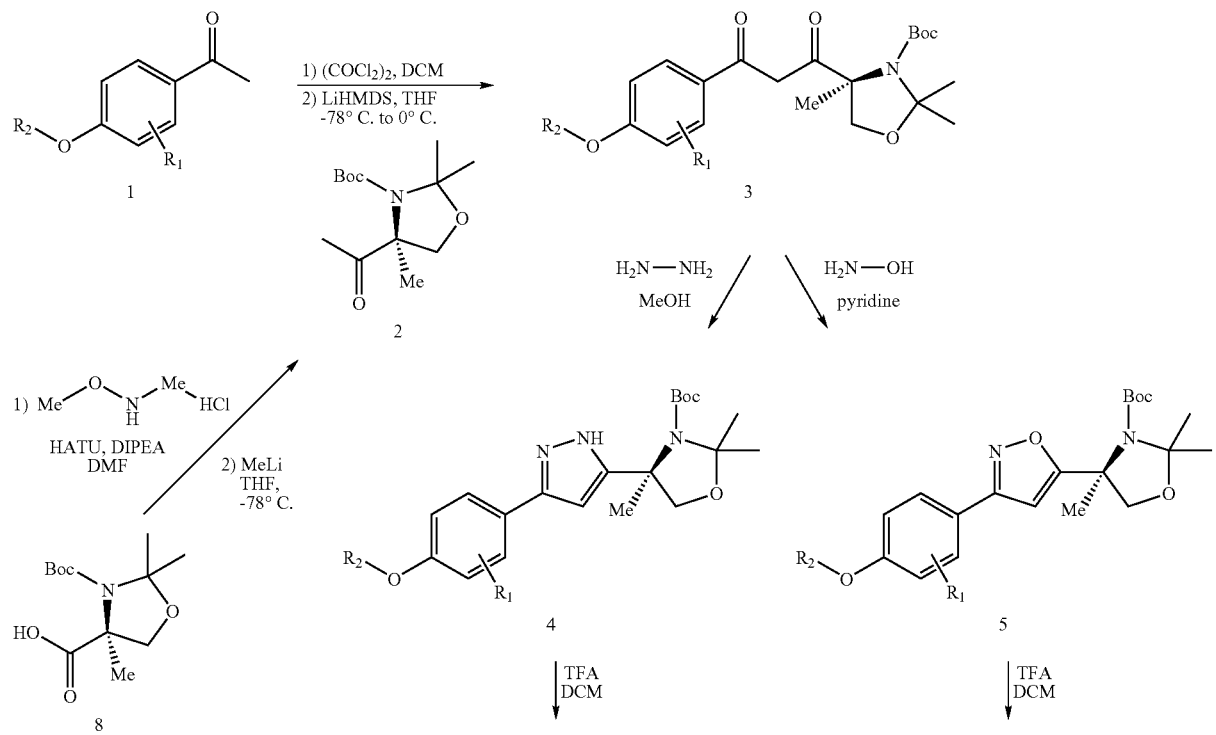

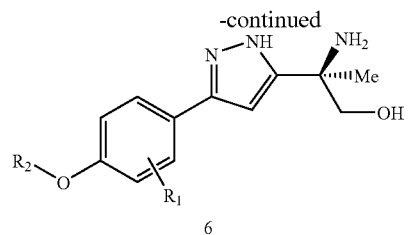

6

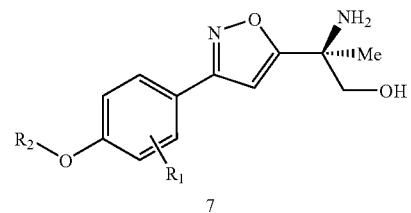

7

(R)-tert-Butyl 4-acetyl-2,2,4-trimethyloxazolidine-3-carboxylate (2)

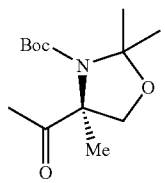

To a solution of (R)-3-(tert-butoxycarbonyl)-2,2,4-trimethyloxazolidine-4-carboxylic acid 8 (2.6 g, 10 mmol, 1.0 equiv) in DMF (25 mL) was added HATU (4.6 g, 12 mmol, 1.2 equiv) and DIPEA (8.7 mL, 50 mmol, 5.0 equiv). The reaction mixture was stirred at rt for 10 min and treated with N,O-dimethylhydroxylamine hydrochloride (2.9 g, 30 mmol, 3.0 equiv), stirred for 2 days at rt, quenched with half saturated NaHCO$_3$, extracted with EtOAc. The organics was dried over Na$_2$SO$_4$, concentrated to afford corresponding Weinreb amide in 92% (2.78 g) yield. HPLC retention time on a C18 column (30×4.6 mm, 3.5μ) was 2.20 min with gradient 10-95% acetonitrile-H$_2$O (0.1% TFA) in 3.5 min as mobile phase. MS (ESI, M+H$^+$)=303.3.

The crude corresponding Weinreb amide (2.78 g, 9.2 mmol, 1.0 equiv) was dissolved in THF (50 mL), cooled to −78° C. and treated with a solution of 1.6 M MeLi (14.7 mL, 23 mmol, 2.5 equiv) in ether drop-wise. After being stirred at −78° C. for 3 h, the reaction mixture was allowed to warm to rt, quenched with saturated aqueous NH$_4$Cl, extracted with EtOAc. The organics was dried over Na$_2$SO$_4$, concentrated in vacuo to afforded an oil which was purified by silica gel column chromatograph (n-hexane/EtOAc=85:15) to give (R)-tert-butyl 4-acetyl-2,2,4-trimethyloxazolidine-3-carboxylate as a white solid in 82% (1.94 g) yield. HPLC retention time on a C18 column (30×4.6 mm, 3.5 p) was 2.39 min with gradient 10-95% acetonitrile-H$_2$O (0.1% TFA) in 3.5 min as mobile phase. MS (ESI, M+H$^+$)=258.4; $^1$H NMR (400 MHz, CDCl$_3$) δ 3.95 (d, 1H, J=9.6 Hz), 3.74 (d, 1H, J=9.6 Hz), 2.21 (s, 3H), 1.69 (s, 2H), 1.65-1.64 (m, 1H), 1.61 (s, 2H), 1.57-1.55 (m, 2H), 1.49 (s, 5H), 1.42 (s, 6H).

(S)-tert-Butyl 2,2,4-trimethyl-4-(3-(4-(octyloxy)-3-(trifluoromethyl)phenyl)-3-oxo-propanoyl)oxazolidine-3-carboxylate (3a)

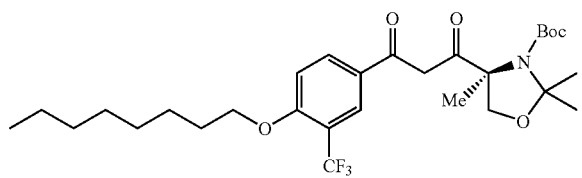

4-(Octyloxy)-3-(trifluoromethyl)benzoic acid (460 mg, 1.0 equiv) was treated with oxalyl chloride (244 μL, 2.0 equiv) for 30 min. The reaction was condensed and part of the reside (81 mg, 1.2 equiv) was dissolved in THF and transferred to a solution of (S)-tert-butyl 4-acetyl-2,2,4-trimethyloxazolidine-3-carboxylate (51 mg, 1.0 equiv) and 1.0M LiHMDS (0.72 mL, 3.0 equiv) in THF at −78° C. The resultant was stirred at 0° C. for 1 hour. The reaction was quenched with aqueous NH$_4$Cl and extracted with ethyl acetate. The organic layer was washed with brine and dried over Na$_2$SO$_4$ and condensed in vacuo. The residue was purified on a silica gel column with ethyl acetate-hexane (0-30%) as eluent system to afford the title compound in 39% (55 mg) yield. MS (ESI, M+H$^+$)=557.9

(R)-2-Amino-2-(5-(4-(octyloxy)-3-(trifluoromethyl)phenyl)-1H-pyrazol-3-yl)propan-1-ol (6a)

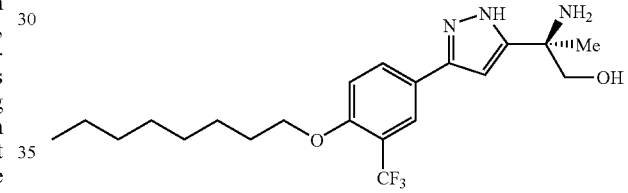

The solution of (S)-tert-butyl 2,2,4-trimethyl-4-(3-(4-(octyloxy)-3-(trifluoromethyl)-phenyl)-3-oxo-propanoyl)oxazolidine-3-carboxylate (27 mg, 0.05 mmol, 1.0 equiv) and hydrazine monohydrate (2.7 μL, 0.055 mmol, 1.1 equiv) in methanol (0.2 mL) was stirred at room temperature for 2 hours. The reaction was condensed and the residue was treated with 20% TFA-DCM for 30 min. After removal of excess amount of TFA and DCM, the crude product was purified by prep. HPLC and afforded the title compound as mono-TFA salt (5.0 mg). MS (ESI, M+H$^+$)=414.0; $^1$H NMR (400 MHz, CD$_3$OD) δ 7.81 (s, 1H), 7.76 (d, 1H, J=9.2 Hz), 7.14 (d, 1H, J=9.2 Hz), 6.56 (s, 1H), 4.03 (t, 2H, J=6.0 Hz), 3.79, 3.67 (AB, 2H, J=12.0 Hz), 1.76-1.69 (m, 2H), 1.59 (s, 3H), 1.46-1.38 (m, 2H), 1.32-1.16 (m, 8H), 0.81 (t, 3H, J=7.2 Hz).

(S)-2-Amino-2-(3-(4-(octyloxy)-3-(trifluoromethyl)phenyl)isoxazol-5-yl)propan-1-ol (7a)

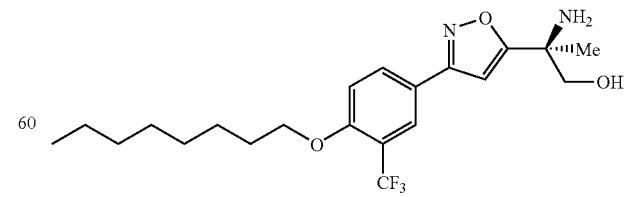

The solution of (S)-tert-butyl 2,2,4-trimethyl-4-(3-(4-(octyloxy)-3-(trifluoromethyl)-phenyl)-3-oxo-propanoyl)oxazolidine-3-carboxylate (27 mg, 0.05 mmol, 1.0 equiv) and hydroxylamine hydrochloride (6.6 mg, 0.10 mmol, 2.0 equiv) in pyridine (0.5 mL) was stirred at 60° C. for 2 days. The reaction was condensed and the residue was treated with 20% TFA-DCM for 30 min. After removal of excess amount of TFA and DCM, the crude product was purified by prep. HPLC and afforded the title compound as mono-TFA salt (6.0 mg). MS (ESI, M+H$^+$)=415.0; $^1$H NMR (400 MHz, CD$_3$OD) δ 8.06 (s, 1H), 8.04 (d, 1H, J=9.6 Hz), 7.31 (d, 1H, J=9.6 Hz), 7.03 (s, 1H), 4.16 (t, 2H, J=6.0 Hz), 4.01, 3.83 (AB, 2H, J=12.0 Hz), 1.87-1.80 (m, 2H), 1.75 (s, 3H), 1.56-1.47 (m, 2H), 1.40-1.32 (m, 8H), 0.91 (t, 3H, J=7.2 Hz).

General Approach to Synthesis of Phenyl-Pyridine Analogs

Synthesis of phenyl-pyridine analogs is described in Scheme 8. Reaction of desired alcohol with substituted halo-benzene 1 afforded the halo-benzene-ether 2. The substituted halo-benzene-ether 2 was then treated with n-butyl lithium, B(OMe)$_3$, and pinacol respectively to afford ester 3. Suzuki cross-coupling of ester 3 with compound 4 gave biaryl 5 which upon reduction and deprotection afforded amino alcohol 6.

Scheme 8:

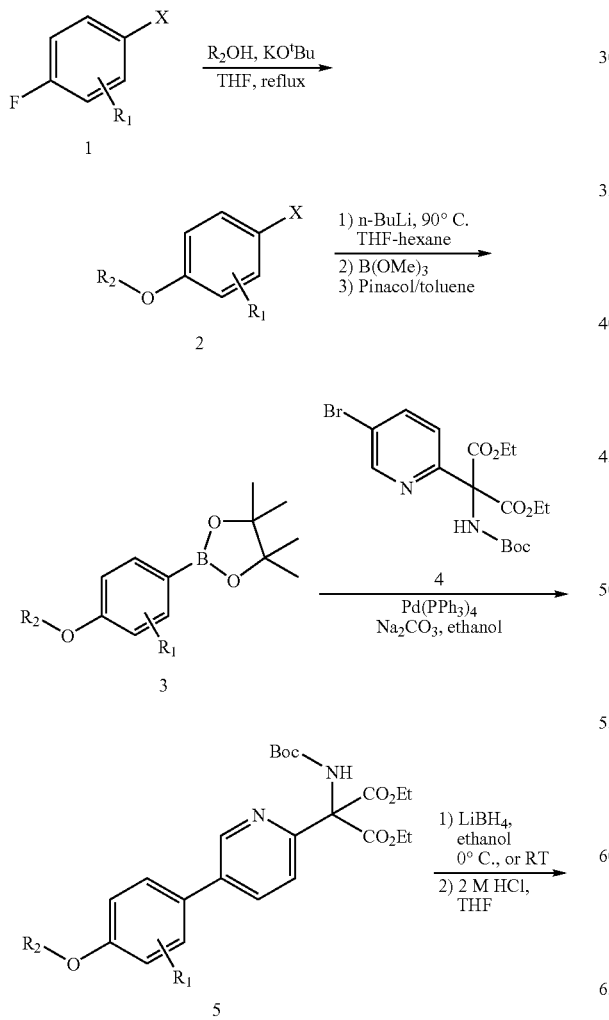

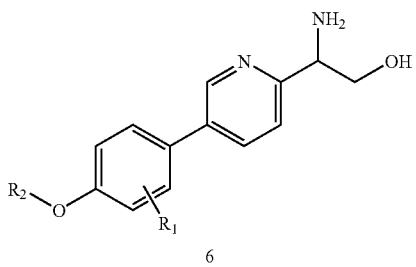

6

4-Bromo-1-(octyloxy)-2-(trifluoromethyl)benzene (2a)

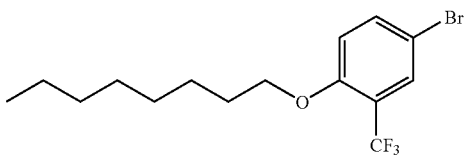

Using 4-bromo-1-fluoro-2-(trifluoromethyl)benzene as starting material, standard aromatic fluoro-substitution with n-octanol provided the title compound in quantitative yield. $^1$H NMR (400 MHz, CDCl$_3$) δ 7.65 (δ, 1H, J=2.4 Hz), 7.55 (dd, 1H, J=8.8 Hz, J=2.4 Hz), 6.85 (d, 1H, J=8.8 Hz), 4.01 (t, 2H, J=6.4 Hz), 1.80 (m, 2H), 1.46 (m, 2H), 1.32 (m, 8H), 0.90 (t, 2H, J=5.6 Hz).

4,4,5,5-Tetramethyl-2-(4-(octyloxy)-3-(trifluoromethyl)phenyl)-1,3,2-dioxaborolane (3a)

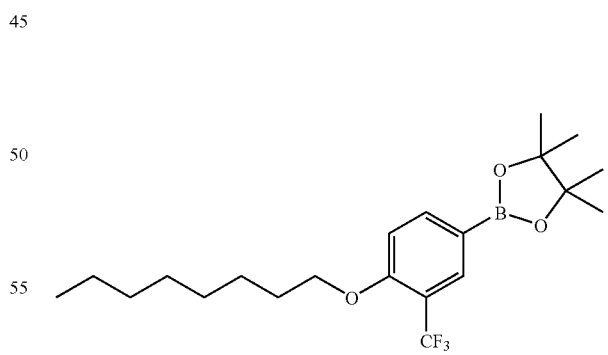

Using 4-bromo-1-(octyloxy)-2-(trifluoromethyl)benzene as starting material, the title compound was prepared using a literature procedure in 96% yield (J. Am. Chem. Soc. 2004, 126, 14316-14317). $^1$H NMR (400 MHz, CDCl$_3$) (7.99 (s, 1H), 7.89 (dd, 1H, J=8.4 Hz, J=1.2 Hz), 6.95 (d, 1H, J=8.4 Hz), 4.06 (t, 2H, J=6.0 Hz), 1.81 (m, 2H), 1.47 (m, 2H), 1.36-1.28 (m, 8H), 0.88 (t, 2H, J=7.2 Hz).

Diethyl 2-(tert-butoxycarbonylamino)-2-(5-(4-(octyloxy)-3-(trifluoromethyl)-phenyl)pyridin-2-yl)malonate (5a)

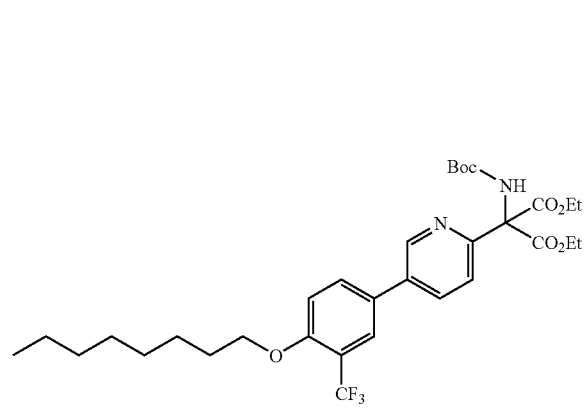

The suspension of 4,4,5,5-tetramethyl-2-(4-(octyloxy)-3-(trifluoromethyl)phenyl)-1,3,2-dioxaborolane 3a (136 mg, 0.34 mmol, 1.5 equiv), diethyl 2-(5-bromopyridin-2-yl)-2-(tert-butoxycarbonylamino)malonate (98 mg, 0.23 mmol, 1.0 equiv), Pd(PPh$_3$)$_4$ (26.3 mg, 0.023 mmol, 0.1 equiv), and Na$_2$CO$_3$ (120 mg, 1.14 mmol, 4.0 equiv) in ethanol-H$_2$O was heated at 80° C. for 1 hour. The reaction mixture was filtered and the filtrate was purified by silica gel column to afford the title compound in 77% (110 mg) yield. MS (ESI, M+H$^+$)=625.1; $^1$H NMR (400 MHz, CDCl$_3$) δ 8.66 (s, 1H), 7.88 (s, 1H), 7.86 (dd, 1H, J=8.4 Hz, J=2.0 Hz), 7.75 (d, J=2.5 Hz), 7.66 (d, 1H, J=8.4 Hz), 7.08 (d, 1H, J=8.4 Hz), 6.82 (s, 1H), 4.30 (m, 4H), 4.09 (t, 2H, J=6.0 Hz), 1.84 (m, 2H), 1.46 (m, 11H), 1.28 (m, 14H), 0.90 (t, 3H, J=7.2 Hz).

2-Amino-2-(5-(4-(octyloxy)-3-(trifluoromethyl)phenyl)pyridin-2-yl)ethanol (6a)

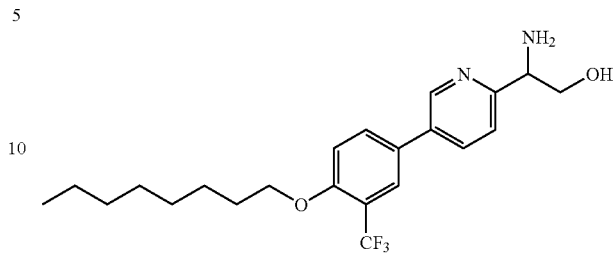

Diethyl 2-(tert-butoxycarbonylamino)-2-(5-(4-(octyloxy)-3-(trifluoromethyl)-phenyl)-pyridin-2-yl)malonate 5a (110 mg, 0.176 mmol, 1.0 equiv) in THF (2.0 mL) was added LiBH$_4$ (57 mg, 2.64 mmol, 15.0 equiv) at 0° C., followed by addition of ethanol (0.8 mL) carefully. The resultant was warmed up to room temperature for 10 minutes. LC-MS indicated the completion of the reaction. The reaction was terminated by addition of water. Extraction with ethyl acetate and the organic layer was washed with brine and dried over sodium sulfate and condensed. The residue (crude reduction product with significant decarboxylation) was treated with 2M HCl in THF to afford the title compound after preparative HPLC purification. MS (ESI, M+H$^+$)=411.1; $^1$H NMR (400 MHz, DMSO-d$_6$) δ 8.95 (d, 1H, J=2.4 Hz), 8.39 (s, 3H), 8.22 (dd, 1H, J=8.4 Hz, J=2.4 Hz), 8.01 (dd, 1H, J=8.4 Hz, J=2.0 Hz), 7.93 (d, 1H, J=2.0 Hz), 7.60 (d, 1H, J=8.4 Hz), 7.39 (d, 1H, J=9.2 Hz), 5.48 (br, 1H), 4.48 (br, 1H), 4.17 (t, 2H, J=6.0 Hz), 3.86-3.72 (m, 2H), 1.75 (m, 2H), 1.44 (m, 2H), 1.29 (m, 8H), 0.86 (t, 3H, J=6.8 Hz).

(R)-t-Butyl 2,2,4-trimethyl-4-(5-(4-(octyloxy)-3-(trifluoromethyl)phenyl)-1,3,4-oxadi-azol-2-yl)oxazolidine-3-carboxylate

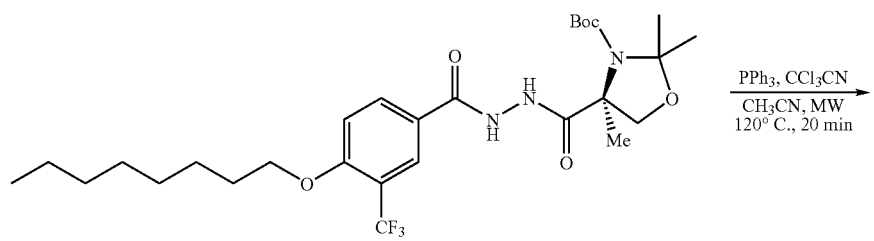

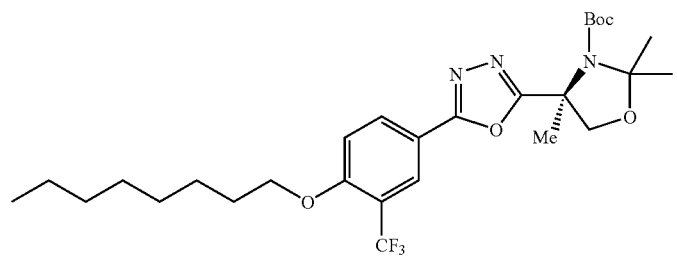

The title compound was prepared from (S)-t-butyl-2,2,4-trimethyl-4-(2-(4-(octyloxy)benzoyl)hydrazinecarbonyl)oxazolidine-3-carboxylate using published procedure (Tet. Letters, 2006, 47, 105-108) in 85% yield. MS (ESI, M+H$^+$)=556.1; $^1$H NMR (400 MHz, CDCl$_3$) δ 8.22 (d, 1H, J=1.6 Hz), 8.14 (d, 1H, J=8.8 Hz), 8.10 (dd, 1H, J=8.8 Hz, J=1.6 Hz), 4.22 (d, 1H, J=8.8 Hz), 4.12 (t, 2H, J=6.0 Hz), 4.01 (m, 1H), 1.94 (s, 3H), 1.85 (m, 2H), 1.76 (s, 3H), 1.72 (s, 3H), 1.51-1.46 (m, 4H), 1.22 (m, 7H), 1.25 (s, 6H), 0.89 (t, 3H, J=7.2 Hz).

(S)-2-Amino-2-(5-(4-(octyloxy)-3-(trifluoromethyl)phenyl)-1,3,4-oxadiazol-2-yl)propan-1-ol

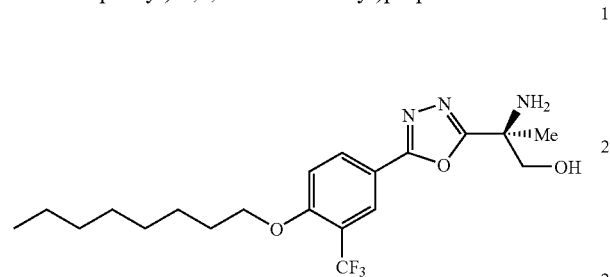

Standard 20% TFA deprotection of (R)-t-butyl 2,2,4-trimethyl-4-(5-(4-(octyloxy)-3-(trifluoromethyl)phenyl)-1,3,4-oxadi-azol-2-yl)oxazolidine-3-carboxylate afforded the title compound in 55% yield. (ESI, M+H$^+$)=416.0; $^1$H NMR (400 MHz, CD$_3$OD) δ 8.18 (d, 1H, J=8.8 Hz), 8.18 (s, 1H), 7.30 (d, 1H, J=8.8 Hz), 4.12 (t, 2H, J=6.0 Hz), 4.01, 3.79 (AB, 2H, J=11.6 Hz), 1.74 (m, 2H), 1.68 (s, 3H), 1.43 (m, 2H), 1.31-1.19 (m, 8H), 0.81 (t, 3H, J=2.8 Hz).

General Approach to Synthesis of Ether-Phenyl-Thiazoles

The synthesis of 2,5-substituted thiazoles is described in Scheme 9. Reaction of the desired alcohol para-methoxybenzyl alcohol (PMB-OH) with substituted 4-fluoroacetophenone 1 afforded the acetophenone intermediate 2. Acetophenone intermediate 2 was then converted to the corresponding bromo-acetophenone using Bu$_4$NBr$_3$ which, upon reaction with NaN$_3$, provided the azido-acetophenone intermediate. Hydrogenation of the azido-acetophenone intermediate afforded amine 3, followed by coupling with orthogonally protected amino acid 4 gave amide 5. Removal of PMB group under hydrogenation gave phenol 6. Mitsunobu reaction of the phenol 6 with the desired alcohol followed by thiazole formation under Lawesson's reagent conditions afforded intermediate 7 in good yield. Removal of the protecting group from intermediate 7 afforded the final amino-alcohol 8.

Scheme 9:

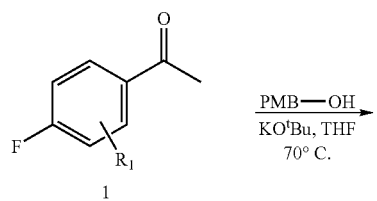

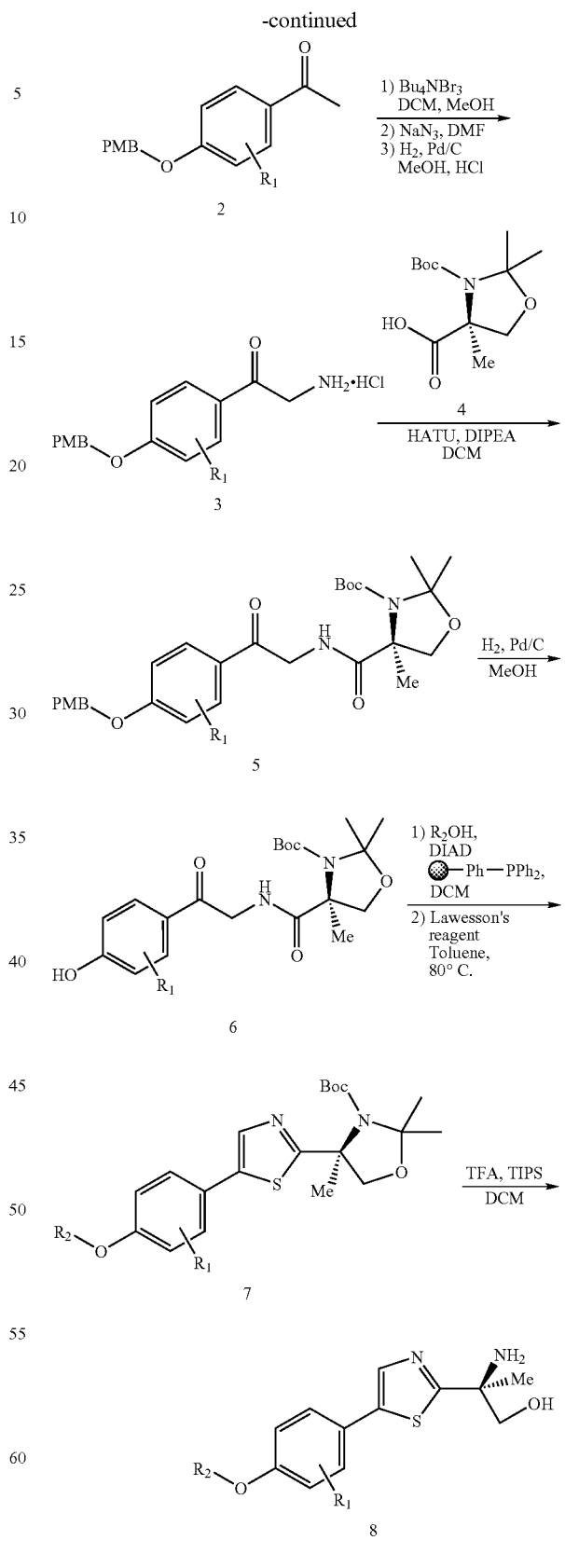

For general protocol for synthesis of compound 2, 3, 4, and 5 refer to scheme 1.

1-(4-(4-Methoxybenzyloxy)-3-(trifluoromethyl)phenyl)ethanone (2a)

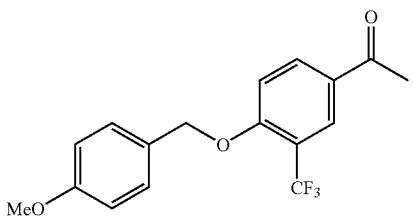

For general protocol for synthesis of compound 2 refer to scheme 1. The product was purified by silica gel column chromatography using the Combi-Flash system (Hex: EtOAc) as colorless oil in 90% (4.25 g). HPLC retention time on a C8(2) column (30×3.00 mm, 3μ) is 2.02 min with gradient 50-98% acetonitrile-$H_2O$ (0.1% TFA) in 4.0 min as mobile phase. TLC (1:3 EtOAc:Hex), $R_f$=0.4; $^1$H NMR (400 MHz, $CDCl_3$) δ 8.20 (d, 1H, J=1.6 Hz), 8.09 (dd, 1H, J=8.8 Hz, J=2.0 Hz), 7.35 (d, 2H, J=8.4 Hz), 7.09 (d, 1H, J=8.4 Hz), 6.93 (d, 2H, J=8.4 Hz), 5.21 (s, 2H), 3.82 (s, 3H), 2.58 (s, 3H).

2-Azido-1-(4-(4-methoxybenzyloxy)-3-(trifluoromethyl)phenyl)ethanone

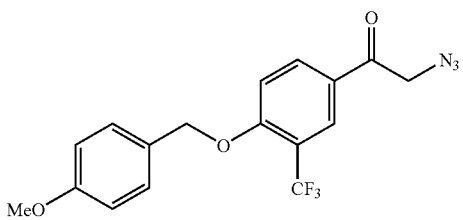

For general protocol for synthesis of azido intermediate refer to scheme 1. The product was purified by silica gel column chromatography using the Combi-Flash system (Hex:EtOAc) as yellow solid in 76% (3.64 g) yield from acetophenone 2a. HPLC retention time on a C8(2) column (30×3.00 mm, 3μ) is 2.20 min with gradient 50-98% acetonitrile-$H_2O$ (0.1% TFA) in 4.0 min as mobile phase. TLC (1:3 EtOAc:Hex), $R_f$=0.3; $^1$H NMR (400 MHz, $CDCl_3$) δ 8.15 (d, 1H, J=2.0 Hz), 8.05 (dd, 1H, J=8.8 Hz, J=2.4 Hz), 7.33-7.36 (m, 2H), 7.12 (d, 1H, J=8.8 Hz), 6.90-6.94 (m, 2H), 5.22 (s, 2H), 4.51 (s, 2H), 3.82 (s, 3H).

(R)-tert-Butyl 4-(2-(4-(4-methoxybenzyloxy)-3-(trifluoromethyl)phenyl)-2-oxoethylcarbamoyl)-2,2,4-trimethyloxazolidine-3-carboxylate (5a)

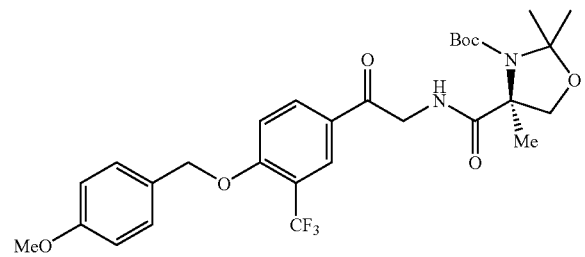

For general protocol for synthesis of compound 5 refer to scheme 1. The reaction was stirred at room temperature for 2 hours. The product was purified by silica gel column chromatography using the Combi-Flash system (Hex:EtOAc) as yellow foam in 72% (2.44 g) yield from amino-acetophenone 3a. HPLC retention time on a C8(2) column (30×3.00 mm, 3μ) is 2.51 min with gradient 50-98% acetonitrile-$H_2O$ (0.1% TFA) in 4.0 min as mobile phase. TLC (1:1 EtOAc:Hex), $R_f$=0.5; $^1$H NMR (400 MHz, $CDCl_3$) δ 8.24 (br s, 1H), 8.09 (br d, 1H, J=8.4 Hz), 7.32-7.39 (m, 2H), 7.12 (d, 1H, J=8.4 Hz), 6.90-6.97 (m, 2H), 5.22 (s, 2H), 4.70 (t, 2H, J=5.2 Hz), 4.30 (br s, 1H), 3.78-3.86 (m, 5H), 1.38-1.85 (m, 18H).

(R)-tert-Butyl 4-(2-(4-hydroxy-3-(trifluoromethyl)phenyl)-2-oxoethylcarbamoyl)-2,2,4-trimethyloxazolidine-3-carboxylate (6a)

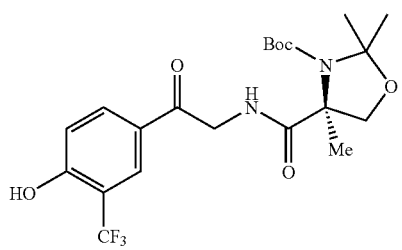

To a solution of (R)-tert-butyl 4-(2-(4-(4-methoxybenzyloxy)-3-(trifluoromethyl)phenyl)-2-oxoethylcarbamoyl)-2,2,4-trimethyloxazolidine-3-carboxylate (4) (2.4 g, 4.1 mmol, 1.0 equiv) in methanol (20 mL) was added 10% Pd/C (240 mg). The reaction mixture was stirred for 3 hours at rt under $H_2$ atmosphere using a $H_2$ balloon, filtered through celite and concentrated to give (R)-tert-butyl 4-(2-(4-hydroxy-3-(trifluoromethyl)phenyl)-2-oxoethylcarbamoyl)-2,2,4-trimethyloxazolidine-3-carboxylate (6a) as a white foam in quantitative yield. HPLC retention time on a C18 column (30×4.6 mm, 3.5μ) was 2.62 min with gradient 10-95% acetonitrile-$H_2O$ (0.1% TFA) in 3.5 min as mobile phase. MS (ESI, $M+H^+$)=461.4.

(R)-tert-Butyl 2,2,4-trimethyl-4-(2-oxo-2-(4-(6-phenylhexyloxy)-3-(trifluoromethyl)phenyl)ethylcarbamoyl)oxazolidine-3-carboxylate

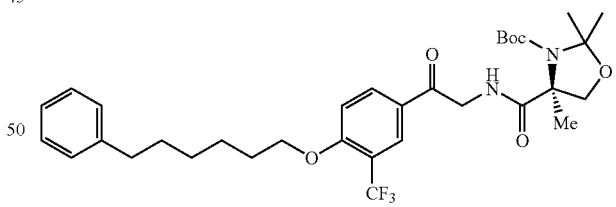

To a solution of (R)-tert-butyl 4-(2-(4-hydroxy-3-(trifluoromethyl)phenyl)-2-oxoethylcarbamoyl)-2,2,4-trimethyloxazolidine-3-carboxylate (114 mg, 0.25 mmol, 1.0 equiv) and 6-phenylhexan-1-ol (45 mg, 0.25 mmol, 1.0 equiv) in DCM (1 mL) was added polymer bond $PPh_3$ (125 mg, 0.75 mmol, 3.0 equiv). The reaction mixture was stirred at rt for 0.5 hour and cooled to 0° C. A solution of DIAD (0.053 mL, 0.25 mmol, 1.0 equiv) in DCM (0.5 mL) was added drop wise to the reaction mixture. The reaction mixture was stirred at rt for 2 hours, filtered and evaporated under reduced pressure to give a residue, which was purified by $SiO_2$ column chromatograph (30-50% EtOAc in hexanes) to give (R)-tert-butyl 2,2,4-trimethyl-4-(2-oxo-2-(4-(6-phenylhexyloxy)-3-(trifluoromethyl)phenyl)ethylcarbamoyl)oxazolidine-3-carboxylate in 75% (155 mg) yield. HPLC retention time on a C18 column (30×4.6 mm, 3.5μ) was 3.31 min with gradient 50-95% acetonitrile-H$_2$O (0.1% TFA) in 3.5 min as mobile phase. MS (ESI, M+H$^+$)=621.6.

(R)-tert-Butyl 2,2,4-trimethyl-4-(2-oxo-2-(3-(trifluoromethyl)-4-(5-(4-(trifluoromethyl)phenyl)pentyloxy)phenyl)ethylcarbamoyl)oxazolidine-3-carboxylate

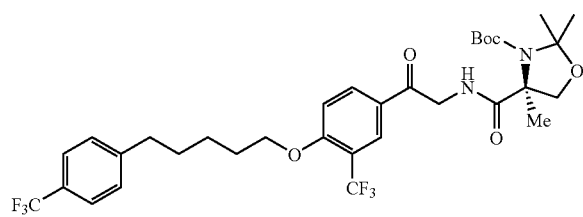

The title compound was prepared from (R)-tert-butyl 4-(2-(4-hydroxy-3-(trifluoromethyl)phenyl)-2-oxoethylcarbamoyl)-2,2,4-trimethyloxazolidine-3-carboxylate (0.25 mmol, 1.0 equiv) and 5-(4-(trifluoromethyl)phenyl)pentan-1-ol (0.25 mmol, 1.0 equiv) according to the general procedure in 31% yield. HPLC retention time on a C18 column (30×4.6 mm, 3.5 V) was 3.26 min with gradient 50-95% acetonitrile-H$_2$O (0.1% TFA) in 3.5 min as mobile phase. MS (ESI, M+H$^+$)=675.6.

(R)-tert-Butyl 2,2,4-trimethyl-4-(5-(4-(6-phenylhexyloxy)-3-(trifluoromethyl)phenyl)thiazol-2-yl)oxazolidine-3-carboxylate (7a)

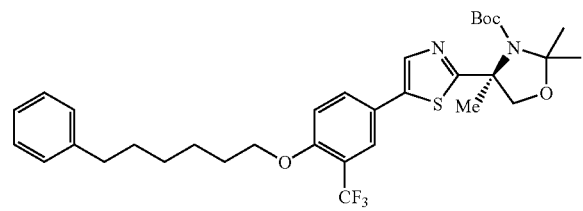

To a solution of (R)-tert-butyl 2,2,4-trimethyl-4-(2-oxo-2-(4-(6-phenylhexyloxy)-3-(trifluoromethyl)phenyl)ethylcarbamoyl)oxazolidine-3-carboxylate (49 mg, 0.079 mmol, 1.0 equiv) in toluene (1 mL) was added Lawesson's reagent (32 mg, 0.087 mmol, 1.1 equiv). The reaction mixture was heated at 80° C. for 3 h. The crude product was purified directly by SiO$_2$ column chromatograph (EtOAc/hexanes, 3:7) to give (R)-tert-butyl 2,2,4-trimethyl-4-(5-(4-(6-phenylhexyloxy)-3-(trifluoromethyl)phenyl)thiazol-2-yl)oxazolidine-3-carboxylate. HPLC retention time on a C8(2) column (30×50 mm, 3μ) is 3.29 min with gradient 70-98% acetonitrile-H$_2$O (0.1% TFA) in 3.5 min as mobile phase. MS (ESI, M+H$^+$)=619.0.

(R)-tert-Butyl 2,2,4-trimethyl-4-(5-(3-(trifluoromethyl)-4-(5-(4-(trifluoromethyl)phenyl)pentyloxy)phenyl)thiazol-2-yl)oxazolidine-3-carboxylate (7b)

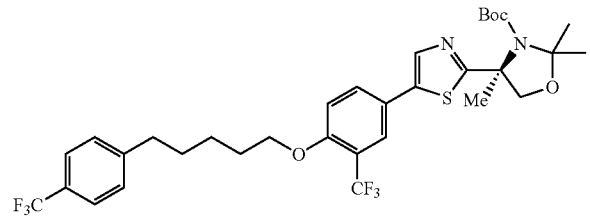

The title compound was prepared from (R)-tert-butyl 2,2,4-trimethyl-4-(2-oxo-2-(3-(trifluoromethyl)-4-(5-(4-(trifluoromethyl)phenyl)pentyloxy)phenyl)ethylcarbamoyl)-oxazolidine-3-carboxylate. HPLC retention time on a C8(2) column (30×50 mm, 3μ) is 3.29 min with gradient 70-98% acetonitrile-H$_2$O (0.1% TFA) in 3.5 min as mobile phase. MS (ESI, M+H$^+$)=673.0.

(S)-2-Amino-2-(5-(4-(6-phenylhexyloxy)-3-(trifluoromethyl)phenyl)thiazol-2-yl)propan-1-ol (8a)

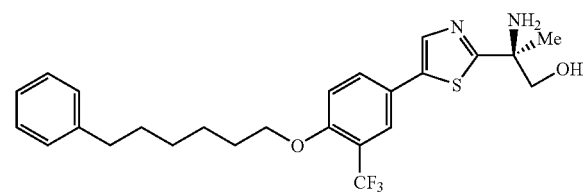

The title compound was prepared from (R)-tert-butyl 2,2,4-trimethyl-4-(5-(4-(6-phenylhexyloxy)-3-(trifluoromethyl)phenyl)thiazol-2-yl)oxazolidine-3-carboxylate. HPLC retention time on a C18 column (30×4.6 mm, 3.5μ) was 2.41 min with gradient 10-95% acetonitrile-H$_2$O (0.1% TFA) in 3.5 min as mobile phase. MS (ESI, M+H$^+$)=479.4; $^1$H NMR (400 MHz, CDCl$_3$) δ 7.76 (s, 1H), 7.65 (d, 1H, J=2.0 Hz), 7.55 (dd, 1H, J=8.8 Hz, J=2.0 Hz), 7.28-7.23 (m, 2H), 7.18-7.15 (m, 3H), 6.96 (d, 1H, J=9.2 Hz), 4.06-3.99 (m, 4H), 2.62 (t, 2H, J=7.6 Hz), 1.85-1.78 (m, 5H), 1.69-1.62 (m, 2H), 1.56-1.50 (m, 2H), 1.44-1.38 (m, 2H).

(S)-2-Amino-2-(5-(3-(trifluoromethyl)-4-(5-(4-(trifluoromethyl)phenyl)pentyloxy)phenyl)thiazol-2-yl)propan-1-ol (8b)

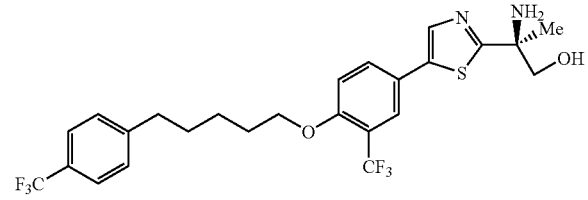

The title compound was prepared from (R)-tert-butyl 2,2,4-trimethyl-4-(5-(3-(trifluoromethyl)-4-(5-(4-(trifluoromethyl)phenyl)pentyloxy)phenyl)thiazol-2-yl)oxazolidine-3- carboxylate. HPLC retention time on a C18 column (30×4.6 mm, 3.5μ) was 2.50 min with gradient 10-95% acetonitrile-H$_2$O (0.1% TFA) in 3.5 min as mobile phase. MS (ESI, M+H$^+$)=533.4; $^1$H NMR (400 MHz, CDCl$_3$) δ 7.77 (s, 1H), 7.66 (d, 1H, J=2.0 Hz), 7.56 (dd, 1H, J=9.0 Hz, J=2.4 Hz), 7.52 (d, 2H, J=8.0 Hz), 7.28 (d, 2H, J=8.0 Hz), 6.97 (d, 1H, J=8.8 Hz), 4.07-4.03 (m, 4H), 2.70 (t, 2H, J=7.8 Hz), 1.89-1.82 (m, 5H), 1.74-1.67 (m, 2H), 1.57-1.50 (m, 2H).

General Method for Phosphate Synthesis

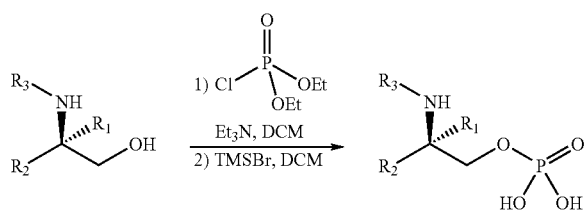

R$_3$=H or protecting group

Synthetic strategy for synthesis of desired phosphates is illustrated above. To a solution of unprotected amino alcohol (1.0 equiv) in dry CH$_2$Cl$_2$ at RT was added excess diethyl chlorophosphate (10.0 equiv) and triethylamine (20.0 equiv) and the reaction stirred for 12-18 hours. The reaction was monitored by LC-MS. The crude reaction mixture was then evaporated to dryness in vacuo. The obtained phospho-diester intermediate was reacted with excess bromotrimethylsilane (10.0-20.0 equiv) in dry CH$_2$Cl$_2$ at RT over a period of 6-10 hours to afford the final phosphate which was purified by reverse-phase preparative HPLC after evaporation of the solvent and excess reagent.

(S)-2-Amino-2-(5-(4-(octylthio)-3-(trifluoromethyl)phenyl)-1,3,4-thiadiazol-2-yl)propyl dihydrogen phosphate (a)

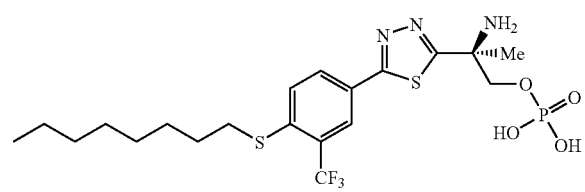

MS (ESI, M+H$^+$)=528.0; HPLC retention time on a C8(2) column (30×3.00 mm, 3μ) is 2.27 min with gradient 30-98% acetonitrile-H$_2$O (0.1% TFA) in 3.5 min as mobile phase.

(S)-2-Amino-2-(5-(4-(nonyloxy)-3-(trifluoromethyl)phenyl)-1,3,4-thiadiazol-2-yl)propyl dihydrogen phosphate (b)

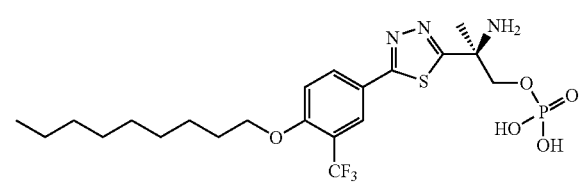

MS (ESI, M+H$^+$)=526.0; HPLC retention time on a Synergi-Max RP column (2×20 mm, 2 μL) is 1.51 min with gradient 30-99% acetonitrile-H$_2$O (0.1% TFA) in 2 min as mobile phase.

(S)-2-Amino-2-(5-(3-(trifluoromethyl)-4-(5-(3-(trifluoromethyl)phenyl)pentyloxy)phenyl)-1,3,4-thiadiazol-2-yl)propyl dihydrogen phosphate (c)

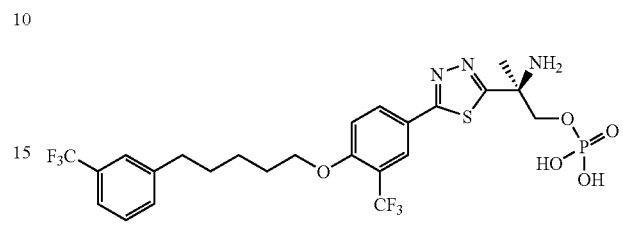

MS (ESI, M+H$^+$)=614.0; HPLC retention time on a Synergi-Max RP column (2×20 mm, 2 μL) is 1.44 min with gradient 30-99% acetonitrile-H$_2$O (0.1% TFA) in 2 min as mobile phase.

(S)-2-Amino-2-(5-(3-(trifluoromethyl)-4-(5-(4-(trifluoromethyl)phenyl)pentyloxy)phenyl)-1,3,4-thiadiazol-2-yl)propyl dihydrogen phosphate (d)

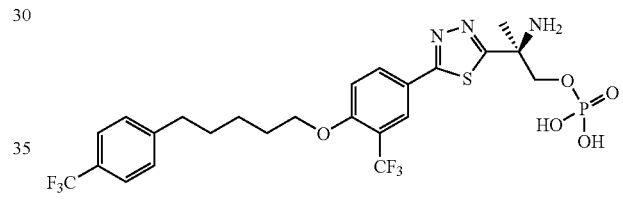

MS (ESI, M+H$^+$)=614.0; HPLC retention time on a Synergi-Max RP column (2×20 mm, 2 μL) is 1.44 min with gradient 30-99% acetonitrile-H$_2$O (0.1% TFA) in 2 min as mobile phase.

(S)-2-Amino-2-(5-(4-((4-phenyl-5-(trifluoromethyl)thiophen-2-yl)methoxy)-3-(trifluoromethyl)phenyl)-1,3,4-thiadiazol-2-yl)propyl dihydrogen phosphate (e)

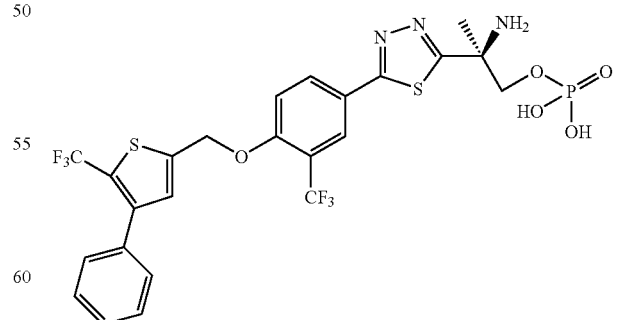

MS (ESI, M+H$^+$)=639.8; HPLC retention time on a Synergi-Max RP column (2×20 mm, 2 μL) is 1.37 min with gradient 30-99% acetonitrile-H$_2$O (0.1% TFA) in 2 min as mobile phase.

(S)-2-Amino-2-(5-(4-(6-phenylhexyloxy)-3-(trifluoromethyl)phenyl)-1,3,4-thiadiazol-2-yl)propyl dihydrogen phosphate (f)

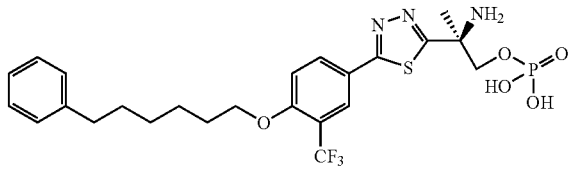

MS (ESI, M+H⁺)=599.9; HPLC retention time on a Synergi-Max RP column (2×20 mm, 2 μL) is 1.41 min with gradient 30-99% acetonitrile-H₂O (0.1% TFA) in 2 min as mobile phase.

(S)-2-Amino-2-(5-(4-(5-(3-fluorophenyl)pentyloxy)-3-(trifluoromethyl)phenyl)-1,3,4-thiadiazol-2-yl)propyl dihydrogen phosphate (g)

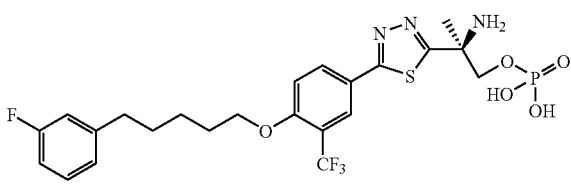

MS (ESI, M+H⁺)=563.9; HPLC retention time on a Synergi-Max RP column (2×20 mm, 2 μL) is 1.53 min with gradient 20-95% acetonitrile-H₂O (0.1% TFA) in 2 min as mobile phase.

(S)-2-Amino-2-(5-(4-(5-(4-fluorophenyl)pentyloxy)-3-(trifluoromethyl)phenyl)-1,3,4-thiadiazol-2-yl)propyl dihydrogen phosphate (h)

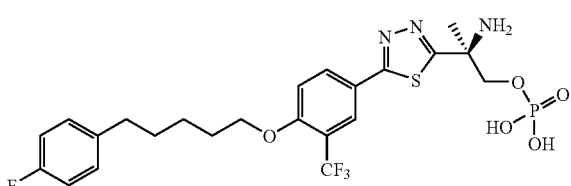

MS (ESI, M+H⁺)=593.9; HPLC retention time on a Synergi-Max RP column (2×20 mm, 2 μL) is 1.57 min with gradient 20-95% acetonitrile-H₂O (0.1% TFA) in 2 min as mobile phase.

(S)-2-Amino-2-(5-(3-(trifluoromethyl)-4-(4-(3-(trifluoromethyl)phenyl)butoxy)phenyl)-1,3,4-thiadiazol-2-yl)propyl dihydrogen phosphate (i)

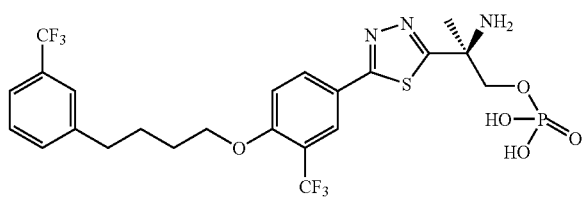

MS (ESI, M+H⁺)=599.9; HPLC retention time on a Synergi-Max RP column (2×20 mm, 2 μL) is 2.03 min with gradient 20-95% acetonitrile-H₂O (0.1% TFA) in 2 min as mobile phase.

(S)-2-Amino-2-(5-(4-(4-(4-fluorophenyl)butoxy)-3-(trifluoromethyl)phenyl)-1,3,4-thiadiazol-2-yl)propyl dihydrogen phosphate (j)

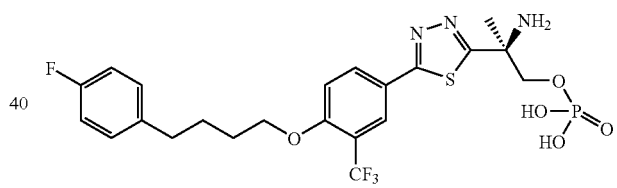

MS (ESI, M+H⁺)=549.9; HPLC retention time on a Synergi-Max RP column (2×20 mm, 2 μL) is 1.51 min with gradient 20-95% acetonitrile-H₂O (0.1% TFA) in 2 min as mobile phase.

(S)-2-Amino-2-(5-(4-(6-(3-fluorophenyl)hexyloxy)-3-(trifluoromethyl)phenyl)-1,3,4-thiadiazol-2-yl)propyl dihydrogen phosphate (k)

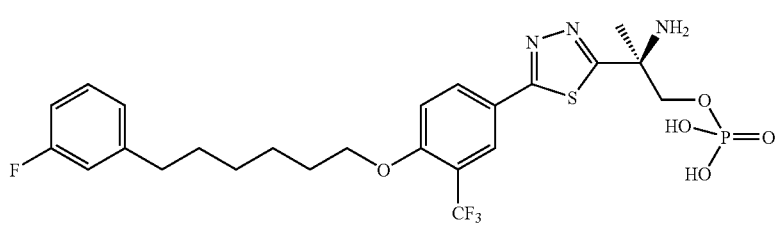

MS (ESI, M+H⁺)=577.9; HPLC retention time on a Synergi-Max RP column (2×20 mm, 2 μL) is 1.65 min with gradient 20-95% acetonitrile-H₂O (0.1% TFA) in 2 min as mobile phase.

(S)-2-Amino-2-(5-(4-(6-(4-fluorophenyl)hexyloxy)-3-(trifluoromethyl)phenyl)-1,3,4-thiadiazol-2-yl)propyl dihydrogen phosphate (l)

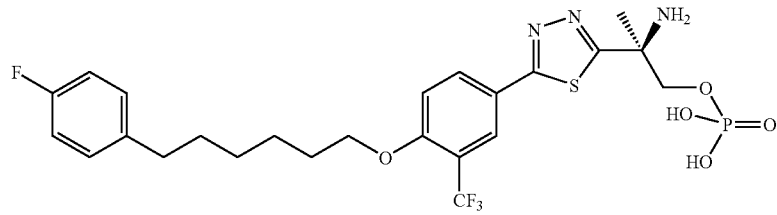

MS (ESI, M+H⁺)=578.0; HPLC retention time on a Synergi-Max RP column (2×20 mm, 2 μL) is 1.63 min with gradient 20-95% acetonitrile-H₂O (0.1% TFA) in 2 min as mobile phase.

(S)-2-Amino-2-(5-(4-(5-(3,4-difluorophenyl)pentyloxy)-3-(trifluoromethyl)phenyl)-1,3,4-thiadiazol-2-yl)propyl dihydrogen phosphate (m)

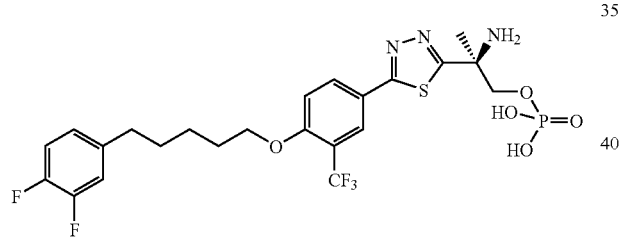

MS (ESI, M+H⁺)=582.0; HPLC retention time on a Synergi-Max RP column (2×20 mm, 2 μL) is 1.58 min with gradient 20-95% acetonitrile-H₂O (0.1% TFA) in 2 min as mobile phase.

(S)-2-Amino-2-(5-(3-(trifluoromethyl)-4-(5-(2,4,5-trifluorophenyl)pentyloxy)phenyl)-1,3,4-thiadiazol-2-yl)propyl dihydrogen phosphate (n)

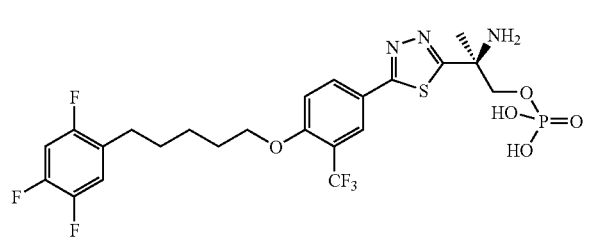

MS (ESI, M+H⁺)=599.9; HPLC retention time on a Synergi-Max RP column (2×20 mm, 2 μL) is 1.59 min with gradient 20-95% acetonitrile-H₂O (0.1% TFA) in 2 min as mobile phase.

(S)-2-Amino-2-(3-(4-(octyloxy)-3-(trifluoromethyl)phenyl)-1,2,4-oxadiazol-5-yl)propyl dihydrogen phosphate (o)

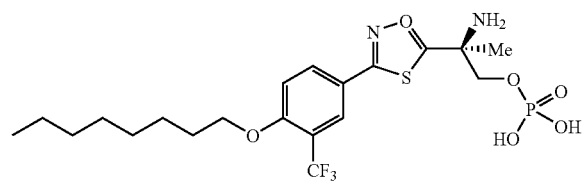

The title product was obtained according to general procedure from compound 7a (Scheme 6). MS (ESI, M+H⁺)=496.0

(R)-2-Amino-2-(3-(4-(octyloxy)-3-(trifluoromethyl)phenyl)-1H-pyrazol-5-yl)propyl dihydrogen phosphate (p)

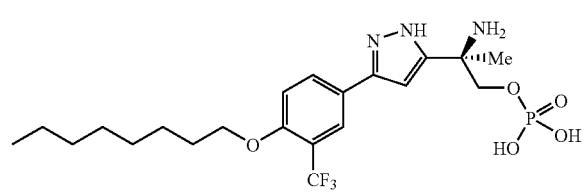

The title product was obtained according to general procedure from compound 3a (Scheme 7). MS (ESI, M+H⁺)=494.1

(S)-2-Amino-2-(3-(4-(octyloxy)-3-(trifluoromethyl)phenyl)isoxazol-5-yl)propyl dihydrogen phosphate (q)

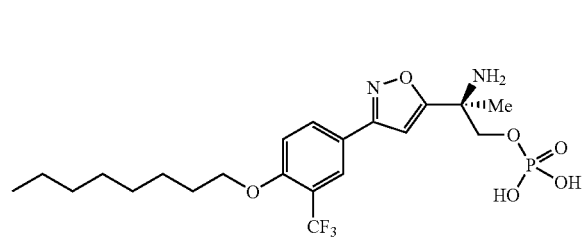

The title product was obtained according to general procedure from compound 3a (Scheme 7). MS (ESI, M+H⁺)=495.0

(S)-2-Amino-2-(5-(4-(octyloxy)-3-(trifluoromethyl)phenyl)-1,3,4-oxadiazol-2-yl)propyl dihydrogen phosphate (q)

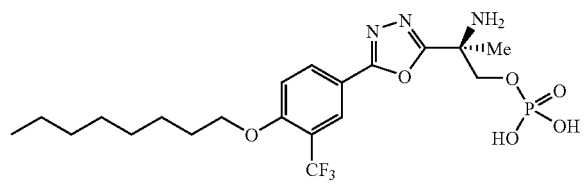

The title product was obtained according to general procedure from the corresponding amino-alcohol. MS (ESI, M+H⁺)=496.0

(S)-2-Amino-2-(5-(4-(6-phenylhexyloxy)-3-(trifluoromethyl)phenyl)thiazol-2-yl)propyl dihydrogen phosphate (r)

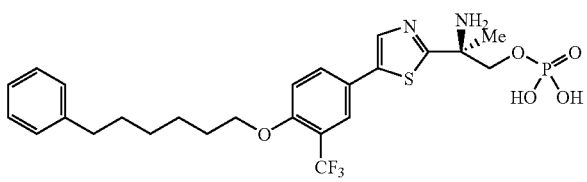

The title compound was prepared from (S)-2-amino-2-(5-(4-(6-phenylhexyloxy)-3-(trifluoromethyl)phenyl)thiazol-2-yl)propan-1-ol. HPLC retention time on a C18 column (30× 4.6 mm, 3.5µ) was 2.48 min with gradient 10-95% acetonitrile-H₂O (0.1% TFA) in 3.5 min as mobile phase. MS (ESI, M+H⁺)=559.5.

(S)-2-Amino-2-(5-(3-(trifluoromethyl)-4-(5-(4-(trifluoromethyl)phenyl)pentyloxy)phenyl)thiazol-2-yl)propyl dihydrogen phosphate (s)

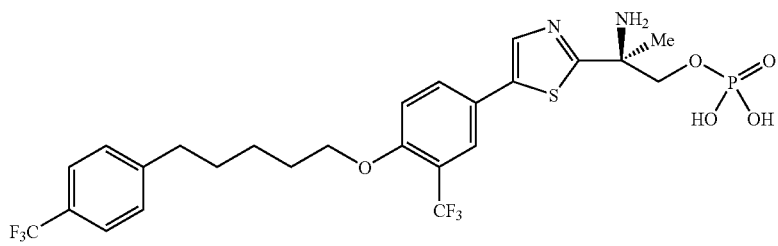

The title compound was prepared from (S)-2-amino-2-(5-(3-(trifluoromethyl)-4-(5-(4-(trifluoromethyl)phenyl)pentyloxy)phenyl)thiazol-2-yl)propan-1-ol. HPLC retention time on a C18 column (30×4.6 mm, 3.5µ) was 2.53 min with gradient 10-95% acetonitrile-H₂O (0.1% TFA) in 3.5 min as mobile phase. MS (ESI, M+H⁺)=613.5.

Examples of specific methods used to make (S)-2-Amino-2-(5-(4-(octyloxy)-3-(trifluoromethyl)phenyl)thiazol-2-yl)propan-1-ol and (S)-2-Amino-2-(5-(4-(octyloxy)-3-(trifluoromethyl)phenyl)-1,3,4-thiadiazol-2-yl)propan-1-ol Description 1

1-(4-(Octyloxy)-3-(trifluoromethyl)phenyl)ethanone (D1)

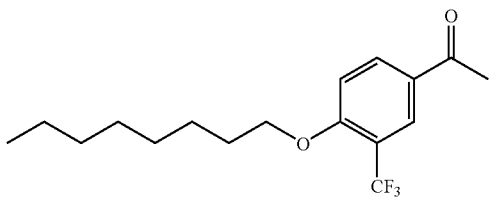

1-octanol (2 mL), 1-[4-fluoro-3-(trifluoromethyl)phenyl]ethanone (2.62 g), potassium tert-butoxide (14 mL, 1.0M) and tetrahydrofuran (30 mL) were heated at 65° C. for 3 hrs to produce the title product as a brownish oil (4.00 g). The product was purified by silica gel column chromatography using the Combi-Flash system (Hex:EtOAc) as white solid in 60% (1.20 g). TLC (1:5 EtOAc:Hex), R$_f$=0.4; ¹H NMR (400 MHz, CDCl₃) δ 8.18 (d, 1H, J=2.0 Hz), 8.10 (dd, 1H, J=8.8 Hz, J=2.3 Hz), 7.02 (d, 1H, J=8.8 Hz), 4.12 (t, 2H, J=6.4 Hz), 2.58 (m, 3H), 1.80-1.89 (m, 2H), 1.42-1.54 (m, 2H), 1.22-1.40 (m, 8H), 0.89 (t, 3H, J=6.7 Hz).

Description 1 Alternative Method (D1A)

1-(4-(Octyloxy)-3-(trifluoromethyl)phenyl)ethanone (D1)

A solution of n-octanol (13.3 g, 0.102 mol), in THF (224 mL) was treated with 1.0 M potassium t-butoxide in THF (112 mL, 1.1 equiv) at room temperature and heated to 65° C. After 15 minutes, a solution of 1-[4-fluoro-3-(trifluoromethyl)phenyl]ethanone (21 g, 1.0 equiv) in THF (224 mL) was charged slowly over 30 minutes. Vigorous gas evolution was noted during the addition. The reaction was monitored by HPLC and deemed complete after 1.5 h. The reaction mixture was cooled to ambient temperature, treated with 10% aqueous citric acid (250 mL), extracted with MTBE (2×500 mL), dried, and concentrated to afford the product (31.99 g, 99.3%, 88.1% AUC by HPLC). This reaction was repeated with slight modification as described above (reducing the amount of THF used to dissolve the acetophenone to 3 mL/g from 10.7 mL/g with improved control of gas evolution) on a 100 g scale to give 137.1 g, >100% yield). The two lots were combined and purified by column chromatography using silica-gel (1 kg), eluted with 10% ethyl acetate: 90% heptane to afford the title product (105 g, 75% yield) as a pale yellow color oil. Impure fractions were collected and provided 22.8 g (16.3% yield) of the product.

Description 2

2-Amino-1-(4-(octyloxy)-3-(trifluoromethyl)phenyl)ethanone hydrochloride (D2)

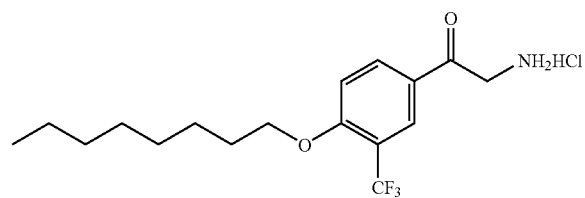

To a solution of 1-(4-(Octyloxy)-3-(trifluoromethyl)phenyl)ethanone (D1) (0.5 g, 1.0 equivalent) in CH$_2$Cl$_2$/MeOH (4:1, 10 mL) was added Bu$_4$NBr$_3$ (0.76 g, 1.0 equiv). The reaction mixture was stirred at room temperature for 3 hours. TLC (4:1, Hex/EtOAc), R$_f$=0.6. The solvent was removed in vacuo, and re-dissolved in DMF (10 mL). NaN$_3$ (0.31 g, 3.0 equiv) was added to the reaction and the resulting mixture was then stirred at room temperature for 2 hrs. The solvent was removed in vacuo and the product was purified by silica gel column chromatography using the Combi-Flash system (Hex:EtOAc) to give the azido-acetophenone product. TLC (4:1, Hex/EtOAc), R$_f$=0.4. The residue was then dissolved in concentrated HCl (1.0 mL) and MeOH (20 mL). 10% Pd/C (100 mg) was added and the mixture stirred under an atmosphere of H$_2$ (g) for 3 hours. The reaction mixture was then filtered and evaporated to dryness to give the title product as a yellow solid 98% (570 mg yield). TLC (4:1, Hex/EtOAc), R$_f$=0.6.

Description 2 Alternative Method (D2A)

2-Amino-1-(4-(octyloxy)-3-(trifluoromethyl)phenyl)ethanone hydrochloride (D2)

A 5 L round bottom flask was charged with 1-(4-(Octyloxy)-3-(trifluoromethyl)phenyl)ethanone (D1A) (128 g, 0.40 mol), anhydrous dichloromethane (3.2 L), tetrabutylammonium tribromide (175 g, 0.36 mol, 0.9 equiv), methanol (640 mL) and stirred for 1 hour at room temperature (18 to 23° C.) and then treated with additional tetrabutylammonium tribromide (20 g, 0.1 equiv) and held for five additional hours. The reaction was deemed complete by TLC analysis (10% ethyl acetate in toluene) and concentrated to a residue. The residue was purified by column chromatography using silica gel (2.7 kg), eluted with 10% ethyl acetate: 90% heptane to afford a foamy solid (128 g, 80% yield). A 3 L round bottom flask was charged with a solution of the foamy solid (128 g, 0.32 mol) in acetonitrile (1 L) and sodium diformylamide (36.9 g, 0.38 mol, 1.2 equiv), and heated to 65° C. for 2 hours. The reaction was assayed by TLC and appeared to be approximately 50% complete. The reaction was allowed to continue for a further 10 hours, at which point was found to be complete by TLC. The mixture was cooled to room temperature (18 to 23° C.) and charged with MTBE (1 L), stirred for 15 minutes, filtered, the solids washed twice with MTBE (2×250 mL). The filtrates were combined and concentrated to thick oil. The oil was taken up in reagent alcohol (1.1 L), charged with 10 N HCl (100 mL) and heated to 70° C. and held for 3 hours, at which point TLC indicated the reaction to be complete. The mixture was cooled to 40-50° C. and transferred to a rotavap and the ethanol removed, and azeotroped three times with toluene (3×1 L) to afford the title product (149 g, quantitative yield) as gummy oil.

Description 3

(R)-3-(tert-Butoxycarbonyl)-2,2,4-trimethyloxazolidine-4-carboxylic acid (D3)

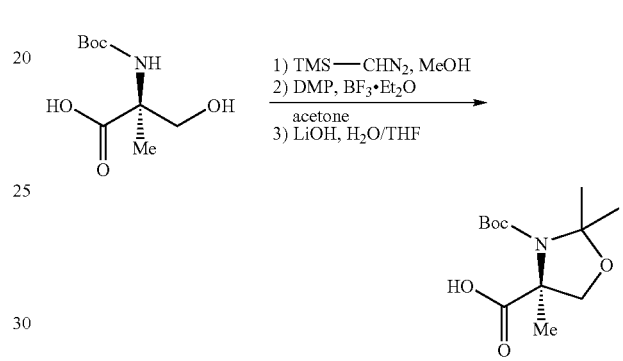

To a solution of the (S)-2-(tert-butoxycarbonylamino)-3-hydroxy-2-methylpropanoic acid (5.0 g, 1.0 equiv) in CH$_2$Cl$_2$/MeOH (4:1, 50 mL) at 0° C. was added a solution of TMS-CHN$_2$ (2.0 M in diethyl ether or hexanes, 12.5 mL, 1.1 equiv) drop-wise until the colourless solution turned a light yellow colour. The reaction mixture was stirred for 20 minutes at 0° C. then a few drops of acetic acid were added to quench the last unreacted TMS-CHN$_2$ (the solution turns colourless from light yellow). The solvent was removed in vacuo. TLC (2:1, Hex/EtOAc), R$_f$=0.4.

The residue was dissolved in acetone (30 mL), 2,2-dimethoxypropane (DMP) (12 mL) and BF$_3$.OEt$_2$ (2 mL). The solution was stirred at RT for 4 hours. The solvent was removed in vacuo and the product was purified by silica gel column chromatography using the Combi-Flash system (Hex:EtOAc). TLC (3:1, Hex/EtOAc), R$_f$=0.6; $^1$H NMR (400 MHz, CDCl$_3$) δ 4.06-4.12 (m, 1H), 3.73-3.83 (m, 4H), 1.55-1.64 (m, 9H), 1.48 (br s, 3H), 1.41 (br s, 6H).

The purified residue was dissolved in THF (40 mL) and to the solution was added LiOH (1.15 g, 1.20 equiv) in H$_2$O (20 mL). The solution was heated at reflux for 6 hours then stirred overnight, then concentrated in vacuo to remove most of the THF. The solution was diluted with H$_2$O (150 mL) and washed with Et$_2$O (2×150 mL). The aqueous layer was cooled to 0° C. then acidified to pH2 using concentrated HCl, then extracted with EtOAc (2×200 mL). The EtOAc layers were combined, dried (MgSO$_4$), filtered, and the solvent was removed in vacuo to afford the carboxylate title compound as a white solid in 64% yield (3.78 g). TLC (1:1 EtOAc:Hex), R$_f$=0.2; $^1$H NMR (400 MHz, CDCl$_3$) δ (rotamers) 4.47 (br d, 0.5H, J=8.8 Hz), 4.17 (br d, 0.5H, J=8.8 Hz), 3.85 (br d, 0.5H, J=8.8 Hz), 3.78 (br d, 0.5H, J=8.8 Hz), 1.38-1.67 (m, 18H).

Description 3 Alternative Method (D3A)

(R)-3-(tert-Butoxycarbonyl)-2,2,4-trimethyloxazolidine-4-carboxylic acid (D3)

A 22 L round bottom flask was inerted and charged with (S)-2-(tert-butoxycarbonylamino)-3-hydroxy-2-methylpropanoic acid (564 g, 2.57 mol), acetone (8.4 L) and stirred. The mixture was slowly charged with 1,8-Diazabicyclo[5.4.0]undec-7-ene (770 mL, 5.1 mol, 2 equiv.). The addition was exothermic and the temperature was maintained below 25° C. The mixture was stirred for 45 minutes at ambient conditions, and then cautiously charged with iodomethane (320 mL, 5.1 mol, 2 equiv). The addition was exothermic and the temperature was maintained below 25° C. The mixture was allowed to stir overnight at room temperature (18 to 23° C.). After 16 hours, TLC indicated starting material remained. The reaction was charged with iodomethane (320 mL, 5.1 mol, 2 equiv), warmed to 30° C. for 4 hours, and then allowed to stir overnight at room temperature (18 to 23° C.). After 16 hours, assay by TLC indicated the reaction was complete. The reaction mixture was combined with another reaction mixture of a scale of 275 g. The combined reaction mixtures were concentrated under vacuum to a residue, transferred into a reactor, charged with water (8.4 L), ethyl acetate (8.4 L), mixed thoroughly, phases split, extracted aqueous phase once more with ethyl acetate (8.4 L), combined organic phases, washed with 5% w/v citric acid (900 mL), brine (1 L), dried with magnesium sulfate, filtered over Celite, and concentrated to afford an oil (925 g, 104% yield). A 22 L round bottom flask was charged with this crude product (925 g, 3.8 mol based on theoretical output from previous step), dichloromethane (10 L), 2,2-Dimethoxypropane (2.6 L), and mixed. Boron trifluoride diethyl etherate (200 mL, 1.62 mol, 0.42 equiv) in dichloromethane (1.2 L) was cautiously charged over 45 minutes. The resulting dark solution was stirred over night at room temperature (18 to 23° C.). After 16 hours TLC indicated the reaction was complete. The mixture was slowly quenched with saturated sodium bicarbonate (3.5 L) while maintaining the temperature below 25° C. Once the quench was complete, the mixture was stirred for 30 minutes, the phases separated, and the aqueous extracted with dichloromethane (3.5 L), the organic phases were combined, washed with saturated sodium bicarbonate (3 L), concentrated to obtain compound a yellow oil (1070 g, quantitative). A 22 L round bottom flask was charge with lithium hydroxide monohydrate (482 g, 11.4 mol, 3 equiv), water (2.3 L), methanol (2.1 L), a solution of crude yellow oil (1046 g—based on theoretical output of previous step, 3.82 mol) in tetrahydrofuran (6.5 L). The mixture was stirred for 72 hours at room temperature (18 to 23° C.). TLC indicated the reaction was complete. The mixture was concentrated under vacuum at 40° C., the residue was charged with water (10 L), MTBE (6 L), mixed thoroughly, and the phases split. The organic phase was washed with water (4 L), the aqueous phases were combined, and solid citric acid was charged in portions until a pH of 3 was obtained. The aqueous was extracted with ethyl acetate (2×10 L), ethyl acetate phases were combined, washed with brine (7 L), dried with magnesium sulfate, filtered over Celite, and concentrated to afford the title product (770 g, 77.6% yield) as an off white solid.

Description 4

(R)-tert-Butyl 2,2,4-trimethyl-4-(5-(4-(octyloxy)-3-(trifluoromethyl)phenyl)thiazol-2-yl)oxazolidine-3-carboxylate (D4)

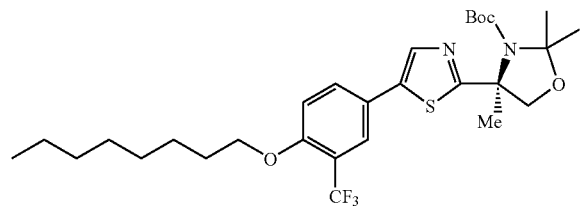

To a solution of (R)-3-(tert-Butoxycarbonyl)-2,2,4-trimethyloxazolidine-4-carboxylic acid (D3) (100 mg, 1 equiv), HATU (220 mg, 1.5 equiv), and DIEA (0.67 mL, 10 equiv) in DCM (5 mL) was added 2-amino-1-(4-(octyloxy)-3-(trifluoromethyl)phenyl)ethanone hydrochloride (D2) (142 mg, 1.0 equivalents). The solvent removed in vacuo and the product was purified with silica gel column chromatography using the Combi-Flash system (Hex:EtOAc). This resulted in a colourless, thick oil which was dissolved in toluene (5 mL) with Lawesson's reagent (280 mg, 3 equiv). The resultant mixture was heated at 120° C. for 2 hours to produce the title product as a colourless oil 41% yield (90 mg). TLC (1:2 EtOAc:Hex), $R_f$=0.3; MS (ESI, M+Na)=572.99; $^1$H NMR (400 MHz, CDCl$_3$) δ 8.21 (s, 1H), 8.11 (d, 1H, J=8.4 Hz), 7.05 (d, 1H, J=8.4 Hz), 4.62-4.79 (m, 2H), 4.13 (t, 2H, J=6.4 Hz), 3.28 (br s, 1H), 1.22-1.90 (m, 30H), 0.89 (t, 3H, J=6.4 Hz).

Description 4 Alternative Method (D4A)

(R)-tert-Butyl 2,2,4-trimethyl-4-(5-(4-(octyloxy)-3-(trifluoromethyl)phenyl)thiazol-2-yl)oxazolidine-3-carboxylate (D4)

A 5 L, round bottom flask was charged with HATU (147 g, 0.38 mol, 1.2 equiv), methylene chloride (600 mL), N,N-dimethylformamide (300 mL), diisopropylethylamine (83.5 g, 0.64 mol, 2 equiv) and the mixture cooled to 10-15° C. A solution of (R)-3-(tert-Butoxycarbonyl)-2,2,4-trimethyloxazolidine-4-carboxylic acid (D3A) (83.7 g, 0.32 mol, 1 equiv) in methylene chloride (600 mL) was charged over a period of 30 minutes. The mixture was warmed to room temperature (18 to 23° C.) and stirred for 1 hour. A separate flask was charged with solution of 2-Amino-1-(4-(octyloxy)-3-(trifluoromethyl)phenyl)ethanone hydrochloride (D2A) (149 g, 0.32 mol—based on theoretical output) in methylene chloride (1 L), N,N-dimethylformamide (400 mL) and diisopropylethylamine (125 g, 0.96 mol, 3 equiv). The solution of the second flask was slowly charged to the first flask over a period of 35 minutes. The resulting brown solution was stirred for 1 hour, at which point TLC analysis indicated the reaction was complete. The mixture was transferred to a rotavap and concentrated to remove the methylene chloride. The mixture was transferred once more to the round bottom flask and charge with MTBE (3 L), 10% w/v aqueous sodium chloride solution (3 L), stirred for 10 minutes, phases separated, and the aqueous extracted once more with MTBE (1 L). The organic phases were combined, washed twice with 10% w/v aqueous sodium chloride solution (2×1 L), dried with magnesium sulfate, and concentrated to a residue which was purified by column chromatography using silica-gel (1.3 kg), eluted with 5% ethyl acetate: 95% heptane to 30% ethyl acetate: 70% heptane to afford the product as a yellow-coloured oil (137.5 g, 74% yield). A 5 L round bottom flask was charged with Lawesson's reagent (116.2 g, 0.28 mol, 1.2 equiv), a solution of the yellow-coloured oil (137 g, 0.239 mol) in toluene (2 L). The resulting slurry was heated to 80° C. which after 30 minutes became a clear solution. The solution was held at 80° C. for another 2 hours, at which point TLC (25% ethyl acetate: 75% heptane) indicated the reaction was complete. The reaction mixture was cooled to room temperature (18 to 23° C.), charged with saturated sodium bicarbonate solution (1 L), 10% w/v sodium chloride (1 L), ethyl acetate (1 L), and stirred for 30 minutes. The phases were separated and the aqueous extracted once more with ethyl acetate (1 L). The organic phases were combined and concentrated to a residue. The residue was purified by column chromatography using silica-gel (1.3 kg), eluted with 100% heptane to 30% ethyl acetate: 70% heptane to afford the title product (91.1 g, 67% yield, 96.6% AUC by HPLC) as a brown oil.

Description 5

4-(Octyloxy)-3-(trifluoromethyl)benzoic acid (D5)

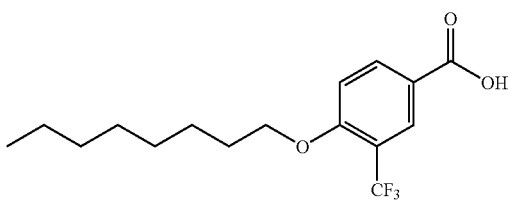

1-octanol (315 μL, 2.0 mmol), THF (5 mL), potassium t-butoxide (5 mL, 1M solution in THF), 4-Fluoro-3-trifluoromethylbenzoic acid (417 mg, 2.0 mmol) were mixed and heated at 75° C. for 3-4 hrs. The reaction mixture was then diluted with ethyl acetate and washed with water. The water layer was acidified and extracted with ethyl acetate. The organic layer was washed with brine and dried over $Na_2SO_4$ and concentrated to afford the title compound (632 mg, HPLC purity >95%), which was used for next reaction without further purification. HPLC retention time on a C8(2) column (30×3.00 mm, 3μ) was 3.28 min with gradient 50-98% acetonitrile-$H_2O$ (0.1% trifluoroacetic acid (TFA)) in 3.5 min as mobile phase.

Description 5 Alternative Method A (D5A)

4-(Octyloxy)-3-(trifluoromethyl)benzoic acid (D5)

A 12 L round bottom flask was inerted and charged with 1-octanol (103 g, 0.793 mol, 1 equiv), THF (2 L), 1 M potassium tert-butoxide (2 L, 2.5 equiv) and heated to 65° C. and held for 45 minutes. The reaction was charged over 1 hour with 4-fluoro-3-trifluoromethyl benzoic acid (165 g, 0.793 mol) while maintaining the temperature at 64 to 67° C. After 2 hours, the reaction mixture was sampled. The sample was concentrated, quenched into 1 N HCl, extracted with ethyl acetate, removed the ethyl acetate, diluted with acetonitrile and injected in to the HPLC. The reaction was complete. The reaction mixture was stirred overnight at 18 to 23° C. The mixture was cooled to 5 to 10° C. and cautiously quenched with water (1.6 L). The quench was exothermic and the temperature was maintained at T<10° C. The resulting mixture was concentrated under vacuum until no noticeable THF was coming off. The resulting aqueous mixture was acidified to pH 1 to 2 using 6 N HCl (400 mL). The mixture was extracted with MTBE (2×2.5 L). The MTBE phases were combined, washed with brine (2 L), dried with magnesium sulfate, filtered over Celite, concentrated to afford the title product (279 g, 111% yield, 95.6% AUC by HPLC) as a tan solid.

Description 6

4-(Octyloxy)-3-(trifluoromethyl)benzohydrazide (D6)

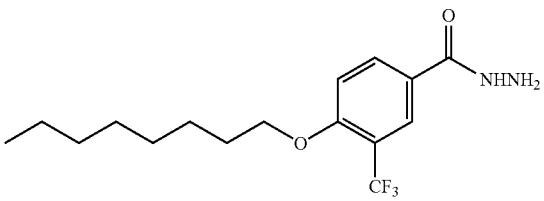

4-(Octyloxy)-3-(trifluoromethyl)benzoic acid (D5) (600 mg, 1 equiv) was stirred with HATU (859 mg, 1.2 equiv) and DIEA (1.63 mL, 5 equiv) in $CH_2Cl_2$-DMF (10 mL, 4:1, 3 equivalents) followed by addition of hydrazine (282 μL, 3 equiv). The reaction mixture was then diluted with ethyl acetate and washed with water and brine. The organic layer was dried over $Na_2SO_4$ and concentrated in vacuo to afford the title compound (661 mg). MS (ESI): 333.08 ($MH^+$)

Another batch was also made using D5 (32 mg, 1 equivalent), HATU (46 mg, 1.2 equivalents), DIEA (87 μL, 5 equiv) in $CH_2Cl_2$-DMF (1.5 mL, 2:1) followed by addition of hydrazine (15 μL, 3 equiv).

Description 6 Alternative Method (D6A)

4-(Octyloxy)-3-(trifluoromethyl)benzohydrazide (D6)

A 5 L 3 neck, round bottom flask was inerted and charged with CDI (153 g, 0.94 mol, 1.2 equiv), 4-(Octyloxy)-3-(trifluoromethyl)benzoic acid (D5A) (250 g based on theoretical output of previous step, 0.78 mol), THF (2.5 L) and stirred at 18 to 23° C. for 1 hour. A separate 12 L round bottom flask was inerted and charged with hydrazine monohydrate (235 g, 4.71 mol, 6 equiv) and THF (1.2 L). The contents of the first flask was charged to the second flask over 1 hour. During the addition, the temperature was maintained at T<25° C. Once the addition was complete, the mixture was stirred for 2 hours at 18 to 23° C., at which point TLC indicated the reaction was complete. The mixture was concentrated under vacuum at 35 to 40° C. until approximately 10 to 15% of the original volume was attained. Water (2 L) and brine (2 L) were charged to the mixture which was then extracted with dichloromethane (2×2.5 L). There was a small emulsion during each extraction. The organic phases were combined, washed with brine (500 mL), dried with magnesium sulfate, filtered over Celite, and concentrated to afford the title product (247 g, 94% yield, 96% AUC by HPLC) as a yellow solid.

Description 7

(R)-3-(tert-Butoxycarbonyl)-2,2,4-trimethyloxazolidine-4-carboxylic acid (D7)

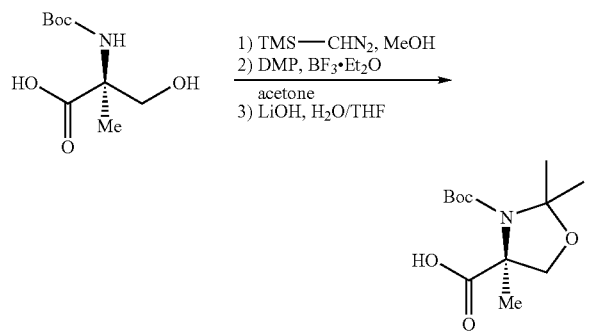

To a solution of the (S)-2-(tert-butoxycarbonylamino)-3-hydroxy-2-methylpropanoic acid (5.0 g, 1.0 equiv) in $CH_2Cl_2$/MeOH (4:1, 50 mL) was added a solution of TMS-$CHN_2$.

The residue was dissolved in acetone (30 mL), 2,2-dimethoxypropane (DMP) (12 mL) and $BF_3 \cdot OEt_2$ (2 mL). The solution was stirred at RT for 4 hours. The solvent was removed in vacuo and the product was purified by silica gel column chromatography using the Isco system (0-30% Hex: EtOAc) to give the oxazoline methyl ester intermediate.

The purified residue was dissolved in $H_2O$-THF (1:4) and to the solution was added LiOH (1.16 g). The solution was heated at refluxed for overnight, cooled to room temperature and condensed to remove the THF. The aqueous material was diluted with $H_2O$ (~100 mL), acidified to pH2 with 110% $KHSO_4$ and then extracted with EtOAc. The Eorganic layers were dried over $Na_2SO_4$, and condensed to afford the title compound in 66% yield (3.29 g).

Description 8

(S)-tert-Butyl 2,2,4-trimethyl-4-(2-(4-(octyloxy)-3-(trifluoromethyl)benzoyl)-hydrazinecarbonyl)oxazolidine-3-carboxylate (D8)

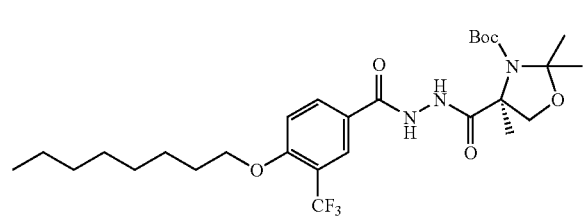

(R)-3-(tert-Butoxycarbonyl)-2,2,4-trimethyloxazolidine-4-carboxylic acid (D7) (210 mg, 0.81 mmol), HATU (372 mg, 0.98 mmol), diisopropylethyl amine (DIEA) (0.705 mL, 4.1 mmol), $CH_2Cl_2$-DMF and 4-(octyloxy)-3-(trifluoromethyl)benzohydrazide (D6) (270 mg, 0.81 mmol) were mixed together. The reaction was condensed, diluted with ethyl acetate, washed with water and brine, and condensed again. Another batch was made using this method with (D7) (0.1 mmol), HATU (46 mg, 0.12 mmol), DIEA (87 mL, 0.5 mmol), $CH_2Cl_2$-DMF and 4-(octyloxy)-3-(trifluoromethyl) benzohydrazide (D6) (>6 mg, 0.1 mmol). The batches were chromatographed and combined to provide the title product (428 mg). MS (ESI): 573.84 (MH$^+$); $^1$H NMR (400 MHz, $CDCl_3$) δ 9.43 (br, 2H), 8.06 (d, 1H, J=2.0 Hz), 7.94 (dd, 1H, J=8.8 Hz, J=2.0 Hz), 6.96 (d, 1H, J=8.8 Hz), 4.52 (br, 1H), 4.07 (t, 2H, J=6.4 Hz), 3.76 (br, 1H), 1.82 (m, 2H), 1.67 (s, 6H), 1.57 (s, 3H), 1.51 (s, 9H), 1.51-1.43 (m, 4H), 1.38-1.24 (m, 6H), 0.88 (t, 3H, J=7.2 Hz).

Description 8 Alternative Method (D8A)

(S)-tert-Butyl 2,2,4-trimethyl-4-(2-(4-(octyloxy)-3-(trifluoromethyl)benzoyl)-hydrazinecarbonyl)oxazolidine-3-carboxylate (D8)

A 5 L round bottom flask was inerted and charged with HATU (199 g, 0.52 mol, 1.2 equiv), N,N-dimethylformamide (380 mL), and mixed. A solution of (R)-3-(tert-butoxycarbonyl)-2,2,4-trimethyloxazolidine-4-carboxylic acid (D3A) (133.1 g, 0.43 mol, 1 equiv), dichloromethane (870 mL), and N,N-diisopropylethylamine (155 mL, 0.88 mol, 2 equiv) was charged to the flask over 15 minutes. The resulting mixture was stirred at 18 to 23° C. for 1 hour. A solution of benzohydrazide (D6) (145 g, 0.43 mol, 1 equiv) in dichloromethane (1120 mL), and N,N-Dimethylformamide (420 mL) was charged over 15 minutes then stirred at 18 to 23° C. for 1 hour. After 1 hour, TLC indicated the reaction was complete. The mixture was concentrated, partitioned between ethyl acetate (2.5 L) and water (2.5 L). The phases were split and the aqueous extracted once more with ethyl acetate (1 L). The organic phases were combined, washed with 10% w/v sodium chloride (2×1 L), dried with magnesium sulfate, filtered over Celite, and concentrated under vacuum to afford the crude product (367 g, 146% yield). The crude material was purified using a silica-gel column (2 kg) which was eluted with 5 to 25% ethyl acetate in heptane to give the title product (270 g, 108% yield, 95.9% AUC by HPLC) as a yellow oil.

Description 9

(R)-tert-Butyl 2,2,4-trimethyl-4-(5-(4-(octyloxy)-3-(trifluoromethyl)phenyl)-1,3,4-thiadiazol-2-yl)oxazolidine-3-carboxylate (D9)

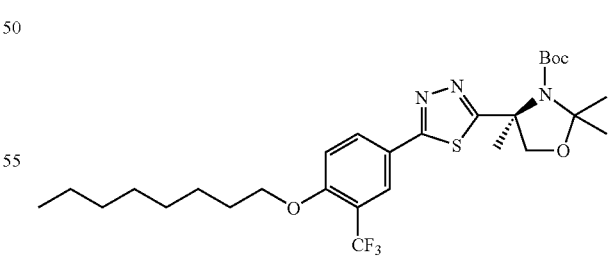

A solution of (S)-tert-butyl 2,2,4-trimethyl-4-(2-(4-(octyloxy)-3-(trifluoromethyl)-benzoyl)hydrazinecarbonyl)oxazolidine-3-carboxylate (D8) (228 mg, 0.39 mmol) in toluene (5 mL) was treated with Lawesson's reagent (321 mg, 0.79 mmol). The reaction was chromatographed on a silica gel column eluted with ethyl acetate-hexane to afford the title compound (~156 mg). MS (ESI): 572.17 (MH$^+$), $^1$H NMR (400 MHz, CDCl$_3$) δ 8.10 (d, 1H, J=8.8 Hz), 8.08 (d, 1H, J=6.8 Hz), 7.06 (d, 1H, J=8.0 Hz), 4.41 (d, 1H, J=8.0 Hz), 4.18 (d, 1H, J=9.6 Hz), 4.13-4.07 (m, 3H), 2.00 (s, 3H), 1.85 (m, 2H), 1.78 (s, 3H), 1.68 (m, 4H), 1.51 (s, 3H), 1.47 (m, 2H), 1.39-1.28 (m, 13H), 0.89 (t, 3H, J=7.2 Hz).

Description 9 Alternative Method (D9A)

(R)-tert-Butyl 2,2,4-trimethyl-4-(5-(4-(octyloxy)-3-(trifluoromethyl)phenyl)-1,3,4-thiadiazol-2-yl)oxazolidine-3-carboxylate (D9)

A 12 L, round bottom flask was inerted and charged with Lawesson's reagent (211.5 g, 0.52 mol, 1.2 equiv), a solution of (S)-tert-butyl 2,2,4-trimethyl-4-(2-(4-(octyloxy)-3-(trifluoromethyl)benzoyl)-hydrazinecarbonyl)oxazolidine-3-carboxylate (D8A) (250 g—based on theoretical output, 0.43 mol) in toluene (2.5 L), and the resulting slurry was heated to 80° C. and held for 3 hours. TLC indicated the reaction was complete. The mixture was cooled to 18-23° C., charged with saturated NaHCO$_3$ solution (2 L), which was slightly exothermic. The aqueous was extracted twice with ethyl acetate (2 L, 1.5 L), the organic phases were combined, concentrated, dissolved in dichloromethane (500 mL), charged with silica-gel (500 g), concentrated to remove dichloromethane, and purified using a silica-gel (2.5 kg) column which was eluted with 5% ethyl acetate: 95% heptane to afford the title product (185 g, 74% yield, 95% AUC by HPLC) as a yellow color oil.

Example 1

(S)-2-Amino-2-(5-(4-(octyloxy)-3-(trifluoromethyl)phenyl)thiazol-2-yl)propan-1-ol (E1)

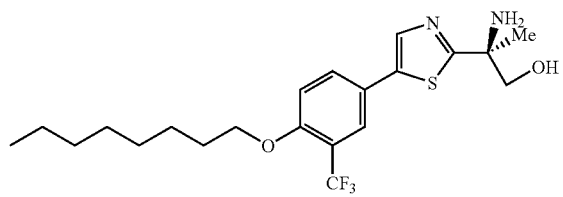

(R)-tert-Butyl 2,2,4-trimethyl-4-(5-(4-(octyloxy)-3-(trifluoromethyl)phenyl)thiazol-2-yl)oxazolidine-3-carboxylate (D4) (90 mg, 1 equiv) and para toluenesulfonic acid (PTSA, 300 mg, 10 equiv) in MeOH (6 mL) was refluxed for 4 hours. The solvent was removed from ⅔ of the reaction mixture and the product was purified by preparative HPLC to give the title product as the trifluoroacetate salt (35 mg). MS (ESI, M+H$^+$)=431.01; $^1$H NMR (400 MHz, DMSO-d$_6$) δ 8.27 (s, 1H), 7.88 (dd, 1H, J=8.8 Hz, J=2.4 Hz), 7.85 (d, 1H, J=2.4 Hz), 7.34 (d, 1H, J=8.4 Hz), 5.77 (br s, 1H), 4.14 (t, 2H, J=6.4 Hz), 3.76 (dd, 1H, J=11.2, Hz, J=1.2 Hz), 3.66 (dd, 1H, J=11.2 Hz, J=1.2 Hz), 1.73 (q, 2H, J=6.8 Hz), 1.58 (s, 3H), 1.36-1.48 (m, 2H), 1.20-1.36 (m, 8H), 0.85 (t, 3H, J=6.4 Hz).

Example 1

Alternative Method E1A (S)-2-Amino-2-(5-(4-(octyloxy)-3-(trifluoromethyl)phenyl)thiazol-2-yl)propan-1-ol (E1)

(R)-tert-Butyl 2,2,4-trimethyl-4-(5-(4-(octyloxy)-3-(trifluoromethyl)phenyl)thiazol-2-yl)oxazolidine-3-carboxylate (47 g, 82.35 mmol), was reacted with p-TSA (2 equiv) in methanol (470 mL) at reflux for 4 h at which point HPLC indicated the reaction was complete. The mixture was cooled to rt, concentrated to a residue, and triturated with IPAc (235 mL). The resulting solid was filtered, washed with IPAc (470 mL) to afford PPI-5325 p-TSA salt (45 g) as a white solid. The solid was converted to freebase by treating with 6 N NaOH and DCM as a solvent.

To form a hydrochloride salt of E1, the freebase (30 g, 69.84 mmol) was taken up in 4 M HCl in dioxane (70 mL) and stirred at rt for 0.25 hours. The 1,4-dioxane was concentrated to dryness and the crude was triturated with acetonitrile (200 mL). The resulting mixture was stirred for 1 h and filtered the white solid (23.3 g, 60%, $^1$H-NMR was consistent with structure).

Example 2

(S)-2-amino-2-(5-(4-(octyloxy)-3-(trifluoromethyl)phenyl)thiazol-2-yl)propyl dihydrogen phosphate (E2)

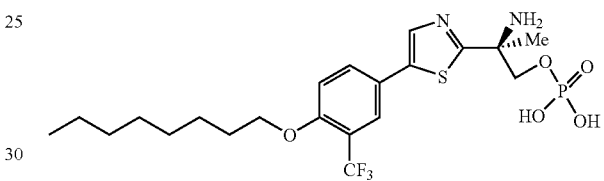

E1 (25 mg, 1.0 equiv), DCM (5 mL), diethyl chlorophosphate (85 μL, 10.0 equiv) and triethylamine (165 μL, 20.0 equiv) were stirred overnight. The obtained phospho-diester intermediate was reacted with excess bromotrimethylsilane in DCM for 5 hrs. The resulting phosphate was purified by preparative HPLC as the trifluoroacetate salt (10 mg). MS (ESI, M+H$^+$)=511.1.

Example 3

(S)-2-Amino-2-(5-(4-(octyloxy)-3-(trifluoromethyl)phenyl)-1,3,4-thiadiazol-2-yl)propan-1-ol (E3)

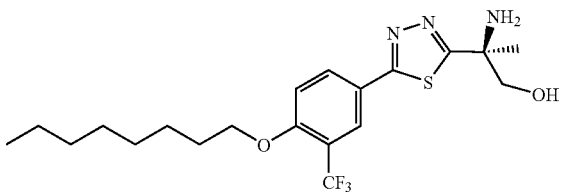

A solution of (S)-tert-butyl 2,2,4-trimethyl-4-(2-(4-(octyloxy)-3-(trifluoromethyl)-benzoyl)hydrazinecarbonyl)oxazolidine-3-carboxylate (D9) (156 mg, 0.27 mmol) in methanol (10 mL) was treated with p-toluenesulfonic acid monohydrate (259 mg, 1.36 mmol) at 70° C. for 3 hours. Two thirds of the reaction mixture was then purified by prep HPLC on a C8(2) column ((Luna, 5μ, 100×21.10 mm) with acetonitrile-H$_2$O (0.1% TFA) as mobile phase and gradient 30-98% in 20 min. The title compound was obtained as the bis-TFA salt (24 mg). MS (ESI): 432.00 (MH$^+$); $^1$H NMR (400 MHz, DMSO-d$_6$) δ 8.21 (dd, 1H, J=2.0 Hz, J=8.8 Hz), 8.15 (d, 1H, J=2.0 Hz), 8.09 (br s, 2H), 7.45 (d, 1H, J=8.8 Hz), 5.96 (t, 1H, J=4.8 Hz), 4.21 (t, 2H, J=6.4 Hz), 3.81 (dd, 1H, J=11.2 Hz, J=5.2 Hz), 3.73 (dd, 1H, J=11.2 Hz, J=5.2 Hz), 1.76 (m, 2H), 1.66 (s, 3H), 1.44 (m, 2H), 1.28 (m, 8H), 0.86 (t, 3H, J=6.8 Hz).

The remaining third of the reaction was condensed and the residue re-dissolved in ethyl acetate and washed with aqueous NaHCO3, brine, dried over brine and condensed again to provide crude product for use in Example 4.

Example 3

Alternative Method E3A)

(S)-2-Amino-2-(5-(4-(octyloxy)-3-(trifluoromethyl)phenyl)-1,3,4-thiadiazol-2-yl)propan-1-ol (E3)

A 5 L round bottom flask was inerted and charged with p-toluene sulfonic acid monohydrate (208 g, 1.09 mol, 5 equiv) and a solution of (R)-tert-Butyl 2,2,4-trimethyl-4-(5-(4-(octyloxy)-3-(trifluoromethyl)phenyl)-1,3,4-thiadiazol-2-yl)oxazolidine-3-carboxylate (125 g, 0.22 mol) in methanol (2.5 L), and heated to reflux. After 1.5 h HPLC indicated reaction complete. The heat was turned off and the mixture was allowed to cool to room temperature (18 to 23° C.) and stirred for 12 hours. The mixture was concentrated under vacuum to a residue to provide the title product.

The residue was taken up in dioxane (2 L), charged with 4 M HCl in dioxane (820 mL, 3.28 mol, 15 equiv), heated to 50° C. for 45 minutes, cooled to 18-23° C., stirred for 2 hours, filtered over a glass flitted filter, displaced once with MTBE (300 mL), slurried once with MTBE (300 mL), and dried on the filter to afford a hydrochloride of E3 (72 g, solvent wet).

Three batches of the hydrochloride of E3 synthesised using this method were combined (totaling 143 g, solvent wet), slurried twice in MTBE (750 mL, 500 mL), the solvent was filtered off each time, the material was transferred to a vacuum oven and dried overnight at room temperature (18 to 23° C.). $^1$H-NMR indicated the presence of dioxane (0.24% by weight). Further drying at an increased temperature of 30 to 35° C. for 72 hours afforded a hydrochloride (135 g, 98.6% AUC by HPLC) as a white solid.

Example 4

(S)-2-Amino-2-(5-(4-(octyloxy)-3-(trifluoromethyl)phenyl)-1,3,4-thiadiazol-2-yl)propyl dihydrogen phosphate (E4)

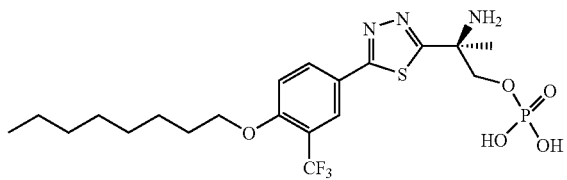

Crude product from E3 (30 mg, 0.069 mmol) was added to diethylchlorophosphate (100 μL, 0.69 mmol) and triethylamine (194 μL, 1.39 mmol,) in DCM and stirred for approx 36 hrs. The reaction mixture was then condensed and treated with bromotrimethylsilan (0.3 mL) in DCM (5 mL) to provide the title compound (~2 mg). MS (ESI): 511.98 (MH$^+$),

What is claimed is:

1. (S)-2-Amino-2-(5-(4-(octyloxy)-3-(trifluoromethyl)phenyl)-1,3,4-thiadiazol-2-yl)propan-1-ol or a pharmaceutically acceptable salt, phosphate derivative, phosphate mimic, or a phosphate precursor analog thereof.

2. (S)-2-Amino-2-(5-(4-(octyloxy)-3-(trifluoromethyl)phenyl)-1,3,4-thiadiazol-2-yl)propyl dihydrogen phosphate or a pharmaceutically acceptable salt thereof.

3. A pharmaceutical composition comprising a compound as defined claim in 1 or a pharmaceutically acceptable salt, phosphate derivative, phosphate mimic, or phosphate precursor analog thereof.

4. A pharmaceutical composition comprising a compound as defined in claim 2 or a pharmaceutically acceptable salt, phosphate derivative, phosphate mimic, or phosphate precursor analog thereof.

* * * * *